US00RE49699E

(19) United States
(12) Reissued Patent
Bouyssou et al.

(10) Patent Number: US RE49,699 E
(45) Date of Reissued Patent: Oct. 17, 2023

(54) INHIBITORS OF TRPC6

(71) Applicants: Boehringer Ingelheim International GmbH, Ingelheim am Rhein (DE); Hydra Biosciences, LLC, Belmont, MA (US)

(72) Inventors: Thierry Bouyssou, Ingelheim am Rhein (DE); Dirk Gottschling, Ingelheim am Rhein (DE); Niklas Heine, Ingelheim am Rhein (DE); Lana Louise Smith Keenan, Poughquag, NY (US); Michael D. Lowe, Pleasantville, NY (US); Hossein Razavi, Danbury, CT (US); Christopher Ronald Sarko, San Ramon, CA (US); Simon Surprenant, Boisbriand (CA); Hidenori Takahashi, LaGrangeville, NY (US); Michael Robert Turner, Danbury, CT (US); Xinyuan Wu, Newton, MA (US)

(73) Assignees: Boehringer Ingelheim International GmbH, Ingelheim am Rhein (DE); Hydra Biosciences, LLC, Belmont, MA (US)

(21) Appl. No.: 17/334,097

(22) Filed: May 28, 2021

Related U.S. Patent Documents

Reissue of:
(64) Patent No.: 10,800,757
Issued: Oct. 13, 2020
Appl. No.: 16/170,154
Filed: Oct. 25, 2018

U.S. Applications:
(60) Provisional application No. 62/628,313, filed on Feb. 9, 2018, provisional application No. 62/577,883, filed on Oct. 27, 2017.

(51) Int. Cl.

| | |
|---|---|
| ***C07D 401/14*** | (2006.01) |
| ***A61K 31/45*** | (2006.01) |
| ***A61K 31/501*** | (2006.01) |
| ***C07D 213/04*** | (2006.01) |
| ***C07D 451/02*** | (2006.01) |
| ***C07D 487/08*** | (2006.01) |
| ***C07D 498/08*** | (2006.01) |

(52) U.S. Cl.
CPC ..... *C07D 401/14* (2013.01); *A61K 31/45* (2013.01); *A61K 31/501* (2013.01); *C07D 213/04* (2013.01); *C07D 451/02* (2013.01); *C07D 487/08* (2013.01); *C07D 498/08* (2013.01)

(58) Field of Classification Search
CPC .. C07D 401/14; C07D 213/04; C07D 451/02; C07D 487/08; C07D 498/08; C07D 401/12; A61K 31/45; A61K 31/501; A61K 31/496; A61P 3/10; A61P 9/00; A61P 11/00; A61P 13/12; A61P 25/28
See application file for complete search history.

(56) References Cited

U.S. PATENT DOCUMENTS

| | | | |
|---|---|---|---|
| 6,673,799 | B1 | 1/2004 | Taniguchi et al. |
| 7,332,495 | B2 | 2/2008 | Li et al. |
| 8,816,079 | B2 | 8/2014 | Maeda et al. |
| 10,800,757 | B2 | 10/2020 | Bouyssou et al. |
| 10,889,568 | B2 | 1/2021 | Bouyssou et al. |
| 2004/0016224 | A1 | 1/2004 | Haaken et al. |
| 2007/0021472 | A1 | 1/2007 | Zhu et al. |
| 2010/0234603 | A1 | 9/2010 | Linghu et al. |
| 2011/0257196 | A1 | 10/2011 | Lu et al. |
| 2021/0163449 | A1 | 6/2021 | Bouyssou et al. |

FOREIGN PATENT DOCUMENTS

| | | | |
|---|---|---|---|
| CL | 202001097 | A1 | 8/2020 |
| CN | 1381449 | A | 11/2002 |
| CN | 103360343 | A | 10/2013 |
| CN | 106317050 | A | 1/2017 |
| CN | 107176927 | A | 9/2017 |
| CN | 107540636 | A | 1/2018 |
| EP | 1396487 | A1 | 3/2004 |
| JP | 2003-64057 | A | 3/2003 |
| JP | 2007-254391 | A | 10/2007 |
| JP | 2008-239568 | A | 10/2008 |
| JP | 2013-107881 | A | 6/2013 |
| JP | 2016-520105 | A | 7/2016 |
| JP | 2021-8503 | A | 1/2021 |
| TW | 201930264 | A | 8/2019 |
| WO | WO 91/09594 | A1 | 7/1991 |
| WO | WO 93/00313 | A2 | 1/1993 |

(Continued)

OTHER PUBLICATIONS

Extended European Search Report dated Feb. 3, 2021 in connection with EP Application No. 20197194.2.

(Continued)

*Primary Examiner* — Jerry D Johnson
(74) *Attorney, Agent, or Firm* — Wolf, Greenfield & Sacks, P.C.

(57) ABSTRACT

The invention related to compounds of formula (I), (I)

and pharmaceutically acceptable salts thereof, wherein $R^1$ to $R^2$, A, Y and L are as defined herein. The invention also relates to pharmaceutical compositions comprising these compounds, methods of using these compounds in the treatment of various diseases and disorders, processes for preparing these compounds and intermediates useful in these processes.

40 Claims, No Drawings

(56) References Cited

FOREIGN PATENT DOCUMENTS

| | | | |
|---|---|---|---|
| WO | WO 94/12461 | A1 | 6/1994 |
| WO | WO 00/17163 | A1 | 3/2000 |
| WO | WO 02/08221 | A2 | 1/2002 |
| WO | WO 02/102778 | A1 | 12/2002 |
| WO | WO 03/090752 | A1 | 11/2003 |
| WO | WO 2006/044174 | A2 | 4/2006 |
| WO | WO 2007/053394 | A1 | 5/2007 |
| WO | WO 2007/075629 | A2 | 7/2007 |
| WO | WO 2008/110611 | A1 | 9/2008 |
| WO | WO 2010/080357 | A1 | 7/2010 |
| WO | WO 2011/019798 | A1 | 2/2011 |
| WO | WO 2011/044001 | A1 | 4/2011 |
| WO | WO 2011/062939 | A1 | 5/2011 |
| WO | WO 2011/109059 | A1 | 9/2011 |
| WO | WO 2011/136292 | A1 | 11/2011 |
| WO | WO 2011/143365 | A1 | 11/2011 |
| WO | WO 2012/016217 | A1 | 2/2012 |
| WO | WO 2012/158784 | A2 | 11/2012 |
| WO | WO 2013/066714 | A1 | 5/2013 |
| WO | WO 2014/139144 | A1 | 9/2014 |
| WO | WO 2014/191336 | A1 | 12/2014 |
| WO | WO 2015/048547 | A2 | 4/2015 |
| WO | WO 2015/101957 | A2 | 7/2015 |
| WO | WO 2016/073774 | A2 | 5/2016 |
| WO | WO 2016/138114 | A1 | 9/2016 |
| WO | WO 2017/066705 | A1 | 4/2017 |
| WO | WO 2017/161028 | A1 | 9/2017 |
| WO | WO 2017/222930 | A1 | 12/2017 |
| WO | WO 2018/159827 | A1 | 9/2018 |
| WO | WO 2018/170225 | A1 | 9/2018 |
| WO | WO 2019/081637 | A1 | 5/2019 |

OTHER PUBLICATIONS

International Search Report and Written Opinion dated Jan. 21, 2019 for Application No. PCT/EP2018/079276.

Alessandri-Haber et al., TRPC1 and TRPC6 channels cooperate with TRPV4 to mediate mechanical hyperalgesia and nociceptor sensitization. J Neurosci. May 13, 2009;29(19):6217-28. doi: 10.1523/JNEUROSCI.0893-09.2009.

Antigny et al., Transient receptor potential canonical channel 6 links Ca2+ mishandling to cystic fibrosis transmembrane conductance regulator channel dysfunction in cystic fibrosis. Am J Respir Cell Mol Biol. Jan. 2011;44(1):83-90. doi: 10.1165/rcmb.2009-0347OC. Epub Mar. 4, 2010.

Bergdahl et al., Plasticity of TRPC expression in arterial smooth muscle: correlation with store-operated Ca2+ entry. Am J Physiol Cell Physiol. Apr. 2005;288(4):C872-80. Epub Nov. 23, 2004.

Bernaldo De Quiros et al., Identification of TRPC6 as a possible candidate target gene within an amplicon at 11q21-q22.2 for migratory capacity in head and neck squamous cell carcinomas. BMC Cancer. Mar. 14, 2013;13:116. doi: 10.1186/1471-2407-13-116.

Chigurupati et al., Receptor channel TRPC6 is a key mediator of Notch-driven glioblastoma growth and invasiveness. Cancer Res. Jan. 1, 2010;70(1):418-27. doi: 10.1158/0008-5472.CAN-09-2654. Epub Dec. 22, 2009.

Clapham et al., The TRP ion channel family. Nat Rev Neurosci. Jun. 2001;2(6):387-96. Review.

Clapham, TRP channels as cellular sensors. Nature. Dec. 4, 2003;426(6966):517-24. Review.

Clarson et al., Store-operated Ca2+ entry in first trimester and term human placenta. J Physiol. Jul. 15, 2003;550(Pt 2):515-28. Epub May 23, 2003.

Davis et al., A TRPC6-dependent pathway for myofibroblast transdifferentiation and wound healing in vivo. Dev Cell. Oct. 16, 2012;23(4):705-15. doi: 10.1016/j.devcel.2012.08.017. Epub Sep. 27, 2012.

Desai et al., TRP channels and mice deficient in TRP channels. Pflugers Arch. Oct. 2005;451(1):11-8. Epub Aug. 3, 2005. Review.

Dhennin-Duthille et al., High expression of transient receptor potential channels in human breast cancer epithelial cells and tissues: correlation with pathological parameters. Cell Physiol Biochem. 2011;28(5):813-22. doi: 10.1159/000335795. Epub Dec. 15, 2011.

Ding et al., Pyrazolo[1,5-a]pyrimidine TRPC6 antagonists for the treatment of gastric cancer. Cancer Lett. Sep. 28, 2018;432:47-55. doi: 10.1016/j.canlet.2018.05.041. Epub May 31, 2018.

Ding et al., Essential role of TRPC6 channels in G2/M phase transition and development of human glioma. J Natl Cancer Inst. Jul. 21, 2010;102(14):1052-68. doi: 10.1093/jnci/djq217. Epub Jun. 16, 2010.

Eckel et al., TRPC6 enhances angiotensin II-induced albuminuria. J Am Soc Nephrol. Mar. 2011;22(3):526-35. doi: 10.1681/ASN.2010050522. Epub Jan. 21, 2011.

Finney-Hayward et al., Expression of transient receptor potential C6 channels in human lung macrophages. Am J Respir Cell Mol Biol. Sep. 2010;43(3):296-304. doi: 10.1165/rcmb.2008-0373OC. Epub Oct. 20, 2009.

Hafner et al., (+)-Larixol Congener with High Affinity and Subtype Selectivity toward TRPC6. ChemMedChem. May 23, 2018; 13(10):1028-1035. doi: 10.1002/cmdc.201800021. Epub Apr. 26, 2018.

Hofmann et al., Direct activation of human TRPC6 and TRPC3 channels by diacylglycerol. Nature. Jan. 21, 1999;397(6716):259-63.

Iyer et al., Receptor channel TRPC6 orchestrate the activation of human hepatic stellate cell under hypoxia condition. Exp Cell Res. Aug. 1, 2015;336(1):66-75. doi: 10.1016/j.yexcr.2015.03.023. Epub Apr. 4, 2015.

Johansson et al., Cerebrovascular endothelin-1 hyper-reactivity is associated with transient receptor potential canonical channels 1 and 6 activation and delayed cerebral hypoperfusion after forebrain ischaemia in rats. Acta Physiol (Oxf). Jul. 2015;214(3):376-89. doi: 10.1111/apha.12519. Epub Jun. 4, 2015.

Krall et al., Podocyte-specific overexpression of wild type or mutant trpc6 in mice is sufficient to cause glomerular disease. PLoS One. Sep. 20, 2010;5(9):e12859. doi: 10.1371/journal.pone.0012859.

Ku et al., Expression of transient receptor channel proteins in human fundal myometrium in pregnancy. J Soc Gynecol Investig. Apr. 2006;13(3):217-25. Epub Mar. 9, 2006.

Kunichika et al., Bosentan inhibits transient receptor potential channel expression in pulmonary vascular myocytes. Am J Respir Crit Care Med. Nov. 15, 2004;170(10):1101-7. Epub Aug. 18, 2004.

Kuwahara et al., TRPC6 fulfills a calcineurin signaling circuit during pathologic cardiac remodeling. J Clin Invest. Dec. 2006;116(12):3114-26. Epub Nov. 9, 2006.

Lei et al., The role of mechanical tension on lipid raft dependent PDGF-induced TRPC6 activation. Biomaterials. Mar. 2014;35(9):2868-77. doi: 10.1016/j.biomaterials.2013.12.030. Epub Jan. 4, 2014.

Maier et al., Discovery and pharmacological characterization of a novel potent inhibitor of diacylglycerol-sensitive TRPC cation channels. Br J Pharmacol. Jul. 2015;172(14):3650-60. doi: 10.1111/bph.13151. Epub May 19, 2015.

Moller et al., Induction of TRPC6 channel in acquired forms of proteinuric kidney disease. J Am Soc Nephrol. Jan. 2007;18(1):29-36. Epub Dec. 13, 2006.

Motoyama et al., Discovery of a bicyclo[4.3.0]nonane derivative DS88790512 as a potent, selective, and orally bioavailable blocker of transient receptor potential canonical 6 (TRPC6). Bioorg Med Chem Lett. Jul. 1, 2018;28(12):2222-2227. doi: 10.1016/j.bmcl.2018.03.056. Epub Mar. 22, 2018.

Reiser et al., TRPC6 is a glomerular slit diaphragm-associated channel required for normal renal function. Nat Genet. Jul. 2005;37(7):739-44. Epub May 27, 2005.

Rosenbaum et al., Hypercholesterolemia inhibits re-endothelialization of arterial injuries by TRPC channel activation. J Vase Surg. Oct. 2015;62(4):1040-1047.e2. doi: 10.1016/j.jvs.2014.04.033. Epub May 10, 2014.

Sadowski et al., A single-gene cause in 29.5% of cases of steroid-resistant nephrotic syndrome. J Am Soc Nephrol. Jun. 2015;26(6):1279-89. doi: 10.1681/ASN.2014050489. Epub Oct. 27, 2014.

(56) References Cited

OTHER PUBLICATIONS

Schlondorff et al., TRPC6 mutations associated with focal segmental glomerulosclerosis cause constitutive activation of NFAT-dependent transcription. Am J Physiol Cell Physiol. Mar. 2009;296(3):C558-69. doi: 10.1152/ajpcell.00077.2008. Epub Jan. 7, 2009.
Seo et al., Combined TRPC3 and TRPC6 blockade by selective small-molecule or genetic deletion inhibits pathological cardiac hypertrophy. Proc Natl Acad Sci U S A. Jan. 28, 2014;111(4):1551-6. doi: 10.1073/pnas. 1308963111. Epub Jan. 22, 2014. Erratum in: Proc Natl Acad Sci U S A. Apr. 22, 2014;111(16):6115.
Sharma et al., Review of Transient Receptor Potential Canonical (TRPC5) Channel Modulators and Diseases. J Med Chem. Apr. 17, 2019. doi: 10.1021/acs.jmedchem.8b01954.
Song et al., Critical role of TRPC6 channels in the development of human renal cell carcinoma. Mol Biol Rep. Aug. 2013;40(8):5115-22. doi: 10.1007/s11033-013-2613-4. Epub May 23, 2013.
Tauseef et al., TLR4 activation of TRPC6-dependent calcium signaling mediates endotoxin-induced lung vascular permeability and inflammation. J Exp Med. Oct. 22, 2012;209(11):1953-68. doi: 10.1084/jem.20111355. Epub Oct. 8, 2012.
Thilo et al., Pulsatile atheroprone shear stress affects the expression of transient receptor potential channels in human endothelial cells. Hypertension. Jun. 2012;59(6):1232-40. doi: 10.1161/HYPERTENSIONAHA.111.183608. Epub May 7, 2012.
Thilo et al., VEGF regulates TRPC6 channels in podocytes. Nephrol Dial Transplant. Mar. 2012;27(3):921-9. doi: 10.1093/ndt/gfr457. Epub Aug. 24, 2011.
Urban et al., Identification and Validation of Larixyl Acetate as a Potent TRPC6 Inhibitor. Mol Pharmacol. Jan. 2016;89(1):197-213. doi: 10.1124/mol.115.100792. Epub Oct. 23, 2015.
Wang et al., Effects of chronic exposure to cigarette smoke on canonical transient receptor potential expression in rat pulmonary arterial smooth muscle. Am J Physiol Cell Physiol. Feb. 15, 2014;306(4):C364-73. doi: 10.1152/ajpcell.00048.2013. Epub Dec. 11, 2013.
Washburn et al., The discovery of potent blockers of the canonical transient receptor channels, TRPC3 and TRPC6, based on an anilino-thiazole pharmacophore. Bioorg Med Chem Lett. Sep. 1, 2013;23(17):4979-84. doi: 10.1016/j.bmcl.2013.06.047. Epub Jun. 26, 2013.
Weissmann et al., Activation of TRPC6 channels is essential for lung ischaemia-reperfusion induced oedema in mice. Nat Commun. Jan. 31, 2012;3:649. doi: 10.1038/ncomms1660.
Wen et al., Regulation of Multi-drug Resistance in hepatocellular carcinoma cells is TRPC6/Calcium Dependent. Sci Rep. Mar. 24, 2016;6:23269. doi: 10.1038/srep23269.
Winn et al., A mutation in the TRPC6 cation channel causes familial focal segmental glomerulosclerosis. Science. Jun. 17, 2005;308(5729):1801-4. Epub May 5, 2005.
Wu et al., TRPC channels are necessary mediators of pathologic cardiac hypertrophy. Proc Natl Acad Sci U S A. Apr. 13, 2010;107(15):7000-5. doi: 10.1073/pnas.1001825107. Epub Mar. 29, 2010.
Xie et al., Soluble Klotho Protects against Uremic Cardiomyopathy Independently of Fibroblast Growth Factor 23 and Phosphate. J Am Soc Nephrol. May 2015;26(5):1150-60. doi: 10.1681/ASN.2014040325. Epub Dec. 4, 2014.
Xie et al., Cardioprotection by Klotho through downregulation of TRPC6 channels in the mouse heart. Nat Commun. 2012;3:1238. doi: 10.1038/ncomms2240.
Yu et al., Enhanced expression of transient receptor potential channels in idiopathic pulmonary arterial hypertension. Proc Natl Acad Sci U S A. Sep. 21, 2004; 101(38):13861-6. Epub Sep. 9, 2004.
Zhang et al., High expression of transient potential receptor C6 correlated with poor prognosis in patients with esophageal squamous cell carcinoma. Med Oncol. 2013;30(3):607. doi: 10.1007/S12032-013-0607-7. Epub May 18, 2013.
Zhang et al., MicroRNA-26a prevents endothelial cell apoptosis by directly targeting TRPC6 in the setting of atherosclerosis. Sci Rep. Mar. 24, 2015;5:9401. doi: 10.1038/srep09401.
U.S. Appl. No. 16/170,178, filed Oct. 25, 2018, Bouyssou et al.

INHIBITORS OF TRPC6

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION(S)

This Application *is a reissue of U.S. Pat. No. 10,800,757, issued on Oct. 13, 2020, filed as U.S. patent application Ser. No. 16/170,154 on Oct. 25, 2018, which* is a Non-Provisional application and claims priority under 35 USC 119(e) of U.S. Application Ser. No. 62/628,313, filed Feb. 9, 2018, and U.S. Application Ser. No. 62/577,883, filed Oct. 27, 2017. The entire contents of these applications are incorporated herein by reference in their entirety.

FIELD OF THE INVENTION

The present invention relates to pharmaceutical compounds, compositions, and methods for the treatment of cardiac and respiratory conditions, renal disease, liver disease, muscular dystrophy, fibrotic disorders, pain ischemia or ischemic reperfusion injury, and cancer, as well as inhibiting the Transient Receptor Potential C6 ion channel (TRPC6).

BACKGROUND

A variety of ion channel proteins exist to mediate ion flux across cellular membranes. The proper expression and function of ion channel proteins is essential for the maintenance of cellular function, intracellular communication, and the like. An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. Numerous diseases are the result of dysregulation of membrane potential or aberrant calcium handling. Given the central importance of ion channels in modulating membrane potential and ion flux in cells, identification of agents that can promote or inhibit particular ion channels is of great interest as research tools and as possible therapeutic agents.

One such channel is the Transient Receptor Potential C6 (TRPC6) channel. TRPC6 belongs to the larger family of TRP ion channels (see, Desai et al., 2005 Eur J Physiol 451:11-18; Clapham et al., 2001 Nat Neurosci 2:387-396; Clapham, 2003 Nature 426: 517-524; Clapham et al., 2002 IUPHAR Compendium). TRPC6 is a calcium permeable channel, specifically a non-selective calcium permeable cation channel. In addition to calcium ions, TRPC6 channels are permeable to other cations, for example sodium. Thus, TRPC6 channels modulate not only intracellular calcium concentration, but also membrane potential by modulating the flux of cations including calcium and sodium ions. Although non-selective cation channels such as TRPC6 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels such as TRPC6 are generally signal transduction gated, long-lasting, and produce less rapid changes in ion concentration. They show increased activity in response to the production of the second messenger, diacylglycerol (Hofmann et al., 1999). In addition, TRPC6 can respond to changes in pressure. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

TRPC6 function has been implicated in, among other things, the modulation of myogenic tone. TRPC6 is highly expressed in smooth muscle cells, vascular smooth muscle cells, cardiomyocytes, pulmonary arteries, the aorta, heart, liver, brain, and kidney. The expression of TRPC6, along with experiments conducted in knock-out mice and cells in culture, suggest that TRPC6 may provide a useful target for the treatment of hypertension and other cardiac and vascular conditions, preeclampsia.

Mutation in the human TRPC6 channel can cause focal segmental glomerulscierosis (FSGS) (Winn et al., 2005, Reiser et al., 2005). These mutations that are reported to be gain-of-function (Reiser et al 2005), are sufficient to induce disease. In addition, elevated TRPC6 expression has been associated with nephrotic syndrome, minimal change disease, and diabetic nephropathy (Moller et al., 2006, Ilatovskaya et al., 2013, Thilo et al., 2011), or other kidney conditions.

Based on its expression and work implicating it in TGF-B signaling; TRPC6 is also thought to be important in respiratory conditions, restenosis, liver disease, muscular dystrophy, fibrotic disorders, pain, ischemia and ischemic reperfusion injury, and certain forms of cancer.

Yue et al. studied TRPC6 channels for a role in mediating the pulmonary artery smooth muscle cell proliferation that can lead to idiopathic pulmonary arterial hypertension (IPAH). Pulmonary vascular medial hypertrophy caused by excessive pulmonary artery smooth muscle cell (PASMC) proliferation is a major cause for the elevated pulmonary vascular resistance in patients with IPAH. The authors found that TRPC6 was highly expressed and TRPC3 was minimally expressed in PASMC from healthy lung tissue. However, in lung tissue from IPAH patients, mRNA and protein expression of TRPC3 and TRPC6 were significantly elevated in comparison to that in normotensive patients. Furthermore, proliferation of PASMC cells derived from IPAH patients was markedly reduced following incubation with TRPC6 siRNA. Based on these results, the authors concluded that TRPC6 may be important in mediating proper PASMC proliferation, and that dysregulation of TRPC6 may lead to increased PASMC proliferation and pulmonary vascular medial hypertrophy observed in IPAH patients (Yu et al., 2004 Proc Natl Acad Sci 101(38):13861-6), Further support is provided by the observation that in IPAH patients the frequency of a single-nucleotide polymorphism in the promoter of TRPC6 which increases expression was significantly higher when compared to normal subjects (Yue, et al, 2009 Circulation 119: 2313-22).

Additional evidence implicating TRPC6 dysregulation in IPAH comes from studies of bosentan; a dual endothelin receptor blocker, that has been used clinically to treat IPAH. This inhibitor decreases proliferation of PASMCs, but the mechanism by which this occurs is unclear. Interestingly, bosentan both decreases proliferation of PASMC and also decreases expression of TRPC6 in lung tissue of IPAH patients (Kunichika et al., 2004 Am J Respir Crit Care Meal 170(10):1101-7).

Chronic exposure of cigarette smoke (CS) to rats resulted in an increase in TRPC6 mRNA and protein expression in distal pulmonary arteries and similar erects were observed using PASMCs in vitro. Nicotine treatment of cultured rat PASMCs upregulated TRPC6 expression and increased intracellular calcium levels, both of which were reduced by TRPC6 siRNA silencing (Wang et al., 2014 Ant J Physiol Cell Physiol 306:C364-73). These results suggest a role for TRPC6 in CS-induced lung injury.

Evidence supports a role of TRPC6 in additional pulmonary disorders. In alveolar macrophages from patients with chronic obstructive pulmonary disease (COPD), TRPC6 expression was found to be elevated when compared with controls (Finney-Hayward et al., 2010 Am J Respir Cell Mol Biol 43:296-304). In human cystic fibrosis epithelial cells, the TRPC6-mediated calcium influx is abnormally increased and may contribute to the hypersecretion of mucus. siRNA-TRPC6 was able to reduce this abnormal calcium influx (Antigny et al. 2011 Am J Resp Cell Mol Biol, 44:83-90). In mouse lung fibroblasts, the pro-fibrotic activity of PDGF is dependent on the activation of TRPC6, suggesting that TRPC6 inhibition would reduce lung fibrosis (Lei et al., 2014 Biomaterials 35:2868-77). A role of TRPC6 in pulmonary endothelial cell function was demonstrated in mouse lung models of ischemic-reperfusion induced-edema and lipopolysaccharide-induced inflammation in which TRPC6 deficiency was able to reduce acute lung injury by preserving endothelial barrier function (Weissmann et al., 2011 Nat Comm, 3:649-58 and Tauseef et al., 2012 J Exp Med 209:1953-68).

Recent studies also implicate the role of TRPC6 in other cardiac conditions, including cardiac hypertrophy. The hearts of patients with dilated cardiomyopathy have elevated TRPC6 mRNA expression when compared with normal hearts (Kuwahara et al., 2006 J Clin Invest 116:3114-26). In mouse models of cardiac hypertrophy, TRPC6 cardiac mRNA levels are elevated by pressure overload (Kuwahara et al., 2006 J Clin invest 176:3114-26), chronic isoproterenol treatment (Xie et al., 2012 Nat Commun 3:1238), and uremic cardiomyopathy induced by partial nephrectomy (Xie et al., 2015 J Am Soc Nephrol 26:1150-60). Furthermore, cardiac specific overexpression of TRPC6 in the cardiomyoctes of transgenic mice induced cardiac hypertrophy and premature death (Kuwahara et al., 2006 J Clin Invest 116:3114-26).

Wu and colleagues found that transgenic mice expressing dominant-negative TRPC6 in a cardiac-specific fashion had an attenuated cardiac hypertrophic response following either neuroendocrine agonist infusion or pressure-overload simulation, indicating that TRPC6 is a component of channel complexes that are essential mediators of hypertrophy (Wu et al., 2010 Proc Nati Acad Sci. 107:7000-05). Small molecule drugs targeting TRPC6 have also recently begun to show promise in treating cardiac conditions. For example, Seo and coworkers demonstrated that TRPC6 and TRPC3 antagonists (GSK2332255B and GSK833503A) exhibited dose-dependent inhibition of cell hypertrophy signaling in neonatal and adult cardiac myncytes (Seo et al., 2014 Proc Natl Acad Sci 111:1551-1556). Similarly, mice deficient for TRPC6 were protected from isoproterenol-induced cardiac hypertrophy (Xie et al., 2012 Nat Commun 3:1238).

Reducing TRPC6 activity may be beneficial for the treatment of cardiovascular disease. In vitro, atheroprone shear stress-induces increased TRPC6 mRNA levels in human vascular endothelial cells (EC) when compared to atheroprotective flow conditions (Thilo, et al., 2072 Hypertension 59:1232-40). EC migration is important for healing after arterial injury, and lysophosphatidylcholine-mediated ihhibition of EC migration was prevented in vitro in cells from TRPC6 deficient mice. Furthermore, high cholesterol diet combined with carotid injury did not impair healing in TRPC6 deficient mice when compared with wild-type controls (Rosenbaum et al., 2015 J Vasc Surg 62:1040-47 and Chaudhuri et al., 2008 Mol Biol Cell 19: 3203-11). Similarly, balloon dilatation-induced injury of human internal mammary arteries ex vivo resulted in increased TRPC6 mRNA levels when compared with undilated arteries (Bergdahl et al, 2005 Am J Physiol Cell Physiol 288:C872-80). Apoptosis of endothelial cells is involved in the initiations and progression of atherosclerotic lesions, and oxidized low-density lipoprotein-induced apoptosis of human aortic ECs was demonstrated to be dependent on TRPC6 (Zhang et al, 2015 Sci Rep 5:9401-10). In a rat model of forebrain ischaemia, TRPC6 mRNA levels were increased in vascular SMCs and correlated with reduced cerebral blood flow (Johannson et al., 2015 Acta Physiol 214:376-89).

Studies by Reiser, Winn, and Schlöndorff identified mutations in TRPC6 in patients as being causative in FSGS (Reiser et al., 2005 Nature Genet 37:739-744; Winn et al, 2005 Science 308:1801-1804; Schlöndorff et al., 2009 Am J Physiol Cell Physiol 296:C558-69). Subsequent studies identified additional TRPC6 mutations associated with steroid-resistant nephrotic syndrome (C. Sadowski et al., 2014 J Am Soc Nephrol 26:7279-89). Further studies demonstrated that TRPC6 is important in normal podocyte function by controlling calcium influx and nuclear factor of activated T cell activation in which elevated current through the channel is associated with renal injury and the induction of proteinuria (Moller et al., 2007 J Am Soc Nephrol 18:29-36 and Schlöndorff et al., 2009 Am J Physiol Cell Physiol 296:C558-69). In addition to Gain of Function mutations, it has been shown that expression of TRPC6 is elevated in human chronic kidney diseases including FSGS, minimal change disease, membraneous glomerulonephritis, and diabetic nephropathy (Moller et al., 2007 J Am Soc Nephrol 18:29-36 and Thilo et al., 2011 Nephrol. Dial. Transplant 27:921-9) as well as in mouse models of podocyte injury (Moller et al., 2007 J Soc Nephrol 18:29-36). TRPC6 deficient mice have been demonstrated to have reduced angiotensin II (Ang II)-induced albuminuria (Eckel et al., 2011 J Am Soc Nephrol 22:526-35) whereas transgenic podocyte-specific expression of human GoF mutations in mice induces albuminuria and glomerular lesions (Krall et al., 2010 PLoS ONE e12859 and Canales et al., 2015 Brit J Medicine Med. Res 5:1198-1212). Consequently, inhibition of TRPC6 may be useful in the treatment of chronic kidney diseases, These findings not only suggest that TRPC6 normally functions to maintain proper kidney function, but also implicates TRPC6 as a specific cause of at least certain cases of FSGS. Based on the likely role of TRPC6 in kidney function, TRPC6 inhibitor compounds can be used in treating or ameliorating chronic kidney diseases or conditions caused (in whole or in part) by TRPC6 dysfunction. Additionally, TRPC6 inhibitor compounds can be used in treating or ameliorating symptoms of kidney diseases (e.g., hypertension, proteinuria, etc.), regardless of the cause of the disease.

TRPC6 is expressed in the myometrium and placenta during pregnancy (Ku et al, 2006 J Soc Gynecol Investig 13:217-225; Clarson et al., 2003 J Physiol 550:515-528). As such TRPC6 may contribute to maintaining proper myogenic tone in the placenta and/or in maintaining proper fetal and maternal blood pressure during pregnancy.

Recent evidence has emerged implicating TRPC6 in certain forms of cancer. Several groups have established that TRPC6 expression is elevated in cells taken from patients with gliobastortia muitiforme, the most frequent and incurable type of brain cancer (Chigurupati, et al., 2010 Cancer Res, 70:418-427; Ding et al., 2010 J Nati Cancer Inst. 102:1052-1068).

Similarly, Ding et al, found elevated levels of TRPC6 in human glioma cells, and inhibition of TRPC6 pharmacologically or with a dominant negative mutant suppressed cell growth in vitro. In two xenograft models of human gliomas, lentiviral-mediated expression of dominant-negative TRPC6 in the tumor cells prior subcutaneous or intracranial implantation reduced tumor volume when compared to controls (Ding et al., J. Natl. Cancer Inst. 2010, 102, 1052-1068). Increased levels of TRPC6 was also found to be associated with cervical cancer (Wan et al, 2012 Onco Targets Ther 5:171-176), breast cancer (Dhennin-Duthille et al., 2011 Cell Physiol Biochem 28:813-822), renal cell carcinoma (Song et al, 2013 Mol Biol Rep 40:5115-5122), head and neck squamous cell carcinoma (de Quiros, et al. 2013 BMC Cancer 13:116-127), and esophageal squamous cell carcinoma (Zhang et al., 2013 Med Oncol 30:607), among others. In hepatocellular carcinoma cells, it was demonstrated that doxoruhicin, hypoxia, and ionizing radiation increased TRPC6 mRNA expression, and that TRPC6 is found at higher levels in tumor tissues than in the non-involved tissues. Elevated TRPC6 was associated with drug resistance which was diminished by TRPC6 RNA silencing in vitro. Lentiviral delivery of TRPC6 specific short hairpin RNA into Huh7 tumor cells prior to implantation in a mouse subcutaneous xenograft model reduced tumor growth and sensitized the tumors to doxorubicin (Wen et al, 2016 Sci Rep 6:23269). These findings suggest that TRPC6 may be a promising therapeutic target for cancer treatment.

Liver diseases including non-alcoholic steatohepatitis may be treated by reducing TRPC6 activity. Hypoxia increased TRPC6 expression in a human hepatic stellate cell line when compared to normoxic conditions. Using these cells, TRPC6 RNA silencing down-regulated transcripts for alpha smooth muscle actin and collagen 1A1, both of which are associated with fibrosis, in response to hypoxia Oyer et al., 2015 Exp Cell Res 336:66-75).

Inhibition of TRPC6 may provide benefit to patients with Duchenne muscular dystrophy (DMD). In the mdx/utrn$^{+/-}$ model of DMD using isolated cardiomyoctes, TRPC6 deficiency restored the stress-stimulated contractility force and calcium transient response to normal when compared with mice possessing the wild-type TRPC6 gene, suggesting that TRPC6 inhibition will preserve cardiac function in DMD patients (Seo et al., 2014 Circ Res 114:823-32).

Fibrotic disorders may be treated with TRPC6 inhibitors. Overexpression of TRPC6 induced myofibroblast activation while deletion of TRPC6 reduced transforming growth factor beta-induced myofibroblast transformation. Furthermore, TRPC6 deficient mice demonstrated reduced dermal and cardiac wound healing (Davis et al., 2012 Dev Cell 23:705-15).

TRPC6 inhibitors may be useful for the treatment of pain. Spinal delivery of TRPC6 antisense oligonucleotides reduced hyperalgesia induced by mechanical, hypotonic, and thermal stimuli in preclinical pain models (Alessandri-Haber et al., 2000 J Neurosci 29:6217-28).

Modulating a function of TRPC6 provides a means for modulating calcium :homeostasis, sodium homeostasis, intracellular calcium levels, membrane polarization (resting membrane potential), and/or cation levels in a cell. Compounds that can modulate one or more TRPC6 functions are useful in many aspects including, but not limited to, maintaining calcium homeostasis; maintaining sodium homeostasis; modulating intracellular calcium levels; modulating membrane polarization (membrane potential); modulating cation levels; anchor treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or dysregulation of TRPC6 expression or function.

There is a need for highly selective TRPC6 antagonists for treating diseases or disorders that can be alleviated by modulating TRPC6.

BRIEF SUMMARY OF THE INVENTION

The present invention provides novel compounds that modulate TRPC6 and thus are useful for treating a variety of diseases and disorders that can be alleviated by modulating TRPC6 including hypertension, preeclampsia, restenosis, a cardiac or respiratory condition, renal disease, liver disease, muscular dystrophy, fibrotic disorders, pain, ischemia or ischemic reperfusion injury, and cancer. This invention also relates to pharmaceutical compositions comprising these compounds, methods of using these compounds in the treatment of various diseases and disorders, processes for preparing these compounds and intermediates useful in these processes.

In one embodiment (embodiment one), the invention relates to a compound of formula (1), (I)

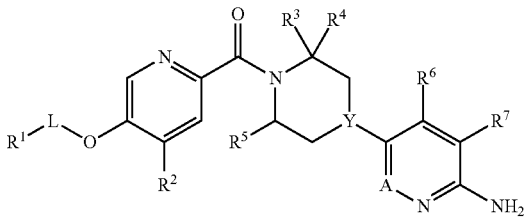

wherein

L is absent or is methylene or ethylene;

Y is CH or N;

A is CH or N;

$R^1$ is selected from the group consisting of:

$C_{1-6}$alkyl optionally substituted with 1 to 3 groups independently selected from the group consisting of halo, $C_{3-6}$cycloalkyl and $OC_{3-6}$cycloalkyl;

phenyl optionally substituted with 1 to 3 groups independently selected from the group consisting of $CF_3$, halo, $C_{3-6}$cycloalkyl, $OC_{3-6}$cycloalkyl, alkyl optionally substituted with one to three halo; and $C_{3-6}$cycloalkyl optionally substituted with 1 to 3 groups independently selected from the group consisting of halo and optionally substituted with 1 to 3 halo;

$R^2$ is selected from the group consisting of H, $C_{1-6}$alkyl, $OCF_3$, $C_{3-6}$cycloalkyl, $OC_{1-6}$alkyl, $OC_{3-6}$cycloalkyl;

$R^3$ is selected from the group consisting of H, $C_{1-6}$alkyl, $C_{3-6}$cycloalkyl, $OC_{3-6}$ cycloalkyl; wherein each of the $C_{1-6}$alkyl, $C_{3-6}$cycloalkyl, $OC_{3-6}$cycloalkyl of the $R^3$ group may be optionally substituted with one to three groups each independently selected from the group consisting of halo, OH, $OC_{1-6}$alkyl, $SC_{1-6}$alkyl, $N(C_{1-6}alky)_2$; and wherein one to three carbon atoms of the $C_{1-6}$alkyl of the $R^3$ group may optionally be replaced one or two moieties selected from the group consisting of NH, $N(C_{1-6}$alkyl), O, and S;

$R^4$ and $R^5$ are each independently selected from the group consisting of H or $C_{1-6}$alkyl;

$R^3$ and $R^4$ can together with the atom to which they are attached join to form a 3 to 9-membered carbocyclyl ring which optionally may contain one to three heteroatoms selected from the group consisting of N, O, and S; or $R^3$ and $R^5$ can together form a 3 to 9-membered bicyclic ring which optionally may contain one to three heteroatoms selected from the group consisting of N, O, and S;

$R^6$ is selected from the group consisting of H, $C_{1-6}$alkyl, CN, $CF_3$, $OCF_3$, $C_{3-6}$cycloalkyl, $OC_{1-6}$alkyl, and $OC_{3-6}$cycloalkyl;

$R^7$ is selected from the group consisting of H and $OC_{1-6}$ alkyl;

or a pharmaceutically acceptable salt thereof.

In another embodiment (embodiment two), the invention relates to a compound according to the first embodiment above, wherein $R^1$ is selected from the group consisting of:

$C_{1-6}$alkyl optionally substituted with 1 to 3 groups independently selected from the group consisting of halo, $C_{3-6}$cycloalkyl;

phenyl optionally substituted with 1 to 3 groups independently selected from the group consisting of $CF_3$, halo, $OC_{3-6}$cycloalkyl, and $OC_{1-6}$alkyl optionaly substituted with one to three halo; and $C_{3-6}$cycloalkyl optionally substituted with 1 to 3 halo groups;

$R^2$ is $OC_{1-6}$alkyl;

$R^3$ is selected from the group consisting of H, $C_{1-6}$alkyl optionally substituted with OH or $OC_{1-6}$alkyl, $R^4$ is H;

$R^5$ is H;

$R^3$ and $R^4$ can together with the atom to which they are attached join to form a 3 to 9-membered carbocyclyl ring which optionally may contain one to three heteroatoms selected from the group consisting of N and O; or $R^3$ and $R^5$ can together thrm a 3 to 9-membered bicyclic which optionally may contain one to three heteroatoms selected from the group consisting of N and O;

$R^6$ is selected from the group consisting of H, $C_{1-6}$alkyl, $OC_{1-6}$ alkyl and $OC_{3-6}$ cycloalkyl, $R^7$ is selected from the group consisting of H and $OC_{1-6}$ alkyl, or a pharmaceutically acceptable salt thereof.

In another embodiment (embodiment three), the invention relates to a compound according to embodiment one or two above, wherein A is CH and Y is N; or A is CH and Y is CH; or A is N and Y is CH;

or a pharmaceutically acceptable salt thereof.

In another embodiment (embodiment four), the invention relates to a compound according to any one of embodiments one to three above, wherein $R^1$ is selected from the group consisting phenyl optionally substituted with a group selected from the group consisting of $CF_3$, $OCF_3$, halo, $OC_{1-6}$cycloalkyl, and $OC_{1-6}$alkyl optionally substituted with one to three halo; and, $R^2$ is $OC_{1-6}$ alkyl;

$R^3$ is selected from the group consisting of F, $C_{1-6}$alkyl optionally substituted with OH, or $OC_{1-6}$alkyl;

$R^4$ is H;

$R^5$ is H;

$R^3$ and $R^4$ can together with the atom to which they are attached join to form a 3 to 9-membered carbocyclyl ring which optionally may contain one to three heteroatoms selected from the group consisting of N, O; or $R^3$ and $R^5$ can together form a 3 to 9-membered bicyclic which optionally may contain one to three heteroatoms selected from the group consisting of N and O;

$R^6$ is selected from the group consisting of H, $C_{1-6}$alkyl, $OC_{1-6}$ alkyl, and $OC_{3-6}$cycloalkyl; pos $R^7$ is selected front the group consisting of H and $OC_{1-6}$alkyl;

or a pharmaceutically acceptable salt thereof.

In another embodiment (embodiment five), the invention relates to a compound according to any one of embodiments one to four above, wherein $R^1$ is selected from the group consisting phenyl optionally substituted with a group selected from the group consisting of $CF_3$, $OCF_3$, F, and methoxy;

$R^2$ is selected from the group consisting of methoxy or ethoxy;

$R^3$ is selected from the group consisting of H, 2-hydroxymethyl, methoxymethyl, 1-hydroxyethyl;

$R^4$ is H;

$R^5$ is H;

or $R^3$ is ethyl, and $R^3$ and $R^4$ join to form a spirocyclic ring; or $R^3$ is ethyl or methoxymethyl, and $R^3$ and $R^5$ join to form a bicyclic ring;

$R^6$ is selected from the group consisting of H, methyl, methoxy, ethoxy, propoxy, and cyclylpropyloxy;

$R^7$ is selected from the group consisting of H and methoxy;

or a pharmaceutically acceptable salt thereof.

In another embodiment (embodiment six), the invention relates to a compound according to any one of embodiments one to five above, wherein $R^1$ together with L represent a group selected from the group consisting of phenyl, 4-chlorophenyl, 4-fluorophenyl, 4-methoxyphenyl, 4-isopropoxyphenyl, 4-trifluoromethylphenyl, 4-difluoromethoxyphenyl 4-cyclopropyloxyphenyl, cyclopropyl, cyclopentyl, cyclohexyl, benzyl, 2-fluorobenzyl, and phenylethyl;

$R^2$ is methoxy or ethoxy;

or a pharmaceutically acceptable salt thereof.

In another embodiment (embodiment seven), the invention relates to a compound according to any one of embodiments one to six above, wherein Y is CH and A is N;

$R^1$ together with L represent a group selected from the group consisting of phenyl, 4-chlorophenyl, 4-fluorophenyl, 4-methoxyphenyl, 4-isopropoxyphenyl, 4-trifluoromethylphenyl, 4-difluoromethoxyphenyl 4-cyclopropyloxyphenyl, benzyl, 2-fluorobenzyl, and phenylethyl;

$R^2$ is methoxy or ethoxy;

$R^3$, $R^4$ and $R^5$ are each H;

$R^6$ is H, methyl, methoxy or ethoxy;

$R^7$ is H;

or a pharmaceutically acceptable salt thereof.

In another embodiment (embodiment eight), the invention relates to a compound according to any one of embodiments one to six above, wherein Y is CH and A is CH;

$R^1$ together with L represent a group selected from the group consisting of phenyl, 4-chlorophenyl, 4-fluorophenyl, 4-methoxyphenyl, 4-trifluoromethylphenyl, cyclopendyl, cyclohexyl, benzyl, 2-fluorobenzyl, phentylethyl;

$R^2$ is methoxy or ethoxy;

$R^3$, $R^4$ and $R^5$ are each H;

$R^6$ is H, methyl, methoxy, or ethoxy;

$R^7$ is H;

or a pharmaceutically acceptable salt thereof.

In another embodiment (embodiment nine), the invention relates to a compound according to any one of embodiments one to five above, wherein Y is N and A is CH;

$R^1$ together with L represent a group selected from the group consisting of phenyl, and 4-fluorophenyl;

$R^2$ is methoxy;

$R^3$ is selected from the group consisting H, 2-hydroxymethyl, and hydroxyethyl, $R^4$ is H;

$R^5$ is H;

$R^3$ and $R^4$ may join to form a spirocyche ring;

or $R^3$ and $R^5$ may join to form a bicyclic ring;

$R^6$ is selected from the group consisting of H and methoxy;

$R^7$ is H;

or a pharmaceutically acceptable salt thereof.

In another embodiment (embodiment ten), the invention relates to a compound according to any one of embodiments one to four above, wherein $R^1$ is $C_{1-6}$alkyl optionally substituted with 1 to 3 groups independently selected from the group consisting of halo and $C_{3-6}$cycloalkyl;

$R^2$ is alkyl;

$R^3$, $R^4$ and $R^5$ are each H;

$R^6$ is selected from-the group consisting of H, $C_{1-6}$alkyl, and $OC_{1-6}$alkyl;

$R^7$ is H;

or a pharmaceutically acceptable salt thereof.

In another embodiment (embodiment eleven), the invention relates to a compound according to any one of embodiments one to four and ten above, wherein $R^1$ together with L represent a group selected from the group consisting ethyl, propyl, isopropyl, isobutyl, cyclopropylmethyl, cyclobutylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2-difluorocyclobutylmethyl, 3,3-difliuorocyclobutylmethyl, 3-(trifluoromethyl)cyclobutylmethyl, and 3,3,3-trifluoro-2-methyl-propyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment twelve), the invention relates to a compound according to any one of embodiments one to fou, ten and eleven above, wherein Y is CH and A is N;

$R^1$ together with L represent a group selected from the group consisting propyl, isopropyl, isobutyl, cyclopropylmethyl, cyclobutylmethyl, 2,2-dimethylpropyl, 1-cyclopropylethyl, 2-cyclopropylethyl, and cyclohexyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment thirteen), the invention relates to a compound according to any one of embodiments one to four, ten and eleven above, wherein Y is CH and A is CH;

$R^1$ together with L represent a group selected from the group consisting ethyl, propyl, isopropyl, isobutyl, cyclopropylmethyl, cyclobutylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2-difluorocyclobutylmethyl, 3,3-difluorocyclobutylmethyl, 3-(trifluoromethyl)cyclobutylmethyl, and 3,3,3-trifluoro-2-methyl-propyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment fourteen), the invention relates to a compound according to embodiment one above, wherein $R^3$ and $R^4$ together with the atom to which they are attached join to form a 3-membered carbocyclyl ring;

or a pharmaceutically acceptable salt thereof.

In another embodiment (embodiment fifteen), the invention relates to a compound according to embodiment one above, wherein $R^3$ and $R^5$ together form a 3 to 9-membered bicyclic; ring which optionally may contain one to two heteroatoms independently selected front the group consisting of N and O, and or a pharmaceutically acceptable salt thereof.

In another embodiment (embodiment sixteen), the invention relates to a compound according to embodiment one above, wherein Y is C; A is N;

$R^2$ is $OCH_3$; and $R^3$, $R^4$, $R^5$ and $R^7$ are each H;

or a pharmaceutically acceptable salt thereof.

In another embodiment (embodiment seventeen), the invention relates to a compound according to embodiment one or sixteen above, wherein L is absent;

$R^1$ is phenyl optionally substituted with 1 to 3 groups independently selected from the group consisting of $CF_3$, halo, $C_{3-6}$cycloalkyl, $OC_{36}$cycloalkyl, $OC_{1-6}$alkyl optionally substituted with one to three halo; and $R^6$ is H; or $OCH_3$;

or a pharmaceutically acceptable salt thereof.

In another embodiment (embodiment eighteen, the invention relates to a compound according to any one of embodiments one or sixteen above, wherein $R^1$ is selected from the group consisting of phenyl optionally substituted with 1 to 3 groups independently selected from the group consisting of $CF_3$, halo, $OC_{3-6}$cycloalkyl, and $OC_{1-6}$ alkyl optionally substituted with one to three halo;

$R^2$ is $OCH_3$ or $OCH_2CH_3$;

$R^3$, $R^4$, $R^5$, $R^6$, and $R^7$ are each H; and or a pharmaceutically acceptable salt thereof.

In another embodiment (embodiment nineteen), the invention relates to a compound according to any one of embodiments one or sixteen above, wherein $R^1$ is selected from the group consisting of phenyl optionally substituted with 1 to 3 groups independently selected from the group consisting of $CF_3$, halo, $OC_{3-6}$cycloalkyl, and $OC_{1-6}$alkyl optionally substituted with one to three halo;

$R^2$ is OCH, of $OCH_2CH_3$;

$R^3$, $R^4$, $R^5$ and $R^7$ are each H;

$R^6$ is $CH_3$ or $OCH_3$;

Y is CH; and

A is N;

or a pharmaceutically acceptable salt thereof.

In another embodiment (embodiment twenty), the invention relates to any one of embodiments one or sixteen to nineteen, wherein L is absent;

or a pharmaceutically acceptable salt thereof.

In another embodiment (embodiment twentyone), the invention relates to a compound according to embodiment one above, wherein the compound is selected from the group consisting of any one of compounds 1-95 in Table 1, or a pharmaceutically acceptable salt thereof.

In another embodiment (embodiment twentytwo), the invention relates to a pharmaceutical composition comprising any one of the compounds according to embodiments one to twentyone above, or a pharmaceutically acceptable salt thereof, and optionally a pharmaceutically acceptable excipient.

In another embodiment (embodiment twentythree), the invention relates to a method of treating a disease or disorder that can be alleviated TRPC6 inhibition comprising administering a therapeutically effective amount of any one of the compounds according to any one of embodiments one to twentyone above, or a pharmaceutically acceptable salt thereof, to a patient in need thereof.

In another embodiment (embodiment twentvfour), the invention relates to a method according to embodiment twentythree, wherein the disease or disorder is selected from the group consisting of cardiac hypertrophy, ischemia, schemic reperfusion injury, hypertension, pulmonary arterial hypertension, idiopathic pulmonary arterial hypertension, restenosis, chronic obstructive pulmonary disease, cystic fibrosis. Alzheimer's disease. Parkinson's disease, Huntington's disease, amyotrophic lateral sclerosis (ALS), trauma induced brain disorders, asthma, chronic obstructive pulmonary disease, rheumatoid arthritis, osteoarthritis, inflammatory bowel disease, multiple sclerosis, muscular dystrophy, Duchenne muscular dystrophy, preeclampsia and pregnancy-induced hypertension, non-alcoholic steatohepatitis, minimal change disease, focal segmental glomerulosclerosis (FSGS), nephrotic syndrome, diabetic nephropathy or diabetic kidney disease (DKD), renal insufficiency, end stage renal disease, ischemia or an ischemic reperfusion injury, cancer, IPF (idiopathic pulmonary fibrosis), ARDS (acute respiratory disease syndrome), emphysema and diabetes.

DETAILED DESCRIPTION OF THE INVENTION

Table 1shows the compounds of the invention which can be made by the synthetic schemes and the examples shown in the Synthetic Examples section below, and known methods in the art.

TABLE 1

| Cpd No. | Structure | Compound Name |
|---|---|---|
| 1 | 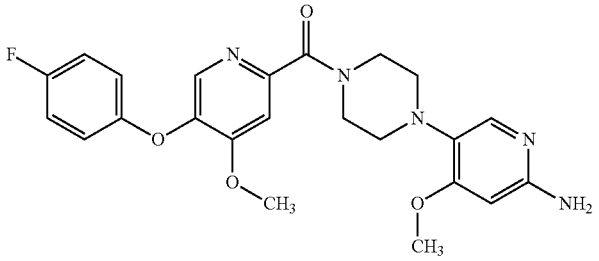 | [4-(6-Amino-4-methoxy-pyridin-3-yl)-piperazin-1-yl]-[5-(4-fluoro-phenoxy)-4-methoxy-pyridin-2-yl]-methanone |
| 2 | 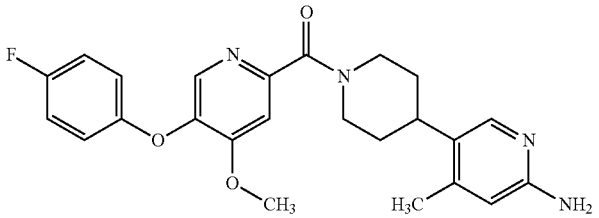 | (6-Amino-4-methyl-3',4',5',6'-tetrahydro-2'H-[3,4']bipyridinyl-1'-yl)-[5-(4-fluoro-phenoxy)-4-methoxy-pyridin-2-yl]-methanone |
| 3 | 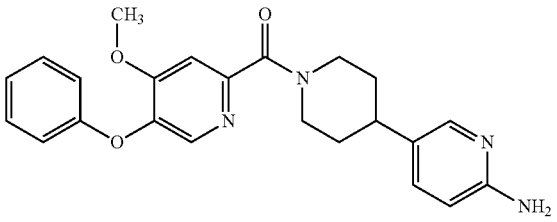 | (6-Amino-3',4',5',6'-tetrahydro-2'H-[3,4']bipyridinyl-1'-yl)-(4-methoxy-5-phenoxy-pyridin-2-yl)-methanone |

TABLE 1-continued

| Cpd No. | Structure | Compound Name |
|---|---|---|
| 4 | 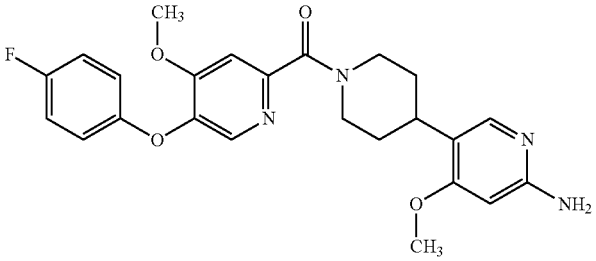 | (6-Amino-4-methoxy-3',4',5',6'-tetrahydro-2'H-[3,4']bipyridinyl-1'-yl)-[5-(4-fluoro-phenoxy)-4-methoxy-pyridin-2-yl]methanone |
| 5 | 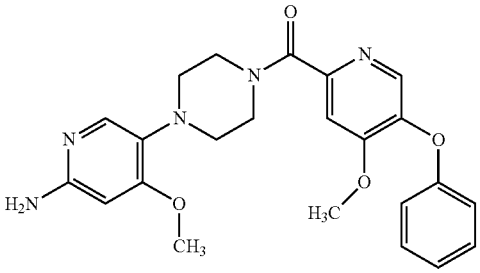 | [4-(6-Amino-4-methoxy-pyridin-3-yl)-piperazin-1-yl]-(4-methoxy-5-phenoxy-pyridin-2-yl)-methanone |
| 6 | 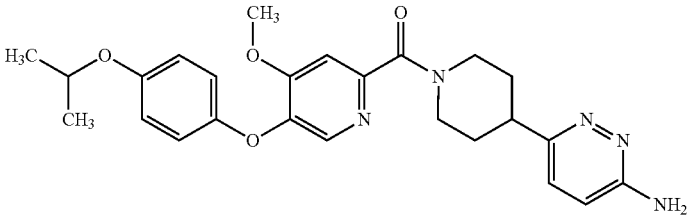 | [4-(6-Amino-pyridazin-3-yl)-piperidin-1-yl]-[5-(4-isopropoxy-phenoxy)-4-methoxy-pyridin-2-yl]-methanone |
| 7 | 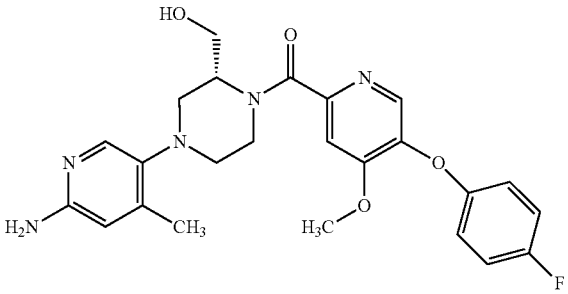 | [(R)-4-(6-Amino-4-methyl-pyridin-3-yl)-2-hydroxymethyl-piperazin-1-yl]-[5-(4-fluoro-phenoxy)-4-methoxy-pyridin-2-yl]-methanone |
| 8 | 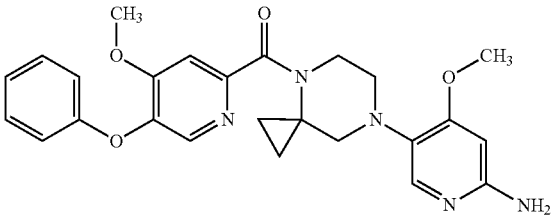 | [7-(6-Amino-4-methoxy-pyridin-3-yl)-4,7-diaza-spiro[2.5]oct-4-yl]-(4-methoxy-5-phenoxy-pyridin-2-yl)-methanone |
| 9 | 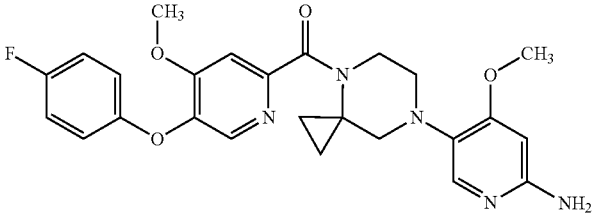 | [7-(6-Amino-4-methoxy-pyridin-3-yl)-4,7-diaza-spiro[2.5]oct-4-yl]-[5-(4-fluoro-phenoxy)-4-methoxy-pyridin-2-yl]-methanone |

TABLE 1-continued

| Cpd No. | Structure | Compound Name |
|---|---|---|
| 10 | 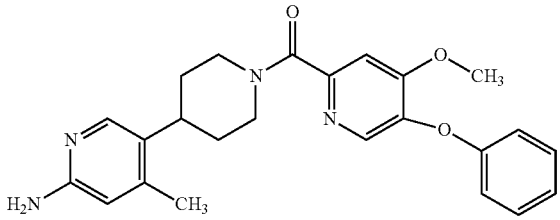 | (6-Amino-4-methyl-3',4',5',6'-tetrahydro-2'H-[3,4']bipyridinyl-1'-yl)-(4-methoxy-5-phenoxy-pyridin-2-yl)-methanone |
| 11 | 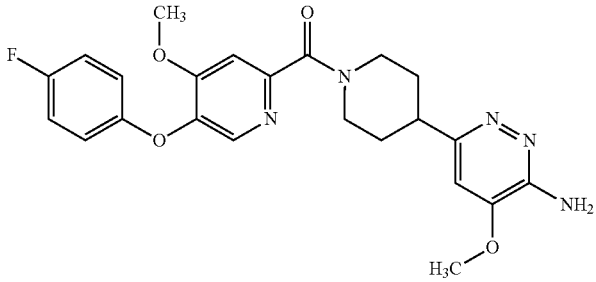 | [4-(6-Amino-5-methoxy-pyridazin-3-yl)-piperidin-1-yl]-[5-(4-fluoro-phenoxy)-4-methoxy-pyridin-2-yl]-methanone |
| 12 | 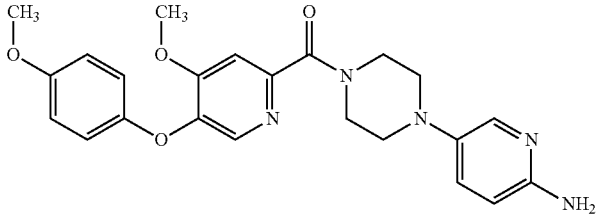 | [4-(6-Amino-pyridin-3-yl)-piperazin-1-yl]-[4-methoxy-5-(4-methoxy-phenoxy)-pyridin-2-yl]-methanone |
| 13 | 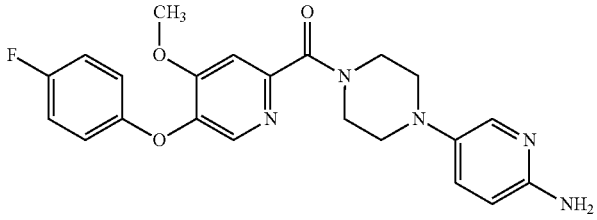 | [4-(6-Amino-pyridin-3-yl)-piperazin-1-yl]-[5-(4-fluoro-phenoxy)-4-methoxy-pyridin-2-yl]-methanone |
| 14 | 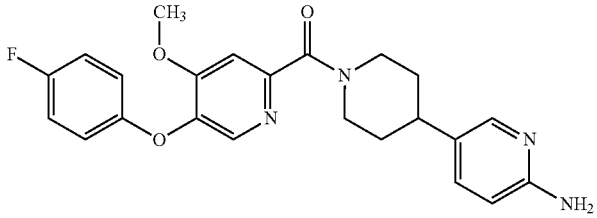 | (6-Amino-3',4',5',6'-tetrahydro-2'H-[3,4']bipyridinyl-1'-yl)-[5-(4-fluoro-phenoxy)-4-methoxy-pyridin-2-yl]-methanone |
| 15 | 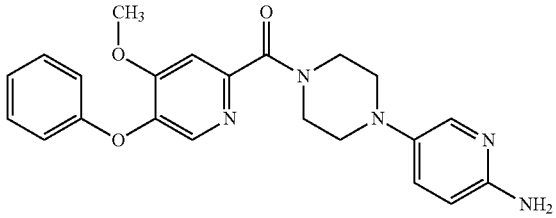 | [4-(6-Amino-pyridin-3-yl)-piperazin-1-yl]-(4-methoxy-5-phenoxy-pyridin-2-yl)-methanone |

TABLE 1-continued

| Cpd No. | Structure | Compound Name |
|---|---|---|
| 16 | 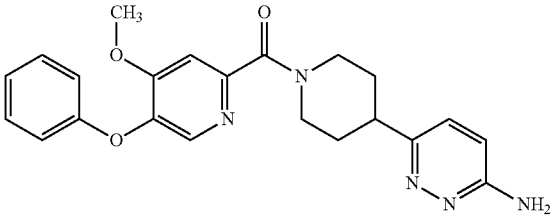 | [4-(6-Amino-pyridazin-3-yl)-piperidin-1-yl]-(4-methoxy-5-phenoxy-pyridin-2-yl)-methanone |
| 17 | 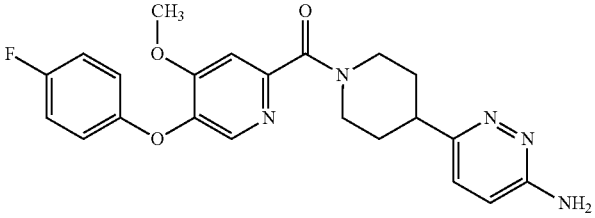 | [4-(6-Amino-pyridazin-3-yl)-piperidin-1-yl]-[5-(4-fluoro-phenoxy)-4-methoxy-pyridin-2-yl]-methanone |
| 18 | 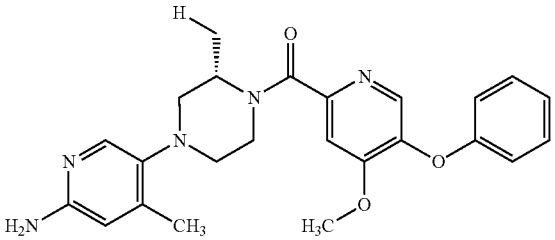 | [(R)-4-(6-Amino-4-methyl-pyridin-3-yl)-2-hydroxymethyl-piperazin-1-yl]-(4-methoxy-5-phenoxy-pyridin-2-yl)-methanone |
| 19 | 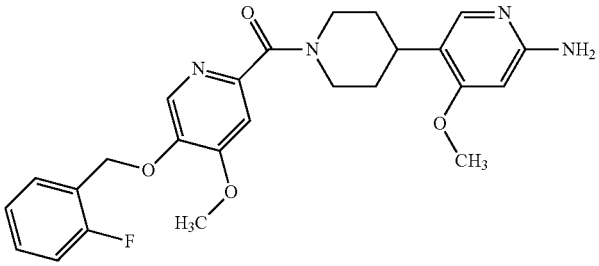 | (6-Amino-4-methoxy-3',4',5',6'-tetrahydro-2'H-[3,4']bipyridinyl-1'-yl)-[5-(2-fluoro-benzyloxy)-4-methoxy-pyridin-2-yl]-methanone |
| 20 | 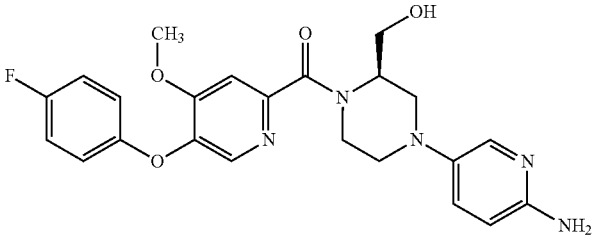 | [(R)-4-(6-Amino-pyridin-3-yl)-2-hydroxymethyl-piperazin-1-yl]-[5-(4-fluoro-phenoxy)-4-methoxy-pyridin-2-yl]-methanone |
| 21 | 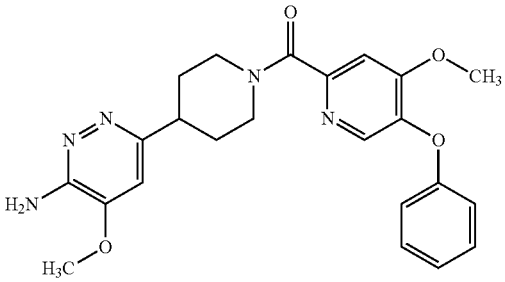 | [4-(6-Amino-5-methoxy-pyridazin-3-yl)-piperidin-1-yl]-(4-methoxy-5-phenoxy-pyridin-2-yl)-methanone |

TABLE 1-continued

| Cpd No. | Structure | Compound Name |
|---|---|---|
| 22 | 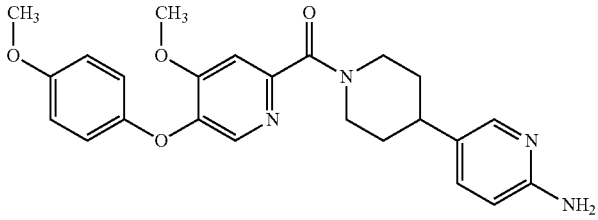 | (6-Amino-3',4',5',6'-tetrahydro-2'H-[3,4']bipyridinyl-1'-yl)-[4-methoxy-5-(4-methoxy-phenoxy)-pyridin-2-yl]-methanone |
| 23 | 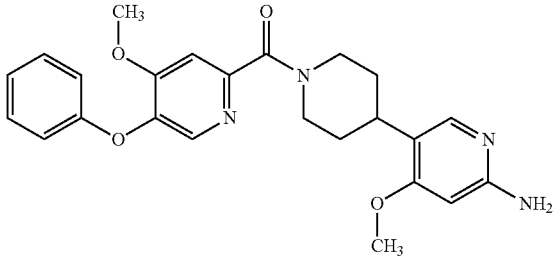 | (6-Amino-4-methoxy-3',4',5',6'-tetrahydro-2'H-[3,4']bipyridinyl-1'-yl)-(4-methoxy-5-phenoxy-pyridin-2-yl)-methanone |
| 24 | 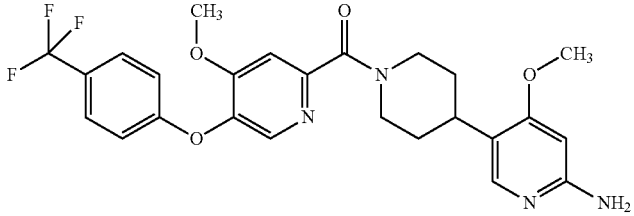 | (6-Amino-4-methoxy-3',4',5',6'-tetrahydro-2'H-[3,4']bipyridinyl-1'-yl)-[4-methoxy-5-(4-trifluoromethyl-phenoxy)-pyridin-2-yl]-methanone |
| 25 | 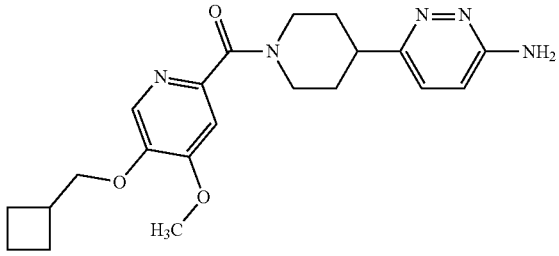 | [4-(6-Amino-pyridazin-3-yl)-piperidin-1-yl]-(5-cyclobutylmethoxy-4-methoxy-pyridin-2-yl)-methanone |
| 26 | 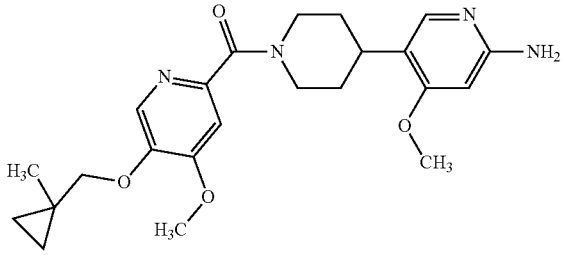 | (6-Amino-4-methoxy-3',4',5',6'-tetrahydro-2'H-[3,4']bipyridinyl-1'-yl)-[4-methoxy-5-(1-methyl-cyclopropylmethoxy)-pyridin-2-yl]-methanone |
| 27 | 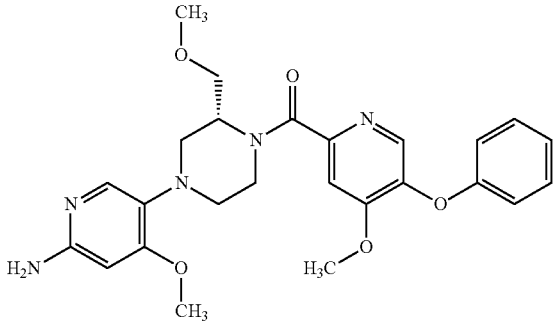 | [(R)-4-(6-Amino-4-methoxy-pyridin-3-yl)-2-methoxymethyl-piperazin-1-yl]-(4-methoxy-5-phenoxy-pyridin-2-yl)-methanone |

TABLE 1-continued

| Cpd No. | Structure | Compound Name |
|---|---|---|
| 28 | 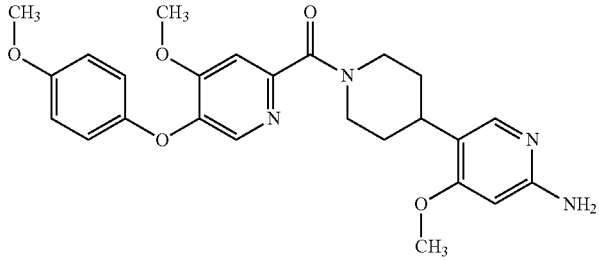 | (6-Amino-4-methoxy-3',4',5',6'-tetrahydro-2'H-[3,4']bipyridinyl-1'-yl)-[4-methoxy-5-(4-methoxy-phenoxy)-pyridin-2-yl]-methanone |
| 29 | 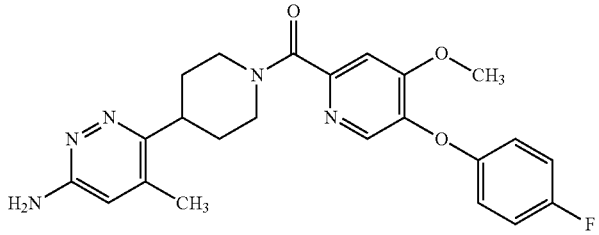 | [4-(6-Amino-4-methyl-pyridazin-3-yl)-piperidin-1-yl]-[5-(4-fluoro-phenoxy)-4-methoxy-pyridin-2-yl]-methanone |
| 30 | 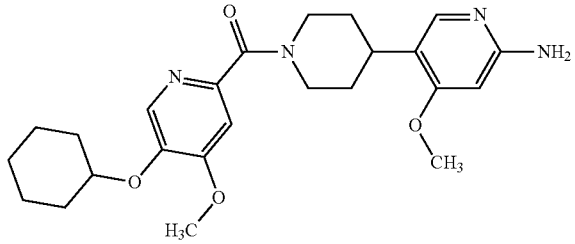 | (6-Amino-4-methoxy-3',4',5',6'-tetrahydro-2'H-[3,4']bipyridinyl-1'-yl)-(5-cyclohexyloxy-4-methoxy-pyridin-2-yl)-methanone |
| 31 | 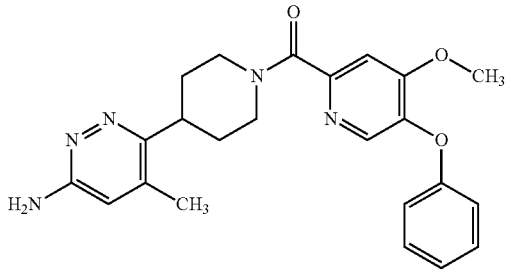 | [4-(6-Amino-4-methyl-pyridazin-3-yl)-piperidin-1-yl]-(4-methoxy-5-phenoxy-pyridin-2-yl)-methanone |
| 32 | 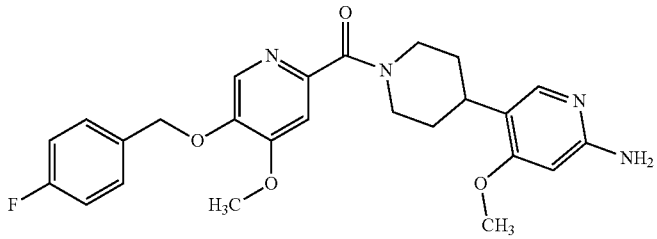 | (6-Amino-4-methoxy-3',4',5',6'-tetrahydro-2'H-[3,4']bipyridinyl-1'-yl)-[5-(4-fluoro-benzyloxy)-4-methoxy-pyridin-2-yl]-methanone |
| 33 | 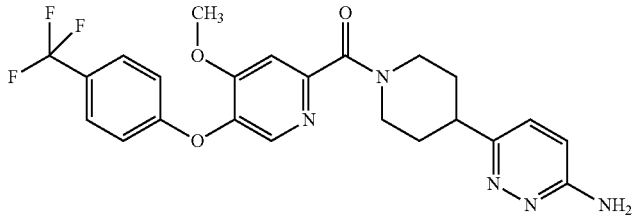 | [4-(6-Amino-pyridazin-3-yl)-piperidin-1-yl]-[4-methoxy-5-(4-trifluoromethyl-phenoxy)-pyridin-2-yl]-methanone |

TABLE 1-continued

| Cpd No. | Structure | Compound Name |
|---|---|---|
| 34 | 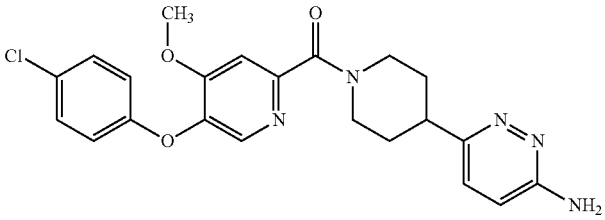 | [4-(6-Amino-pyridazin-3-yl)-piperidin-1-yl]-[5-(4-chloro-phenoxy)-4-methoxy-pyridin-2-yl]-methanone |
| 35 | 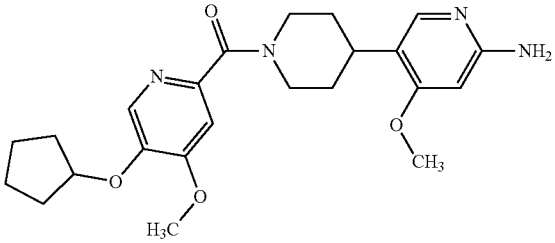 | (6-Amino-4-methoxy-3',4',5',6'-tetrahydro-2'H-[3,4']bipyridinyl-1'-yl)-(5-cyclopentyloxy-4-methoxy-pyridin-2-yl)-methanone |
| 36 | 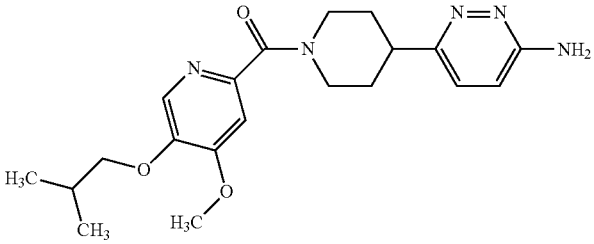 | [4-(6-Amino-pyridazin-3-yl)-piperidin-1-yl]-(5-isobutoxy-4-methoxy-pyridin-2-yl)-methanone |
| 37 | 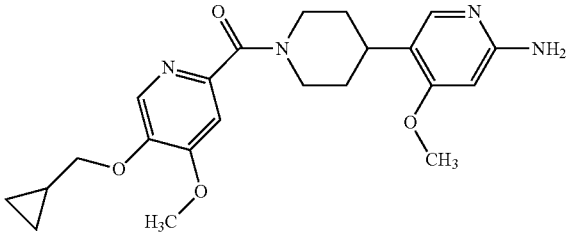 | (6-Amino-4-methoxy-3',4',5',6'-tetrahydro-2'H-[3,4']bipyridinyl-1'-yl)-(5-cyclopropylmethoxy-4-methoxy-pyridin-2-yl)-methanone |
| 38 | 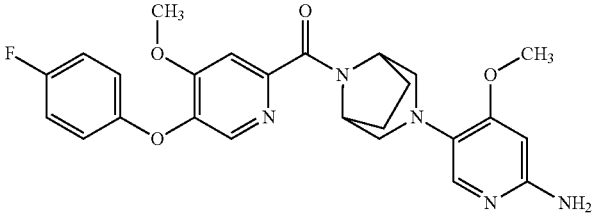 | [3-(6-Amino-4-methoxy-pyridin-3-yl)-3,8-diaza-bicyclo[3.2.1]oct-8-yl]-[5-(4-fluoro-phenoxy)-4-methoxy-pyridin-2-yl]-methanone |
| 39 | 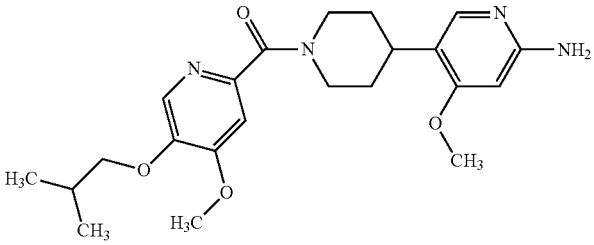 | (6-Amino-4-methoxy-3',4',5',6'-tetrahydro-2'H-[3,4']bipyridinyl-1'-yl)-(5-isobutoxy-4-methoxy-pyridin-2-yl)-methanone |

TABLE 1-continued

| Cpd No. | Structure | Compound Name |
|---|---|---|
| 40 | 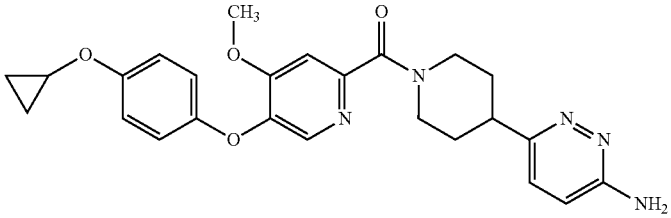 | [4-(6-Amino-pyridazin-3-yl)-piperidin-1-yl]-[5-(4-cyclopropoxy-phenoxy)-4-methoxy-pyridin-2-yl]-methanone |
| 41 | 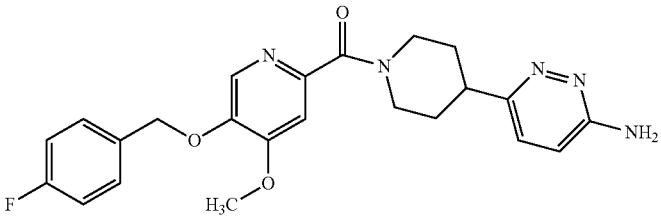 | [4-(6-Amino-pyridazin-3-yl)-piperidin-1-yl]-[5-(4-fluoro-benzyloxy)-4-methoxy-pyridin-2-yl]-methanone |
| 42 | 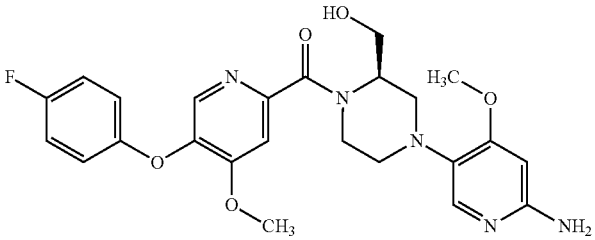 | [(R)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |
| 43 | 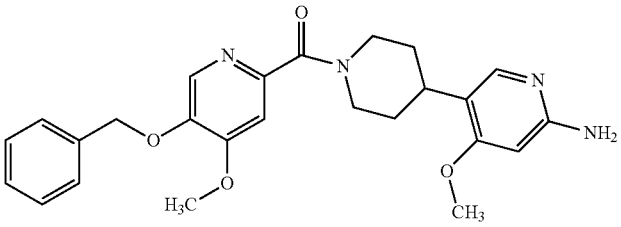 | (6-Amino-4-methoxy-3',4',5',6'-tetrahydro-2'H-[3,4']bipyridinyl-1'-yl)-(5-benzyloxy-4-methoxy-pyridin-2-yl)-methanone |
| 44 | 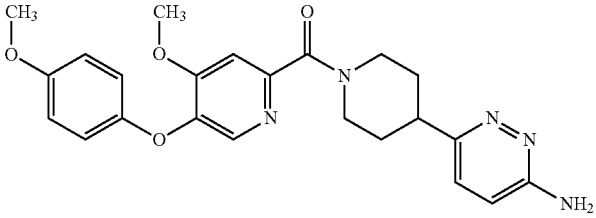 | [4-(6-Amino-pyridazin-3-yl)-piperidin-1-yl]-[4-methoxy-5-(4-methoxy-phenoxy)-pyridin-2-yl]-methanone |
| 45 | 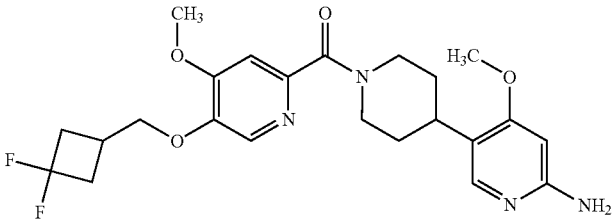 | (6-Amino-4-methoxy-3',4',5',6'-tetrahydro-2'H-[3,4']bipyridinyl-1'-yl)-[5-(3,3-difluoro-cyclobutylmethoxy)-4-methoxy-pyridin-2-yl]-methanone |

TABLE 1-continued

| Cpd No. | Structure | Compound Name |
|---|---|---|
| 46 | 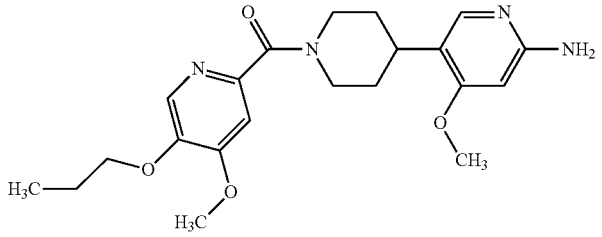 | (6-Amino-4-methoxy-3',4',5',6'-tetrahydro-2'H-[3,4']bipyridinyl-1'-yl)-(4-methoxy-5-propoxy-pyridin-2-yl)-methanone |
| 47 | 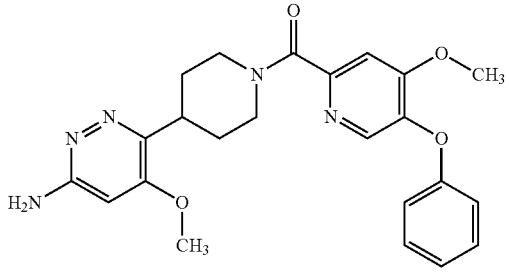 | [4-(6-Amino-4-methoxy-pyridazin-3-yl)-piperidin-1-yl]-(4-methoxy-5-phenoxy-pyridin-2-yl)-methanone |
| 48 | 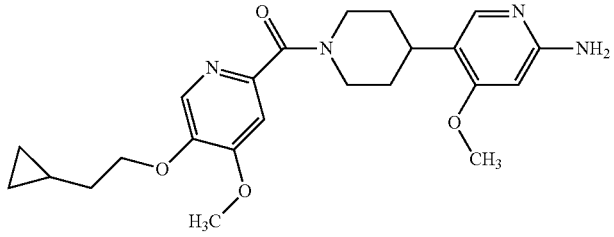 | (6-Amino-4-methoxy-3',4',5',6'-tetrahydro-2'H-[3,4']bipyridinyl-1'-yl)-[5-(2-cyclopropyl-ethoxy)-4-methoxy-pyridin-2-yl]-methanone |
| 49 | 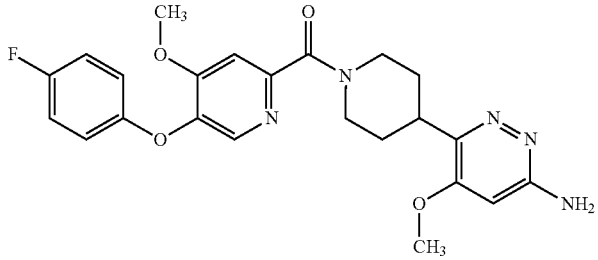 | [4-(6-Amino-4-methoxy-pyridazin-3-yl)-piperidin-1-yl]-[5-(4-fluoro-phenoxy)-4-methoxy-pyridin-2-yl]-methanone |
| 50 | 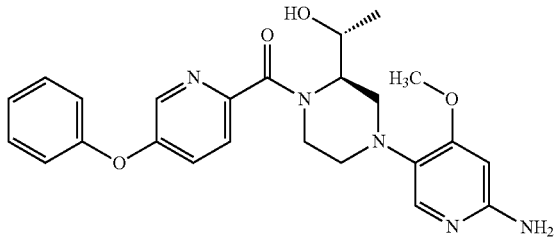 | (1R)-1-[(2R)-4-(6-amino-4-methoxypyridin-3-yl)-1-(5-phenoxypyridine-2-carbonyl)piperazin-2-yl]ethan-1-ol |
| 51 | 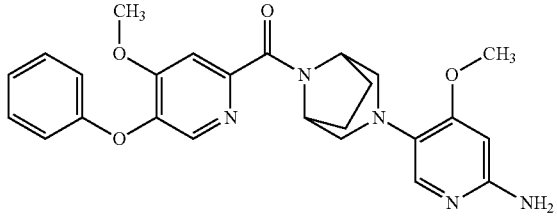 | [3-(6-Amino-4-methoxy-pyridin-3-yl)-3,8-diaza-bicyclo[3.2.1]oct-8-yl]-(4-methoxy-5-phenoxy-pyridin-2-yl)-methanone |

TABLE 1-continued

| Cpd No. | Structure | Compound Name |
|---|---|---|
| 52 | 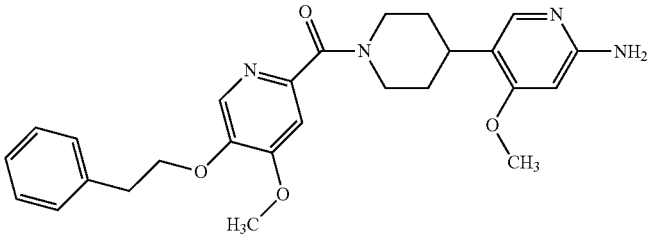 | (6-Amino-4-methoxy-3',4',5',6'-tetrahydro-2'H-[3,4']bipyridinyl-1'-yl)-(4-methoxy-5-phenethyloxy-pyridin-2-yl)-methanone |
| 53 | 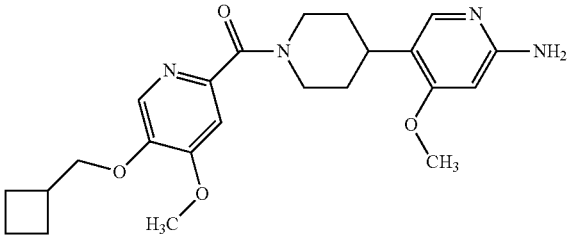 | (6-Amino-4-methoxy-3',4',5',6'-tetrahydro-2'H-[3,4']bipyridinyl-1'-yl)-(5-cyclobutylmethoxy-4-methoxy-pyridin-2-yl)-methanone |
| 54 | 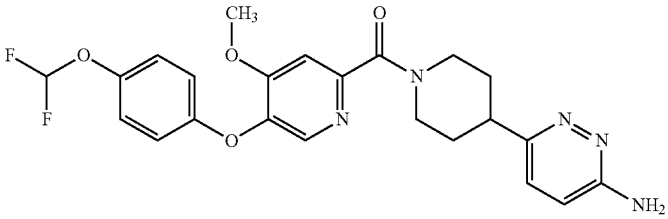 | [4-(6-Amino-pyridazin-3-yl)-piperidin-1-yl]-[5-(4-difluoromethoxy-phenoxy)-4-methoxy-pyridin-2-yl]-methanone |
| 55 | 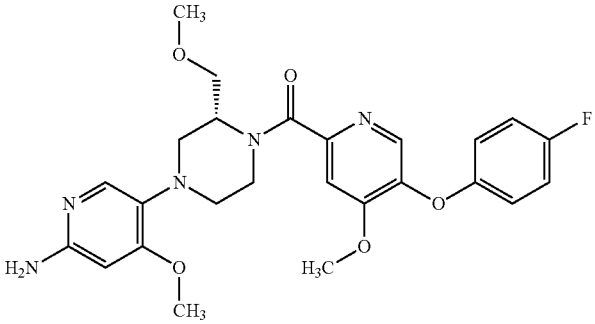 | [(R)-4-(6-Amino-4-methoxy-pyridin-3-yl)-2-methoxymethyl-piperazin-1-yl]-[5-(4-fluoro-phenoxy)-4-methoxy-pyridin-2-yl]-methanone |
| 56 | 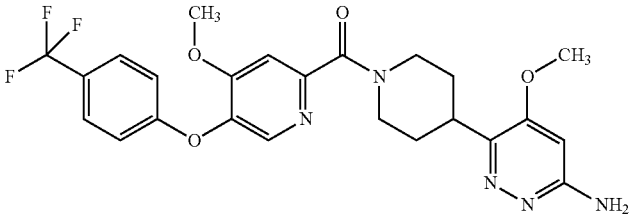 | [4-(6-Amino-4-methoxy-pyridazin-3-yl)-piperidin-1-yl]-[4-methoxy-5-(4-trifluoromethyl-phenoxy)-pyridin-2-yl]-methanone |
| 57 | 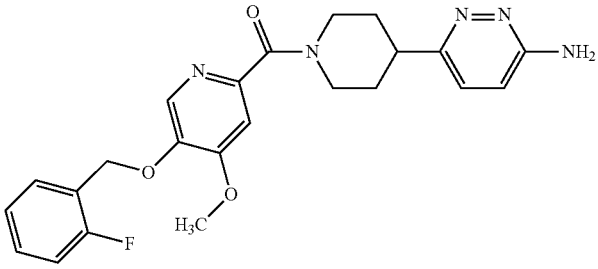 | [4-(6-Amino-pyridazin-3-yl)-piperidin-1-yl]-[5-(2-fluoro-benzyloxy)-4-methoxy-pyridin-2-yl]-methanone |

TABLE 1-continued

| Cpd No. | Structure | Compound Name |
|---|---|---|
| 58 | 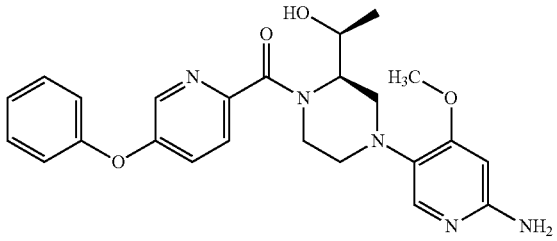 | (1S)-1-[(2R)-4-(6-amino-4-methoxypyridin-3-yl)-1-(5-phenoxypyridine-2-carbonyl)piperazin-2-yl]ethan-1-ol |
| 59 | 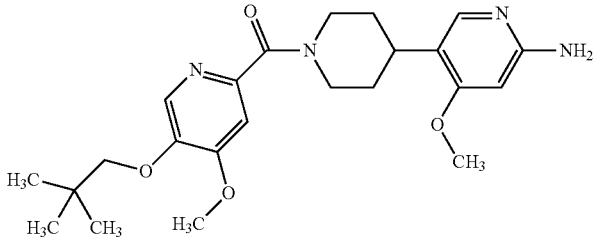 | (6-Amino-4-methoxy-3',4',5',6'-tetrahydro-2'H-[3,4']bipyridinyl-1'-yl)-[5-(2,2-dimethyl-propoxy)-4-methoxy-pyridin-2-yl]-methanone |
| 60 | 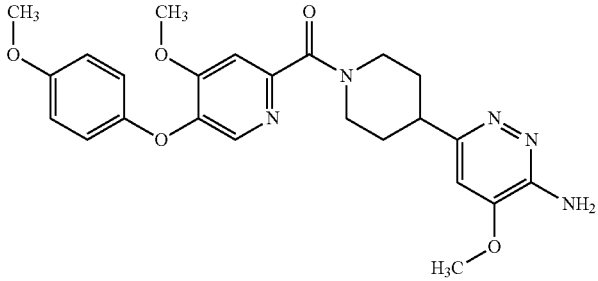 | [4-(6-Amino-5-methoxy-pyridazin-3-yl)-piperidin-1-yl]-[4-methoxy-5-(4-methoxy-phenoxy)-pyridin-2-yl]-methanone |
| 61 | 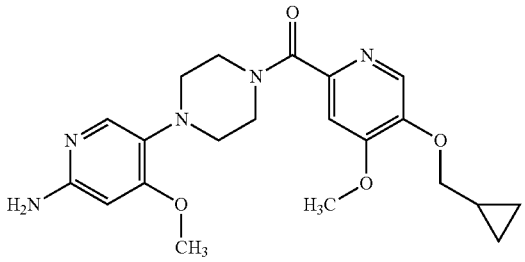 | [4-(6-Amino-4-methoxy-pyridin-3-yl)-piperazin-1-yl]-(5-cyclopropylmethoxy-4-methoxy-pyridin-2-yl)-methanone |
| 62 | 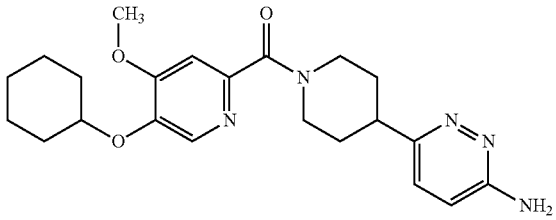 | [4-(6-Amino-pyridazin-3-yl)-piperidin-1-yl]-(5-cyclohexyloxy-4-methoxy-pyridin-2-yl)-methanone |
| 63 | 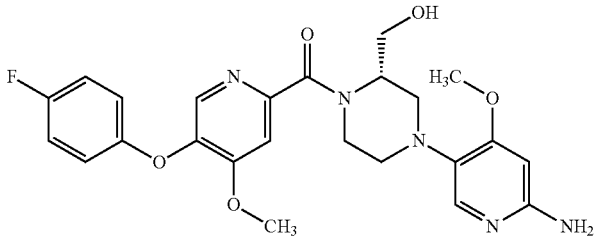 | [(S)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |

TABLE 1-continued

| Cpd No. | Structure | Compound Name |
|---|---|---|
| 64 | 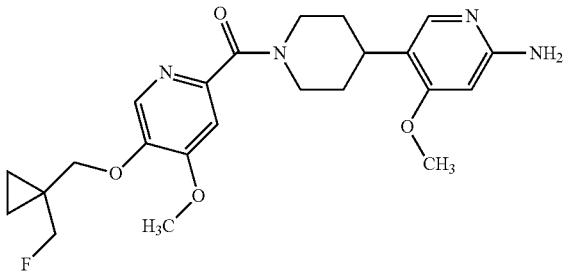 | (6-Amino-4-methoxy-3',4',5',6'-tetrahydro-2'H-[3,4']bipyridinyl-1'-yl)-[5-(1-fluoromethyl-cyclopropylmethoxy)-4-methoxy-pyridin-2-yl]-methanone |
| 65 | 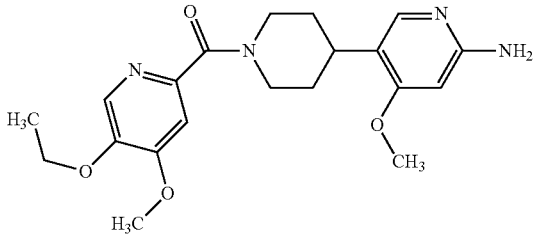 | (6-Amino-4-methoxy-3',4',5',6'-tetrahydro-2'H-[3,4']bipyridinyl-1'-yl)-(5-ethoxy-4-methoxy-pyridin-2-yl)-methanone |
| 66 | 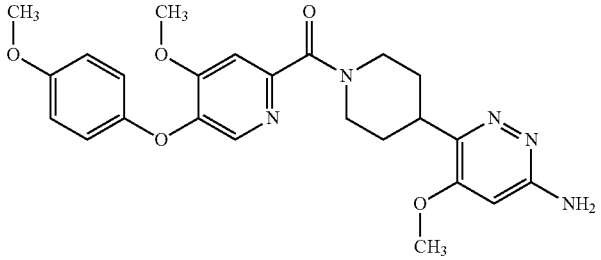 | [4-(6-Amino-4-methoxy-pyridazin-3-yl)-piperidin-1-yl]-[4-methoxy-5-(4-methoxy-phenoxy)-pyridin-2-yl]-methanone |
| 67 | 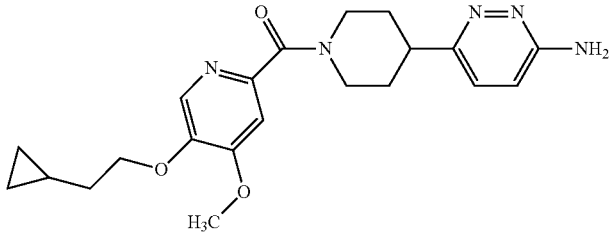 | [4-(6-Amino-pyridazin-3-yl)-piperidin-1-yl]-[5-(2-cyclopropyl-ethoxy)-4-methoxy-pyridin-2-yl]-methanone |
| 68 | 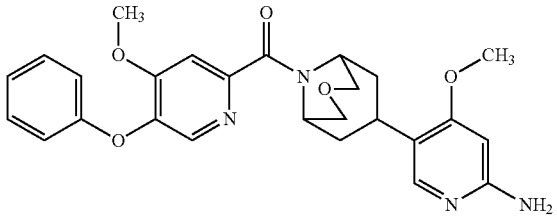 | [7-(6-Amino-4-methoxy-pyridin-3-yl)-3-oxa-9-aza-bicyclo[3.3.1]non-9-yl]-(4-methoxy-5-phenoxy-pyridin-2-yl)-methanone |
| 69 | 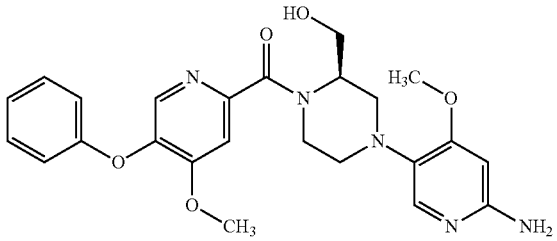 | [(R)-4-(6-Amino-4-methoxy-pyridin-3-yl)-2-hydroxymethyl-piperazin-1-yl]-(4-methoxy-5-phenoxy-pyridin-2-yl)-methanone |

TABLE 1-continued

| Cpd No. | Structure | Compound Name |
|---|---|---|
| 70 | 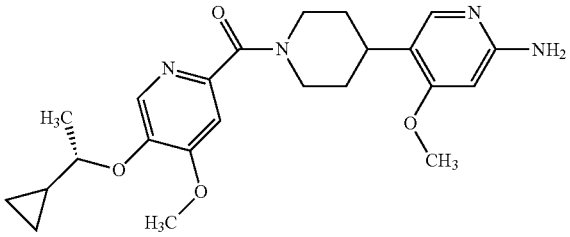 | (6-Amino-4-methoxy-3',4',5',6'-tetrahydro-2'H-[3,4']bipyridinyl-1'-yl)-[5-((S)-1-cyclopropyl-ethoxy)-4-methoxy-pyridin-2-yl]-methanone |
| 71 | 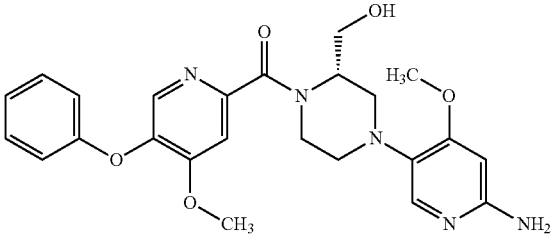 | [(S)-4-(6-Amino-4-methoxy-pyridin-3-yl)-2-hydroxymethyl-piperazin-1-yl]-(4-methoxy-5-phenoxy-pyridin-2-yl)-methanone |
| 72 | 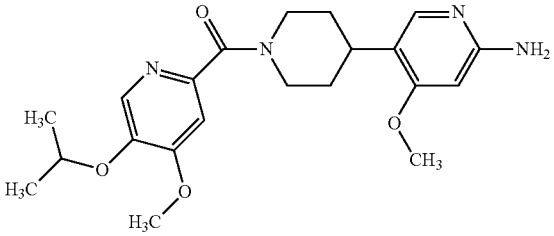 | (6-Amino-4-methoxy-3',4',5',6'-tetrahydro-2'H-[3,4']bipyridinyl-1'-yl)-(5-isopropoxy-4-methoxy-pyridin-2-yl)-methanone |
| 73 | 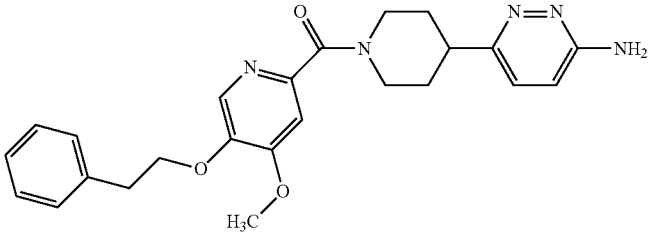 | [4-(6-Amino-pyridazin-3-yl)-piperidin-1-yl]-(4-methoxy-5-phenethyloxy-pyridin-2-yl)-methanone |
| 74 | 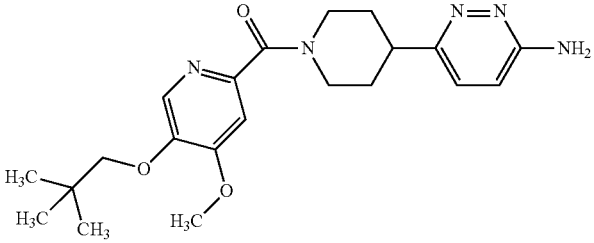 | [4-(6-Amino-pyridazin-3-yl)-piperidin-1-yl]-[5-(2,2-dimethyl-propoxy)-4-methoxy-pyridin-2-yl]-methanone |
| 75 | 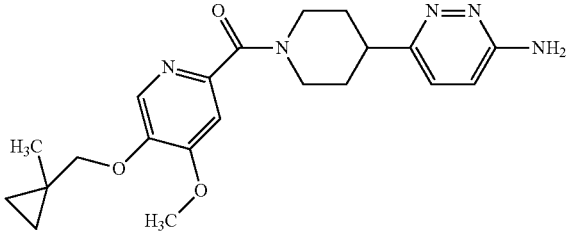 | [4-(6-Amino-pyridazin-3-yl)-piperidin-1-yl]-[4-methoxy-5-(1-methyl-cyclopropylmethoxy)-pyridin-2-yl]-methanone |

TABLE 1-continued

| Cpd No. | Structure | Compound Name |
|---|---|---|
| 76 | 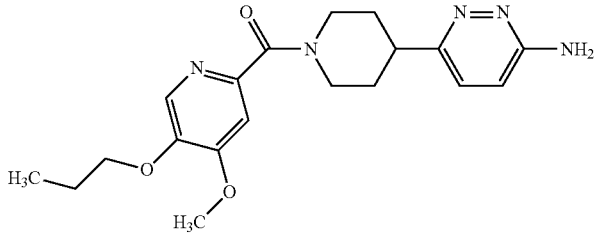 | [4-(6-Amino-pyridazin-3-yl)-piperidin-1-yl]-(4-methoxy-5-propoxy-pyridin-2-yl)-methanone |
| 77 | 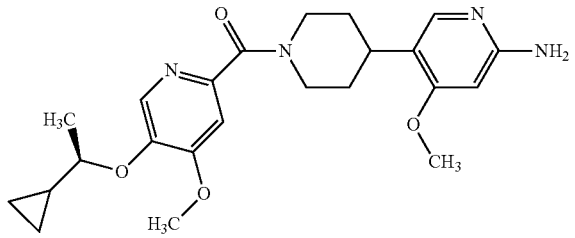 | (6-Amino-4-methoxy-3',4',5',6'-tetrahydro-2'H-[3,4']bipyridinyl-1'-yl)-[5-((R)-1-cyclopropyl-ethoxy)-4-methoxy-pyridin-2-yl]-methanone |
| 78 | 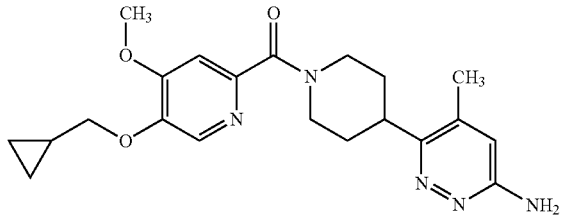 | [4-(6-Amino-4-methyl-pyridazin-3-yl)-piperidin-1-yl]-(5-cyclopropylmethoxy-4-methoxy-pyridin-2-yl)-methanone |
| 79 | 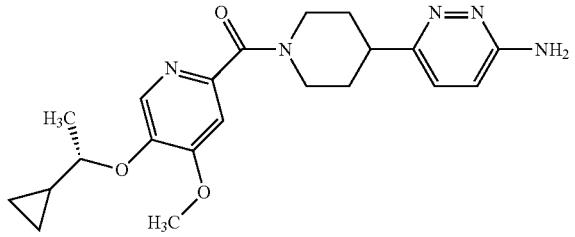 | [4-(6-Amino-pyridazin-3-yl)-piperidin-1-yl]-[5-((S)-1-cyclopropyl-ethoxy)-4-methoxy-pyridin-2-yl]-methanone |
| 80 | 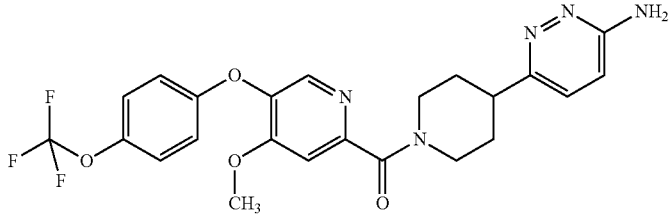 | [4-(6-Amino-pyridazin-3-yl)-piperidin-1-yl]-[4-methoxy-5-(4-trifluoromethoxy-phenoxy)-pyridin-2-yl]-methanone |
| 81 | 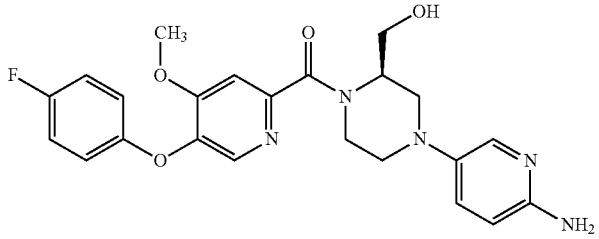 | [(R)-4-(6-Amino-pyridin-3-yl)-2-hydroxymethyl-piperazin-1-yl]-(4-methoxy-5-phenoxy-pyridin-2-yl)-methanone |

TABLE 1-continued

| Cpd No. | Structure | Compound Name |
|---|---|---|
| 82 | 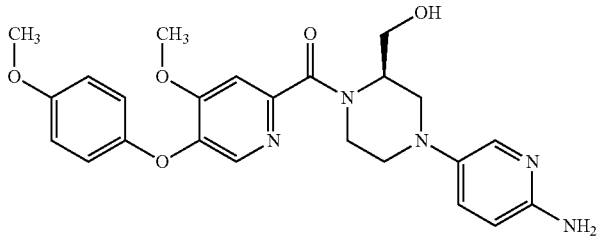 | [(R)-4-(6-Amino-pyridin-3-yl)-2-hydroxymethyl-piperazin-1-yl]-[4-methoxy-5-(4-methoxy-phenoxy)-pyridin-2-yl]-methanone |
| 83 | 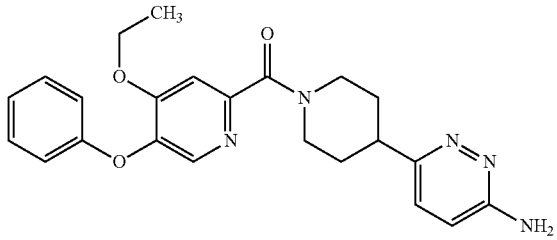 | [4-(6-Amino-pyridazin-3-yl)-piperidin-1-yl]-[5-(phenoxy)-4-ethoxy-pyridin-2-yl]-methanone |
| 84 | 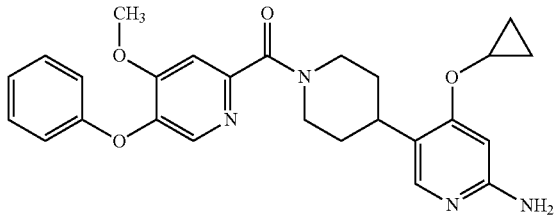 | (6-Amino-4-cyclopropoxy-3',4',5',6'-tetrahydro-2'H-[3,4']bipyridinyl-1'-yl)-[5-(phenoxy)-4-methoxy-pyridin-2-yl]-methanone |
| 85 | 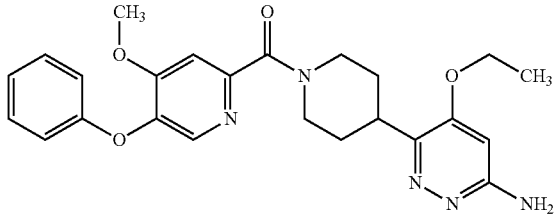 | [4-(6-Amino-4-ethoxy-pyridazin-3-yl)-piperidin-1-yl]-[4-methoxy-5-(phenoxy)-pyridin-2-yl]-methanone |
| 86 | 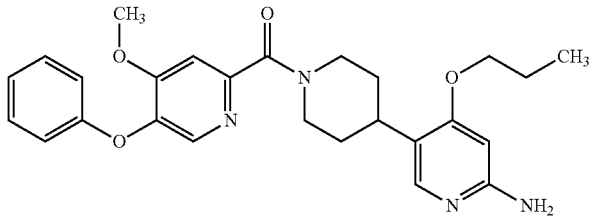 | (6-Amino-4-propoxy-3',4',5',6'-tetrahydro-2'H-[3,4']bipyridinyl-1'-yl)-[5-(phenoxy)-4-methoxy-pyridin-2-yl]-methanone |
| 87 | 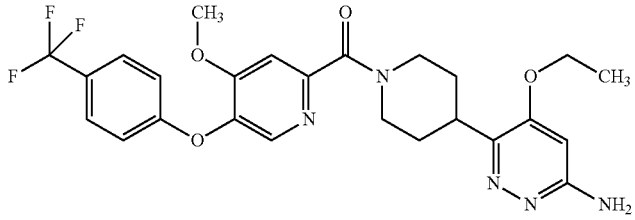 | 5-ethoxy-6-(1-[4-methoxy-5-[4-trifluoromethyl)phenoxy]pyridine-2-carbonyl]piperidin-4-yl)pyridazine-3-amine |

TABLE 1-continued

| Cpd No. | Structure | Compound Name |
|---|---|---|
| 88 | 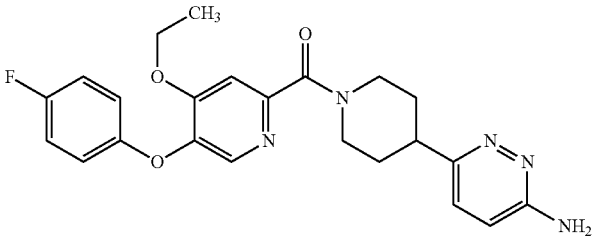 | [4-(6-Amino-pyridazin-3-yl)-piperidin-1-yl]-[5-(4-fluoro-phenoxy)-4-ethoxy-pyridin-2-yl]-methanone |
| 89 | 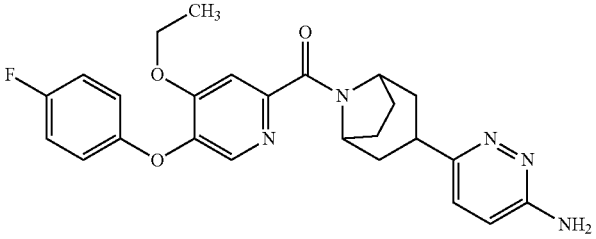 | [3-(6-Amino-pyridazin-3-yl)-8-aza-bicyclo[3.2.1]oct-8-yl]-[4-ethoxy-5-(4-fluoro-phenoxy)-pyridin-2-yl]-methanone |
| 90 | 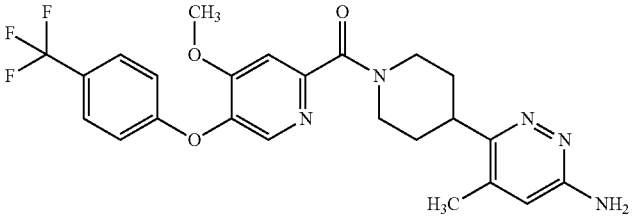 | 6-(1-{4-Methoxy-5-[4-(trifluoromethyl)phenoxy]pyridine-2-carbonyl}piperidin-4-yl)-5-methylpyridazin-3-amine |
| 91 | 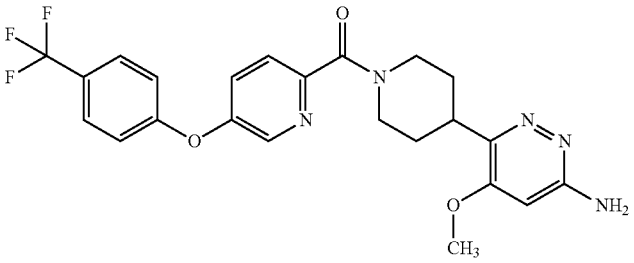 | 5-Methoxy-6-(1-{5-[4-(trifluoromethyl)-phenoxy]-pyridine-2-carbonyl}piperidin-4-yl)-pyridazin-3-amine |
| 92 | 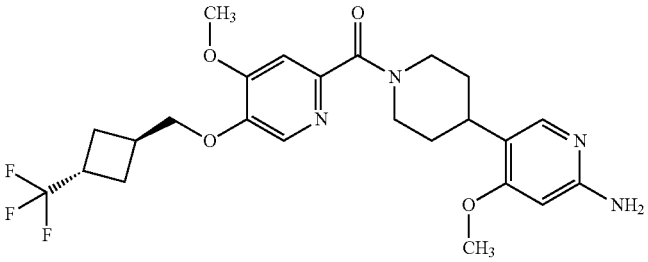 | 4-Methoxy-5-[1-(4-methoxy-5-{[trans-3-(trifluoromethyl)cyclobutyl]-methoxy}pyridine-2-carbonyl)-piperidin-4-yl]pyridin-2-amine |
| 93 | 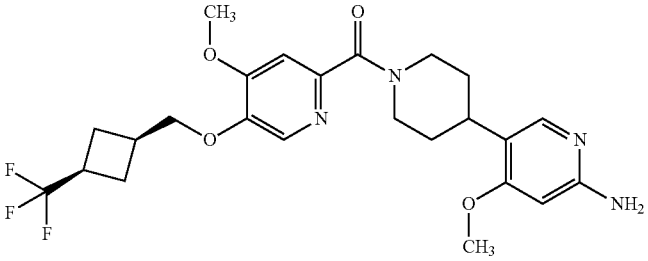 | 4-Methoxy-5-[1-(4-methoxy-5-{[(cis-3-(trifluoromethyl)-cyclobutyl]methoxy}-pyridine-2-carbonyl)piperidin-4-yl]pyridin-2-amine |

TABLE 1-continued

| Cpd No. | Structure | Compound Name |
|---|---|---|
| 94 | 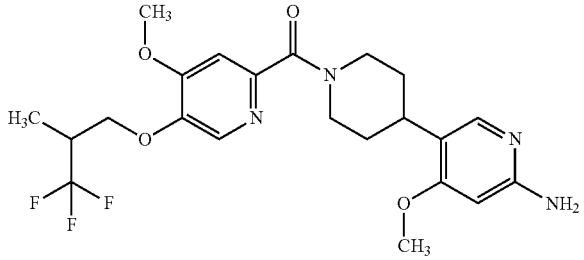 | 4-Methoxy-5-(1-{4-methoxy-5-[(2)-3,3,3-trifluoro-2-methylpropoxy]-pyridine-2-carbonyl}piperidin-4-yl)pyridin-2-amine |
| 95 | 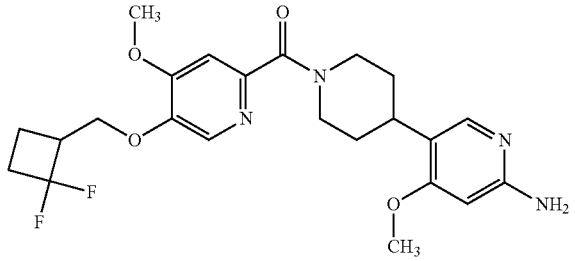 | 5-(1-{5-[(2,2-Difluorocyclobutyl)-methoxy]-4-methoxy-pyridine-2-carbonyl}-piperidin-4-yl)-4-methoxypyridin-2-amine |

In one embodiment, the invention relates to any of the compounds 1 to 95 depicted in Table 1 above, and the pharmaceutically acceptable salts thereof.

In another embodiment, the invention relates to any one of compounds 6, 16, 17, 33, 34, 40, 41, 44, 54, 57, 80, 83 and 88 depicted in Table 1; and the pharmaceutically acceptable salts thereof.

In another embodiment, the invention relates to any one of compounds 29, 31, 49, 56, 66, 85, 87, and 90 depicted in Table 1; and the pharmaceutically acceptable salts thereof.

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, NC(cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas as to indicate the bond which is connected to the core molecule as defined.

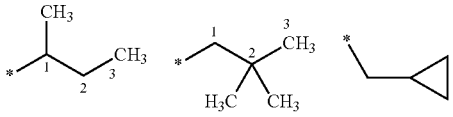

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing limns where such isomers and enantiomers exist, as well as salts, including pharmaceutically acceptable salts thereof and solvates thereof such as for instance hydrates including solvates of the free compounds or solvates of a salt of the compound.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by cnantioselcctivc crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio. As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, formic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid tartaric acid, and trifluoroacetic acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods, Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts, formates) also comprise a part of the invention.

The term halogen generally denotes fluorine, chlorine, bromine and iodine

The term "$C_{1-6}$alkyl", wherein n is an integer selected from the group consisting of 2, 3, 4, 5 or 6, preferably 4 or 6, either alone or in combination with another radical denotes an acyclic, saturated, branched or linear hydrocarbon radical with 1 to n C atoms. For example the term $C_{1-5}$alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—, $H_3C$—$CH_2$—$CH_2$—$CH(CH_3)$—, $H_3C$—$CH_2$—$CH(CH_3)$—$CH_2$, $H_3C$—$(CH_3)$—$CH_2$—$CH_2$—, $H_3C$—$CH_2$—$C(CH_3)_2$—, $H_3C$—$C(CH_2)_2$—$CH_2$—, $H_3C$—$CH(CH_3)$—$CH(CH_3)$— and $H_3C$—$CH_2$—$CH(CH_3CH_3)$—.

The term "$C_{3-6}$-cycloalkyl", wherein n is an integer from 4 to n, either alone or in combination with another radical denotes a cyclic, saturated, unbranched hydrocarbon radical with 3 to n C atoms. For example the term $C_{3-7}$cycloalkyl includes cyclopropyl, cyclobutyl, cyclopentyl, cyclohexyl and cycloheptyl.

By the term "halo" added to an "alkyl", "alkylene" or "cycloalkyl" group (saturated or unsaturated) is such an alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC$—, $HF_2C$—, $F_3C$—.

Analogously, the term "halo" added to an aryl group (e.g., phenyl) means that one or more hydrogen atoms are replaced by a halogen atom selected from among fluorine, chlorine or bromine, preferably fluorine and chlorine, particularly preferred is fluorine.

The term "carbocyclyl" as used either alone or in combination with another radical, means a mono- bi- or tricyclic ring structure consisting of 3 to 9 carbon atoms and optionally a heteroatom selected from the group consisting of N, O, and S. The term "carhocyclyl" refers to fully saturated ring systems and encompasses fused, bridged and spirocyclic systems.

Many of the terms given above may be used repeatedly in the definition of a formula or group and in each case have one of the meanings given above, independently of one another.

The present application provides compounds that can modulate TRPC6 function. Methods employing these compounds are also provided. Certain embodiments provide a method of modulating a TRPC6 function in a cell or animal comprising administering an effective amount of a compound that inhibits a TRPC6 function, wherein the compound inhibits a TRPC6-mediated ion flux. Certain embodiments provide a method of modulating a TRPC6 function in a cell or animal comprising administering an effective amount of a compound that inhibits a TRPC6 function, wherein the compound inhibits a TRPC6-mediated calcium influx. Certain embodiments provide a method of modulating a TRPC6 function in a cell or animal comprising administering an effective amount of a compound that inhibits a TRPC6 function, wherein the compound inhibits a TRPC6-mediated cytoskeletal reorganization or alteration in cell morphology. Certain embodiments provide a method of modulating a TRPC6 function in a cell comprising administering to the cell an effective amount of a compound that inhibits TRPC6 fraction, wherein the compound inhibits outward current mediated by TRPC6. Certain embodiments provide a method of modulating a TRPC6 function in a cell comprising administering to the cell an effective amount of a compound that inhibits TRPC6 function, wherein the compound inhibits inward current mediated by TRPC6. Certain embodiments provide a method of modulating a TRPC6 function in a cell comprising administering to the cell an effective amount of a compound that inhibits TRPC6 function, wherein the compound inhibits both the inward and outward currents mediated by TRPC6. Certain embodiments provide a method of modulating a TRPC6 function in a cell comprising administering to the cell an effective amount of a compound that inhibits TRPC6 function, wherein the compound inhibits TRPC6 mediated increases in intracellular calcium concentration. Certain embodiments provide a method of modulating a TRPC6 function in a cell comprising administering to the cell an effective amount of a compound that inhibits TRPC6 function, wherein the compound inhibits alterations in cell morphology. Certain embodiments also provide a method of preventing or treating a disease or condition related to TRP(function in a subject comprising administering to the subject a therapeutically effective amount of a compound that inhibits TRPC6 function, wherein the compound inhibits the inward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the outward current mediated by TRPC6. Certain embodiments also provide a method of preventing or treating a disease or condition related to TRPC6 function in a subject comprising administering to the subject a therapeutically effective amount of a compound that inhibits TRPC6 function, wherein the compound inhibits both the inward and outward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the ion flux mediated by TRPC6. Note that inhibition of a particular current refers to the ability of a compound to inhibit that current (e.g., inward and/or outward) in either an in vitro or an in vivo assay. Inhibition of a particular current in either an in vivo or an in vitro assay serves as a proxy for the particular functional activity of the particular compound.

The present invention provides methods of treating a TRPC6 mediated disorder in a subject, the method comprising administering an effective amount of a compound of the invention Wherein each of the variables above are described herein, for example, in the detailed description below.

The present invention further provides a method for treating a TRPC6 mediated disorder in a subject, wherein the method comprises administering a composition comprising a compound of the invention and a pharmaceutically acceptable excipient, diluent or carrier.

The present invention further provides a method for treating a TRPC6 mediated disorder in a subject, wherein the method comprises administering a composition comprising a compound of the invention and a pharmaceutically acceptable excipient, diluent or carrier, and the TRPC6 mediated disorder is selected from the group consisting of cardiac hypertrophy, ischemia, ischemic reperfusion injury, hypertension, pulmonary arterial hypertension, idiopathic pulmonary arterial hypertension, restenosis, chrome obstructive pulmonary disease, cystic fibrosis, Alzheimer's disease, Parkinson's disease, Huntington's disease, amyotrophic lateral sclerosis (ALS), trauma induced brain disorders, asthma, chronic obstructive pulmonary disease, rheumatoid arthritis, osteoarthritis, inflammatory bowel disease, multiple sclerosis, muscular dystrophy, preeclampsia and pregnancy-induced hypertension, non-alcoholic steatohepatitis, focal segmental glomerulosclerosis, nephrotic syndrome, diabetic nephropathy or diabetic kidney disease, renal insufficiency, end stage renal disease, ischemia or an ischemic reperfusion injury, cancer, IPF (idiopathic pulmonary fibrosis), ARDS (acute respiratory disease syndrome), emphysema and diabetes.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds in Table 1 can exist in more than one tautomeric form. The invention includes methods for using all such tautomers.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof A pharmacologically active metabolite shall be understood to mean any compound of the invention capable of being metabolized enzymatically or chemically. This includes, for example, hydroxylated or oxidized derivative compounds of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, formates, fumarates, gluceptates, glucornates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mutates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, trifluoroacetates, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (Also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above Which for example are useful for purifying or isolating the compounds of the present invention (e.g. trifluoro acetate salts) also comprise a part of the invention.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature, Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}O$, $^{14}O$, $^{15}N$, $^{18}O$, $^{17}O$, $^{31}P$, $^{35}S$, $^{18}F$, and $^{36}Cl$, respectively. An active agent of a combination of the present invention a prodrug thereof, or a pharmaceutically acceptable salt of either which contains one or more of the above-mentioned isotopes and/or other isotopes of other atoms is contemplated to be within the scope of the present invention.

The compounds of the invention are only those which are contemplated to be "chemically stable" as will be appreciated by those skilled in the art. For example, a compound which would have a "dangling valency", or a "carbanion" are not compounds contemplated by the inventive methods disclosed herein.

For all compounds disclosed herein above in this application, in the event the nomenclature is in conflict with the structure, it shall be understood that the compound is defined by the structure.

List of Abbreviations

AA Acetic Acid
ACN/MeCN Acetonitrile
aq. Aqueous
BEH Ethylene bridged hybrid column
BOC Tert-butyloxycarbonyl
° C. Degree Celsius
CDI Di(imidazol-1-yl)methanone
CPhos-3G-palladacycle methane sulfonate Methansulfonato (2-dicyclohexylphosphino-2',6'-bis(dimethylamino)-1,1'-biphenyl)(2'-amino-1,1'-biphenyl-2yl)palladium(II)
DCM Dichloromethane
DIPEA N,N-diisopropylethylamine
DMF N,N-dimethylformamide
DMA N,N-dimethylacetamide
DMSO Dimethylsulfoxide
DTAD Di-tert-butyl azodicarboxylate
EE Diethylether
eq Equivalent
ESI-MS Electrospray ionisation mass spectrometry
EtOH Ethanol
EtOAc/EE Ethyl acetate
h Hour
H2 Hydrogen
H3PO4 Phosphoric acid
HATU N,N,N',N'-tetramethyl-O-(7-azabenzotriazol-1-yl) uranium hexafluorophosphate
HCl Hydrochloric acid
HPLC High performance liquid chromatography
MeOH Methanol
min Minute
MeI Iodomethane
mL Milliliter
MS Mass spectrum
NaH Sodium hydride
NaOH Sodium hydroxide
NMP N-methyl-2-pyrrolidinone
Pd2(dba)3 Tris(dibenzylideneacetone)dipalladium(0)
Pd/C Palladium on carbon
PdCl12(dppf)CH2Cl2 [1,1'-Bis(diphenylphosphino)ferrocene]dichloropalladium(II) dichloromethane
Pd(OH)2 Palladium hydroxide
PE Petroleum ether
RP Reverse phase
rt or RT Room temperature (about 25° C.)
SFC Supercritical fluid chromatography
TBTU Benzotriazolyl tetramethyuronium tetrafluoroborate
TFA Trifluoroacetic acid
THF Tetrahydrofuran
TLC Thin-layer chromatography on SiO2
Xantphos 4,5-Bis(diphenylphosphino)-9,9-dimethylxanthene
Xphos 2nd Gen. Chloro(2-dicyclohexylphosphino-2',4',6'-triisopropyl-1,1'-bi phenyl)[2-(2'-amino-1,1'-biphenyl)] palladium(II)
TPP Triphenylphosphine General Methods:

Unless noted otherwise, all reactions are run at room temperature (about 25° C.), under inert atmosphere (e.g., Argon $N_2$), and under anhydrous conditions. All compounds are characterized by at least one of the following methods: $^{1}$H NMR, HPLC, MS, HPLC-MS, or melting point.

Typically, reaction progress is monitored by thin layer chromatography (TLC) or HPLC-MS. Intermediates and products are purified using at least one of the following methods:

Flash chromatography on silica gel. Recrystallization, Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or Reversed phase HPLC using a C18 semi-preparative column eluting with a gradient of:

MeCN+0.1% TFA and $H_2O$+0.1% TFA.
McCN+0.1% formic acid and $H_2OI$+0.1% formic acid, or
MeCN and $H_2O$ containing 2.5 mM $NH_4HCO_3$
McCN and $H_2O$+0.1% TFA,
MeCN and $H_2O$+0.1% $NH_3$,
McCN and $H_2O$ and 0.1% TFA
McCN and $H_2O$ and 0.1% $NH_3$ Analytical Data The reported mass spectrometry (MS) data is for observed mass (e.g., $[M+H]^+$). The HPLC method used to characterize the compounds of the invention is described in Table 2.

TABLE 2

HPLC Methods

| Method | Mobile Phase A | Mobile Phase B | Gradient Time (min) | % A | % B | Flow (mL/min.) | Column |
|---|---|---|---|---|---|---|---|
| A | 0.1% Formic Acid in Water | 0.1% Formic Acid in MeCN | 0<br>1.0<br>1.3<br>1.4<br>1.7 | 95.0<br>5.0<br>5.0<br>95.0<br>95.0 | 5.0<br>95.0<br>95.0<br>5.0<br>5.0 | 0.8 | BEH 2.5 × 50 mm C18, 1.7 μm particle diameter |

This method is utilized throughout the remainder of the tables in this section for the ESI-MS and retention time data.

If a different HPLC-MS is used, it is indicated in the text

Method 1

ESI +/− ion mode. Column: CSH C18 2.1×50 mm, 1.7 μm particle diameter. Gradient: 90% A to 100% B in 1.19 minutes hold at 100% B to 1.70 minutes. Flow rate 0.8 mL/min A=(95% water+5% acetonitrile+0.05% formic acid) B=(acetonitrile+0.05% formic acid).

Method 2

ESI +/− ion mode. Column: BEH 2.1×50 mm C18, 1.7 μm particle diameter. Gradient: 90% A to 100% B in 4.45 minutes hold at 100% B to 4.58 minutes. Flow rate 0.8 mL/min. A=(95% water+5% acetonitrile+2.5 mM ammonium bicarbonate) B=(acetonitrile).

Method 3

ESI +/− ion mode. Column: BEH 2.1×50 mm C18, 1.7 μm particle diameter. Gradient: 90% A to 95% B in 1.19 minutes hold at 95%6 to 1.70 minutes. Flow rate 0.8 mL/min. A=(95% water+5% acetonitrile+2.5 mM ammonium bicarbonate) B=(acetonitrile).

Method 4

ESI +/− ion mode. Column: HSS T3 2.1××100 mm, 1.8 μm particule diamétre. Gradient: 100% A hold for 1.00 minute, 100% A to 95% B in 4.50 minutes hold at 100% B to 4.91 minutes. Flow rate 0.6 mL/min A=(95% water+5% acetonitrile+0.05% formic acid) B=(acetonitrile+0.05% formic acid).

Method 5

ESI +/− ion mode. Column: CSH C18 2.1×50 mm, 1.7 μm particle diameter: Gradient: 90% A to 100% B in 4.45 minutes hold at 100% B to 4.58 minutes. Flow rate 0.8 mL/min. A=(95% water+5% acetonitrile+0.05% formic acid) B=(acetonitrile+0.05% formic acid).

Method 6

ESI+/− ion mode, Column: HSS T3 2.1×100 mm, 1 8 μm particule diamétre. Gradient: 95% A to 100% B in 3.65 minutes, hold at 100% B to 4.95 minutes. Flow rate 0.6 mL/min. Column temperature 60 degrees Celsius. A=(95% water+5% acetonitrile+0.05% formic acid) B=(acetonitrile+0.05% formic acid), Method 7 (Column Temperature 60° C.)

| Mobile Phase A | Mobile Phase B | Gradient Time (min) | % A | % B | Flow (mL/min.) | Column |
|---|---|---|---|---|---|---|
| 0.1% TFA in water | ACN | 0 | 97.0 | 3.0 | 2.2 | Sun fire C18_3.0 × 30 mm, 2.5 μm particle diameter, |
| | | 0.2 | 97.0 | 3.0 | 2.2 | |
| | | 1.2 | 0.0 | 100.0 | 2.2 | |
| | | 1.25 | 0.0 | 100.0 | 3.0 | |
| | | 1.4 | 0.0 | 100.0 | 3.0 | |

Method 8 (Column Temperature 40° C.)

| Mobile Phase A | Mobile Phase B | Gradient Time (min) | % A | % B | Flow (mL/min.) | Column |
|---|---|---|---|---|---|---|
| Supercritical carbon dioxide | EtOH 20 mM $NH_3$ | 0 | 60 | 40 | 4.0 | CHIRAL ART ® Cellulose SC_4.6 × 250 mm_5 μm particle diameter |
| | | 10 | 60 | 40 | | |

Method 9

| Mobile Phase A | Mobile Phase B | Gradient Time (min) | % A | % B | Flow (mL/min.) | Column |
|---|---|---|---|---|---|---|
| 0.1% TFA in water | ACN 0.08% TFA | 0 | 95.0 | 5.0 | 1.5 | Sun fire C18_3.0 × 30 mm, 2.5 μm particle diameter |
| | | 1.3 | 0.0 | 100.0 | | |
| | | 1.5 | 0.0 | 100.0 | | |
| | | 1.6 | 95.0 | 5.0 | | |

Method 10 (Column Temperature 60° C.)

| Mobile Phase A | Mobile Phase B | Gradient Time (min) | % A | % B | Flow (mL/min.) | Column |
|---|---|---|---|---|---|---|
| 0.1% TFA in Water | ACN | 0 | 97.0 | 3.0 | 2.2 | Zorbax Stable Bond C18_3.0 × 30 mm, 1.8 μm, particle diameter |
| | | 0.2 | 97.0 | 3.0 | 2.2 | |
| | | 1.2 | 0.0 | 100.0 | 2.2 | |
| | | 1.25 | 0.0 | 100.0 | 3.0 | |
| | | 1.4 | 0.0 | 100.0 | 3.0 | |

Method 11

| Mobile Phase A | Mobile Phase B | Gradient Time (min) | % A | % B | Flow (mL/min) | Column | T° |
|---|---|---|---|---|---|---|---|
| 0.1% $NH_3$ in water | ACN | 0 | 97.0 | 3.0 | 2.2 | XBridge C18_3.0 × 30 mm, 2.5 μm particle diameter | 60° C. |
| | | 0.2 | 97.0 | 3.0 | 2.2 | | |
| | | 1.2 | 0.0 | 100.0 | 2.2 | | |
| | | 1.25 | 0.0 | 100.0 | 3.0 | | |
| | | 1.4 | 0.0 | 100.0 | 3.0 | | |

Method 12

| Mobile Phase A | Mobile Phase B | Gradient Time (min) | % A | % B | Flow (mL/min) | Column | T° |
|---|---|---|---|---|---|---|---|
| 0.1% TFA in water | ACN | 0 | 99.0 | 1.0 | 1.5 | Sun fire C18_2.1 × 30 mm, 2.5 μm particle diameter | 60° C. |
| | | 0.02 | 99.0 | 1.0 | 1.5 | | |
| | | 1.00 | 0.0 | 100.0 | 1.5 | | |
| | | 1.10 | 0.0 | 100.0 | 1.5 | | |

Method 13

| Mobile Phase A | Mobile Phase B | Gradient Time (min) | % A | % B | Flow (mL/min) | Column | T° |
|---|---|---|---|---|---|---|---|
| 0.1% $NH_3$ in water | ACN | 0 | 95.0 | 5.0 | 1.5 | XBridge C18_3.0 × 30 mm, 2.5 μm particle diameter | 60° C. |
| | | 1.3 | 0.0 | 100.0 | 1.5 | | |
| | | 1.5 | 0.0 | 100.0 | 1.5 | | |
| | | 1.6 | 95 | 5.0 | 1.5 | | |

| Method 14 | | | | | | | |
|---|---|---|---|---|---|---|---|
| Mobile Phase A | Mobile Phase B | Gradient Time (min) | % A | % B | Flow (mL/min) | Column | T° |
| 0.5% $H_3PO_4$ in water | 0.5% $H_3PO_4$ in ACN | 0 | 95.0 | 5.0 | 1.2 | Halo C18_4.6 mm × 15 cm, 2.7 μm particle diameter | 15° C. |
| | | 1 | 95.0 | 5.0 | 1.2 | | |
| | | 4 | 70.0 | 30.0 | 1.2 | | |
| | | 5 | 62.5 | 37.5 | 1.2 | | |
| | | 7.5 | 61 | 39 | 1.2 | | |
| | | 10 | 2 | 98 | 1.2 | | |
| | | 12 | 2 | 98 | 1.2 | | |

SYNTHETIC EXAMPLES

The examples which follow are illustrative and, as recognized by one skilled in the art, particular reagents or conditions could be modified as needed for individual compounds without undue experimentation.

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

General Synthetic Procedure

The compounds of the invention are generally prepared by reacting a carboxylic acid intermediate of formula INT-1 with an amine intermediate of formula INT-2 under appropriate conditions as depicted below in Scheme 1.

Scheme 1

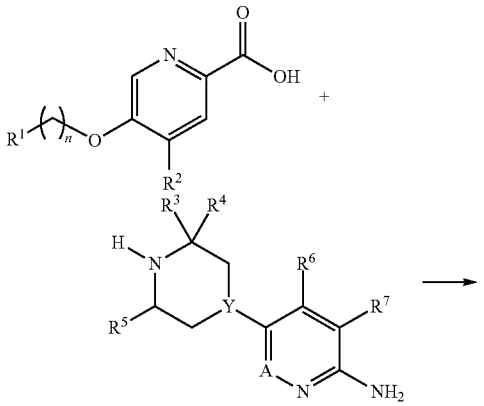

INT-2

-continued

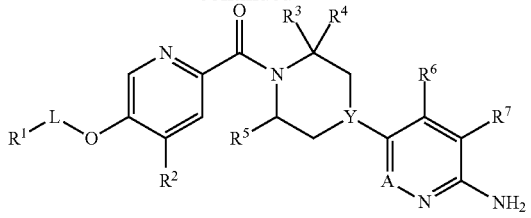

(I)

Intermediates INT-1 and INT-2 are known in the art or can be prepared by the methods described below. The groups/terms $R^1$ to $R^7$, A, Y and L are as defined above for the compound of formula (I).

Synthesis of Intermediates

4-[6-(2,5-Dimethyl-pyrrol-1-yl)-4-methoxy-pyridin-3yl]-piperazine-1-carboxylic acid tert-butyl ester

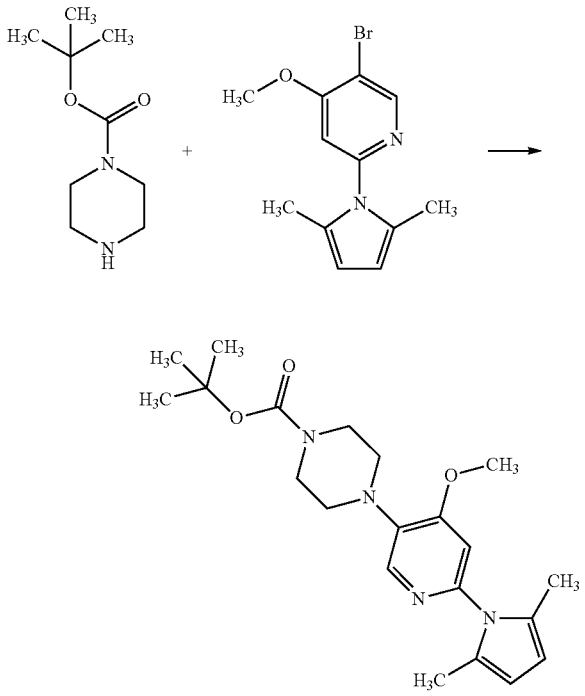

To piperazine-1-carboxylic acid tert-butyl ester (1.0 g, 5.37 mmol) and 5-bromo-2-(2,5-dimethyl-pyrrol-1-yl)-4-methoxy-pyridine (1.5 g, 5.37 mmol) in 1,4-dioxane (15 mL) is added CPhos-G3-palladacycle methane sulfonate and sodium tert-butoxide (216 mg, 16.1 mmol) and degassed with nitrogen for 5 min. The resultant mixture is stirred at 100° C. for 10 h. The reaction mixture is filtered through a pad of silica eluting with EtOAc and concentrated. The crude product is purified by silica gel column chromatography to afford the title compound.

Yield: 2.1 g (88%) $R_t$(HPLC): 1.15 min (Method 1)

4-(6-Amino-4-methoxy-pyridin-3-yl)-piperazine-1-carboxylic acid tert-butyl ester

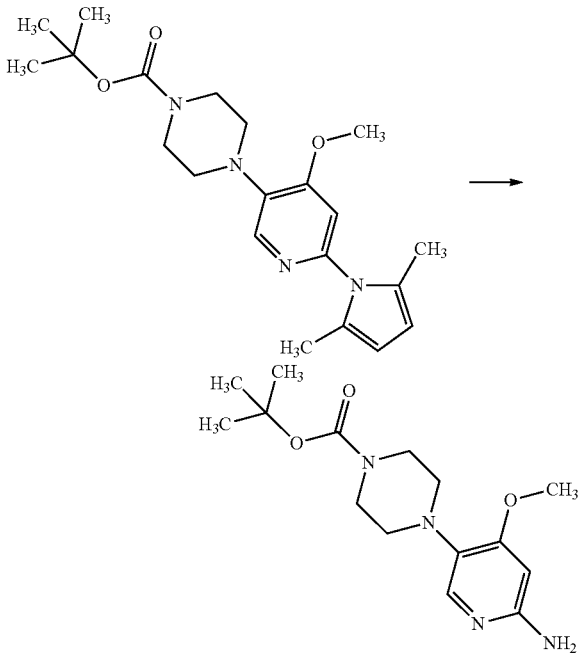

To 4-[6-(2,5-dimethyl-pyrrol-1-yl)-4-methoxy-pyridin-3-yl]-piperazine-1-carboxylic acid tell-butyl ester (2.1 g, 4.73 mmol) in EtOH (10 mL) and water (5 mL) is added hydroxylamine hydrochloride (1.64 g 23.6 mmol and trimethylamine (659 μL, 4.73 mmol) and stirred at 80° C. for 18 h. The reaction mixture is concentrated under reduced pressure. The residue is suspended in DCM and filtered to remove the salts. The filtrate is purified by silica gel column chromatography to afford the title compound.

Yield: 1.07 g (73%)

4-Methoxy-5-piperazin-l-yl-pyridin-2-ylamine dihydrochloride

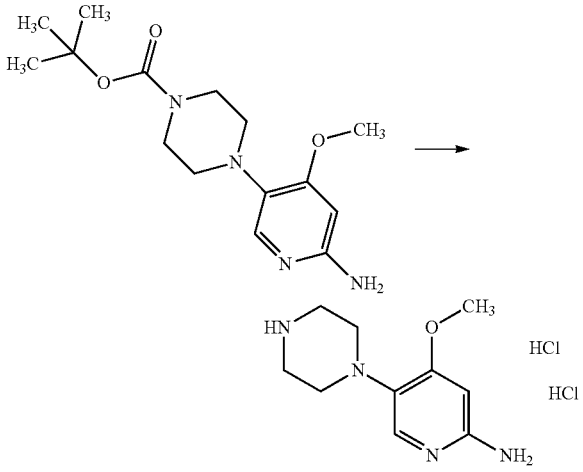

To 4-(6-amino-4-methoxy-pyridin-3-yl)-piperazine-1-carboxylic acid tert-butyl ester (1.07 g. 3.47 mmol) in DCM (12 mL) is added 4M HCl in 1,4-dioxane (4.34 mL, 17.35 mmol) and stirred at RT thr 2 h. The reaction mixture is concentrated under reduced pressure.

Yield: 976 mg (quantitative)

6-Amino-4-methyl-3',6'-dihydro-2'H-[3,4']bipyrinyl-1carboxylic acid tert-butyl ester

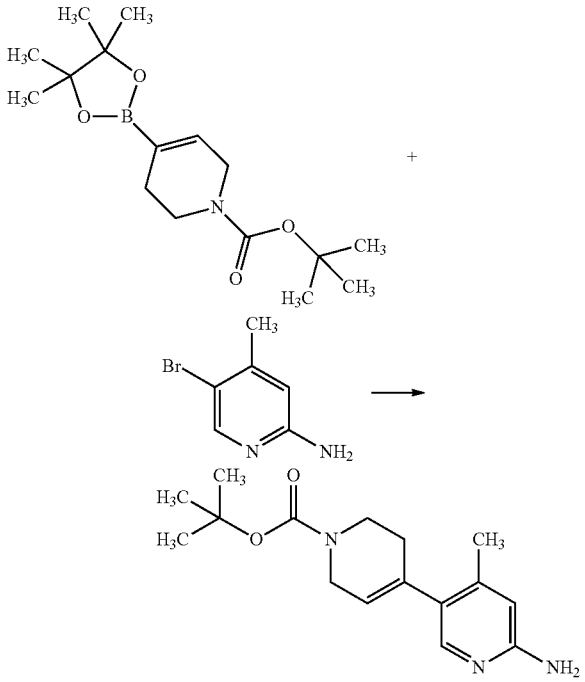

To 4-(4,4,5,5-tetramethyl-[1,3,2]dioxaborolan-2-yl)-3,6-dihydro-2H-pyridine-1-carboxylic acid tert-butyl ester (1,2,4 g, 4.01 mmol) and 5-bromo-4-methyl-pyridin-2-ylamine (750 mg, 4.01 mmol) in 1,4-dioxane is added 2M $Na_2CO_3$ solution (4.01 mL, 8.02 mmol) and PdCl2(dppf) (328 mg, 0.40 mmol). The reaction mixture is degassed with nitrogen for 5 min. and stirred in the microwave at 150° C. for 30 min. The reaction is diluted with EtOAc and water and the layers are separated. The aq. layer is extracted again with EtOAc. The combined organic layers are washed with brine, dried over $MgSO_4$ and concentrated under vacuum. The residue is purified by silica gel chromatography to give the title compound.

Yield: 1.1 g (95%) ESI-MS: m/z=290 $(M+H)^+$ $R_t$(HPLC): 1.82 min (Method 2)

6-Amino-4-methyl-3',4',5',6'-tetrahydro-2'H-[3,4'] bipyridinyl-t-carboxylic acid tert-butyl ester

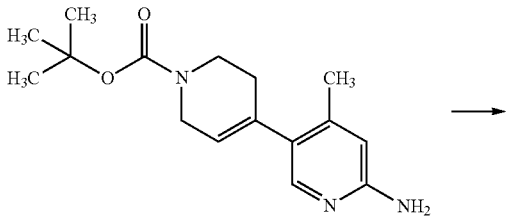

-continued

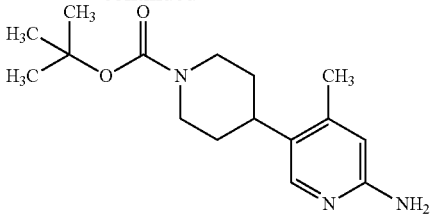

To 6-amino-4-methyl-3',6'-dihydro-2'H-[3,4']bipyridinyl-1'-carboxylic acid tert-butyl ester (1.10 g, 3.80 mmol) in MeOH (10 mL) is added Pd/C (405 mg, 0.38 mmol) under nitrogen. The reaction mixture is degassed and subjected to a balloon of H2. The reaction is filtered and concentrated under reduced pressure. The crude product is purified by silica gel column chromatography to give the title compound.

Yield: 511 mg (46%) ESI-MS: m/z=292 $(M+H)^+$ $R_t$(HPLC): 1.80 min (Method 2)

4-Methyl-1',2',3',4',5',6'-hexahydro-[3,4']bipyridinyl-6-ylamine dihydrochloride

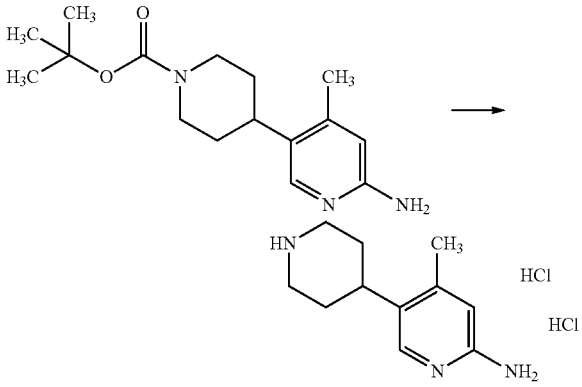

The title compound is synthesized from 6-Amino-4-methyl-3',4',5',6'-tetrahydro-2'H-[3,4']bipyridinyl-1'-carboxylic acid tert-butyl ester (511 mg, 1.75 mmol) according to the procedure described for the synthesis of the intermediate 4-methoxy-5-piperazin-l-yl-pyridin-2-ylamine dihydrochloride.

Yield: 347 mg (75%) ESI-MS: m/z-192 $(M+H)^+$ $R_t$(HPLC): 0.36 min (Method 2)

6-Amino-3',6'-dihydro-2'H-[3,4']bipyridinyl-1'-carboxylic acid tert-butyl ester

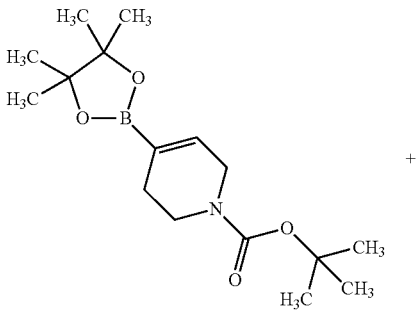

-continued

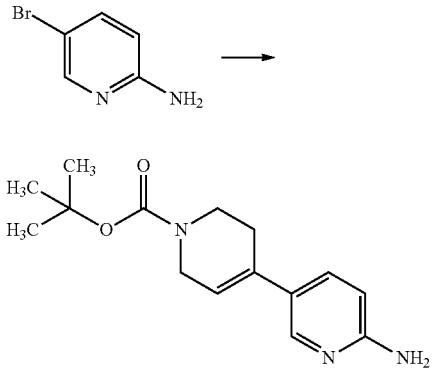

To 4-(4,4,5,5-tetramethyl-[1,3,2]dioxaborolan-2-yl)-3,6-dihydro-2H-pyridine-1-carboxylic acid tert-butyl ester (1.70 g, 5.50 mmol) and 5-bromo-pyridin-2-ylamine (1.00 mg, 5.78 mmol) in 1,4-dioxane is added 2M $Na_2CO_3$ solution (2 mL, 4.00 mmol) and $PdCl_2(dppf)CH_2Cl_2$ (449 mg, 0.55 mmol). The reaction mixture is degassed with nitrogen for 5 min. and stirred at 120° C. for 16 h. All volatiles are evaporated under reduced pressure. The crude material is purified by normal phase chromatography to afford the title compound.

Yield: 1.2 g (79%)

6-Amino-3',4',5',6'-tetrahydro-2'H-[3,4']bipyridinyl-1'-carboxylic acid tert-butyl ester

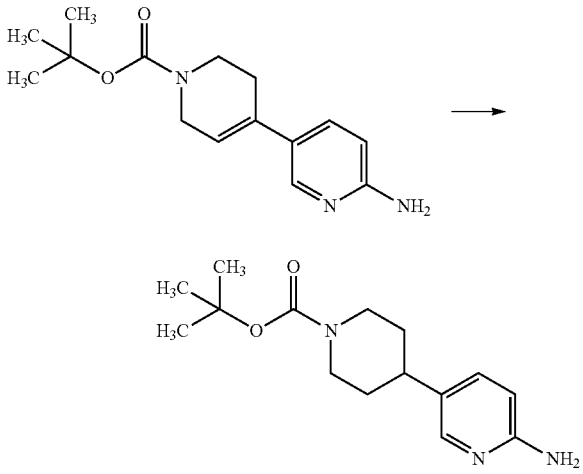

To 6-amino-3',6'-dihydro-2'H-[3,4']bipyridinyl-1'-carboxylic acid tert-butyl ester (45.0 g, 163.4 mmol) in EtOH (1000 mL) is added Pd(OH)2 on carbon (4.5 g, 32.4 imnol) under nitrogen. The reaction mixture is stirred at 30 PSI in PARR SHAKER for 16 h. The reaction is filtered through Celite®. The filtrate is evaporated under reduced pressure and the residue is purified by silica gel column chromatography to get the title compound.

Yield: 23.7 g (79%)

1',2',3',4',5',6'-hexahydro-[3,4']bipyridinyi-6-ylamine dihydrochloride

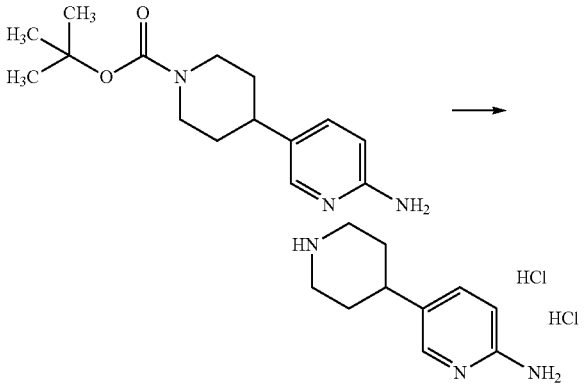

The title compound is synthesized from 6-amino-3',4',5',6'-tetrahydro-2'H-[3,4']-bipyridinyl-1'-carboxylic acid tert-butyl ester (800 mg, 2.88 mmol) according, to the procedure described for the synthesis of the intermediate 4-methoxy-5-piperazin-1yl-pyridin-2-ylamine dihydrochloride.

Yield: 694 mg (96%)

6-Amino-4-methoxy-3',6'-dihydro-2'H-[3,4']bipyridinyl-1-carboxylic acid tert-butyl ester

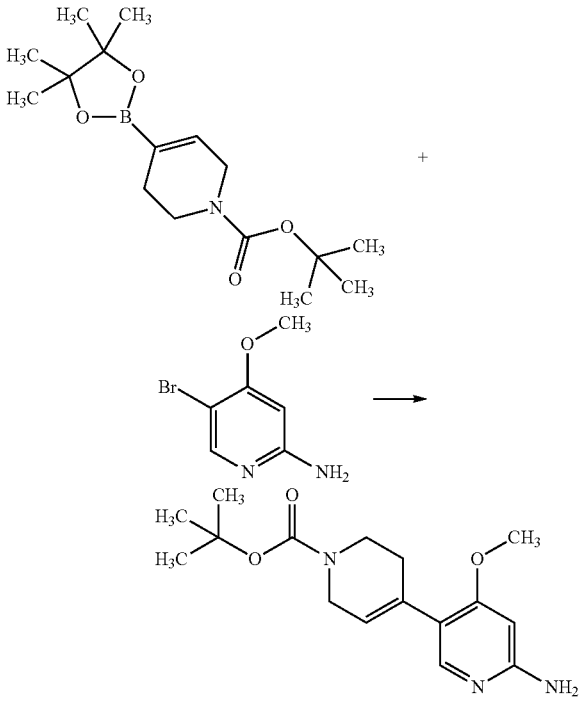

To 4-(4,4,5,5-tetramethyl-[1,3,2]dioxaborolan-2-yl)-3,6-dihydro-2H-pyridine-1-carboxylic acid tert-butyl ester (10.0 g, 49.3 mmol) and 5-bromo-4-methoxy-pyridin-2-ylamine (15.2 g, 49.3 mmol) in 1,4-dioxane (100 mL) is added 2M $Na_2CO_3$ solution (2 mL, 148 mmol) and PdCl2(dppf) $CH_2Cl_2$ (3.93 g, 4.93 mmol). The reaction mixture is degassed with nitrogen for 5 min. and stirred at 120° C. for 16 h. All volatiles are evaporated under reduced pressure. The residue is diluted with water and extracted three times with EtOAc. The combined organic layers are washed with brine, dried over $Na_2SO_4$ and concentrated under reduced pressure. The crude material is purified by normal phase chromatography to afford the title compound.

Yield: 2.50 g (55%)

6-Amino-4-methoxy-3',4',5',6'-tetrahydro-2'H-[3,4']bipyridinyl-1'-carboxylic acid tert-butyl ester

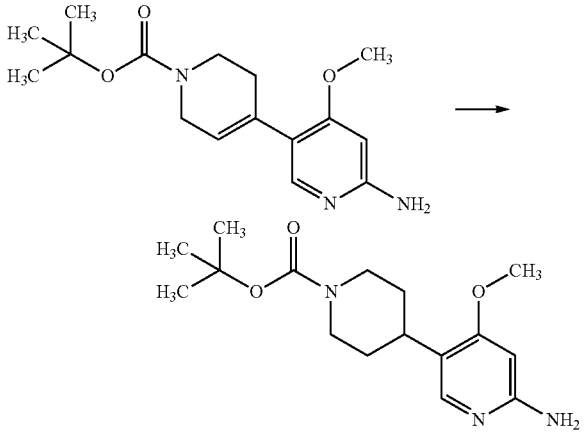

The title compound is synthesized from 6-amino-4-methoxy-3',6'-dihydro-2'H-[3,4']bipyridinyl-1'-carboxylic acid tert-butyl ester (750 mg, 2.46 mmol) according to the procedure described for the synthesis of the intermediate 6-amino-4-methyl-3',4',5',6'-tetrahydro-2'H-[3,4']bipyridinyl-1'-carboxylic acid tert-butyl ester Yield: 715 mg (95%) EST-MS: m/z=308 $(M+H)^+$ $R_t$(HPLC): 0.88 min (Method 5)

4-Methoxy-1',2',3',4',5',6'-hexahydro-[3,4']bipyridinyl-6-ylamine dihydrochloride

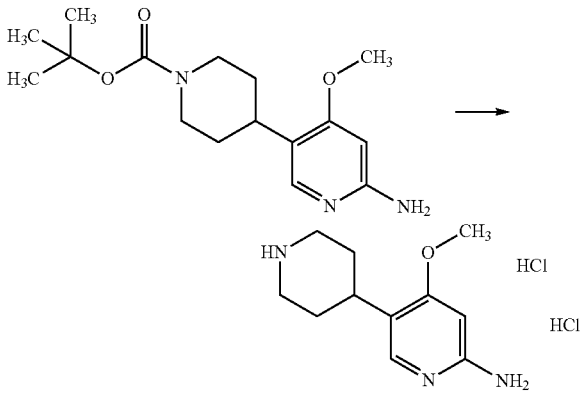

The title compound is synthesized from 6-amino-4-methoxy-3',4',5',6'-tetrahydro-2'H-[3,4'] bipyridinyl-1'-carboxylic acid tert-butyl ester (715 mg, 2.33 mmol) according to the procedure described for the synthesis of the intermediate 4-methoxy-5-piperazin-1-pyridin-2-ylamine dihydrochloride.

Yield: 745 mg (quantitative) ESI-MS: m/z =208 $(M+H)^+$ $R_t$(HPLC): 0.56 min (Method 6)

4-(6-Amino-pyridazin-3-yl)-3,6-dihydro-2H-pyridine-1 -carboxylic acid tert-butyl ester

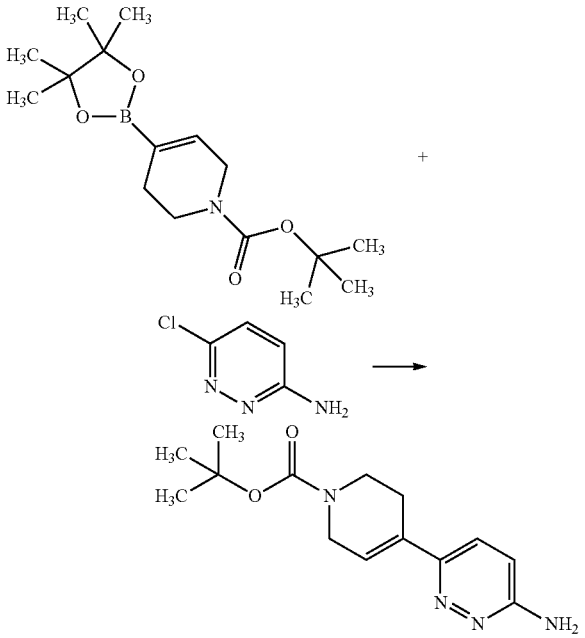

The title compound is synthesized from 4-(4,4,5,5-tetramethyl-[1,3,2]dioxaborolan-2-yl)-3,6-dihydro-2H-pyridine-1-carboxylic acid tert-butyl ester (977 mg, 3.16 mmol) and 6-chloro-pyridazin-3-ylamine (500 mg, 2.87 mmol) according to the procedure described for the synthesis of the intermediate 6-amino-4-methoxy-3',6'-dihhydro-2'H-[3,4'] bipyridinyl-1'-carboxylic acid tert-butyl ester.

Yield: 590 rm (74.3%) ESI-MS: m/z=$(M+H)^+$ $R_t$(HPLC): 0.44 min (Method 1)

4-(6-Amnino-pyridazin-3-yl)-piperidine-1-carboxylic acid tert-butyl ester

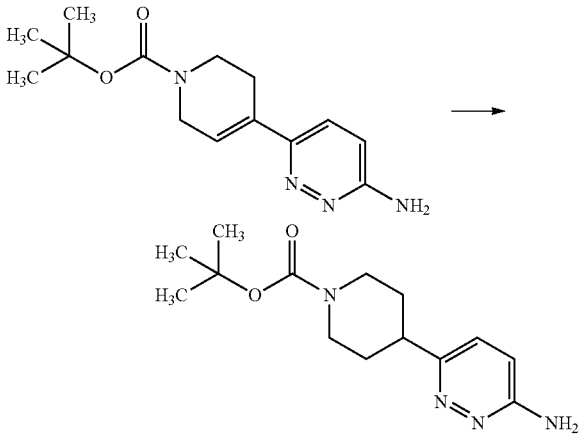

The title compound is synthesized from 4-(6-amino-pyridazin-3-yl)-3,6-dihydro-2H-pyridine-1-carboxylic acid tert-butyl ester (5.40 g, 19.5 mmol) according to the procedure described for the synthesis of the intermediate 6-amino-4-methyl-3',4',5',6'-tetrahydro-2'H-[3,4']bipyridinyl-1'-carboxyli c acid tert-butyl ester.

Yield: 3.93 g (72%) EST-MS: m/z=279 $(M+H)^+$ $R_t$(HPLC): 0.38 min (Method 1)

6-Piperidin-4-yl-pyridazin-3-ylamine dihydrochloride

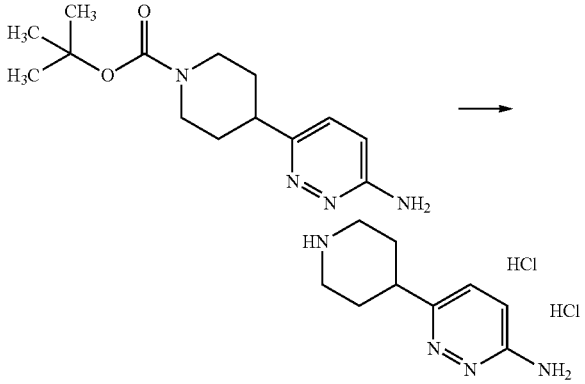

The title compound is synthesized from 4-(6-amino-pyridazon-3-yl)-piperidine-1-carboxylic acid tert-butyl ester (3.60 g, 12.9 mmol) according to the procedure described for the synthesis of the intermediate 4-methoxy-5-piperazin-1-yl-pyridin-2-ylamine dihydrochloride.

Yield: 2.30 g (quantitative) ESI-MS: m/z=179 $(M+H)^+$ $R_t$(HPLC): 0.32 min (Method 1)

(R)-2-(tert-Butyl-dimethyl-silanyloxymethyl)-piperazine-1-carboxylic acid tert-butyl ester

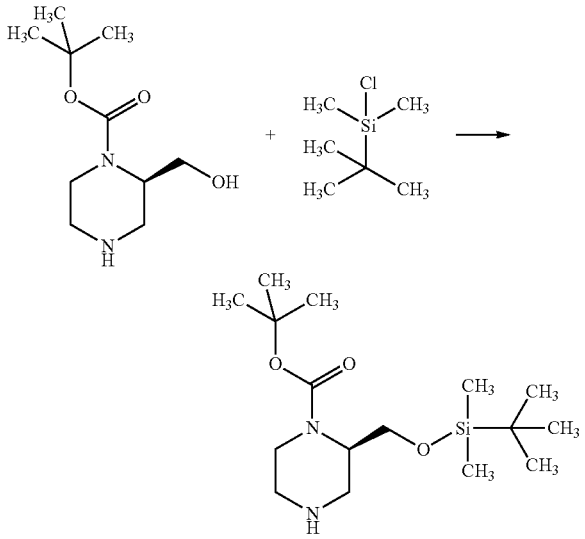

To (R)-2-hydroymethyl-piperazine-1-carboxylic acid tert-butyl ester *(1.00 g, 4.62 mmol) in DMA (10 mL) is added tert-butyl-chloro-dimethyl-silane (1.05 g, 6.94 mmol) and imidazole (944 mg, 13.9 mmol). and the reaction mixture is stirred for 14 h at rt. The reaction mixture is diluted with EtOAc and washed with water and brine, dried over $Na_2SO_4$, filtered and concentrated under reduced pressure. The residue is purified by silica gel column chromatography to give the title compound.

Yield: 1.45 g (95%)

5-Bromo-2-(2,5-dimethyl-pyrrol-1-yl)-4-methyl-pyridine

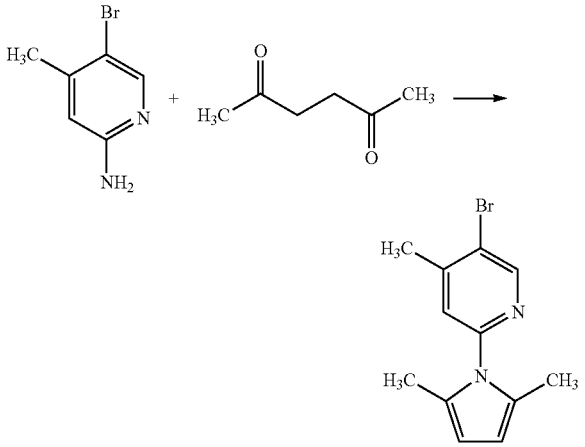

To 5-bromo-4-methyl-pyridin-2-ylamine (2.00 g, 10.7 mmol) and hexane-2,5-dione (1.47 g, 12.8 mmol) in toluene (50 mL) is added para toluene suifonic acid (61.0 mg, 0.32 mmol), and the reaction mixture is stirred for 18 h at 140° C. The reaction mixture is poured into water and diluted in EtOAc. The separated organic layer is washed with brine and dried over $MgSO_4$, filtered and concentrated under reduced pressure. The residue is purified by silica gel column chromatography to give the title compound.

Yield: 2.68 g (95%)

(R)-2-(terL-butyl-dimethyl-silanyloxymethyl)-4-[6-(2,5-dimethyl-pyrrol-1-yl)-4-methyl-pyridin-3-yl]-piperazine-1-carboxylic acid tert-butyl ester

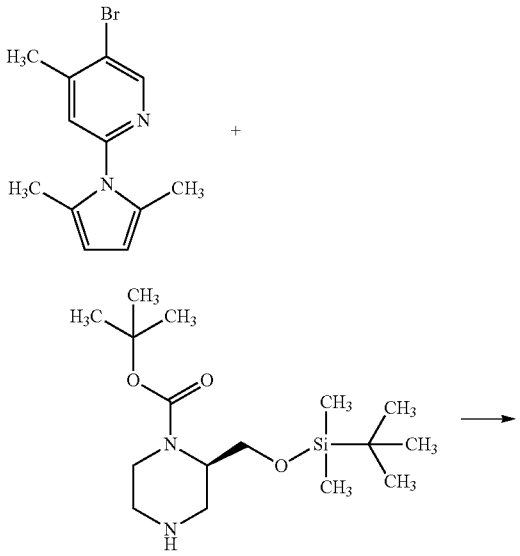

-continued

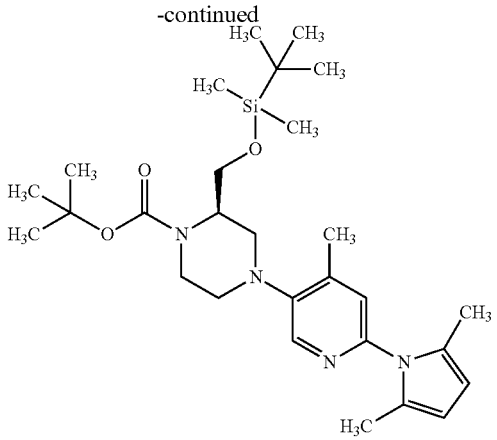

To 5-bromo-2-(2,5-dimethyl-pyrrol-1-yl)-4-methyl-pyridine (1.00 g, 3.77 mmol) and (R)-2-(tert-butyl-dimethylsilanyloxymethyl)-piperazine-1-carboxylic acid tert-butyl ester (1.25 g, 3.77 mmol) 1,4-dioxane (13 mL) is added sodium tert-butoxide (1.09 g, 11.3 mmol) and CPhos-G3-palladacycle methane sulfonate (152 mg, 0.19 mmol. The mixture is degassed with nitrogen for 5 min, and stirred for 18 h at 100° C. The reaction mixture is filtered through a pad of silica gel and eluted with EtOAc. The filtrate is concentrated under reduced pressure to afford the title compound.

Yield: 1.67 g (86%) ESI-MS: m/z=515 $(M+H)^+$ $R_t$(HPLC): 1.56 min (Method 1)

(R)-4-(6-Amino-4-methyl-pyridin-3-yl)-2-hydroxymethyl-piperazine-1 -carboxylic acid tert-butyl ester

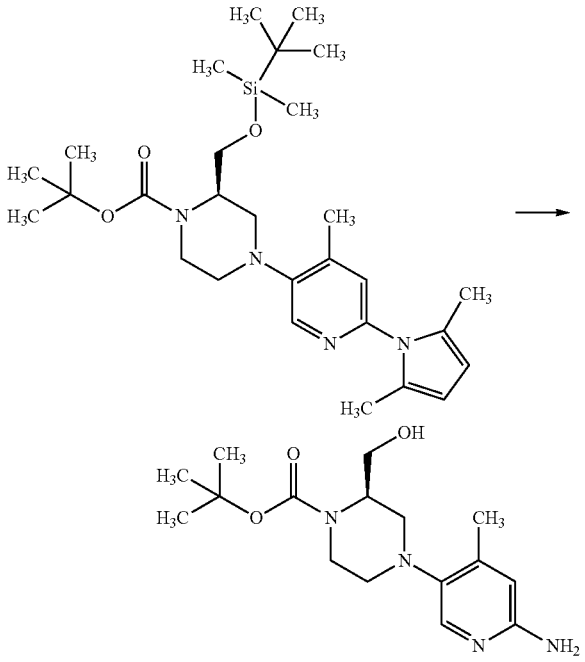

A mixture of (R)-2-(tert-Butyl-dimethyl-silanyloxymethyl)-4-[6-(2,5-dimethyl-pyrrol-1-yl)-4-methyl-pyridin-3-yl]-piperazine-1-carboxylic acid tert-butyl ester (1.67 g, 3.24 mmol), hydroxylamine hydrochloride (1.13 g, 16.2 mmol) and trimethylamine (452 μl, 3.24 mmol) in ethanol (10 mL) and water (5 mL) is stirred for 18 h at 80° C. The reaction mixture is concentrated under reduced pressure and the residue is purified by reverse phase chromatography to afford the title compound.

Yield: 1.67 g (86%) $R_t$(HPLC): 0.66 min (Method 3)

[(R)-4-(6-Amino-4-methyl-pyridin-3-yl)-piperazin-2-yl]-methanol dihydrochloride

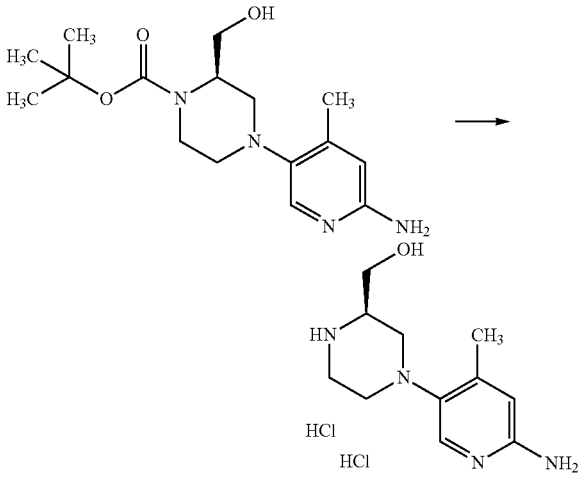

The title compound is synthesized from (R)-4-(6-amino-4-methyl-pyridin-3-yl)-2-hydroxymethyl-piperazine-1-carboxylic acid tert-butyl ester (450 mg, 1.40 mmol) according to the procedure described for the synthesis of the intermediate 4-methoxy-5-piperazin-1-yl-pyridin-2-ylamine dihydrochloride.

Yield: 412 mg (quantitative)

5-Bromo-2-(2,5-dimethyl-pyrrol-1-yl)-4-methoxy-pyridine

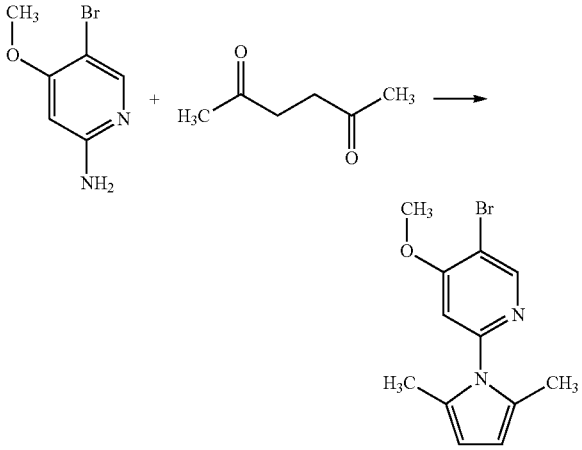

The title compound is synthesized from 5-bromo-4-methoxy-pyridin-2-ylamine (2.00 g, 9.85 mmol) according to the procedure described for the synthesis of the intermediate 5-bromo-2-(2,5-dimethy-pyrrol-1-yl)-4-methyl-pyridine.

Yield: 2.48 g, (90%) ESI-MS: m/z=283 $(M+H)^+$ $R_t$(HPLC): 2.13 min (Method 5)

7-[6-(2,5-Dimethyl-pyrrol-1-yl)-4-methoxy-pyridin-3-yl]-4,7-diaza-spiro[2.5]octane-4-carboxylic acid tert-butyl ester

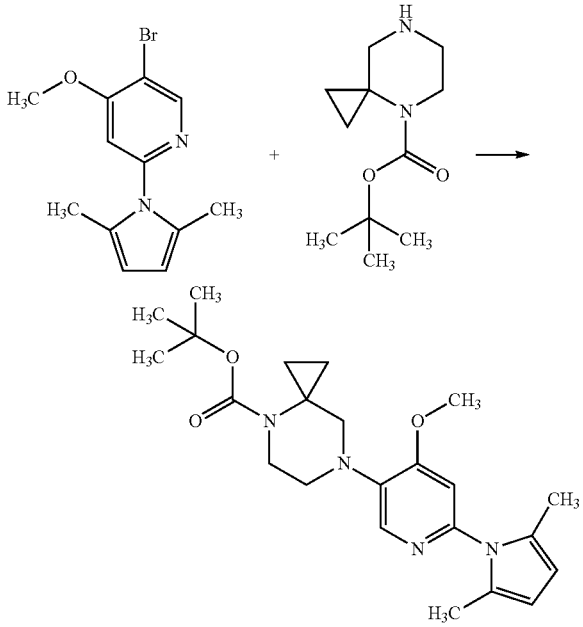

To 5-bromo-2-(2,5-dimethyl-pyrrol-1-yl)-4-methoxy-pyridine (1.25 g, 4.45 mmol) and 4,7-diaza-spiro[2.5]octane-4-carboxylic acid tert-butyl ester (1.13 g, 5.34 mmol) is 1,4-dioxane (13 mL) is added $Cs_2CO_3$ (4.35 g, 13.3 mmol) and CPhos-G3-palladacycie methane sulfonate (359 mg, 0.45 mmol. The mixture is degassed with nitrogen fbr 5 min, and stirred for 18 h at 100° C. The reaction mixture is extracted with EtOAc, washed with brine, dried over $MgSO_4$, filtered and concentrated under reduced pressure. The residue is purified by silica gel column chromatography to afford the title compound.

Yield: 1.51 g (82%) ESI-MS: m/z=413 $(M+H)^+$ $R_t$(HPLC): 2.69 min (Method 5)

7-(6-Amino-4-methoxy-pyridin-3-yl)-4,7-diaza-spiro[2.5]octane-4-carboxylic acid tert-butyl ester

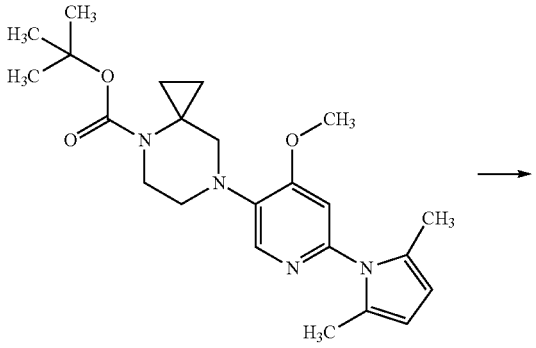

-continued

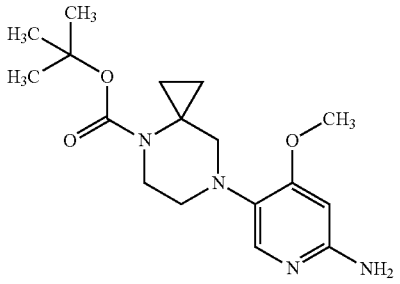

The title compound is synthesized from 7-[6-(2,5-dimethyl-pyrrol-1-yl)-4-methoxy-pyridin-3-yl]-4,7diaza-spiro[2.5]octane-4-carboxylic acid tert-butyl ester (1.51 g, 3.66 mmol) according to the procedure described for the synthesis of the intermediate (R)-4-(6-amino-4-methyl-pyridin-3-yl)-2-hydroxymethyl-piperazine-1-carboxylic acid tert-butyl ester Yield: 1.07 g (87%) ESI-MS: m/z=335 $(M+H)^+$ $R_t$(HPLC): 0.74 min (Method 5)

5-(4,7-Diaza-spiro[2.5]oct-7-yl)-4-methoxy-pyridin-2-ylamine dihydrochioride

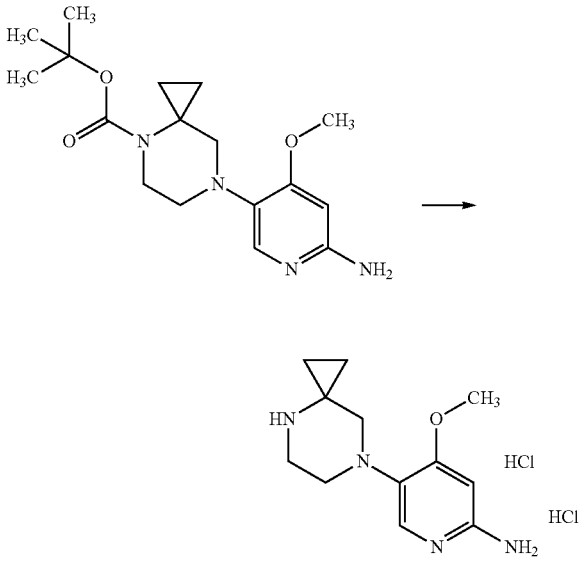

The title compound is synthesized from 7-(6-amino-4-methoxy-pyridin-3-yl)-4,7-diaza-spiro[2.5]octane-4-carboxylic acid tert-butyl ester (1.07 g, 3.19 mmol) according to the procedure described for the synthesis of the intermediate 4-methoxy-5-piperazin-1-yl-pyridin-2-ylamine dihydrochloride.

Yield: 1.10 g (quantitative) ESI-MS: m/z=235 $(M+H)^+$ $R_t$(HPLC): 0.17 min (Method 5)

4-(6-Amino-5-methoxy-pyridazin-3-yl)-3,6-dihydro-2H-pyridine-1-carboxylic acid tert-butyl ester

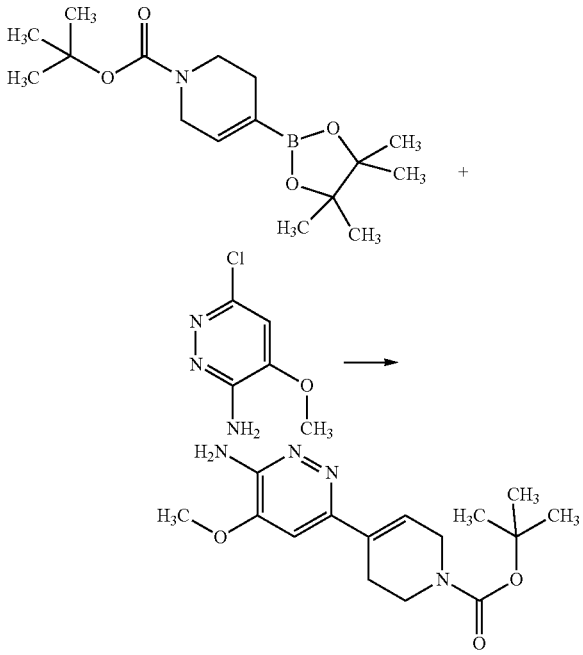

The title compound is synthesized from 4-(4,4,5,5-tetramethyl-[1,3,2]dioxaborolan-2-yl)-3,6-dihydro-2H-pyridine-1-carboxylic acid tert-butyl ester (1.74 g, 5.64 mmol) and 6-chloro-4-methoxy-pyridazin-3-ylamine (900 mg, 5.64 mmol) according to the procedure described for the synthesis of the intermediate 6-amino-4-methoxy-3',6'-dihydro-2'H-[3,4']bipyridinyl-1'-carboxylic acid tert-butyl ester Yield: 787 mg (46%) ESI-MS: m/z=307 $(M+H)^+$ $R_t$(HPLC): 0.59 min (Method 5)

4-(6-Amino-5-methoxy-pyridazin-3-yl)-piperidine-1-carboxylic acid tert-butyl ester

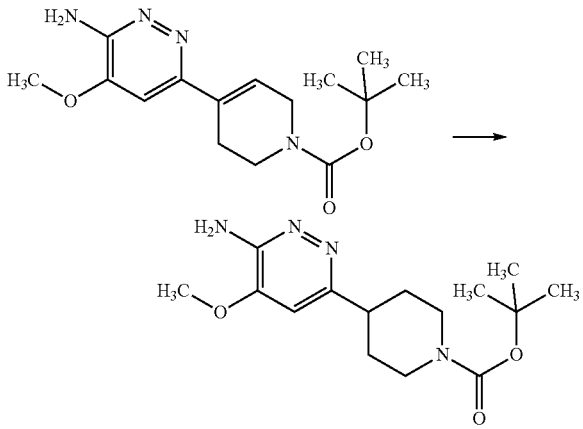

To 4-(6-amino-5-methoxy-pyridazin-3-yl)-3,6-dihydro-2H-pyridine-1-carboxylic acid tert-butyl ester (785 mg, 2.56 mmol) in MeOH (10 mL) and acetic acid (1 mL) is added Pd/C (273 mg, 0.26 mmol) under nitrogen. The reaction mixture is degassed and subjected to a balloon of H2. The reaction is filtered and concentrated under reduced pressure. The crude product is purified by silica gel column chromatography to give the title compound.

Yield: 513 mg (65%) ESI-MS: m/z=309 $(M+H)^+$ $R_t$(HPLC): 0.54 min (Method 5)

4-Methoxy-6-piperidin-4-yl-pyridazin-3-ylamine dihydrochloride

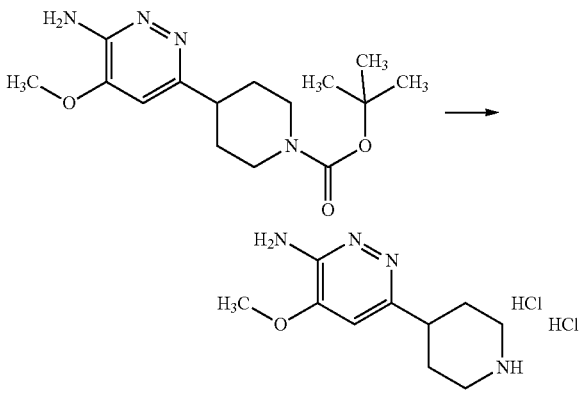

The title compound is synthesized from 4-(6-amino-5-methoxy-pyridazin-3-yl)-piperidine-1-carboxylic acid tert-butyl ester (510 mg, 1.65 mmol) according to the procedure described for the synthesis of the intermediate 4-methoxy-5-piperazin-1-yl-pyridin-2-ylamine dihydrochloride.

Yield: 514 mg (quantitative) ESI-MS: m/z=209 $(M+H)^+$ $R_t$(HPLC): 0.14 min (Method 5)

tert-Butyl 4-(6-{[(tert-butoxy)carbonyl]amino}-4-methoxypyridazin-3-yl)-1,2,3,6-tetrahydropyridine-1-carboxylate

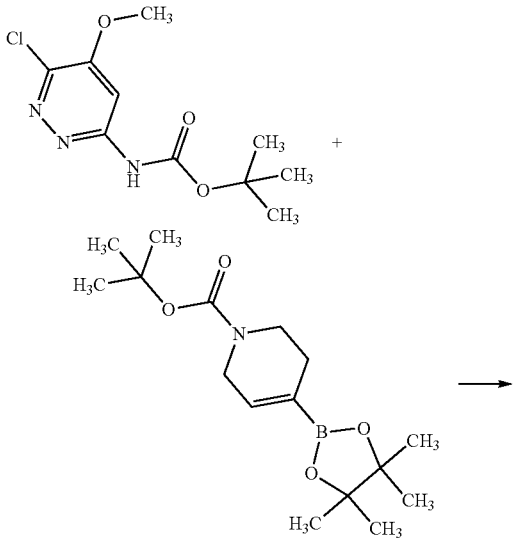

-continued

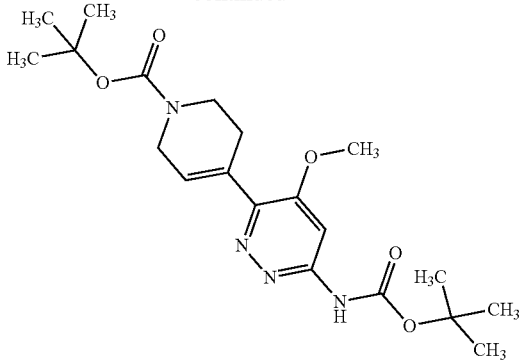

The title compound is synthesized from tert-Butyl 4-(4,4,5,5-tetramethyl-1,3,2-dioxaborolan-2-yl)-1,2,3,6-tetrahydropyridine-1-carboxylate (4.76 g, 20 mmol) and tert-butyl N-(6-chloro-5-methoxypyridazin-3-yl)carbamate (4.00 g, 20 mmol) according to the procedure described for the synthesis of the intermediate 6-amino-4-methoxy-3',6'-dihydro-2'H-[3,4']bipyridiny1'-carboxylic acid tert-butyl ester.

Yield: 4.56 g (59%)

tert-Butyl 4-(6-{[(tert-butoxy)carbonyl]amino}-4-methoxypyridazin-3-yl)piperidine-1-carboxylate

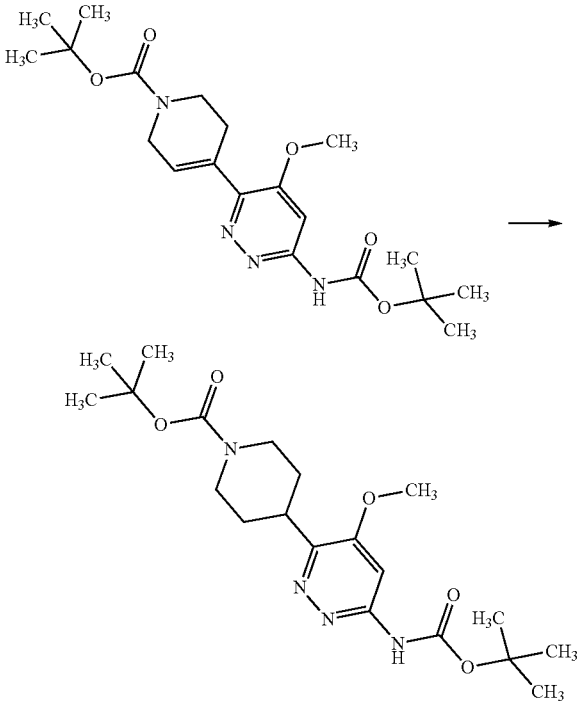

To tert-butyl 4-(6-{[(tert-butoxy)carbonyl]amino}-4-methoxypyridazin-3-yl)-1,2,3,6-tetrahydropyridine-1-carboxylate (1.50 g, 3.69 mmol) in MeOH (15 mL) is added Pd/C (1.18 g, 1.11 mmol) under a nitrogen atmosphere. The reaction mixture is degassed and subjected at 30° C. overnight to a balloon of H2, The mixture is treated with Pd/C (0.3 g) and stirred at 30° C. for 3 h. The reaction is filtered and concentrated under reduced pressure. Yield: 1.42 g (94%)

5-Methoxy-6-(piperidin-4-yl)pyridazin-3-amine dihydrochloride

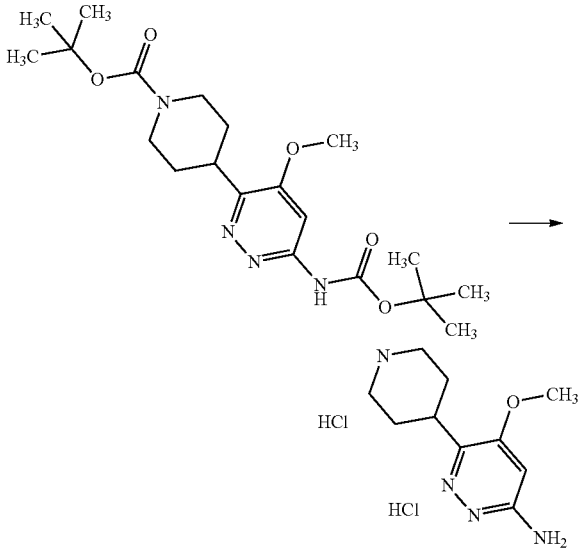

The title compound is synthesized from tert-butyl 4-(6{[(tert-butoxy)carbonyl]amino}-4-methoypyridazin-3yl) piperidine-1-carboxylate (1.42 g, 3.48 mmol) according to the procedure described for the synthesis of 4-methoxy-5-piperazin-1-yl-pyridin-2-ylamine dihydrochloride.

Yield: 0.99 g (quantitative)

4-(6-Nitro-pyridin-3-yl)-piperazine-1-carboxylic acid tert-butyl ester

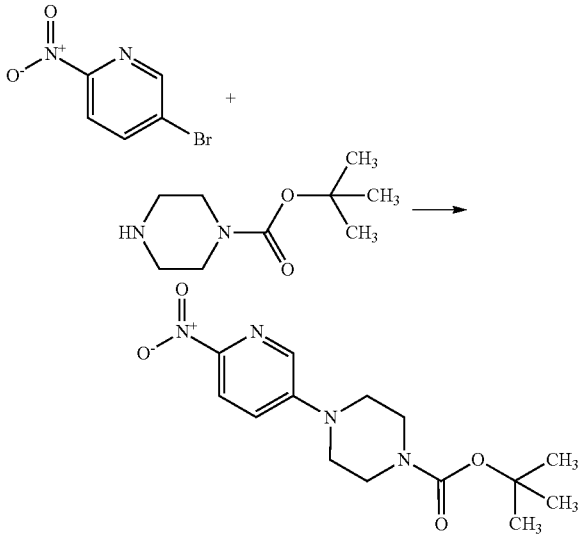

5-Bromo-2-nitro-pyridine (5.00 g, 24.63 mmol) and piperazine-1-carboxylic acid tert-butyl ester (13.7 g, 73.9 mmol) in NMP (50 mL) is stirred for 3 h at 120° C. The reaction mixture is poured into water. The precipitate is filtered, washed with water and dried to give the title compound.

Yield: 6.80 g (90%)

4-(6-Amino-pyridin-3-yl)-piperazine-1-carboxylic acid tert-butyl ester

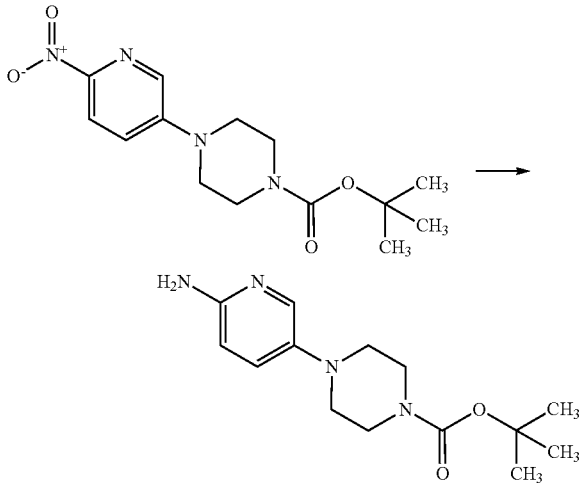

4-(6-Nitro-pyridin-3-yl)-piperazine-1-carboxylic acid tert-butyl ester (2.00 g, 65.9 mmol) and Pd/C (200 mg) in ethanol is stirred with an H2 balloon for 3 h. The reaction mixture is filtered and the filtrate is concentrated under reduced pressure.

Yield: 1.90 g (quantitative)

5-Piperazin-1-pyridin-2-ylamine dihydrochloride

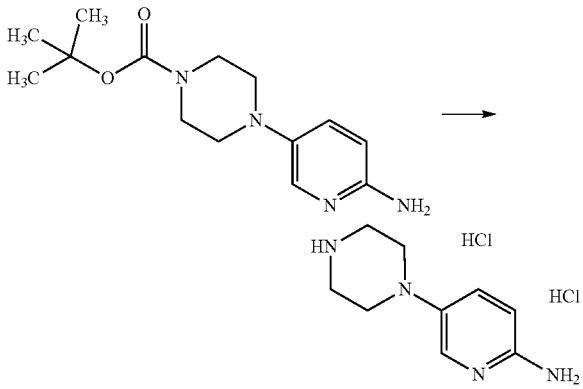

4-(6-Amino-pyridin-3-yl)-piperazine-1-carboxylic acid tert-butyl ester (2.50 g, 8.98 mmol) in DCM (30 mL) and 4M HCl in 1,4-dioxane (11.2 mL, 44.9 mmol) is stirred for 16 h at rt. The reaction mixture is filtered and washed with ether to give the title compound.

Yield: 2.23 g (99%)

(R)-2-(tert-Butyl-dimethyl-silanyloxymethyl)-4-(6-nitro-pyridin-3-yl)-piperazine-1-carboxylic acid tert-butyl ester

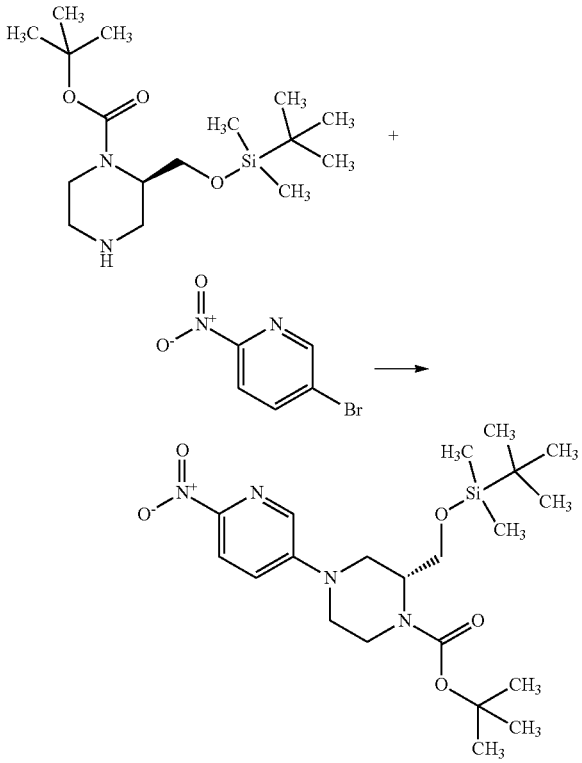

To (R)-2-(tert-butyl-dimethyl-silanyloxymethyl)-piperazine-1-carboxylic acid tert-butyl ester (1.50 g. 4.54 mmol) and 5-bromo-2-nitropyridine (1.00 g, 4.93 mmol) in 1,4-dioxane (12 mL) is added $Cs_2CO_3$ (4.44 g, 13.6 mmol), $Pd2(dba)_3$ (208 mg, 0.23 mmol) and Xantphos (263 mg, 0.45 mmol). The reaction mixture is stirred at 100° C. for 24 h, filtered through Celite®, and concentrated under reduced pressure. The residue is purified by silica gel column chromatography to afford the title compound.

Yield: 1.35 g (66%) ESI-MS: m/z=453 $(M+H)^+$ $R_t$(HPLC): 1.31 min (Method 1)

(R)-4-(6-Amino-pyrdin-3-yl)-2-(tert-butyl-dimethyl-silanyloxymethyl)-piperazine-1-carboxylic acid tert-butyl ester

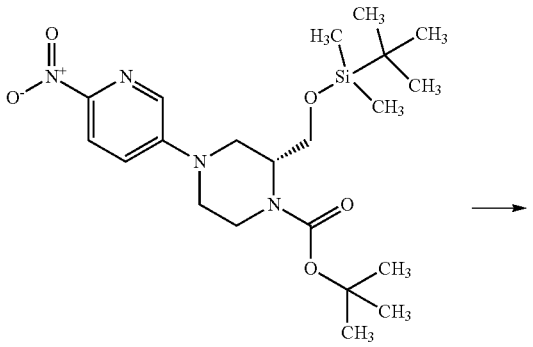

-continued

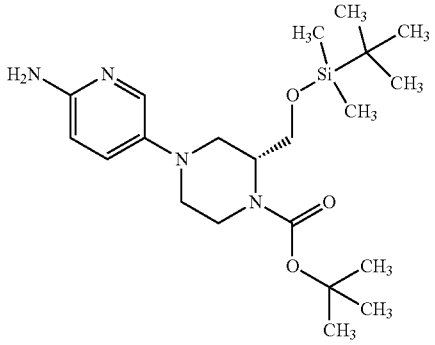

(R)-2-(tert-Butyl-dimethyl-silanyloxymethyl)-4-(6-nitro-pyridin-3-yl)-piperazine-1-carboxylic acid tert-butyl ester (1.35 g, 2.98 mmol) and Pd/C (317 mg, 0.15 mmol) in methanol (20 mL) is stirred with an H2 balloon for 24 h. The reaction mixture is filtered through Celite®, washed with methanol, and the filtrate is concentrated under reduced pressure.

Yield: 1.26 g (quantitative)

[(R)-4-(6-Amino-pyridin-3-yl)-piperazin-2-yl]-methanol dihydrochloride

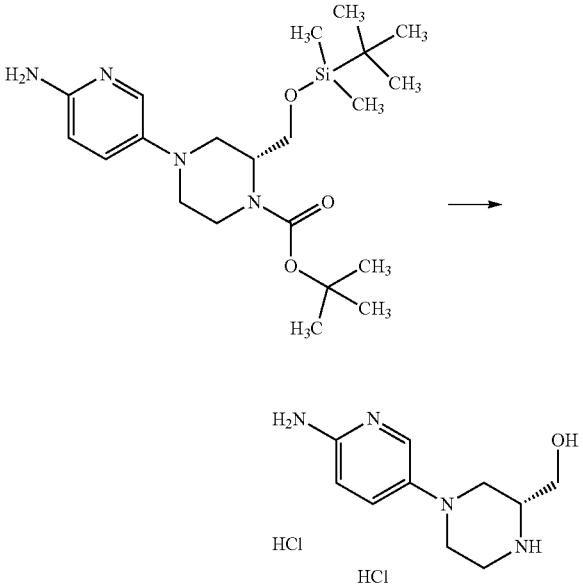

(R)-4-(6-Amino-pyridin-3-yl)-2-(tert-butyl-dimethyl-silanyloxymethyl)-piperazine-1- carboxylic acid tert-butyl ester (1.26 g, 2.98 mmol) in DCM (10 mL) and 4M HCl in 1,4-dioxane (7.5 mL, 30.0 mmol) is stirred for 1 h at rt. The reaction mixture is concentrated under reduced pressure, slurried in ether, filtered and washed with ether to give the title compound.

Yield: 838 mg (quantitative)

(R)-4-[6-(2,5-Dimethyl-pyrrol-1-yl)-4-methyl-pyridin-3-yl]-2-hydroxymethyl-piperazine-1-carboxylic acid tert-butyl ester

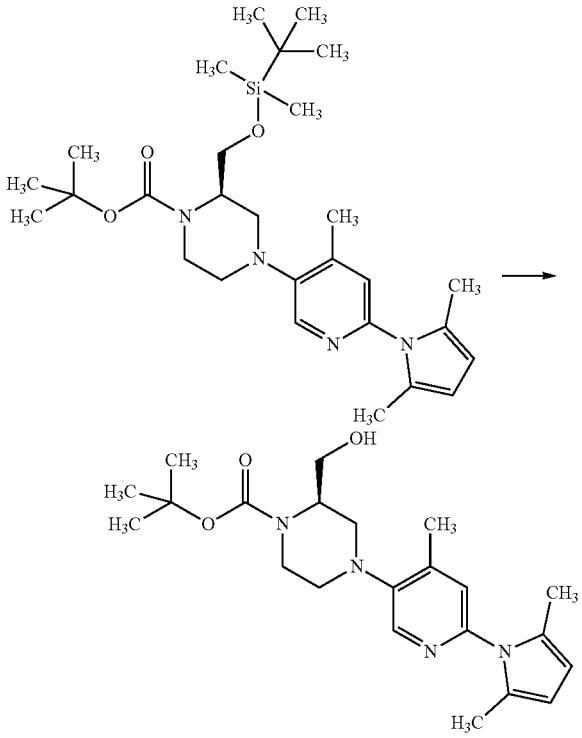

To (R)-2-(tert-Butyl-dimethyl-silanyloxymethyl)-4-[6-(2,5-dimethyl-pyrrol-1-yl)-4-methyl-pyridin-3-yl]-piperazine-1-carboxylic acid tert-butyl ester (8.56 g, 16.1 mmol) in THF (100 mL) is added tetrabutylammonium fluoride (16.1 mL, 16.1 mmol), and the reaction mixture is stirred at RT for 1.5 h. The reaction mixture is concentrated under reduced pressure and the residue is purified by silica gel column chromatography to afford the title compound.

Yield: 6.10 g (91%) ESI-MS: m/z=417 $(M+H)^+$ $R_t$(HPLC): 0.98 min (Method 1)

(R)-4-[6-(2,5-Dimethyl 4-pyrrol-1-yl)-4-methyl-pyridin-3-yl]-2-methoxymethyl-piperazine-1-carboxylic acid tert-butyl ester

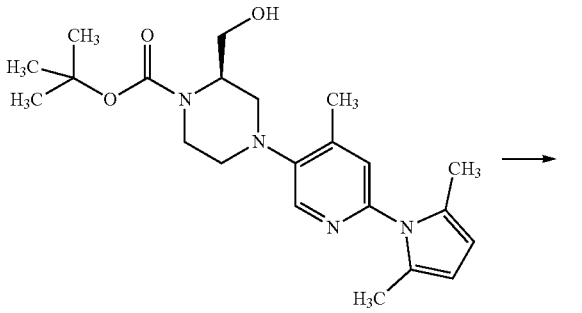

-continued

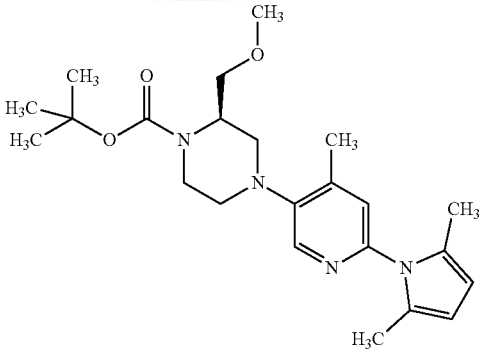

To (R)-4-[6-(2,5-dimethyl-pyrrol-1-yl)-4-methyl-pyridin-3-yl]-2-hydroxymethyl-piperazine-1-carboxylic acid tert-butyl ester (2.00 g, 4.80 mmol) and methyl iodide (915 mg, 7.20 mmol) in DMA (15 mL) is added 60% NaH (230 mg, 5.76 mmol). The reaction mixture is stirred for 2 h at RT and quenched with water. The mixture is extracted three times with EtOAc, the combined organic layers are washed with brine, dried over $MgSO_4$, filtered and concentrated under reduced pressure. The residue is purified by silica gel column chromatography to give the title compound.

Yield: 1.80 g (87%) ESI-MS: m/z=431 $(M+H)^+$ (HPLC): 1.12 min (Method 1)

(R)-4-(6-Amino-4-methyl-pyridin-3-yl)-2-methoxymethyl-piperazine-1-carboxylic acid tert-butyl ester

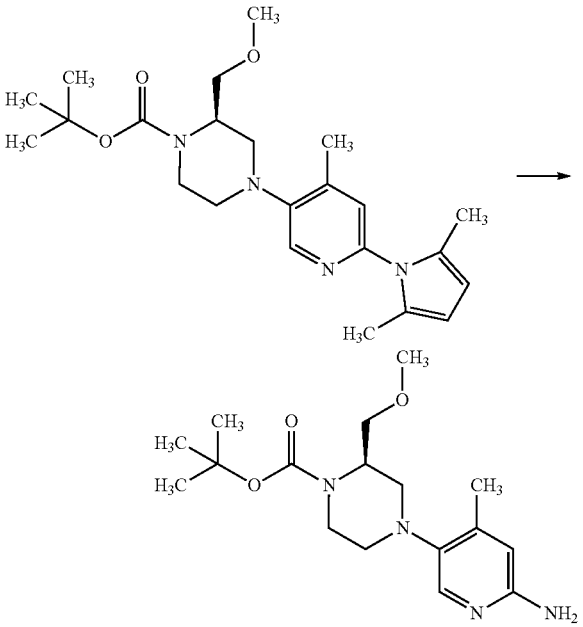

The title compound is synthesized from (R)-4-[6-(2,5-dimethyl-pyrrol-1-yl)-4-methylpyridin-3-yl]-2-methoxymethyl-piperazine-1-carboxylic acid tert-butyl ester (1.80 g, 4.18 mmol) according to the procedure described for the synthesis of the intermediate (R)-4-(6-amino-4-methyl-pyridin-3-yl)-2-hydroxymethyl-piperazine-1-carboxylic acid tert-butyl ester Yield: 1.07 g (87%) ESI-MS: m/z=353 $(M+H)^+$ $R_t$(HPLC): 0.44 mi (Method 1)

5-((R)-3-Methoxymethyl-piperazin-1-yl)-4-methyl-pyridin-2-ylamine dihydrochloride

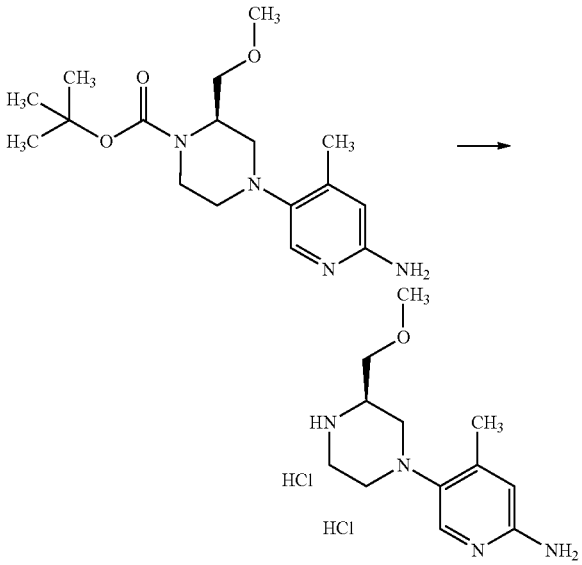

The title compound is synthesized from (R)-4-(6-amino-4-methyl-pyridin-3-yl)-2-methoxymethyl-piperazine-1-carboxylic acid test-butyl ester (440 mg, 1.25 mmol) according to the procedure described for the synthesis of the intermediate 4-methoxy-5-piperazin-1-yl-pyridin-2-ylamine dihydrochloride.

Yield: 406 mg (quantitative)

4-(6-Amino-4-methyl-pyridazin-3-yl)-3,6-dihydro-2H-pyridine-1-carboxylic acid tert-butyl ester

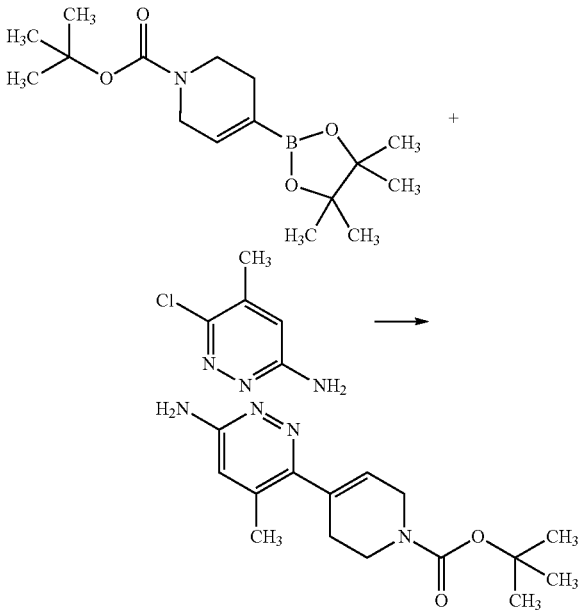

The title compound is synthesized from 4-(4,4,5,5-tetramethyl-[1,3,2]dioxaborolan-2-yl)-3,6-dihydro-2H-pyridine-1-carboxylic acid tert-butyl ester (538 mg, 1.74 mmol) and 6-chloro-5-methyl-pyridazin-3-ylamine (250 mg, 1.74 mmol) according to the procedure described for the synthesis of the intermediate 6-Amino-4-methyl-3',6'-dihydro-2'H-[3,4']bipyridinyl-1'-carboxylic acid tert-butyl ester.

Yield: 326 mg (65%) ESI-MS: m/z=292 $(M+H)^+$ $R_t$(HPLC): 0.51 min (Method 5)

4-(6-Amino-4-methyl-pyridazin-3-yl)-piperidine-1-carboxylic acid tert-butyl ester

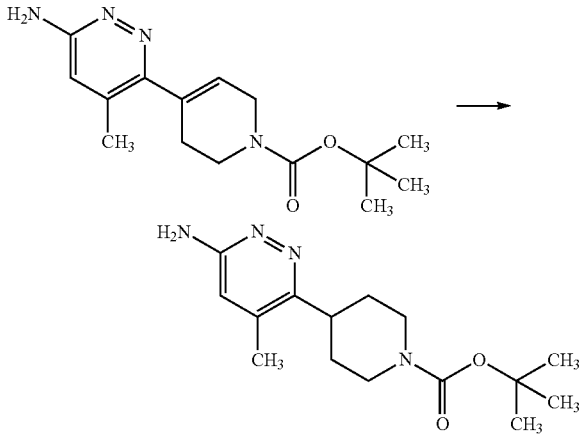

The title compound is synthesized from 4-(6-amino-4-methyl-pyridazin-3-yl)-3,6-dihydro-2H-pyridine-1-carboxylic acid tert-butyl ester (326 mg, 1.12 mmol) according to the procedure described for the synthesis of the intermediate 6-amino-4-methyl-3',4',5',6'-tetrahydro-2'H-[3,4']bipyridinyl-1'-carboxylic acid tert-butyl ester.

Yield: 289 mg (88%) EST-MS: m/z=293 $(M+H)^+$ $R_t$(HPLC): 0.60 min (Method 5)

5-Methyl-6-piperidn-4-yl-pyridazin-3-ylimine dihydrochloride

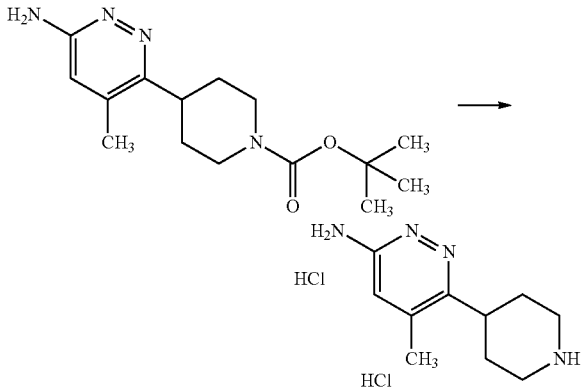

The title compound is synthesized from 4-(6-amino-4-methyl-pyridazin-3-yl)-piperidine-1-carboxylic acid tert-butyl ester (175 mg, 0.60 mmol) according to the procedure described for the synthesis of the intermediate 5-piperazin-1-yl-pyridin-2-ylainine dihydrochioride.

Yield: 154 mg (97%) ESI-MS: m/z=193 $(M+H)^+$ $R_t$(HPLC): 0.46 min (Method 2)

5-Bromo-2-(2,5-ditnethyl-pyrrol-1-yl)-4-methoxy-pyridine

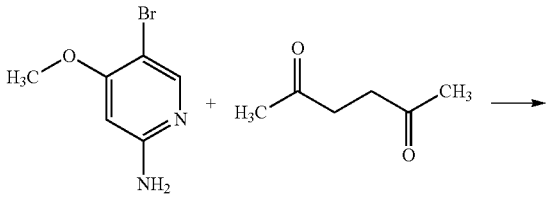

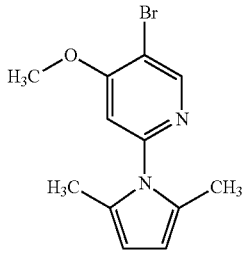

The title compound is synthesized from 5-bromo-4-methoxy-pyridin-2-ylamine (10.6 g, 52.1 mmol) according to the procedure described for the synthesis of the intermediate 5-bromo-2-(2,5-dimethyl-pyrrol-1-yl)-4-methyl-pyridine.

Yield: 14.0 g (96%) ESI-MS: m/z=283 $(M+H)^+$ $R_t$(HPLC): 0.93 min (Method 3)

(R)-2-(tert-Butyl-dimethyl-silanyloxymethyl)-4-[6-(2,5-dimethyl-pyrrol-1-yl)-4-methoxy-pyridin-3-yl]-piperazine-1-carboxylic acid tert-butyl ester

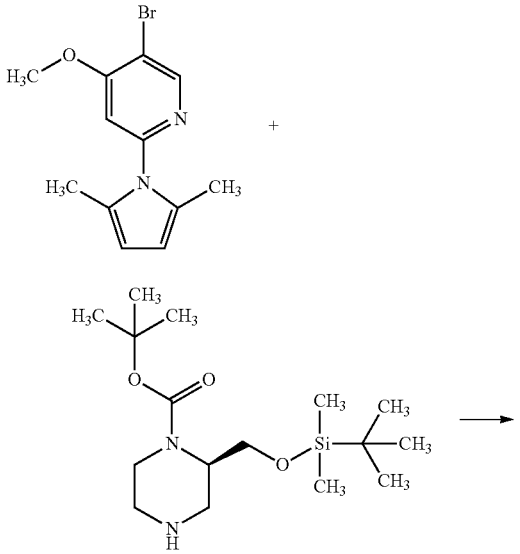

-continued

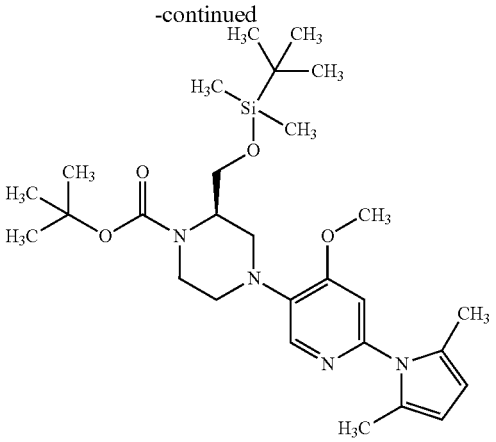

To 5-Bromo-2-(2,5-dimethyl-pyrrol-1-yl)-4-methoxy-pyridine (1.24 g, 4.41 mmol) and (R)-2-(tert-butyl-dimethyl-silanyloxymethyl)-piperazine-1-carboxylic acid tert-butyl ester (1.46 g, 4.41 mmol) in 1,4-dioxane (13 mL) is added sodium tert-butoxide (1.27 g, 13.2 mmol) and CPhos-G3-palladacycle methane sulfonate (178 mg, 0.22 mmol). The mixture is degassed with nitrogen for 5 min, and stirred for 4 h at 100' C. The reaction mixture is filtered through a pad of silica gel and eluted with EtOAc. The filtrate is concentrated under reduced pressure and the residue is purified by reverse phase column chromatography to give the title compound.

Yield: 1.68 g (72%) ESI-MS: m/z=531 $(M+H)^+$ $R_t$(HPLC): 1.43 min (R)-4-(6-Amino-4-methoxy-pyridin-3-yl)-2-hydroxymethyl-piperazine-1-carboxylic acid tert-butyl ester

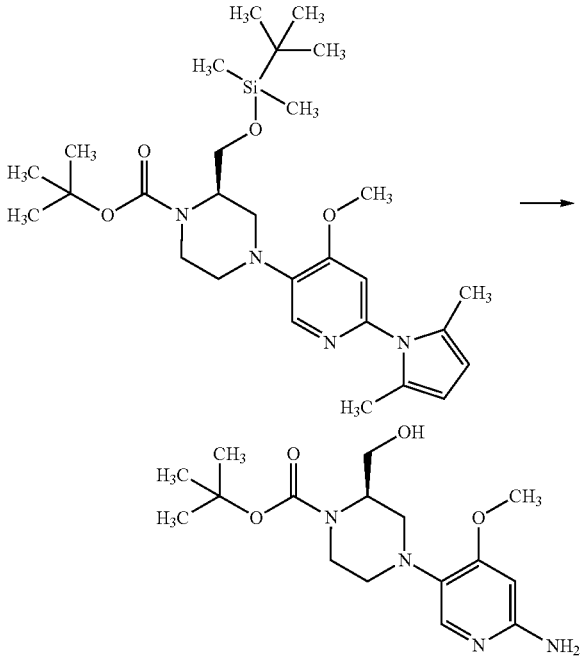

(R)-2-(tert-Butyl-dimethyl-silanyloxymethyl)-4-[6-(2,5-dimethyl-pyrrol-1-yl)-4-methoxy-pyridin-3-yl]-piperazine- 1-carboxylic acid tert-butyl ester (1.68 g, 3.17 mmol), hydroxylamine hydrochloride (1.10 g, 15.8 mmol) and trimethylamine (320 μl, 3.24 mmol) in ethanol (6 mL) and water (3 mL) is stirred for 18 h at 80° C. Hydroxylamine hydrochloride (440 mg, 6.33 mmol) is added again and stirred at 80° C. The reaction mixture is concentrated under reduced pressure and the residue is purified by reverse phase column chromatography (to afford the title compound.

Yield: 620 mg (58%)

[(R)-4-(6-Amino-4-methoxy-pyridin-3-yl)-piperazin-2-yl]-methanol hydrochloride

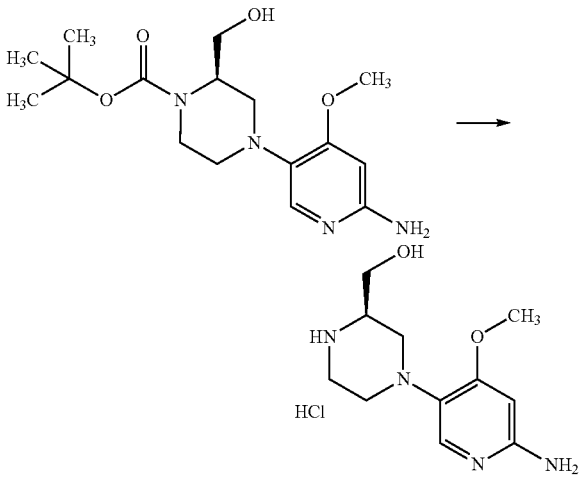

The title compound is synthesized from (R)-4-(6-amino-4-methoxy-pyridin-3-yl)-2-hydroxymethyl-piperazine-1-carboxylic acid tert-butyl ester (620 mg, 1.83 mmol) according to the procedure described for the synthesis of the intermediate 4-methoxy-5-piperazin-1-yl-pyridin-2-ylamine dihydrochloride.

Yield: 503 mg (quantitative)

3-[6-2,5-Dimethyl-pyrrol-1-yl)-4-methoxy-pyridin-3-yl]-3,8-diaza-bicyclo[3.2.1]octane-8-carboxylic acid tert-butyl ester

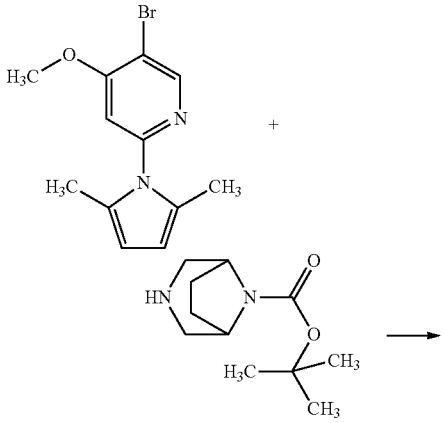

-continued

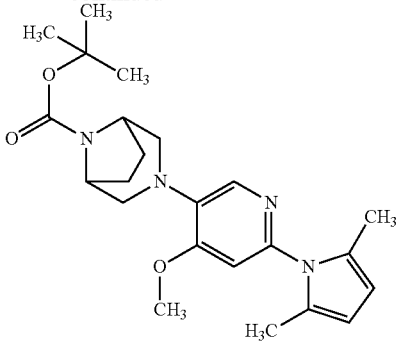

To 5-bromo-2-(2,5-dimethyl-pyrrol-1-yl)-4-methoxypyridine (1.00 g, 3.56 mmol) and 3,8-diaza-bicyclo[3.2.1]octane-8-carboxylic acid tert-butyl ester (830 mg, 3.91 mmol) in 1,4-dioxane (13 mL) is added sodium tert-butoxyide (3.48 g, 10.7 mmol) and CPhos-C3-palladacycle methane sulfonate (287 mg, 0.36 mmol). The mixture is degassed with nitrogen for 5 min, and stirred for 18 h at 80° C. The reaction mixture is extracted with EtOAc, washed with brine, dried over $MgSO_4$, filtered and concentrated u nder reduced pressure. The residue is purified by silica gel column chromatography to give the title compound.

Yield: 760 mg (52%) ESI-MS: m/z=4:12 $(M+H)^+$ $R_t$(HPLC): 1.23 min (Method 1)

3-(6-Amino-4-methoxy-pyridin-3-yl)-3,8-diaza-bicyclo[3.2.1]octane-8-carboxylic acid tert-butyl ester

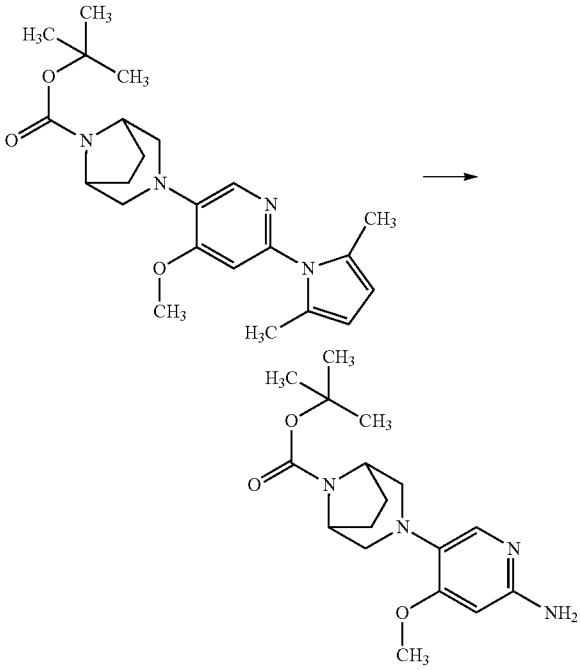

The tide compound is synthesized from 3-[6-(2,5-dimethyl-pyrrol-1- yl)-4-methoxy-pyridin-3-yl]-3,8-diaza-bicyclo[3.2.1]octane-8-carboxylic acid tert-butyl ester (760 mg, 1.84 mmol) according to the procedure described for the synthesis of the intermediate 4-(6-amino-4-methoxy-pyridin-3-yl)-piperazine-1-carboxylic acid tert-butyl ester.

Yield: 330 mg (54%) EST-MS: m/z=335 $(M+H)^+$
$R_t$(HPLC): 1.75 min (Method 6)

5-(3,8-Diaza-bicyclo[3.2.1]oct-3-yl)-4-methoxypyridin-2-ylamine dihydrochloride

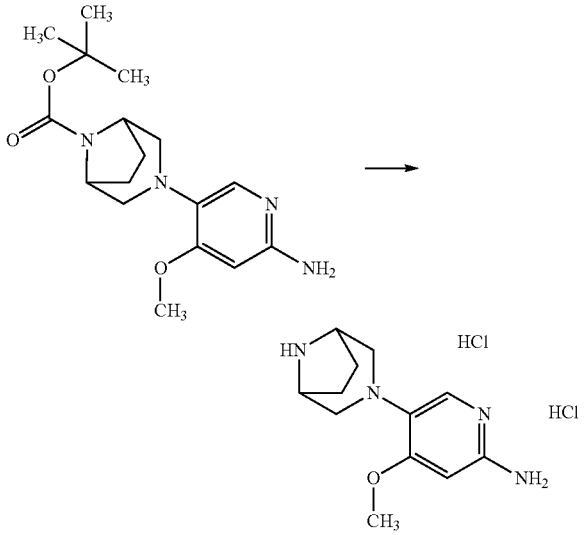

The title compound is synthesized from 3-(6-amino-4-methoxy-pyridin-3-yl)-3,8-diaza-bicyclo[3.2.1]octane-8-carboxylic acid tert-butyl ester (330 mg, 0.99 mmol) according to the procedure described for the synthesis of the intermediate 4-methoxy-5-piperazin-1-yl-pyridin-2-ylamine dihydrochloride.

Yield: 330 mg (quantitative) ESI-MS: m/z=235 $(M+H)^+$
$R_t$(HPLC): 0.15 min (Method 5)

4-Benzyl 1-tert-butyl (2R)-2-[methoxy(methyl)carbamoyl]piperazine-1,4-dicarboxylate

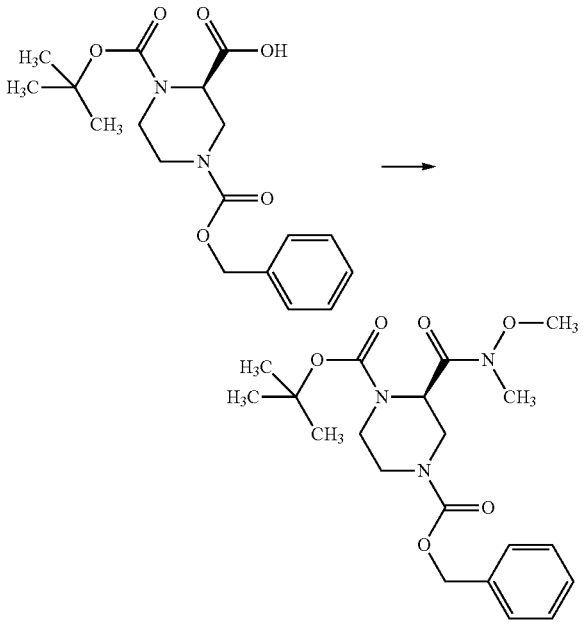

(2R)-4-[(benzyloxy)carbonyl]-1-[(cert-butoxy)carbonyl] piperazine-2-carboxylic, acid (4.00 g, 11.0 mmol), DIPEA (5.1 mL, 27.4 mmol), HATU (5.01 g, 13.2 mmol) and N,O-dimethylhydroxylamine hydrochloride (1.29 g, 13.2 mmol) in DMA (40 mL) are stirred at RT for 3 days. The reaction mixture is diluted with EtOAc, washed with water and brine. The organic layer is dried over $MgSO_4$, filtered and concentrated under reduced pressure. The residue is purified by silica gel column chromatography to give the title compound.

Yield: 4.44 g (99%) ESI-MS m/z=408 $(M+H)^+$

4-Benzyl 1-tert-butyl (2R)-2-acetylpiperazine-1,4-dicarboxylate

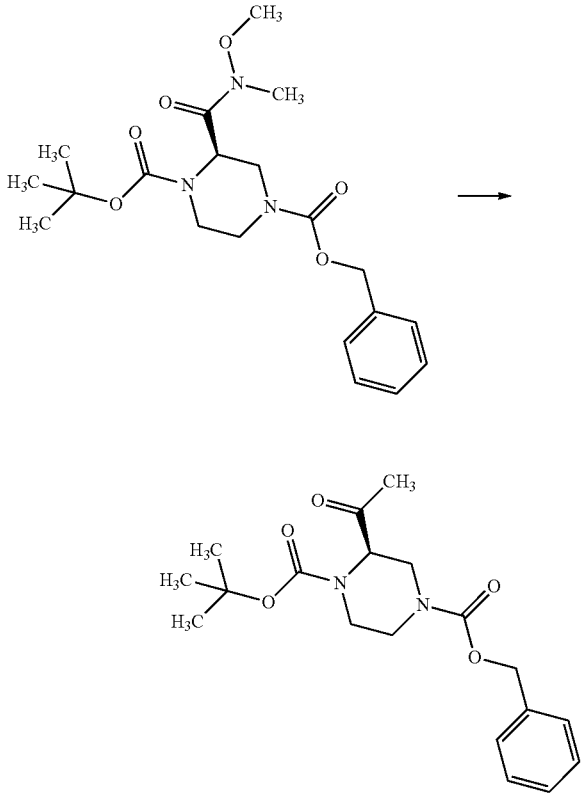

To a −20° C. cooled mixture of 4-benzyl 1-tert-butyl (2R)-2-[methoxy(methyl)carbamoyl]-piperazine-1,4-dicarboxylate (4.40 g, 10.80 mmol) in THF (25 mL) is added dropwise methyl magnesium bromide (5.40 mL. 16.20 mmol) and stirred at −20° C. for 30 min. The reaction mixture is quenched with saturated, aqueous $NH_4Cl$ solution, diluted with EtOAc, and washed with water+1N HCl and brine. The organic layer is dried over $MgSO_4$, filtered and concentrated under reduced pressure. The residue is purified by chromatography to give the desired product. Further purification is done by chiral chromatography separation to give the pure R enantiomer.

Yield: 2.38 g (61%)

85

4-Benzyl 1-tert-butyl (2R)-2-(1-hydroxyethyl)Piperazine-1,4-dicarboxylate

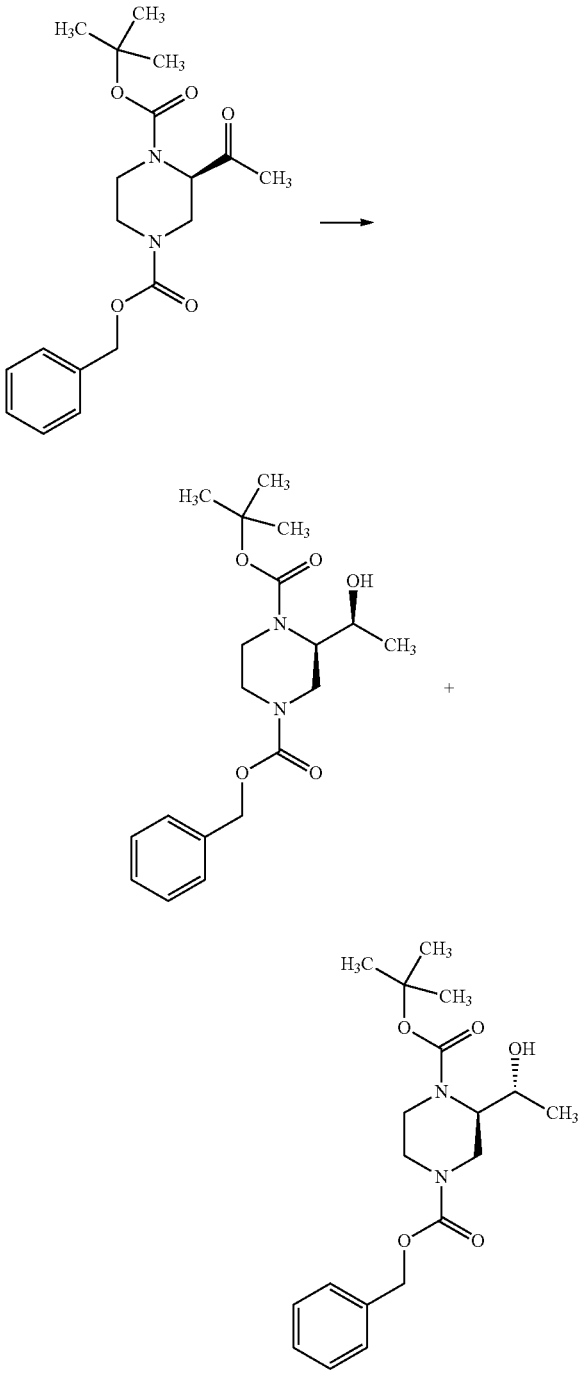

Sodium borohydride (0.36 g, 9.52 mmol) is added to (4-benzyl 1-tert-butyl (2R)-2-acetylpiperazine-1,4-dicarboxylate (2.30 g, 6.35 mmol) in methanol (100 mL). After stirring the reaction mixture for 30 min, the solvent is removed under reduced pressure. The residue is purified by silica chromatography.

Yield: 2.10 g (91%)

86

4-Benzyl 1-tert-butyl (2R)-2-{[(tert-butyldimethylsilyl)oxy]ethyl}piperazine-1,4-dicarboxylate

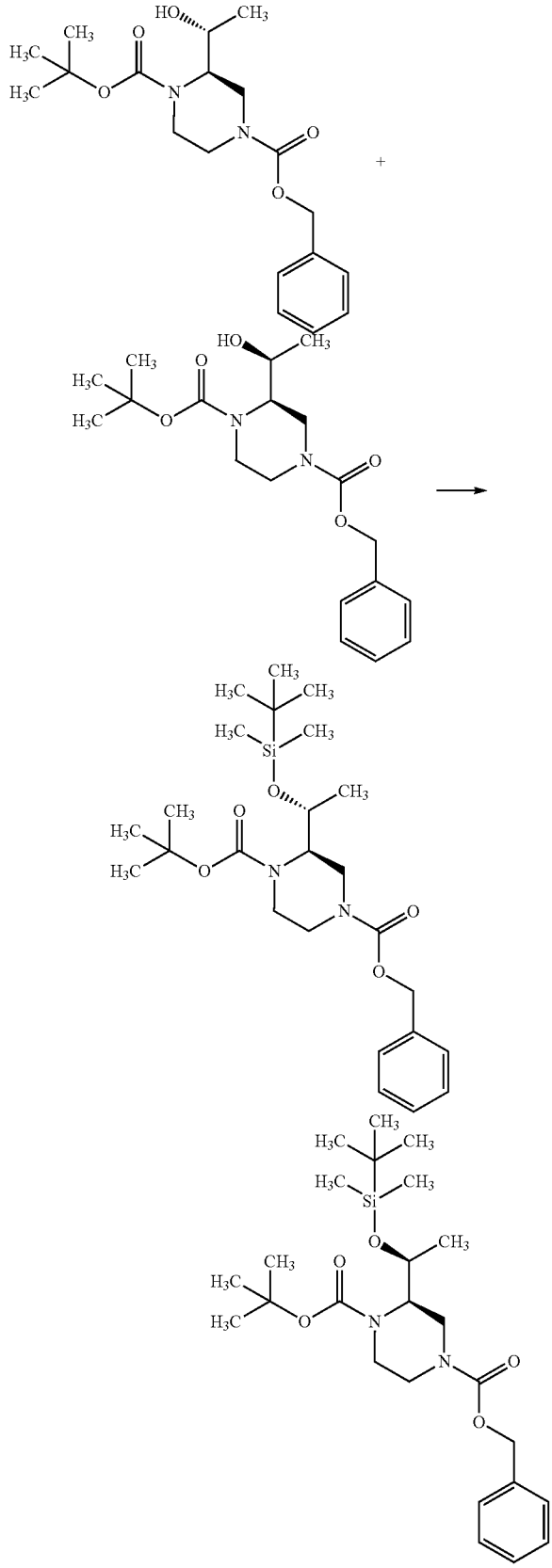

tert-Butyl(chloro)dimethylsilane (1.30 g, 8.64 mmol) is added to 4-benzyl 1-tert-butyl (2R)-2-(1-hydroxyethy)piperazine-1,4-dicarboxylate (2.10 g, 5.76 mmol) and imidazole (1.18 g, 17.29 mmol) it dichloromethane (15 mL). The reaction mixture is stirred overnight. After adding water (10 mL), the aqueous layer is extracted with dichloromethane (2×25 mL). The combined organic layers are washed with brine. The organic layer is dried, filtered and concentrated under reduced pressure. The residue is purified by silica chromatography.

Yield: 2.75 g (99.7%)

tert-Butyl (2R)-2-{1[(tert-butyldimethylsilyl)oxy]ethyl}piperazine-1-carboxylate

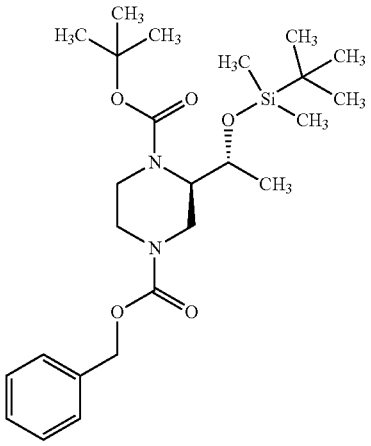

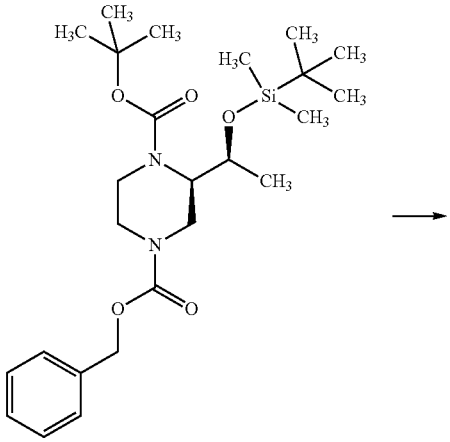

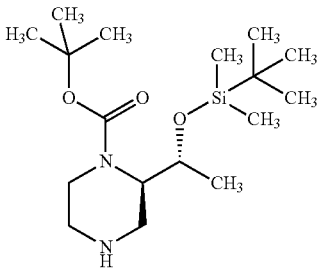

-continued

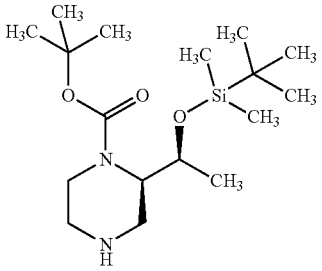

Under an hydrogen atmosphere (balloon) 4-benzyl 1-tert-butyl (2R)-2-{1-[(tert-butyldimethylsilyl)-oxy]ethyl}piperazine-1,4-dicarboxylate (2.75 g, 5.75 mmol) and Pd/C (0.20 g) is stirred at room temperature in ethanol (50 mL) for 2 h. After removal of the catalyst by filtering through Celite®, the solvent is removed under reduced pressure. The residue is filtered through silica eluting with 10% MeOH/dichlormethane.

Yield: 1.89 g (96%)

(tert-Butyl(2R)-2-{1-[(tert-butyldimethylsilyi)oxy]ethyl}-4-[6-(2,5-dimethyl-1H-pyrrol-1-yl)-4methoxypyridin-3-yl]piperazine-1-carboxylate

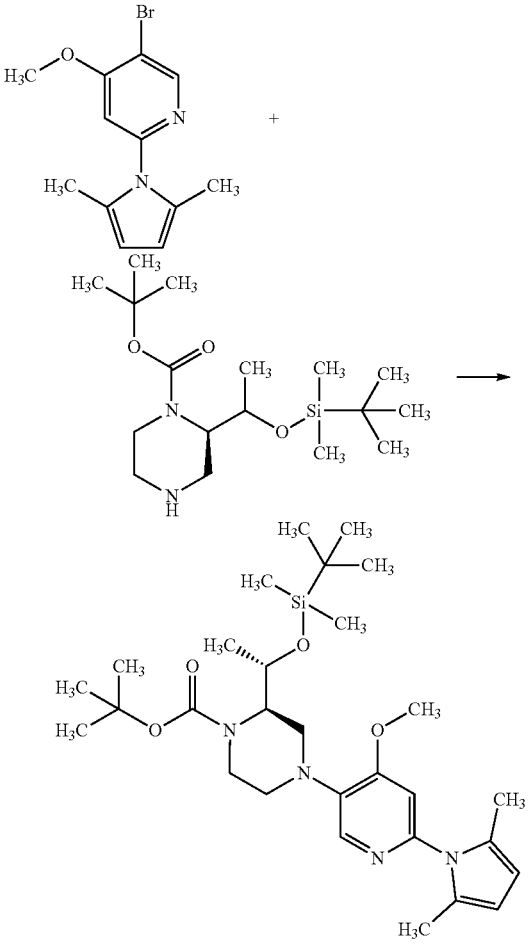

-continued

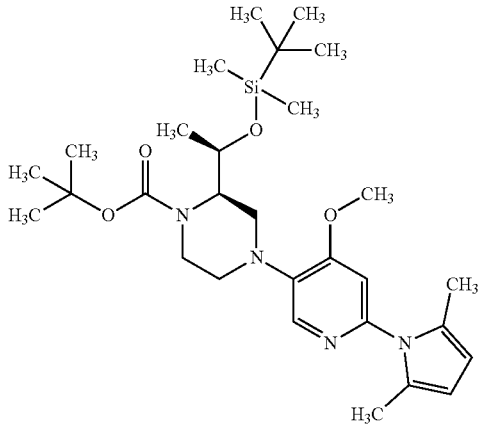

To tert-Butyl (2R)-2-{1-[(tert-butyldimethylsilyl)oxy]ethyl}piperazine-1-carboxylate (1.89 g, 5.49 mmol) and 5-bromo-2-(2,5-dimethyl-pyrrol-1-yl)-4-methoxy-pyridine (1.54 g. 5.49 mmol) in 1,4-dioxane (20 mL) is added CPhos-G3-palladacycle methane sulfonate (0.22 g) and sodium tert-butoxide (1.58 g, 16.5 mmol), and the reaction mixture is sparged with nitrogen. The reaction mixture is stirred at 100° C. for 10 h. The reaction mixture is filtered through a pad of silica eluting with EtOAc and concentrated. The residue is purified twice by silica chromatography to afford the title compounds, Yield:

tert-butyl (2R)-2-[(1S)-1-[(tert-butyldimethylsilyl)oxy]ethy]-4-[6-(2,5-dimethyl-1H-pyrrol-1 -yl)-4-methoxypyridin-3-yl]piperazine-1-carboxylate: 0.57 g (19%) and tert-butyl (2R)-2-[(1R)-1-[(tert-butyldimethylsilyl)oxy]ethyl]-4-[6-(2,5-dimethyl-1H-pyrrol-1-yl)-4-methoxypyridin-3-yl]piperazine-1-carboxylate: 0.78 g (26%)

tert-Butyl (2R)-4-(6-amino-4-methoxypyridin-3-yl)-2-[(1R)-1-hydroxyethyl]piperazine-1-carboxylate

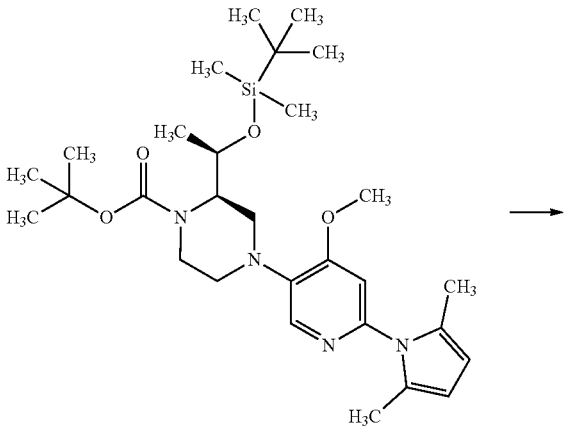

-continued

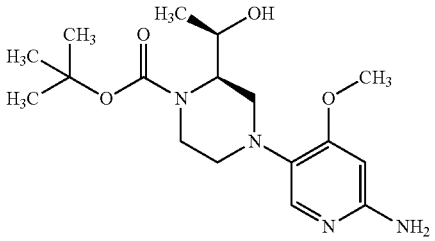

tert-Butyl (2R)-2-[(1R)-1-[(tert-butyldimethylsilyl)oxy]ethyl]-4-[6-(2,5-dimethyl-1H-pyrrol-1-yl)-4-methoxypyridin-3-yl]piperazine-1-carboxylate (0.87 g, 1.60 mmol), hydroxylamine hydrochloride (0.56 g, 7.99 mmol) and trimethylamine (0.22 mL, 1.60 mmol) in 8 mL ethanol and 4 mL water is heated at 80° C. for 42 h. An additional amount of hydroxylamine hydrochloride (0.22 g, 3.19 mmol) is added and the reaction mixture is stirred at 80° C. overnight. The reaction mixture is concentrated under reduced pressure, taken up in dichloromethane and filtered. The desired compound is purified by silica chromatography Yield: 0.20 g (36%), (1R)-1-[(2R)-4-(6-Amino-4-methoxypyridin-3-yl)piperazin-2-yl]ethan-1-ol-dihydrochloride

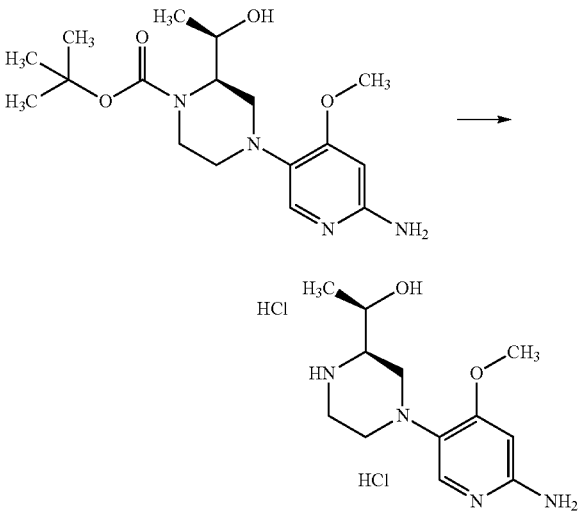

4N HCl in dioxane (0.71 mL, 2.84 mmol) is added to tert-butyl (2R)-4-(6-amino-4-methoxypyridin-3-yl)-2-[(1R)-1-hydroxyethyl]piperazine-1-carboxylate (0.20 g, 0.57 mmol) in 5 mL dichloromethane and stirred at RT for 2 h. Additional 1 ml of 4N HCl in dioxane is added and stirred 1 h at RT. The reaction mixture is concentrated under reduced pressure. The residue is used without further purification.

Yield: 0.18 g (quantitative)

tert-Butyl (2R)-4-(6-amino-4-methoxypyridin-3-yl)-2[(1S)-1-hydroxyethyl]piperazine-1-carboxylate

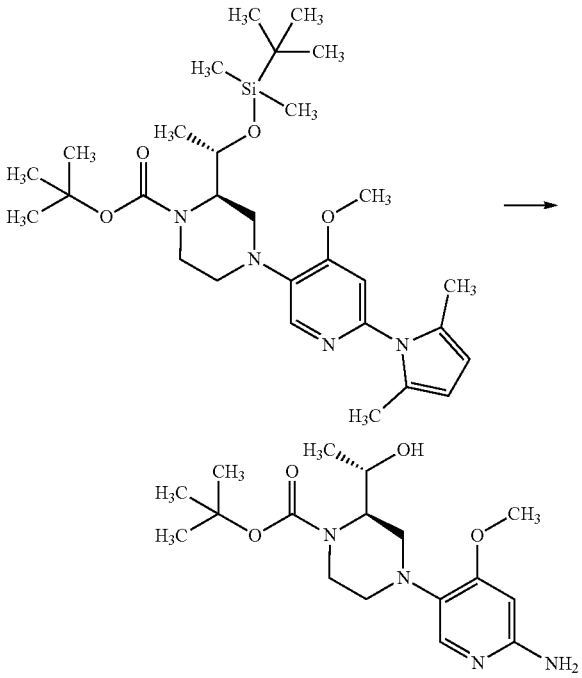

tert-Butyl (2R)-2-R[(1S)-1-[(tert-butyldimethylsilyi)oxy]ethyl]-4-[6-(2,5-dimethyl-1H-pyrrol-1 -yl)-4-methoxypyridin-3-yl]piperazine-1-carboxylate (0.57 g, 1.04 mmol), hydroxylamine hydrochloride (0.36 g, 5.21 mmol) and trimethylamine (0.15 mL, 1.04 mmol) in 4 mL ethanol and 2 mL water is heated at 80° C. for 42 h. Additional amount of hydroxylamine hydrochloride (0.15 g, 2.09 mmol) is added and the reaction mixture is stirred at 80° C. overnight. The reaction mixture is concentrated under reduced pressure, taken up in dichloromethane and filtered. The desired compound is purified by silica chromatography and repurified by HPLC Yield: 0.12 g (33%), (1S)-1-[(2R)-4-(6-Amino-4-methoxypyridin-3yl) piperazin-2-yl]ethan-1-ol dihydrocloloride

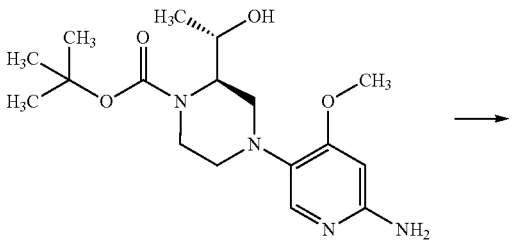

-continued

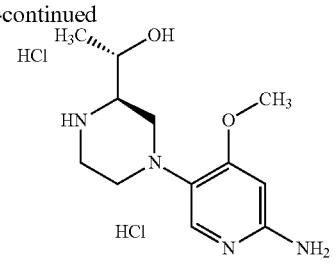

4N HCl in dioxane (0.50 mL, 2.00 mmol) is added to tert-butyl (2R)-4-(6-amino-4-methoxymidin-3-yl)-2-[(1S)-1-hydroxyethyl]piperazine-1-carboxylate (0.12 g, 0.34 mmol) in 1 mL dichloromethane and stirred at RT for 1 h. The reaction mixture is concentrated under reduced pressure. The residue is used without further purification.

Yield: quantitative.

7-(6-Amino-4-methoxy-pyridin-3-yl)-3-oxa-9-aza-bicyclo[3.3.1]non-6-ene-9-carboxylic acid tert-butyl ester

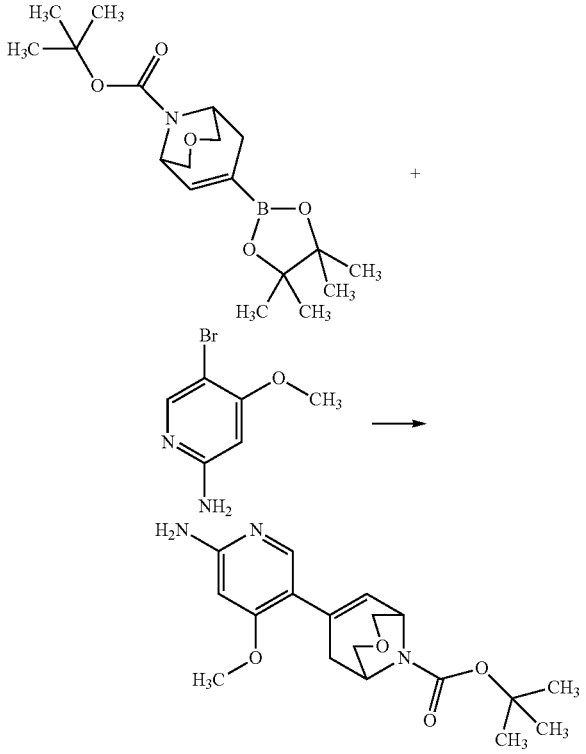

The title compound is synthesized from 5-bromo-4-methoxy-pyridin-2-ylamine (202 mg, 1.00 mmol) and 7-(4,4,5,5-tetramethyl-[1,3,2]dioxaborolan-2-yl)-3-oxa-9-aza-bicyclo[3.3.1]non-6-ene-9-carboxylic acid tert-butyl ester (350 mg, 1.00 mmol) according to the procedure described for the synthesis of the intermediate 6-amino-4-methyl-3', 6'-dihydro-2'H-[3,4]bipyridinyl-1'-carboxylic acid tert-butyl ester.

Yield: 220 mg (64%) ESI-MS: m/z=348 $(M+H)^+$ $R_t$(HPLC): 1.52 min (Method 2)

7 -(6-Amino-4-methoxy-pyridin-3-yl)-3-oxa-9-aza-bicyclo[3.3.1]nonane-9-carboxylic acid tert-butyl ester

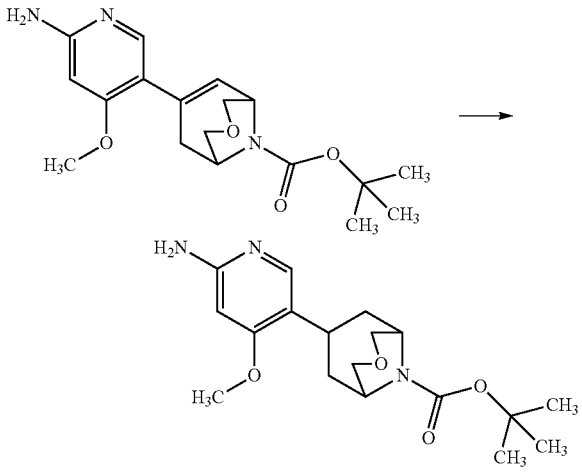

To 7-(6-amino-4-methoxy-pyridin-3-yl)-3-oxa-9-aza-bicyclo[3.3.1]non-6-ene-9-carboxylic acid tert-butyl ester (220 mg, 0.63 mmol) in EtOAc (10 mL) is added Pd/C (67.0 mg, 0.06 mmol) under nitrogen. The reaction mixture is degassed, placed under a balloon of $H_2$ and stirred for 18 h at 50° C. The reaction is filtered through Celite®, concentrated under reduced pressure and purified by silica gel column chromatography to give the title compound.

Yield: 145 mg (66%) ESI-MS: m/z=350 $(M+H)^+$ $R_t$(HPLC): 1.60 min (Method 2)

4-Methoxy-5-(3-oxa-9-aza-bicyclo[3.3.1]non-7-yl) dihydrochloride

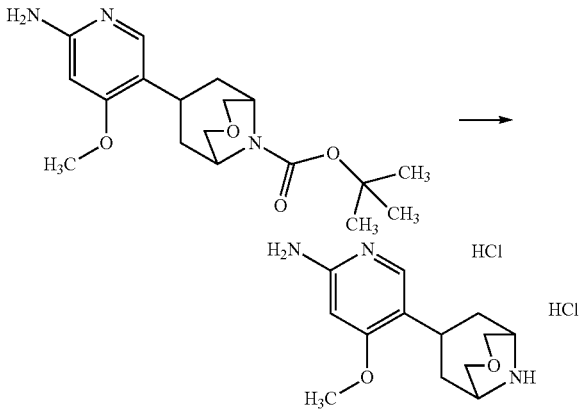

The title compound is synthesized from 7-(6-amino-4-methoxy-pyridin-3-yl)-3-oxa-9-aza-bicyclo[3.3.1]nonane-9-carboxylic acid tert-butyl ester (145 mg, 0.41 mmol) according to the procedure described 16r the synthesis of the intermediate 4 -methoxy-5-piperazin-1-yl-pyridin-2-ylamine dihydrochloride.

Yield: 133 mg (quantitative) ESI-MS: m/z=250 $(M+H)^+$ $R_t$(HPLC): 0.15 min (Method 5)

(S)-2-(tert-Butyl-dimethyl-silanyloxymethyl)-piperazine-1-carboxylic acid tert-butyl ester

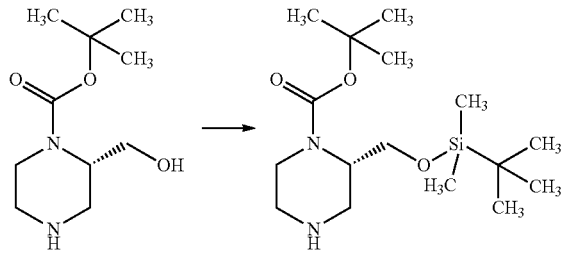

To (S)-2-hydroxymethyl-piperazine-1-carboxylic acid tert-butyl ester (2.00 g, 9.25 mmol) in DMA (10 mL) is added tert-butyl-chloro-dimethyl-silane (2.09 g, 13.9 mmol) and imidazole (1.89 g, 27.7 mmol), and the reaction mixture is stirred for 24 h at rt. The reaction mixture is diluted with $NH_4Cl$-solution and extracted with EtOAc. The organic layer is washed with water and brine, dried over $Na_2SO_4$, filtered and concentrated under reduced pressure. The residue is purified by silica gel column chromatography to give the title compound.

Yield: 2.80 g (92%)

(S)-2-(tert-Butyl-dimethyl-silanyloxymethyl)-4-[6-(2,5-dimethyl-pyrrol-1-yl)-4-methoxy-pyridin-3-yl]-piperazine-1-carboxylic acid tert-butylester

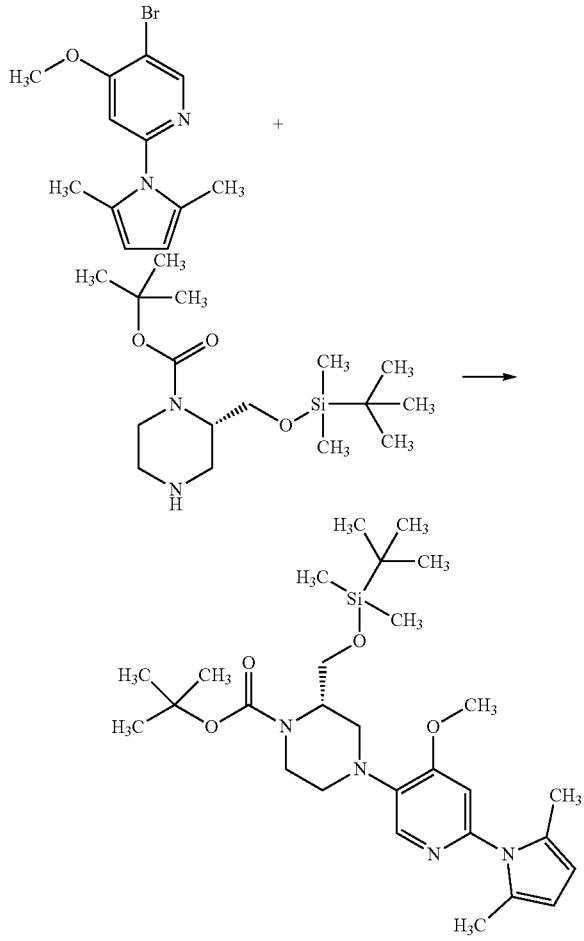

The title compound is synthesized from 5-bromo-2-(2,5-dimethyl-pyrrol-1-yl)-4-methoxy-pyridine (3.25 g, 11.6 mmol) and (S)-2-(tert-butyl-dimethyl-silanyloxymethyl)-piperazine-1-carboxylic acid tert-butyl (3.82 g, 11.6 mmol) ester according to the procedure described for the synthesis of the intermediate 3-[6-(2,5-dimethyl-pyrrol-1-yl)-4-methoxy-pyridin-3-yl]-3,8-diaza-bicyclo[3.2.1]octane-8-carboxylic acid tert-butyl ester.

Yield: 4.94 g (73%) ESI-MS: m/z=531 $(M+H)^+$ $R_t$(HPLC): 1.49 min (Method 3)

(S)-4-(6-Amino-4-methoxy-pyridin-3-yl)-2-hydroxymethyl-piperazine-1-carboxylic acid tert-butyl ester

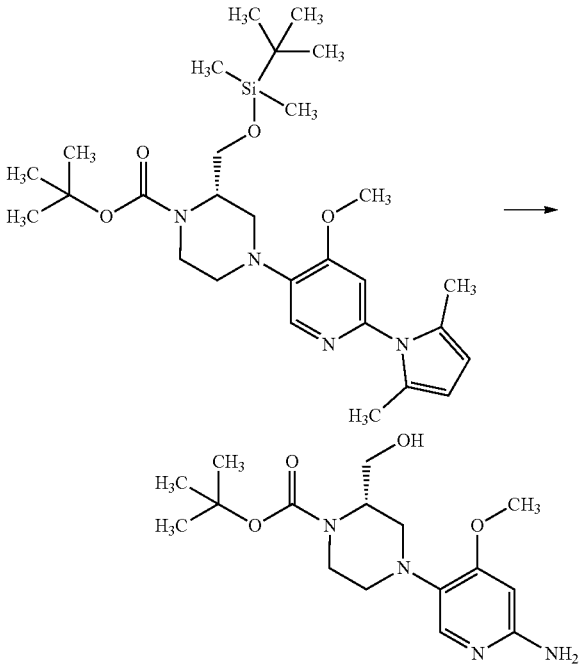

(S)-2-(tert-Butyl-dimethyl-silanyloxymethyl)-4-[6-(2,5-dimethyl-pyrrol-1-yl)-4-methoxypyridin-3-yl]-piperazine-1-carboxylic acid tert-butyl ester (11.9 g, 22.4 mmol), hydroxylamine hydrochloride (3.89 g, 56.0 mmol) and trimethylamine (7.8 mL, 56.0 mmol) in ethanol (30 mL) and water (15 mL) are stirred for 18 h at 80° C. The reaction mixture is concentrated under reduced pressure and the residue is purified by silica gel chromatography to give the title compound.

Yield: 2.57 g (68%)

(S)-4-(6-Amino-4-methoxy-pyridin-3-yl)-piperazin-2-yl1-methanol hydrochloride

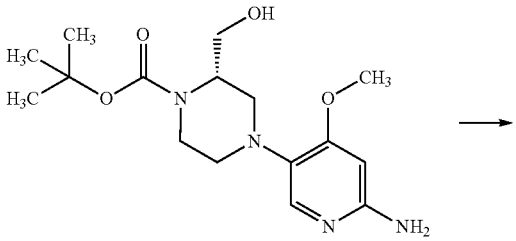

-continued

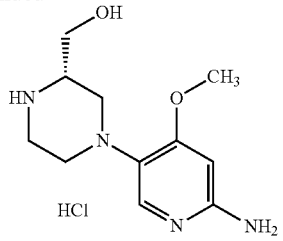

The title compound is synthesized from (S)-4-(6-amino-4-methoxy-pyridin-3-yl)-2-hydroxymethyl-piperazine-1-carboxylic acid tert-butyl ester (264 mg, 0.58 mmol) according to the procedure described for the synthesis of the intermediate 4-methoxy-5-piperazin-1-yl-pyridin-2-ylamine dihydrochloride.

Yield: 160 mg (quantitave)

(R)-4-[6-(2,5-Dimethyl-pyrrol-1-yl)-4-methoxy-pridin-3-yl]-2-hydroxymethyl-piperazine-1-carboxylic acid tert-butyl ester

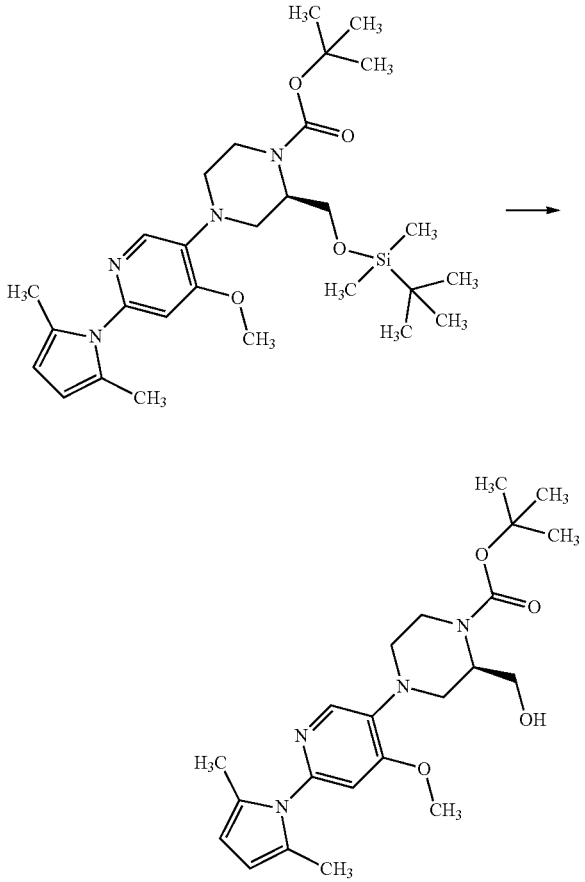

To (R)-2-(tert-butyl-dimethyl-silanyloxymethyl)-4-[6-(2,5-dimethyl-pyrrol-1-yl)-4-methoxy-pyridin-3-yl]-piperazine-1-carboxylic acid tert-butyl ester (8.56 g, 16.1 mmol) in THF (100 mL) is added TBAF (1M in THF, 16.1 mL, 16.1 mmol). The reaction mixture is stirred for 2.5 h at rt. The reaction mixture is concentrated under reduced pressure and the residue is purified by chromatography to get the title product.

Yield: 180 mg (87%)

(R)-4-[6-(2,5-Dimethyl-pyrrol-1-yl)-4-methoxy-pyridin-3-yl]-2-methoxymethyl-piperazine-1-carboxylic acid tert-butyl ester

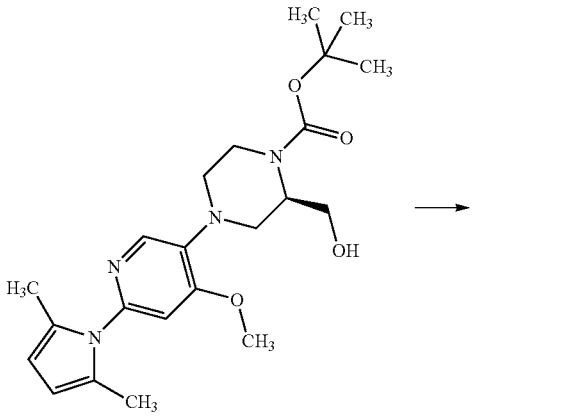

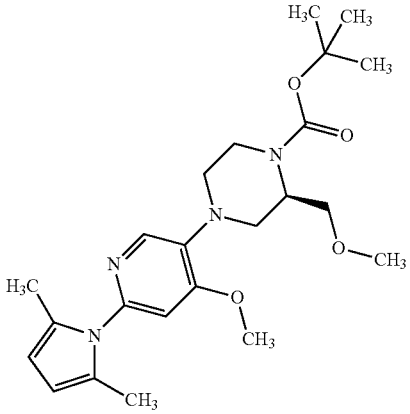

NaH (60%, 230 mg, 9.58 mmol) is added to (R)-4-[6-(2,5-dimethyl-pyrrol-1-yl)-4-methoxy-pyridin-3-yl]-2-hydroxymethyl-piperazine-1 -carboxylic acid tert-butyl ester (2.0 g, 4.80 mmol) and MeI (401 μL, 7.20 mmol) in DMA (20 mL). The reaction mixture is stirred for 2 h at rt. Water is added and the reaction mixture is extracted with EtOAc (3 times). The combined organic layers are washed with brine, dried over $MgSO_4$, filtered and concentrated under reduced pressure. The residue is purified by normal phase chromatography.

Yield: 1.8 g (87%) ESI-MS: m/z=431 $(M+H)^+$ $R_t$(HPLC): 1.11 min (Method 1)

(R)-4-(6-Amino-4-methoxy-pyridin-3-yl)-2-methoxymethyl-piperazine-1-carboxylic acid tert-butyl ester

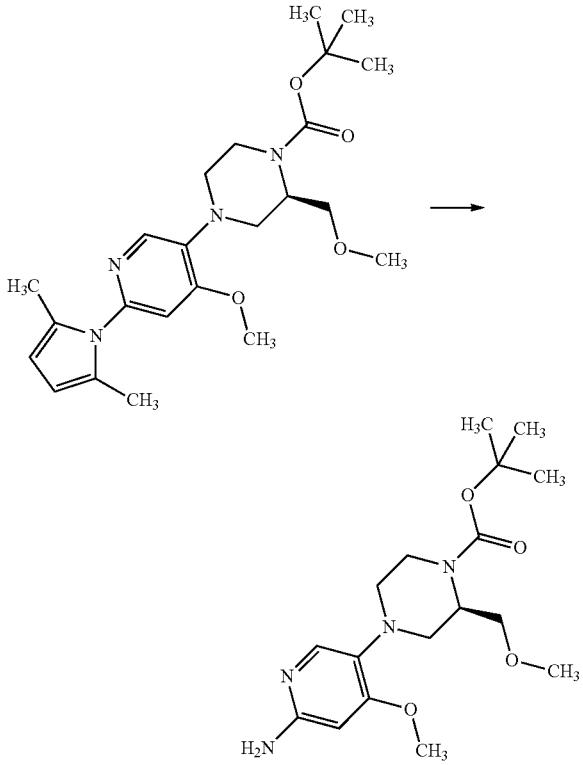

(R)-4-[(6-(2,5-Dimethyl-pyrrol-1-yl)-4-methoxy-pyridin-3-yl]-2-methoxymethyl-piperazine-1-carboxylic acid tert-butyl ester (1.8 g, 4.18 mmol)hydroxylamine hydrochloride (1.45 g, 20.9 mmol) and trimethylamine (0.58 mL, 4.18 mmol) in ethanol (10 mL) and water (5 mL) are stirred at 80° C. for 78 h. The reaction mixture is concentrated under reduced pressure, slurried in DCM, filtered to remove salts and concentrated again under reduced pressure. The residue is purified by normal phase column chromatography to give the title product.

Yield: 440 mg (30%) ESI-MS: m/z=353 $(M+H)^+$ $R_t$(HPLC): 0.44 min (Method 1)

4-Methoxy-5-((R)-3-methoxymethyl-piperazin-1-yl-pyridin-2-ylamine dihydrochloride

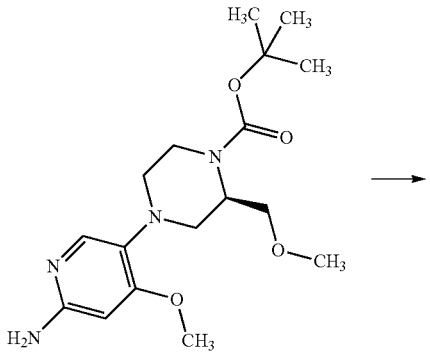

-continued

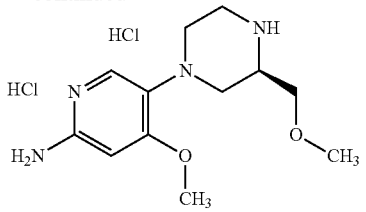

The title compound is synthesized from (R)-4-(6-amino-4-methoxy-pyridin-3-yl)-2-methoxymethyl-piperazine-1-carboxylic acid tert-butyl ester (440 mg, 1.25 mmol) according to the procedure described for the synthesis of the intermediate [(R)-4-(6-amino-4-methoxy-pyridin-3-yl)-piperazin-2-yl]-methanol hydrochloride.

Yield: 406 mg (quantitative)

5-Fluoro-4-methoxy-pyridine-2-carbonitrile

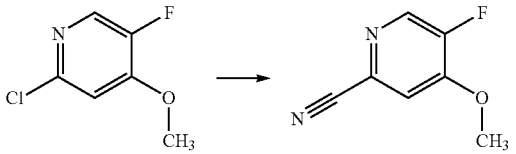

2-Chloro-5-fluoro-4-methoxy-pyridine (1.00 g, 6.19 mmol) is taken in a sealed tube. Zinc cyanide (799 mg, 6.81 mmol) and zinc (40.5 mg, 0.31 mmol) are added and purged with argon. Then PdCl2(dppf)$CH_2Cl_2$ (253 mg, 0.62 mmol) and NMP are added and the mixture is heated for 45 min. at 150° C. in the microwave. Water and EtOAc are added to the reaction mixture and filtered through Celite®. The organic layer is washed with sodium bicarbonate solution, water, brine and dried over $MgSO_4$, filtered and concentrated under reduced pressure. The residue is purified by silica gel column chromatography to afford the title compound.

Yield: 689 mg (73%) ESI-MS: m/z=153 $(M+H)^+$ $R_t$(HPLC): 0.61 min (Method 1)

5-(4-Fluoro-phenoxy)-4-methoxy-pyridine-2-carbonitrile

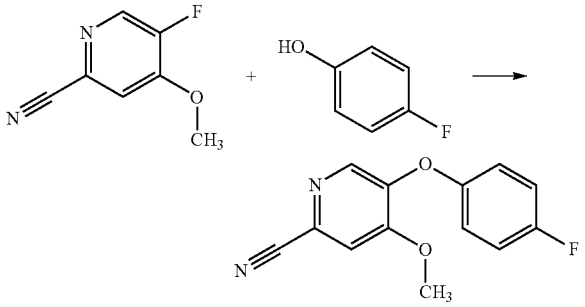

5-Fluoro-4-methoxy-pyridine-2-carbonitrile (6.00 g, 39.4 mmol), 4-fluorophenol (5.31 g, 47.3 mmol) and $K_2CO_3$ (12.0 g, 86.8 mmol) in NMP (12 mL) are heated at 100° C. for 3 h in a sealed tube. The reaction mixture is diluted with water and extracted with EtOAc. The organic layer is washed with brine and dried over $MgSO_4$, filtered and concentrated under reduced pressure. The residue is triturated by ether and heptane to give the title compound.

Yield: 8.99 g (93%) ESI-MS: m/z=245 $(M+H)^+$ $R_t$(HPLC): 0.91 min (Method 1)

5-(4-Fluoro-phenoxy)-4-methoxy-pyridine-2-carboxylic acid

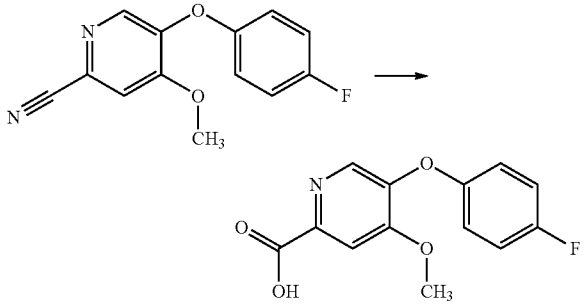

5-(4-Fluoro-phenoxy)-4-methoxy-pyridine-2-carbonittile (8.50 g. 34.8 mmol) in aqueous 2N NaOH solution (90 mL) is stirred at 100° C. for 6 h. The reaction mixture is cooled to RT and the pH of the solution is adjusted to pH 4.5 with 4 N HCl. The precipitate is collected and dried in a drying oven to give the title compound.

Yield: 8.80 g (96%) ESI-MS: m/z=264 $(M+H)^+$ $R_t$(HPLC): 1.58 min (Method 4)

4-Methoxy-5-phenoxy-pyridine-2-carbonitrile

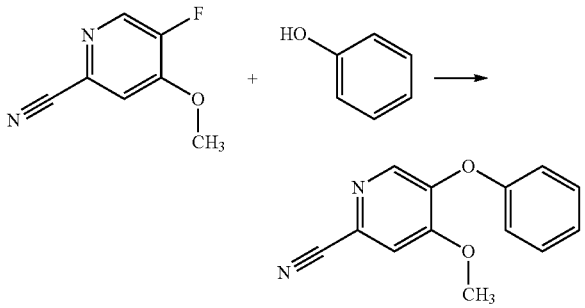

5-Fluoro-4-methoxy-pyridine-2-carbonitrile (8.00 g, 52.6 mmol), phenol (5.94 g, 63.1 mmol) and $K_2CO_3$ (16.0 g, 115 mmol) inn NMP (3 mL) are heated at 10° C. for 3 h in a sealed tube. The reaction mixture is diluted with water and extracted with EtOAc. The organic layer is washed with brine and dried over $MgSO_4$, filtered and concentrated under reduced pressure. The residue is purified by silica gel chromatography to give the title compound.

Yield: 11.5 g (93%) ESI-MS: m/z=227 $(M+H)^+$ $R_t$(HPLC): 0.92 mm (Method 1)

4-Methoxy-5-phenoxy-pyridine-2-carboxylic acid

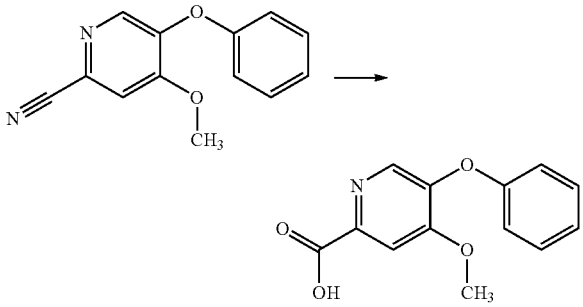

The title compound is synthesized from 4-methoxy-5-phenoxy-pyridine-2-carbonitrile (11.5 g, 50.8 mmol) according to the procedure described for the synthesis of th intermediate 5-(4-fluoro-phenoxy)-4-methoxy-pyridine-2-carboxylic acid.

Yield: 9.57 g (77%) EST-MS: m/z=246 $(M+H)^+$ $R_t$(HPLC): 2,64 min (Method 4)

5-(4-Isopropoxy-phenox)-4-methoxy-pyridine-2-carbonitrile

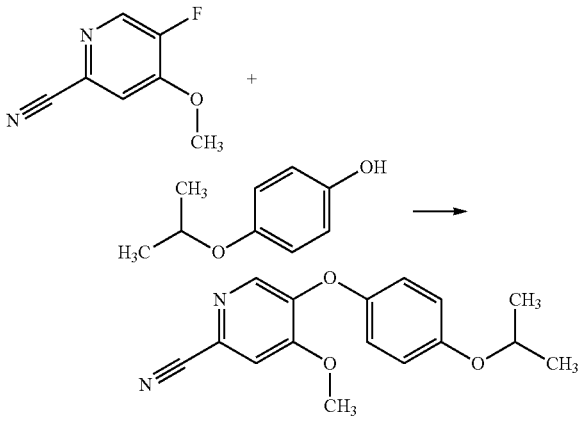

The title compound is synthesized from 5-fluoro-4-methoxy-pyridine-2-carbonitrile (500 mg, 3.29 mmol) and 4-isopropoxy-phenol (600 mg, 3.94 mmol) according to the procedure described for the synthesis of the intermediate 4-methoxy-5-phenoxy-pyridine-2-carbonitrile.

Yield: 850 mg (91%) ESI-MS: m/z=285 $(M+H)^+$ $R_t$(HPLC): 1.02 min (Method 1)

5-(4-Isopropoxy-phenoxy)-4-methoxy-pyridine-2-carboxylic acid

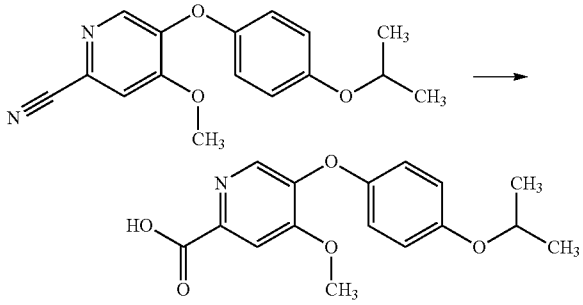

The title compound is synthesized from 5-(4-isopropoxy-phenoxy)-4-methoxy-pyridine-2-carbonitrile (200 mg, 0.70 mmol) according to the procedure described for the synthesis of the intermediate 5-(4-fluoro-phenoxy)-4-methoxy-pyridine-2-carboxylic acid.

Yield: 190 mg (77%) $R_t$(HPLC): 0.73 min (Method 1)

4-Methoxy-5-(4-methoxy-phenoxy)-pyridine-2-carbonitrile

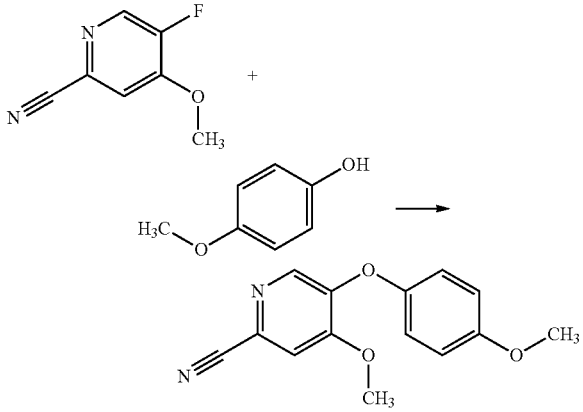

The title compound is synthesized from 5-fluoro-4-methoxy-pyridine-2-carbonitrile (500 mg, 3.29 mmol) and 4-methoxyphenol (490 mg, 3.94 mmol) according to the procedure described for the synthesis of the intermediate 4-methoxy-5-phenoxy-pyridine-2-carbonitrile.

Yield: 740 mg (88%)

4-Methoxy-5-(4-methoxy-phenoxy)-pyridine-2-carboxylic acid

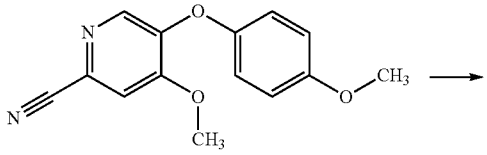

-continued

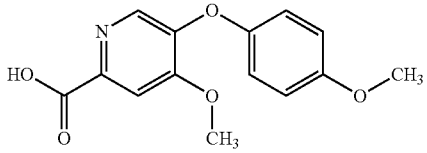

The title compound is synthesized from 4-methoxy-5-(4-methoxy-phenoxy)-pyridine-2-carbonitrile (740 mg, 2.89 mmol) according to the procedure described for the synthesis of the intermediate 5-(4-fluoro-phenoxy)-4-methoxy-pyridine-2-carboxylic acid.

Yield: 610 mg (77%)

4-Methoxy-5-(4-trifluoromethyl-phenoxy)-pyridine-2-carbonitrile

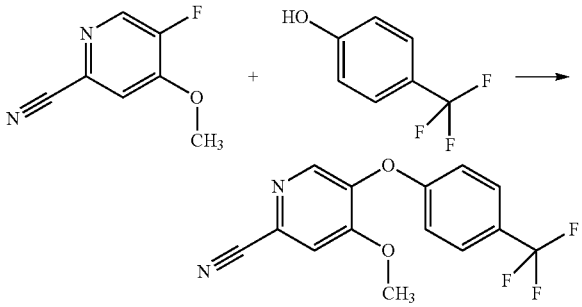

The title compound is synthesized from 5-fluoro-4-methoxy-pyridine-2-carbonitrile (500 mg, 3.29 mmol) and 4-trilfuoromethyl-phenol (639 mg, 3.94 mmol) according to the procedure described for the synthesis of the intermediate 4-methoxy-5-phenoxy-pyridine-2-carbonitrile.

Yield: 320 mg (33%) ESI-MS: m/z=294 $(M+H)^+$ $R_t$(HPLC): 1.06 min (Method 1)

4-Methoxy-5-(4-trfluoromethyl-phenoxy)-pyridine-2-carboxylic acid

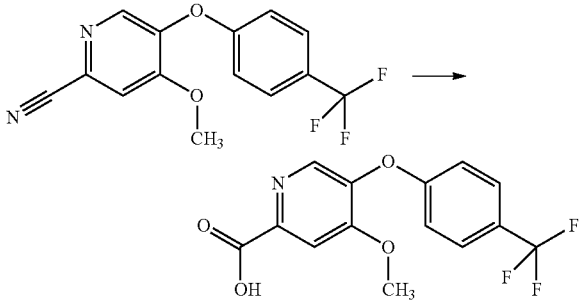

The title compound is synthesized from 4-methoxy-5-(4-trifluoromethyl-phenoxy)-pyridine-2-carbonitrile (151 mg, 0.51 mmol) according to the procedure described for the synthesis of the intermediate 5-(4-fluoro-phenoxy)-4-methoxy-pyridine-2-carboxylic acid.

Yield: 150 mg (93%)

5-(4-Chloro-phenoxy)-4-methoxy-pyridine-2-carbonitrile

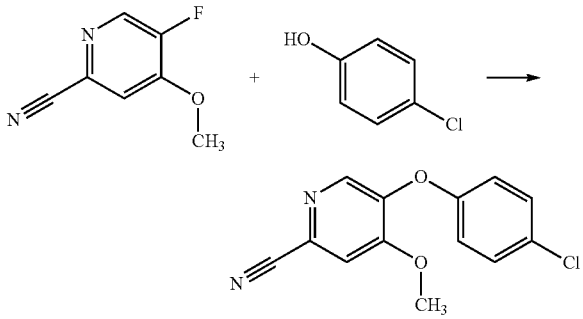

The title compound is synthesized from 5-fluoro-4-methoxy-pyridine-2-carbonitrile (500 mg, 3.29 mmol) and 4-chlorophenol (507 mg, 3.94 mmol) according to the procedure described for the synthesis of the intermediate 4-methoxy-5-phenoxy-pyridine-2-carbonitrile.

Yield: 695 mg (81%)

5-(4-Chloro-phenoxy)-4-methoxy-pyridine-2-carboxylic acid

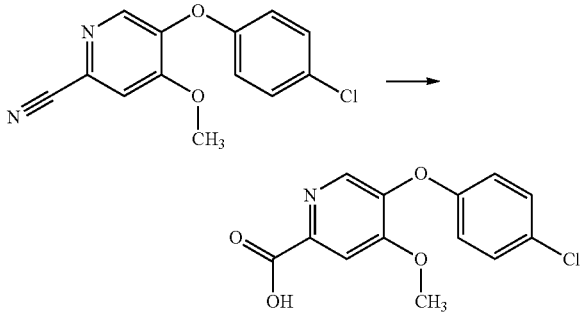

The title compound is synthesized from 5-(4-chloro-phenoxy)-4-methoxy-pyridine-2-carbonitrile (645 mg, 2.47 mmol) according to the procedure described the synthesis of the intermediate 5-(4-fluoro-phenoxy)-4-methoxy-pyridine-2-carboxylic acid.

Yield: 622 mg (90%) ESI-MS: m/z=280 (M+H)+

5-(4-Difluoromethoxy-phenoxy)-4-methoxy-pyridine-2-carbonitrile

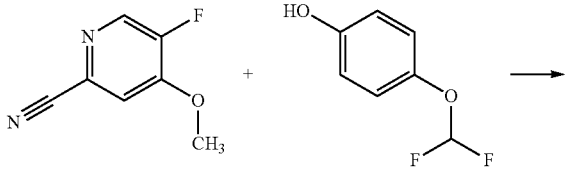

-continued

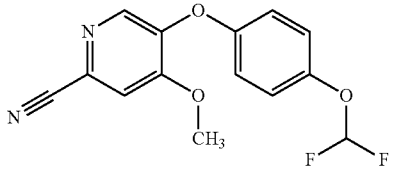

The title compound is synthesized from 5-fluoro-4-methoxy-pyridine-2-carbonitrile (75.0 mg, 0.49 mmol) and 4-difluoromethoxy-phenol (101 mg, 0.63 mmol) according to the procedure described for the synthesis of the intermediate 4-methoxy-5-phenoxy-pyridine-2-carbonitrile.

Yield: 98.0 mg (68%) $R_t$(HPLC): 0.93 min (Method 1)

5-(4-Difluoromethoxy-phenoxy)-4-methoxy-pyridine-2-carboxylic acid

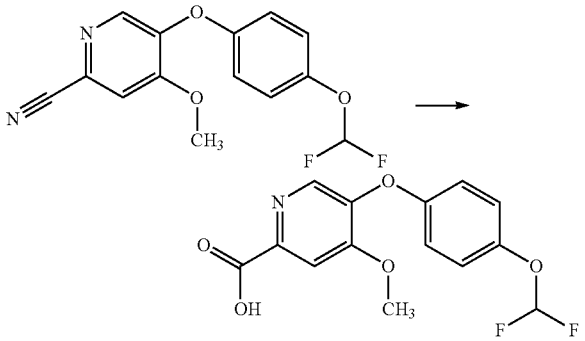

The title compound is synthesized from 5-(4-difluoromethoxy-phenoxy)-4-methoxy-pyridine-2-carbonitrile (98.0 mg, 0.34 mmol) according to the procedure described for the synthesis of the intermediate 5-(4-fluoro-phenoxy)-4-methoxy-pyridine-2-carboxylic acid.

Yield: 94.0 mg (90%) $R_t$(HPLC): 0.60 min (Method 1)

4-Cyclopropoxy-phenol

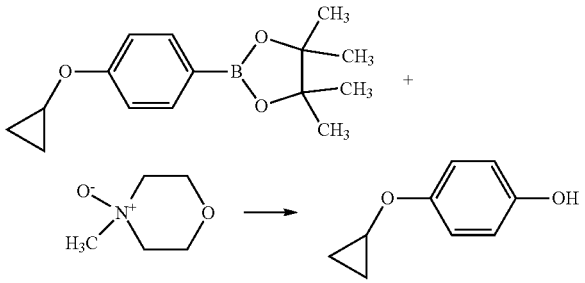

2-(4-Cyclopropoxy-phenyl)-4,4,5,5-tetramethyl-[1,3,2] dioxaborolane 800 mg, 3.08 mmol) and 4-methyl-morpholine 4-oxide (1.03 g, 8.83 mmol) in THF (100 mL) are stirred at 75° C. for 1.5 h and then for 18 h at rt. The reaction mixture is concentrated under vacuum and the residue is purified by silica gel chromatography to afford the title compound.

Yield: 389 mg (84%)

5-(4-Cyclopropoxy-phenoxy)-4-methoxy-pyridine-2-carbonitrile

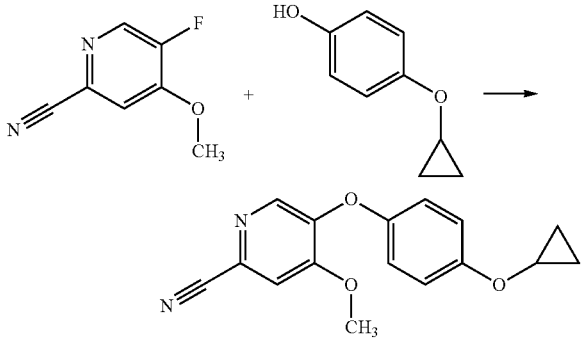

The title compound is synthesized from 5-fluoro-4-methoxy-pyridine-2-carbonitrile (350 mg, 2.30 mmol) and 4-cyclopropoxy-phenol (389 mg, 2.59 mmol) according to the procedure described the synthesis of the intermediate 4-methoxy-5-phenoxy-pyridine-2-carbonitrile.

Yield: 342 mg (53%) $R_t$(HPLC): 1.00 min (Method 1)

5-(4-Cyclopropoxy-phenoxy)-4-methoxy-pyridine-2-carboxylic acid

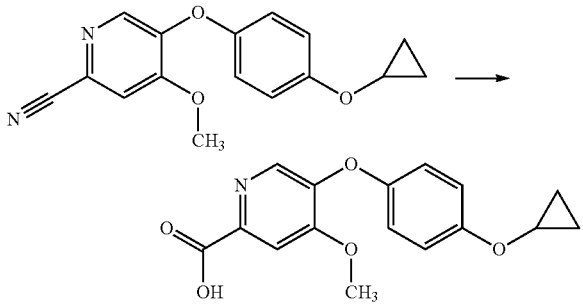

The title compound is synthesized from 5-(4-cyclopropoxy-phenoxy)-4-methoxy-pyridine-2-carbonitrile (100 mg, 0.35 mmol) according to the procedure described for the synthesis of the intermediate 5-(4-fluoro-phenoxy)-4-methoxy-pyridine-2-carboxylic acid.

Yield: 622 mg (90%) $R_t$(HPLC): 0.63 min (Method 1)

4-Methoxy-5-(4-trifluoromethoxy-phenoxy)-pyridine-2-carbonitrile

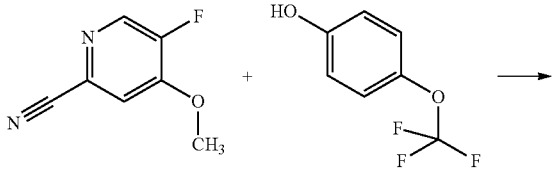

-continued

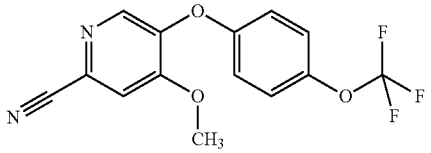

The title compound is synthesized from 5-fluoro-4-methoxy-pyridine-2-carbonitrile (115 mg, 0.76 mmol) and 4-trifluoromethoxy-phenol (162 mg, 0.91 mmol) according to the procedure described for the synthesis of the intermediate 4-methoxy-5-phenoxy-pyridine-2-carbonitrile.

Yield: 140 mg (60%)

4-Methoxy-5-(4-trifluoromethoxy-phenoxy)-pyridine-2-carboxylic acid

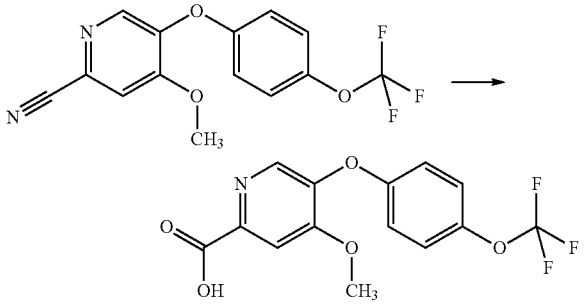

The title compound is synthesized from 4-methoxy-5-(4-trifluoromethoxy-phenoxy)-pyridine-2-cabonitrile (150 mg, 0.48 mmol) according to the procedure described for the synthesis of the intermediate 5-(4-Fluoro-phenoxy)-4-methoxy-pyridine-2-carboxylic acid.

Yield: 120 mg (75%)

5-(2-Fluoro-benzyloxy)-4-methoxy-pyridine-2-carboxylic acid methyl ester

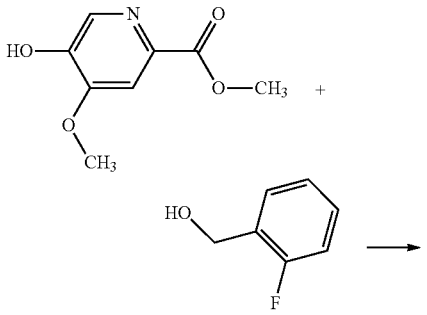

-continued

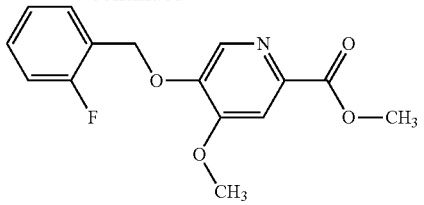

To 5-hydroxy-4-methoxy-pyridine-2-carboxylic acid methyl ester (130 mg, 0.71 mmol), triphenylphosphine (372 mg, 1.42 mmol) and 2-fluorohenzyl alcohol (114 μl, 1.065 mmol) in THF (2 mL) is added diethyl azodicarboxylate (646 μl, 1.42 mmol) at 0° C. The reaction mixture is allowed to warm to RT and stirred for 16 h. The resulting mixture is concentrated under vacuum and the residue is purified by silica gel chromatography to give the title compound.

Yield: 66.0 mg (32%) $R_t$(HPLC): 0.77 min (Method 1)

5-(2-Fluoro-benzyloxy)-4-methoxy-pyridine-2-carboxylic acid

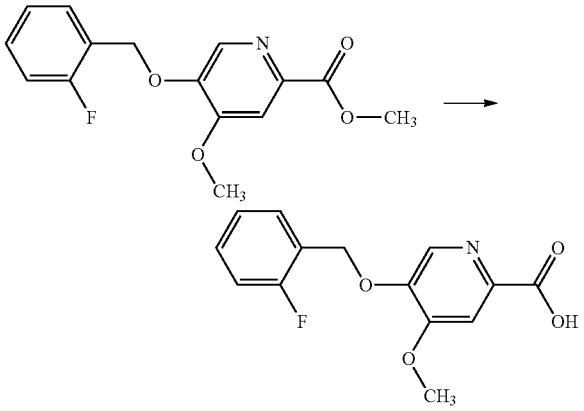

To 5-(2-fluoro-benzyloxy)-4-methoxy-pyridine-2-carboxylic acid methyl ester (66.0 mg, 0.23 mmol) in THF/water/MeOH (3 mL/1 mL/1mL) is added LiOH (38.0 mg, 0.91 mmol), and the reaction mixture is stirred at rt. The reaction mixture is acidified to pH 4.5 with 4 N HCl and concentrated under vacuum. The residue is dissolved in DCM and toluene and concentrated again under reduced pressure. The product was used without further purification.

Yield: 62.0 mg (99%) $R_t$(HPLC): 0.48 min (Method 1)

5-Cyclobutylmethoxy-4-methoxy-pyridine-2-carboxylic acid methyl ester

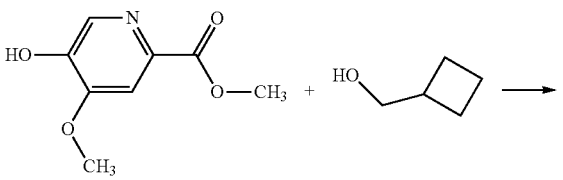

-continued

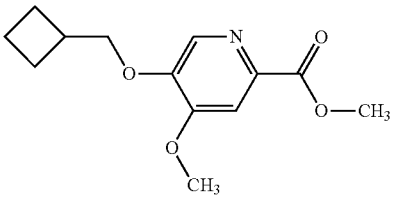

The title compound is synthesized from 5-hydroxy-4-methoxy-pyridine-2-carb-oxylic acid methyl ester (130 mg, 0.71 mmol) and cyclobutyl-methanol (91.7 mg, 1.07 mmol) according to the procedure described for the synthesis of the intermediate 5-(2-fluoro-benzyloxy)-4-methoxy-pyridine-2-carboxylic acid methyl ester.

Yield: 132 mg (74%) $R_t$(HPLC): 0.80 min (Method 1)

5-Cyclobutylmethoxy-4-methoxy-pyridine-2-carboxylic acid

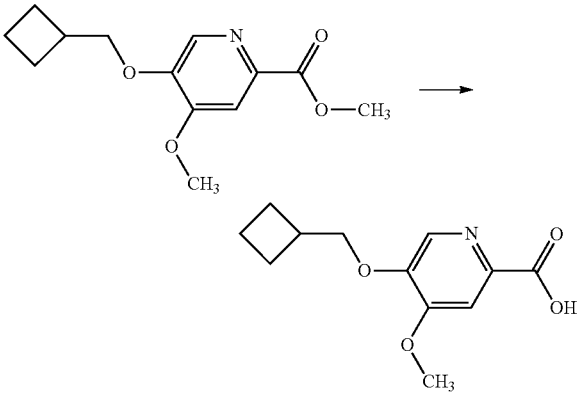

The title compound is synthesized from 5-cyclobutyl-methoxy-4-methoxy-pyridine-2-carboxylic acid methyl ester (132 mg, 0.53 mmol) according to the procedure described for the synthesis of the intermediate 5-(2-fluoro-benzyloxy)-4-methoxy-pyridine-2-carboxylic acid.

Yield: 124 mg (quantitative) $R_t$(HPLC): 0.53 min (Method 1)

4-Methoxy-5-(1-methyl-cyclopropylmethoxy)-pyridine-2-carboxylic acid methyl ester

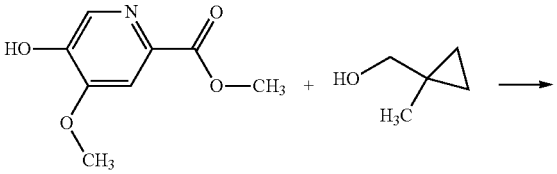

-continued

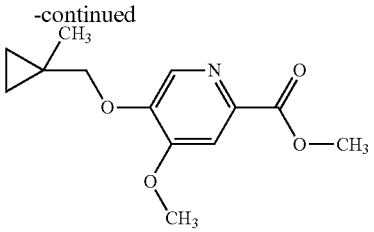

The title compound is synthesized from 5-hydroxy-4-methoxy-pyridine-2-carboxylic acid methyl ester (130 mg, 0.71 mmol) and (1-methyl-cyclopropyl)-methanol (103 mg, 1.07 mmol) according to the procedure described for the synthesis of the intermediate 5-(2-fluoro-benzyloxy)-4-methoxy-pyridine-2-carboxylic acid methyl ester.

Yield: 115 mg (65%) $R_t$(HPLC): 0.81 min (Method 1)

4-Methoxy-5-(1-methyl-cyclopropylmethoxy)-pyridine-2-carboxylic acid

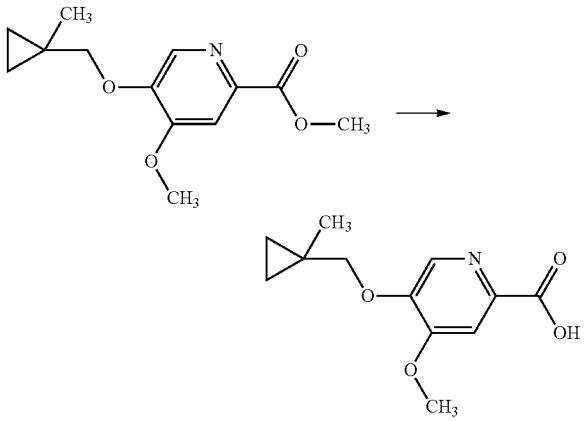

The title compound is synthesized from 5-cyclobutyl-methoxy-4-methoxy-pyridine-2-carboxylic acid methyl ester (115 mg, 0.46 mmol) according to the procedure described for the synthesis of the intermediate 5-(2-fluoro-benzyloxy)-4-methoxy-pyridine-2-carboxylic acid.

Yield: 108 mg (quantiative) $R_f$(HPLC): 0.52 min (Method 1)

5-Cyclohexyloxy-4-methoxy-pyridine-2-carboxylic acid methyl ester

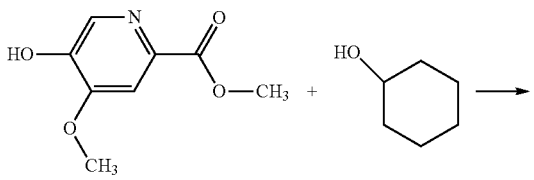

-continued

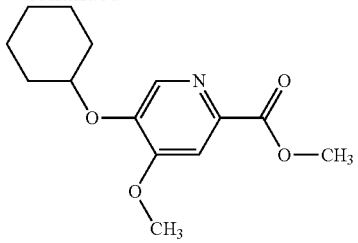

The title compound is synthesized from 5-hydroxy-4methoxy-pyridine-2-carboxylic acid methyl ester (130 mg, 0.71 mmol) and cyclohexanol (111 μL, 1.07 mmol) according to the procedure described for the synthesis of the intermediate 5-(2-fluoro-benzyloxy)-4-methoxy-pyridine-2-carboxylic acid methyl ester.

Yield: 171 mg (91%) $R_t$(HPLC): 0.87 min (Method 1)

5-Cyclohexyloxy-4-methoxy-pyridine-2-carboxylic acid

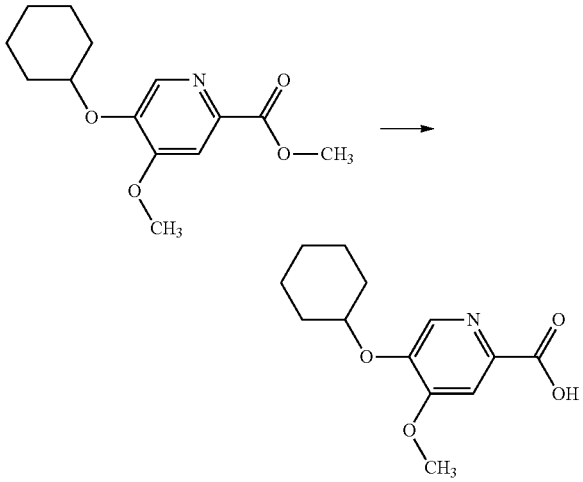

The title compound is synthesized from 5-cyclohexyloxy-4-methoxy-pyridine-2-carboxylic acid methyl ester (131 mg, 0.49 mmol) according to the procedure described for the synthesis of the intermediate 5-(2-fluoro-benzyloxy)-4-methoxy-pyridine-2-carboxylic acid.

Yield: 124 mg (quantitative) $R_t$(HPLC): 0.57 min (Method 1)

5-(4-Fluoro-benzyloxy)-4-methoxy-pyridine-2-carboxylic acid methyl ester

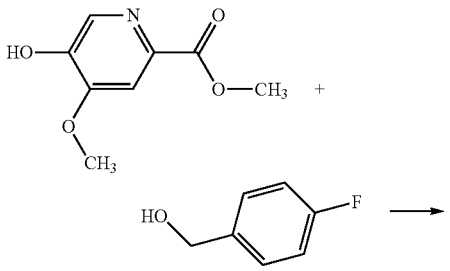

-continued

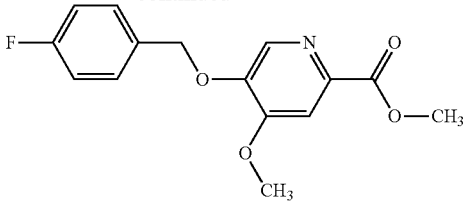

The title compound is synthesized from 5-hydroxy-4-methoxy-pyridine-2-carboxylic acid methyl ester (130 mg, 0.71 mmol) and (4-fluoro-phenyl)-methanol (115 μL, 1.07 mmol) according to the procedure described for the synthesis of the intermediate 5-(2-fluoro-benzyloxy)-4-methoxy-pyridine-2-carboxylic acid methyl ester.

Yield: 150 mg (62%) $R_t$(HPLC): 0.82 min (Method 1)

5-(4-Fluoro-benzyloxy)-4-methoxy-pyridine-2-carboxylic acid

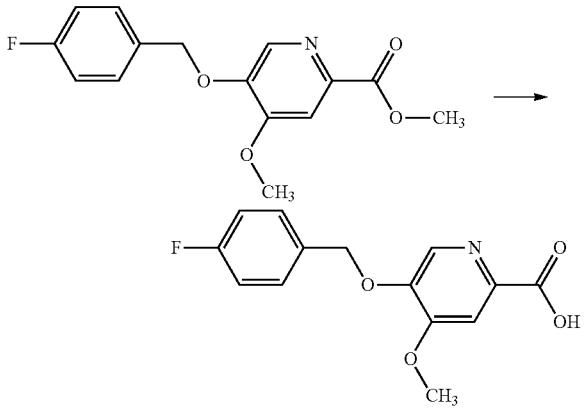

The title compound is synthesized from 5-(4-fluoro-benzyloxy)-4-methoxy-pyridine-2-carboxylic acid methyl ester (150 mg, 0.44 mmol) according to the procedure described for the synthesis of the intermediate 5-(2-fluoro-benzyloxy)-4-methoxy-pyridine-2-carboxylic acid.

Yield: 177 mg (quantative) $R_t$(HPLC): 0.82 min (Method 1)

5-Cyclopentyloxy-4-methoxy-pyridine-2-carboxylic acid methyl ester

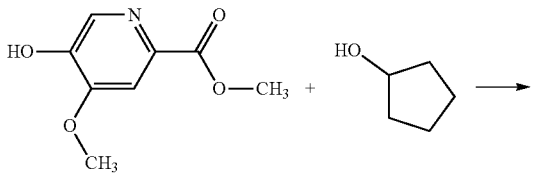

-continued

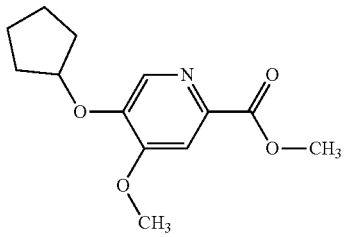

The title compound is synthesized from 5-hydroxy-4-methoxy-pyridine-2-carboxylic acid methyl ester (130 mg, 0.71 mmol) and cyclopentanol (96.7 μL, 1.07 mmol) according to the procedure described for the synthesis of the intermediate 5-(2-fluoro-benzoxy)-4-methoxy-pyridine-2-carboxylic acid methyl ester.

Yield: 170 mg (95%) $R_t$(HPLC): 0.87 min (Method 1)

5-Cyclopentyloxy-4-methoxy-pyridine-2-carboxylic acid

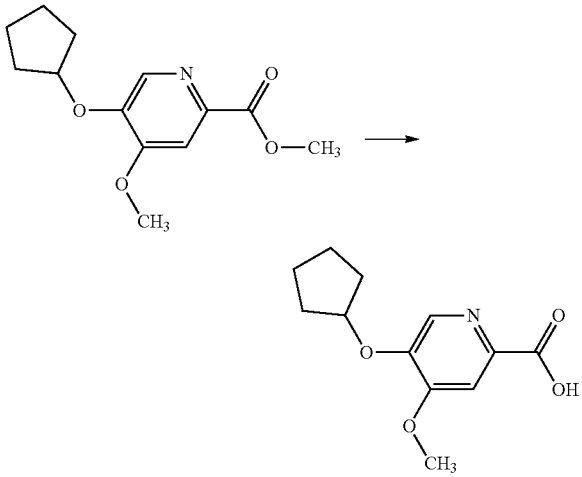

the title compound is synthesized from 5-cyclopentyloxy-4-methoxy-pyridine-2-carboxylic acid methyl ester (130 mg, 0.52 mmol) according to the procedure described for the synthesis of the intermediate 5-(2-fluoro-benzyloxy)-4-methoxy-pyridine-2-carboxylic acid.

Yield: 122 mg (99%) $R_t$(HPLC): 0.49 min (Method 1)

5-hobutoxy-4-methoxy-pyridine-2-carboxylic acid methyl ester

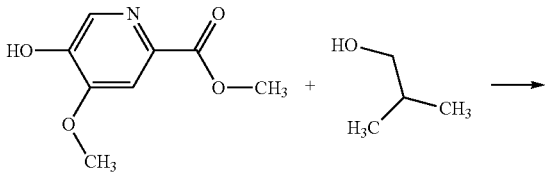

-continued

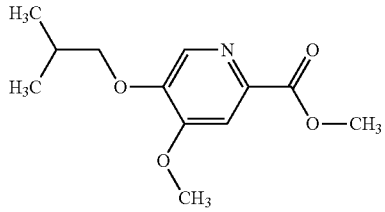

The title compound is synthesized from 5-hydroxy-4-methoxy-pyridine-2-carboxylic acid methyl ester (118 mg, 0.64 mmol) and isobutylalcohol (71.6 mg, 0.97 mmol) according to the procedure described for the synthesis of the intermediate 5-(2-fluoro-benzyloxy)-4-methoxy-pyridine-2-carboxylic acid methyl ester.

Yield: 141 mg (92%) $R_t$(HPLC): 0.78 min (Method 1)

5-Isobutoxy-4-methoxy-pyridine-2-carboxylic acid

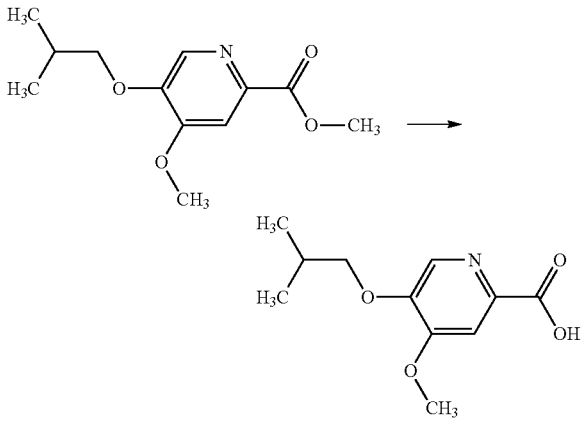

The title compound is synthesized from 5-isobutoxy-4-methoxy-pyridine-2-carboxylic acid methyl ester (141 mg, 0.59 mmol) according to the procedure described for the synthesis of the intermediate 5-(2-fluoro-benzyloxy)-4-methoxy-pyridine-2-carboxylic acid.

Yield: 133 mg (quantitative) $R_t$(HPLC): 0.51 min (Method 1)

5-Cyclopropylmethoxy-4-methoxy-pyridine-2-carboxylic acid methyl ester

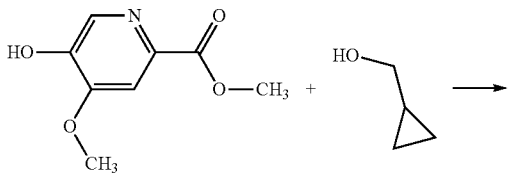

-continued

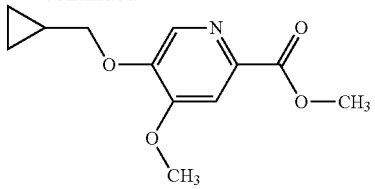

The title compound is synthesized from 5-hydroxy-4-methoxy-pyridine-2-carboxylic acid methyl ester (130 mg, 0.71 mmol) and cyclopropyimethanol (84.2 μL, 1.07 mmol) according to the procedure described for the synthesis of the intermediate 5-(2-fluoro-benzyloxy)-4-methoxy-pyridine-2-carboxylic acid methyl ester.

Yield: 146 mg (87%) $R_t$(HPLC): 0.74 min (Method 1)

5-Cyclopropylmethoxy-4-methoxy-pyridine-2-carboxylic acid

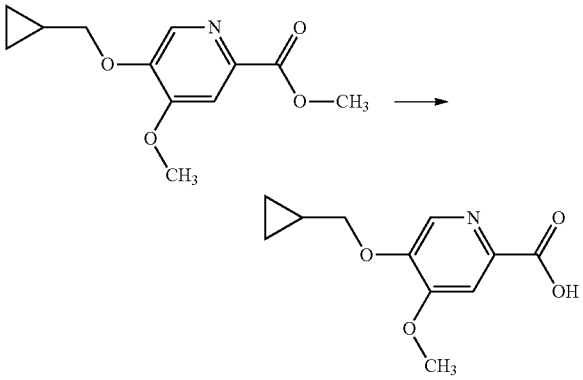

The title compound is synthesized from 5-cyclopropylmethoxy-4-methoxy-pyridine-2-carboxylic acid methyl ester (325 mg, 1.37 mmol) according to the procedure described for the synthesis of the intermediate 5-(2-fluoro-benzyloxy)-4-methoxy-pyridine-2-carboxylic acid.

Yield: 358 mg (quantitative) ESI-MS: m/z=224 $(M+H)^+$ $R_t$(HPLC): 0.40 min (Method 5)

5-Benzyloxy-4-methoxy-pyridine-2-carboxylic acid methyl ester

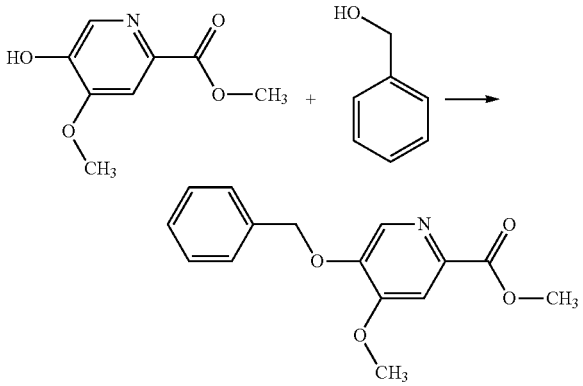

The title compound is synthesized from 5-hydroxy-4-methoxy-pyridine-2-carboxylic acid methyl ester (118 mg, 0.64 mmol) and benzylalcohol (100 μL, 0.97 mmol) according to the procedure described for the synthesis of the intermediate 5-(2-fluoro-benzyloxy)-4-methoxy-pyridine-2-carboxylic acid methyl ester.

Yield: 140 mg (80%) $R_t$(HPLC): 0.79 min (Method 1)

5-Benzyloxy-4-methoxy-pyridine-2-carboxylic acid

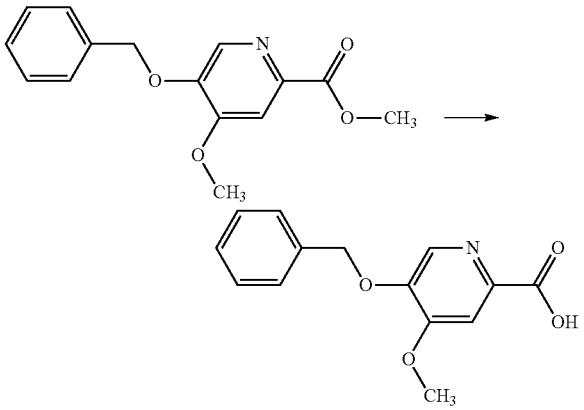

The title compound is synthesized from 5-benzyloxy-4-methoxy-pyridine-2-carboxylic acid methyl ester (140 mg, 0.51 mmol) according to the procedure described for the synthesis of the intermediate 5-(2-fluoro-benzyloxy)-4-methoxy-pyridine-2-carboxylic acid.

Yield: 358 mg (99%) $R_t$(HPLC): 0.54 min (Method 1)

5-(3,3-Difluoro-cyclobutylmethoxy)-4-methoxy-pyridine-2-carboxylic acid methyl ester

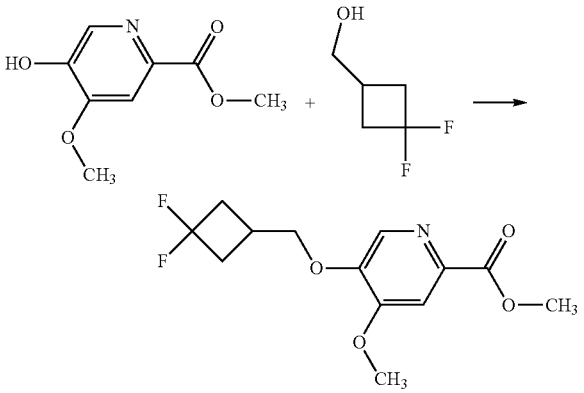

The title compound is synthesized from 5-hydroxy-4-methoxy-pyridine-2-carboxylic acid methyl ester (118 mg, 0.64 mmol) and (3,3-difluoro-cyclobutyl)-methanol (150 mg, 0.82 mmol) according to the procedure described for the synthesis of the intermediate 5((2-fluoro-benzyloxy)-4-methoxy-pyridine-2-carboxylic acid methyl ester.

Yield: 111 mg (47%) ESI-MS: m/z=288 $(M+H)^+$ $R_t$(HPLC): 1.20 min (Method 5)

5-(3,3-Difluoro-cyclobutylmethoxy)-4-methoxy-pyridine-2-carboxylic acid

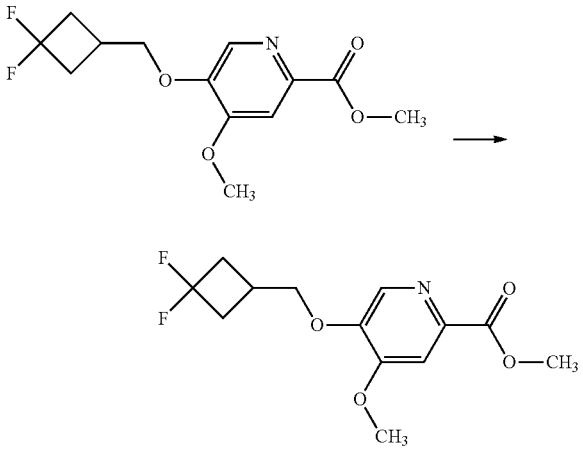

The title compound is synthesized from 5-(3,3-difluoro-cyclobutylmethoxy)-4-methoxy-pyridine-2-carboxylic acid methyl ester (110 mg, 0.38 mmol) according to the procedure described for the synthesis of the intermediate 5-(2-fluoro-benzyloxy)-4-methoxy-pyridine-2-carboxylic acid.

Yield: 73.4 mg (70%) ESI-MS: m/z=274 $(M+H)^+$ $R_t$(HPLC): 0.56 min (Method 5)

4-Methoxy-5-propoxy-pyridine-2-carboxylic acid methyl ester

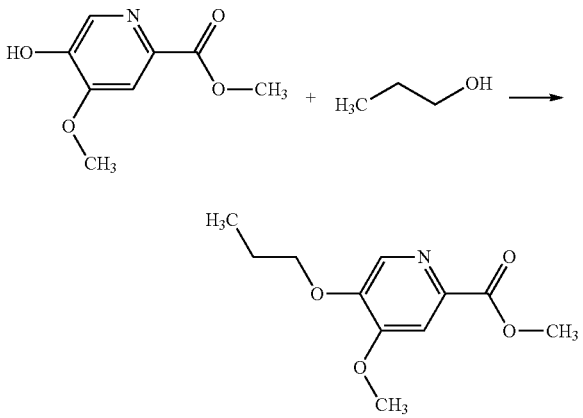

The title compound is synthesized from 5-hydroxy-4-methoxy-pyridine-2-carboxylic acid methyl ester (130 mg, 0.71 mmol) and 1-propanol (80.0 μL, 1.07 mmol) according to the procedure described foir the synthesis of the intermediate 5-(2-fluoro-benzyloxy)-4-methoxy-pyridine-2-carboxylic acid methyl ester.

Yield: 114 mg (71%) $R_t$(HPLC): 0.69 min (Method 1)

4-Methoxy-5-propoxy-pyridine-2-carboxylic acid

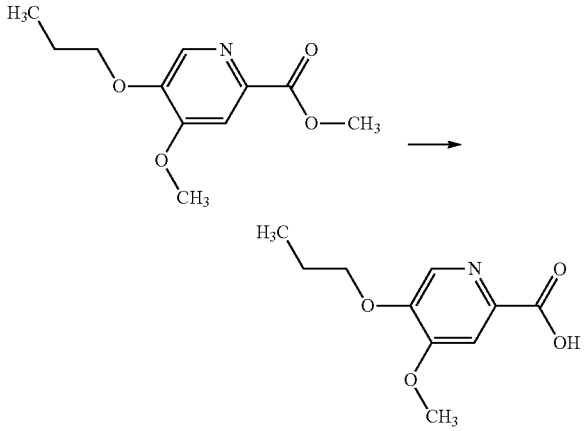

The title compound is synthesized from 4-methoxy-5-propoxy-pyridine-2-carboxylic acid methyl ester (114 mg, 0.51 mmol) according to the procedure described for the synthesis of the intermediate 5-(2-fluoro-benzyloxy)-4-methoxy-pyridine-2-carboxylic acid.

Yield: 106 mg (99%) $R_t$(HPLC): 0.41 min (Method 1)

5-(2-Cyclopropyl-ethoxy)-4-methoxy-pyridine-2-carboxylic acid methyl ester

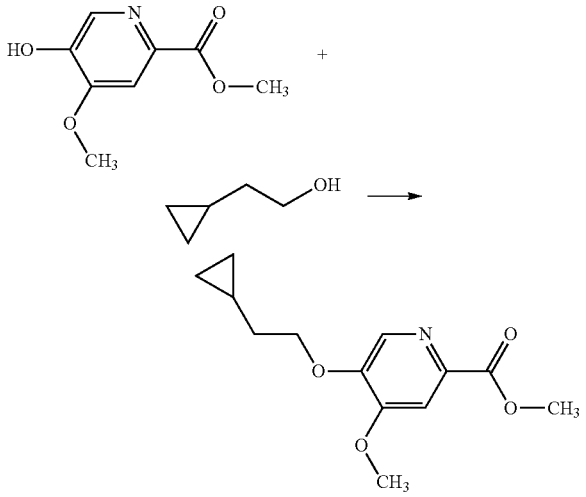

The title compound is synthesized from 5-hydroxy-4-methoxy-pyridine-2-carboxylic acid methyl ester (130 mg, 0.71 mmol) and 2-cyclopropylethanol (91.7 mg, 1.07 mmol) according to the procedure described for the synthesis of the intermediate 5-(2-fluoro-benzyloxy)-4-methoxy-pyridine-2-carboxylic acid methyl ester.

Yield: 130 mg (73%) $R_t$(HPLC): 0.82 min (Method 1)

5-(2-Cyclopropyl-ethoxy)-4-methoxy-pyridine-2-carboxylic acid

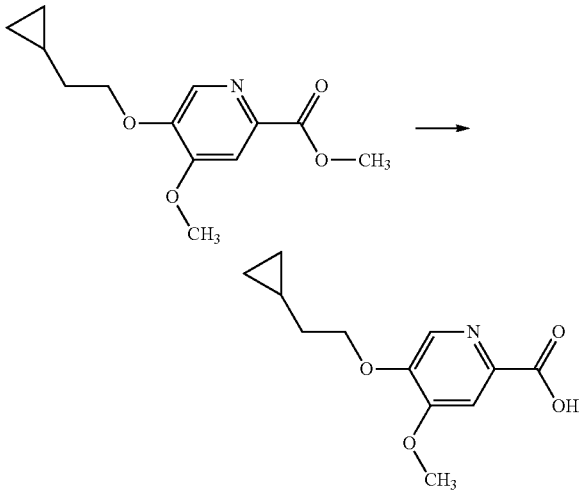

The title compound is synthesized from 5-(2-cyclopropyl-ethoxy)-4-methoxy-pyridine-2-carboxylic acid methyl ester (130 mg, 0.52 mmol) according to the procedure described for the synthesis of the intermediate 5-(2-fluoro-benzyloxy)-4-methoxy-pyridine-2-carboxylic acid.

Yield: 122 mg (99%) $R_t$(HPLC): 0.53 min (Method 1)

4-Methoxy-5-phenethyloxy-pyridine-2-carboxylic acid methyl ester

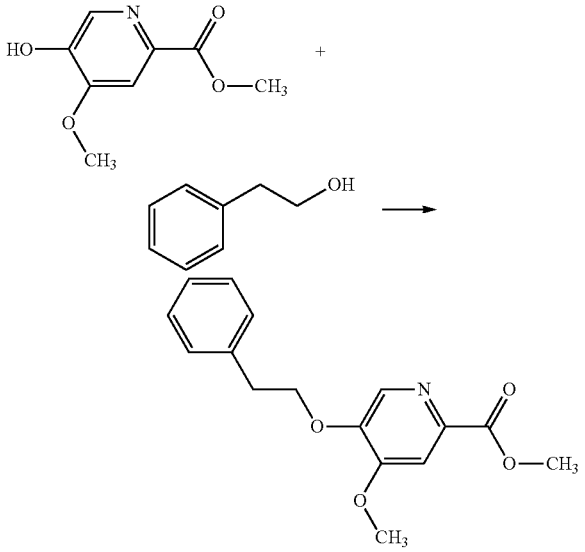

The title compound is synthesized from 5-hydroxy-4-methoxy-pyridine-2-carboxylic acid methyl ester (130 mg, 0.71 mmol) and 2-phenylethanol (128 μL,, 1.07 mmol) according to the procedure described for the synthesis of the intermediate 5-(2-fluoro-benzyloxy)-4-methoxy-pyridine-2-carboxylic acid methyl ester.

Yield: 177 mg (87%) $R_t$(HPLC): 0.90 min (Method 1)

4-Methoxy-5-phenethyloxy-pyridine-2-carboxylic acid

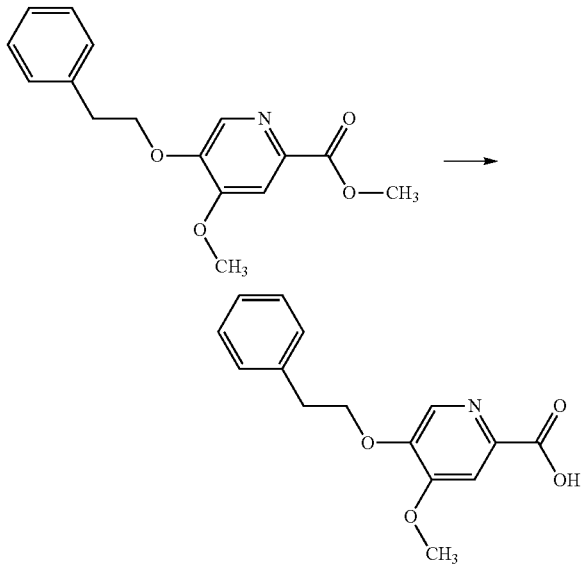

The title compound is synthesized from 4-methoxy-5-phenethyloxy-pyridine-2-carboxylic acid methyl ester (177 mg, 0.62 mmol) according to the procedure described for the synthesis of the intermediate 5-(2-fluoro-benzyloxy)-4-methoxy-pyridine-2-carboxylic acid.

Yield: 168 mg (quantitative) $R_t$(HPLC): 0.63 min (Method 1)

5-(2,2-Dimethyl-propoxy)-4-methoxy-pyridine-2-carboxylic acid methyl ester

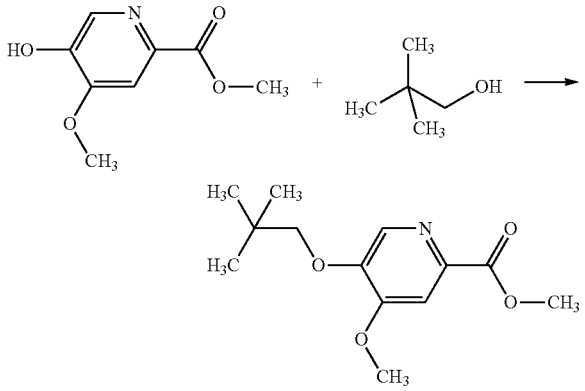

The title compound is synthesized from 5-hydroxy-4-methoxy-pyridine-2-carboxylic acid methyl ester (130 mg, 0.71 mmol) and 2,2-dimethyl-propan-1-ol (93.8 mg, 1.07 mmol) according to the procedure described for the synthesis of the intermediate 5-(2-fluoro-benzyloxy)-4-methoxy-pyridine-2-carboxylic acid methyl ester.

Yield: 160 mg (89%) $R_t$(HPLC): 0.92 min (Method 1)

5-(2,2-Dimethyl-propoxy)-4-methoxy-pyridine-2-carboxylic acid

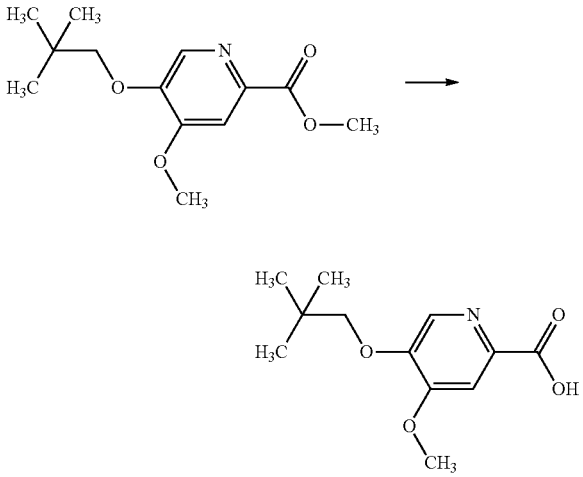

The title compound is synthesized from 5-(2,2-dimethyl-propoxy)-4-methoxy-pyridine-2-carboxylic acid methyl ester (160 mg, 0.63 mmol) according to the procedure described for the synthesis of the intermediate 5-(2-fluoro-benzyloxy)-4-methoxy-pyridine-2-carboxylic acid. po Yield: 150 mg (99%) $R_t$(HPLC): 0.61 min (Method 1)

5-(1-fluoromethyl-cyclopropylmethoxy)-4-methoxy-pyridine-2-carboxylic acid methyl ester

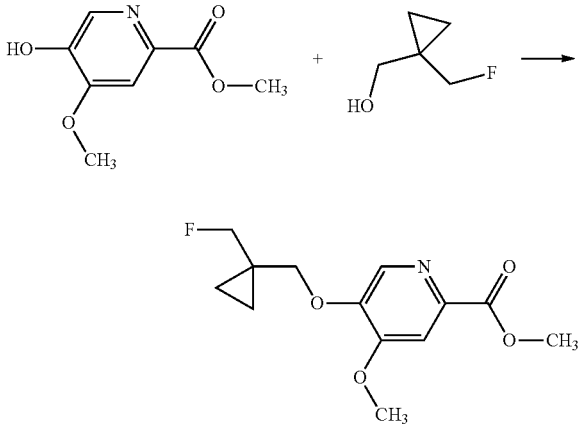

The title compound is synthesized from 5-hydroxy-4-methoxy-pyridine-2-carboxylic acid methyl ester (118 mg, 0.64 mmol) and (1-fluoromethyl-cyclopropyl)-methanol (101 mg, 0.97 mmol) according to the procedure described for the synthesis of the intermediate 5-(2-fluoro-benzyloxy)-4-methoxy-pyridine-2-carboxylic acid methyl ester.

Yield: 159 mg (92%) $R_t$(HPLC): 0.69 min (Method 1)

5-(1-Fluoromethyl-cyclopropylmethoxy)-4-methoxy-pyridine-2-carboxylic acid

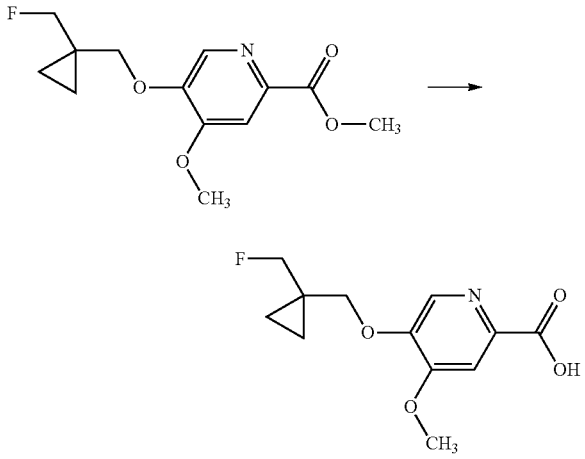

The title compound is synthesized from 5-(1 -fluoromethyl-cyclopropylmethoxy)-4-methoxy-pyridine-2-carboxylic acid methyl ester (159 mg, 0.59 mmol) according to the procedure described for the synthesis of the intermediate 5(2-fluoro-benzyloxy)-4-methoxy-pyridine-2-carboxylic acid.

Yield: 150 mg (quantitative) $R_t$(HPLC): 0.43 min (Method 1)

5-Ethoxy-4-methoxy-pyridine-2-carboxylic acid methyl ester

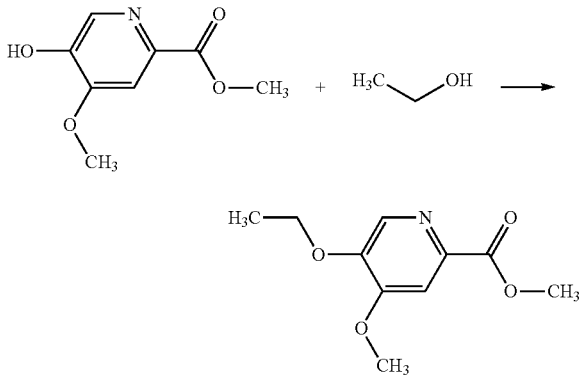

The title compound is synthesized from 5-hydroxy-4-methoxy-pyridine-2-carboxylic acid methyl ester (130 mg, 0.71 mmol) and ethanol (62.1 μL, 1.07 mmol) according to the procedure described for the synthesis of the intermediate 5-(2-fluoro-benzyloxy)-4-methoxy-pyridine-2-carboxylic acid methyl ester.

Yield: 151 mg (100%) $R_t$(HPLC): 0.92 min (Method 1)

5-Ethoxy-4-methoxy-pyridine-2-carboxylic acid

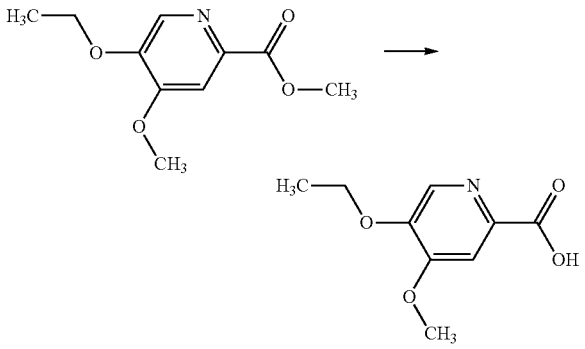

The title compound is synthesized from 5-ethoxy-4-methoxy-pyridine-2-carboxylic acid methyl ester (151 mg, 0.71 mmol) according to the procedure described for the synthesis of the intermediate 5-(2-fluoro-benzyloxy)-4-methoxy-pyridine-2-carboxylic acid, Yield: 140 mg (99%) $R_t$(HPLC): 0.83 min (Method 1)

5-((S)-1-Cyclopropyl-ethoxy)-4-methoxy-pyridine-2-carboxylic acid methyl ester

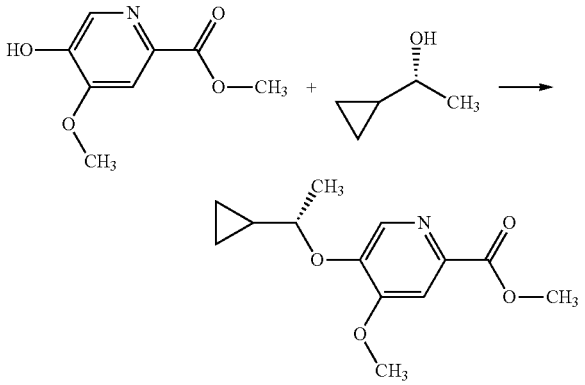

The title compound is synthesized from 5-hydroxy-4-methoxy-pyridine-2-carboxylic acid methyl ester (118 mg, 0.64 mmol) and (R)-1-cyclopropyl-ethanol (83.2 mg, 0.97 mmol) according to the procedure described for the synthesis of the intermediate 5-(2-fluoro-benzyloxy)-4-methoxy-pyridine-2-carboxylic acid methyl ester.

Yield: 102 mg (63%)

5-((S)-1-Cyclopropyl-ethoxy)-4-methoxy-pyeidine-2-carboxylic acid

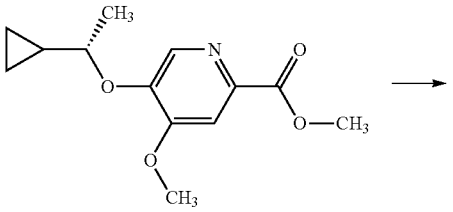

-continued

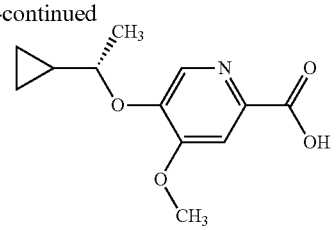

The title compound is synthesized from 5-((S)-1-cyclopropyl-ethoxy)-4-methoxy-pyridine-2-carboxylic acid methyl ester (102 mg, 0.41 mmol) according to the procedure described for the synthesis of the intermediate 5-(2-fluoro-benzyloxy)-4-methoxy-pyridine-2-carboxylic acid.

Yield: 96.0 mg (100%) $R_t$(HPLC): 0.51 min (Method 1)

5-Isopropoxy-4-methoxy-pyridine-2-carboxylic acid methyl ester

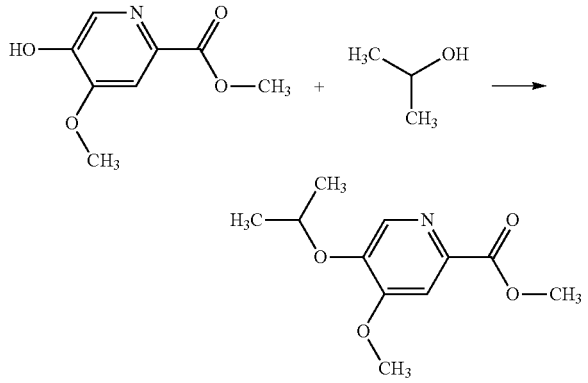

The title compound is synthesized from 5-hydroxy-4-methoxy-pyridine-2-carboxylic acid methyl ester (130 mg, 0.71 mmol) and propan-2-ol (81.5 μL, 0.97 mmol) according to the procedure described for the synthesis of the intermediate 5-(2-fluoro-benzyloxy)-4-methoxy-pyridine-2-carboxylic acid methyl ester, Yield: 154 mg (96%) $R_t$(HPLC): 0.62 min (Method 1)

5-isopropoxy-4-methoxy-pyridine-2-carboxylic acid

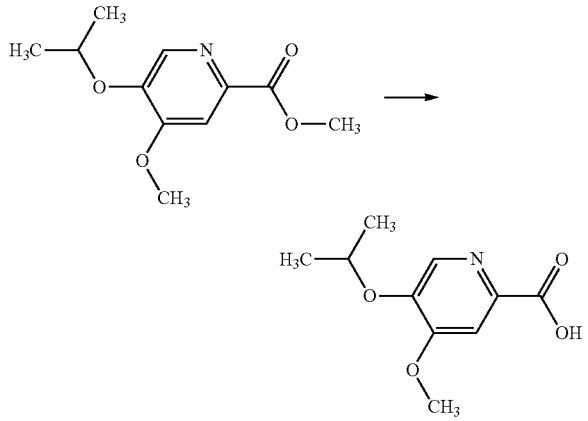

The title compound is synthesized from 5-isopropoxy-4-methoxy-pyridine-2-carboxylic acid methyl ester (154 mg, 0.68 mmol) according to the procedure described for the synthesis of the intermediate 5-(2-fluoro-benzyloxy)-4-methoxy-pyridine-2-carboxylic acid.

Yield: 144 mg (quantitative)

5-((R)-1-Cyclopropyl-ethoxy)-4-methoxy-pyridine-2-carboxylic acid methyl ester

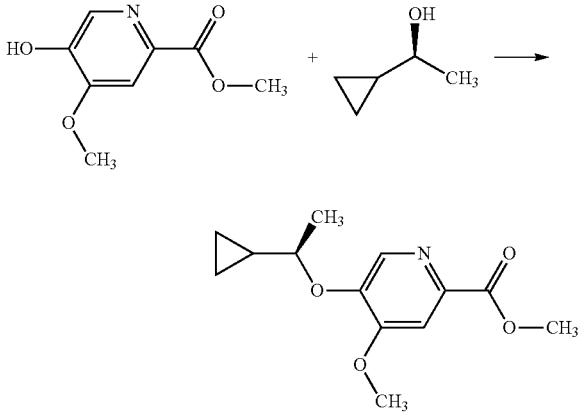

The title compound is synthesized from 5-hydroxy-4-methoxy-pyridine-2-carboxylic acid methyl ester (118 mg, 0.64 mmol) and (S)-1-cyclopropyl-ethanol (83.2 mg, 0.97 mmol) according to the procedure described for the synthesis of the intermediate 5-(2-fluoro-benzyloxy)-4-methoxy-pyridine-2-carboxylic acid methyl ester.

Yield: 101 tug (63%)

5-((R)-1-Cyclopropyl-ethoxy)-4-methoxy-pyridine-2-carboxylic acid

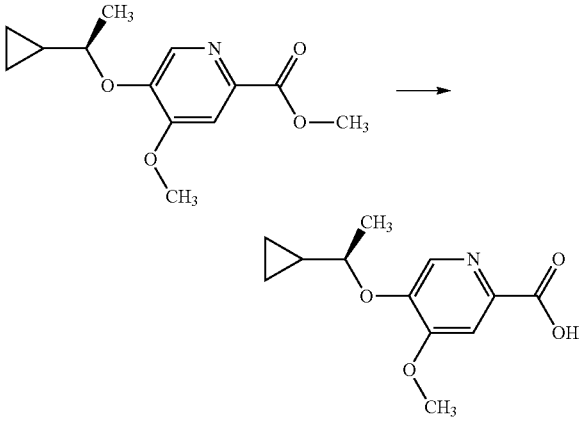

The title compound is synthesized from 5-((R)-1-cyclopropyl-ethoxy)-4-methoxy-pyridine-2-carboxylic acid methyl ester (101 mg, 0.40 mmol) according to the procedure described for the synthesis of the intermediate 5-(2-fluoro-benzyloxy)-4-methoxy-pyridine-2-carboxylic acid.

Yield: 94.0 mg (90%) $R_t$(HPLC): 0.51 min (Method 1)

3-(Trifluoromethyl)cyclobutyl]methanol

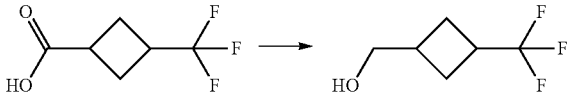

To 3-(trilluoromethy)cyclobutane-1-carboxylic acid (50 mg, 0.29 mmol) in THF (2 mL) is added CDI (57 mg, 0.36 mmol) and stirred at RT for 2 h. Sodium borohydride (12 mg, 0.31 mmol) in water (0.5 mL) is added and the reaction mixture is stirred at RT for 30 min. The reaction mixture is acidified with 1M HCl and extracted with DCM. The combined organic phases are separated and dried over $Na_2SO_4$, filtered and concentrated.

Yield: 45 mg (quantitative)

Methyl 4-methoxy-5{[3-(trifluoromethyl)cyclobutyl]methoxy}pyridine-2-carboxylate

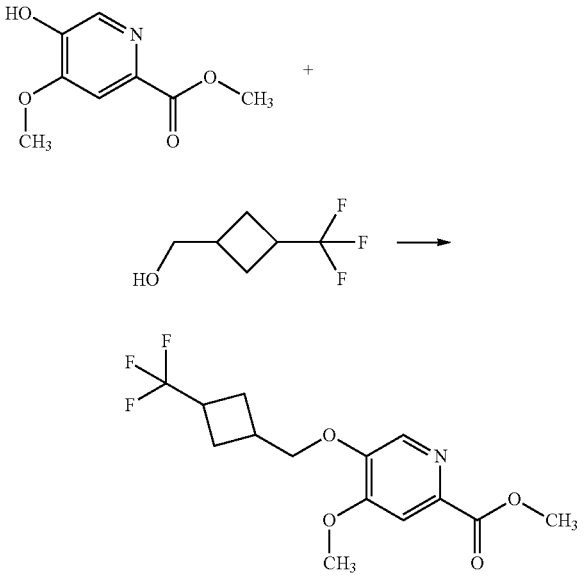

Ihe title compound is synthesized from methyl 5-hydroxy-4-methoxypyridine-2-carboxylate (53 mg, 0.29 mmol) and [3-(trifluoromethyl)cyclobutyl]methanol (45 mg, 0.29 mmol) according to the procedure described for the synthesis of the intermediate 5-(2-fluoro-benzyloxy)-4-methoxy-pyridine-2-carboxylic acid methyl ester.

Yield: 90 mg (97%)

4-Methoxy-5-{[3-(trifluoromethyl)cyclobutyl] methoxy}pyridine-2-carboxylic acid

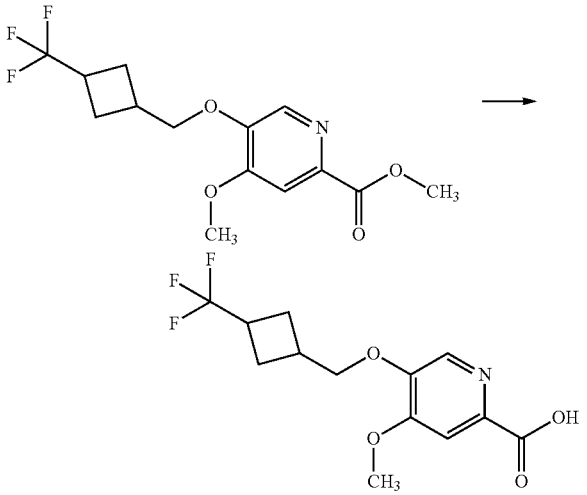

4M aqueous NaH solution (0.55 mL, 2.2 mmol) is added to methyl 4-methoxy-5-{[3-(trifluoromethyl)-cyclobutyl] methoxy}-pyridine-2-carboxylate (350 mg, 1.10 mmol) in 5 mL methanol. The reaction mixture is stirred over night at RT. 4M aqueous HCl solution (0.5 mL) is added and the reaction mixture is stirred 30 min. The reaction mixture is evaporated under reduced pressure, DMF is added to the residue and the desired compound is purified by HPLC.

Yield: 150 mg (45%)

Methyl 4-methoxy-5-(3,3,3-trifluoro-2-methyl-propoxy)pyridine-2-carboxylate

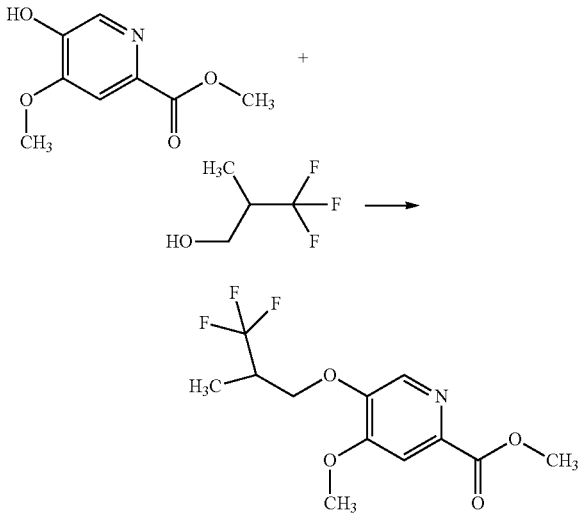

To methyl 5-hydroxy-4-methoxypyridine-2-carboxylate (100 mg, 0.55 mmol) in THF is added 3,3,3-trifluoro-2-methylpropan-1-ol (105 mg, 0.82 mmol) and triphenylphosphine (286 mg, 1.10 mmol) and followed by diisopropylazodicarboxylate (221 mg, 1.10 mmol). The reaction mixture is stirred at RT for 3 h, The reaction mixture is evaporated under reduced pressure and the residue is purified by HPLC. The product containing fractions are combined and lyophilized.

Yield: 160 mg (quantitative)

4-Methoxy-5-(3,3,3-trifluoro-2-methylpropoxy)pyridine-2-carboxylic acid

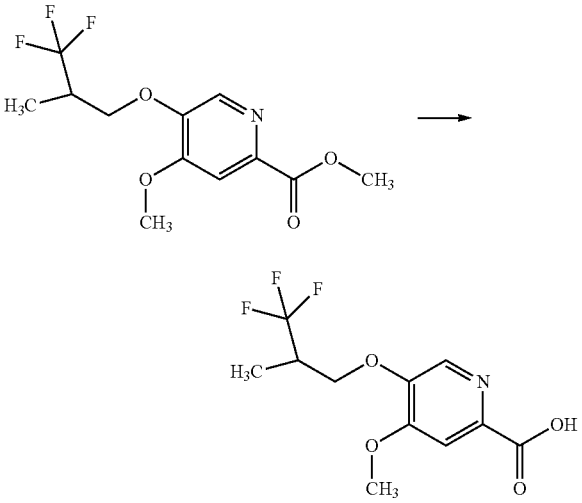

Aqueous 4M NaOH solution (0.52 mL, 2.08 mmol) is added to methyl 4-methoxy-5-(3,3,3-trifluoro-2-methyl-propoxy)pyridine-2-carboxylate (160 mg, 0.55 mmol) in methanol. The reaction mixture is stirred 2 h at RT. The reaction mixture is neutralized with aqueous 4M HCl solution and evaporated under reduced pressure. The residue is used without further purification.

Yield: 150 mg (98%)

General Procedure:

Procedures for preparing compounds of the invention 1-80 are summarized in Table 3A. Analysis of the compounds of the invention 1-80 are summarized in Table 3B.

I: To carboxylic acid (1 eq.) in DMA is added HATU (1.2 eq.) and stirred. Amine (1 eq,) and DIPEA (4.0 eq.) are added and stirred for 18 h at rt. Purification by RP column (ACN/water, acidic or basic conditions) or by silica gel chromatography.

II: Carboxylic acid (1 eq.) and CDI (1.5 eq.) are stirred in DMA for 30 min. at rt. Amine (1 eq.) and DIPEA (2.0 eq.) are added and stirred for 3 h at rt. Purification by RP column (ACN/water, acidic or basic conditions) or by silica gel chromatography.

III: Amine (1.0 eq.), carboxylic acid (0.9 eq.), TBTU (1.0 eq.) and DIPEA (4.0 eq.) in NMP are stirred for 18 h at rt. The filtered reaction mixture is purified by RP column (ACN/water, acidic or basic conditions) or by silica gel chromatograpy.

TABLE 3A
General procedures for preparing compounds of the invention 1-80.
| Cpd No. | Amine Intermediate | Carboxylic acid Intermediate | Genl. Proc. | Yield % |
|---|---|---|---|---|
| 1 | 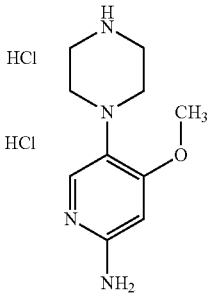 | 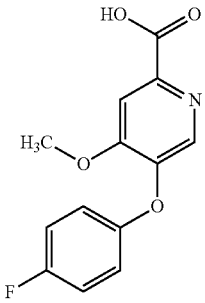 | I | 72 |
| 2 | 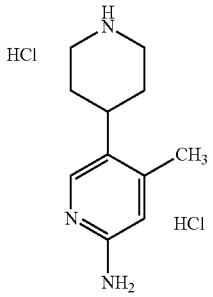 | 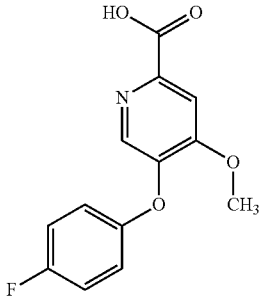 | II | 82 |
| 3 | 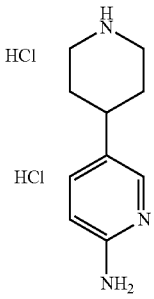 | 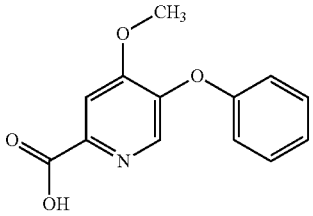 | III | 15 |
| 4 | 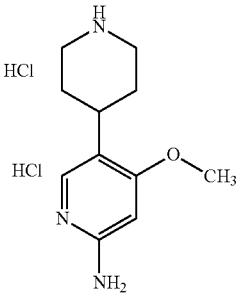 | 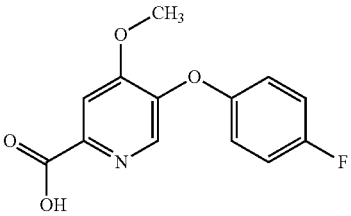 | III | 13 |
| 5 | 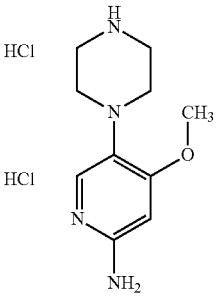 | 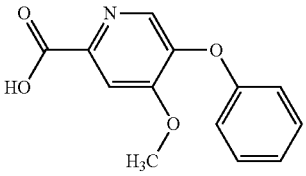 | I | 80 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 6 | 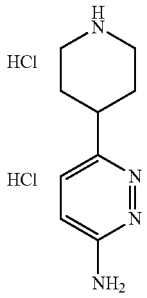 | 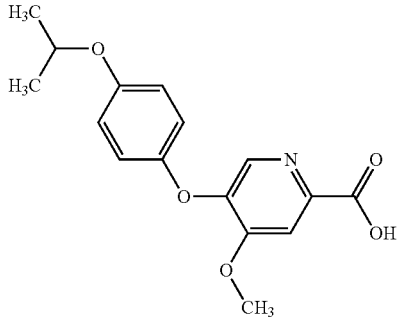 | III | 49 |
| 7 | 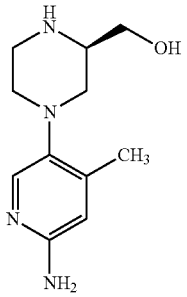 | 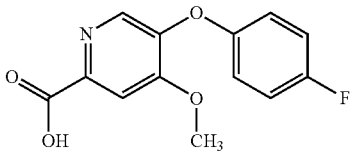 | I | 69 |
| 8 | 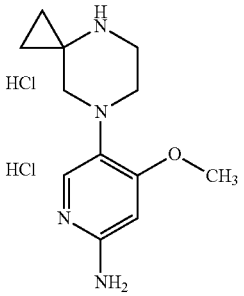 | 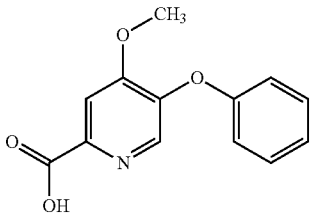 | I | 33 |
| 9 | 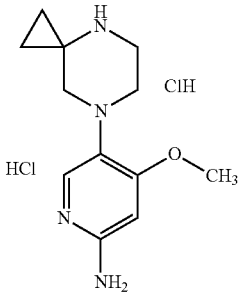 | 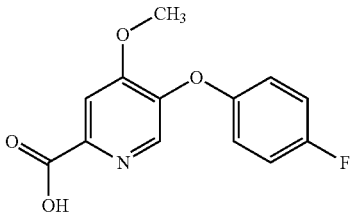 | I | 11 |
| 10 | 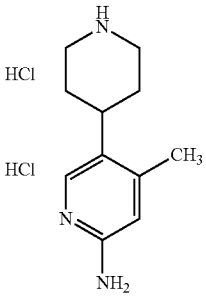 | 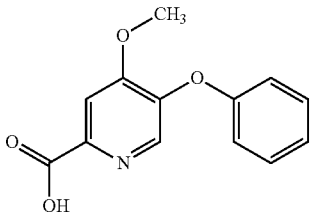 | II | 82 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 11 | 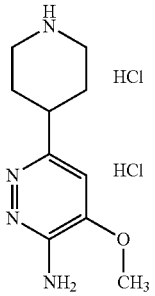 | 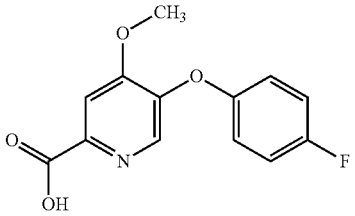 | III | 72 |
| 12 | 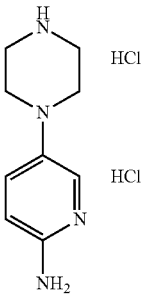 | 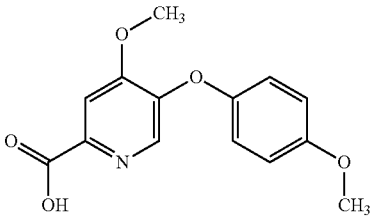 | III | 63 |
| 13 | 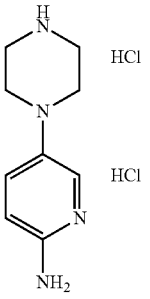 | 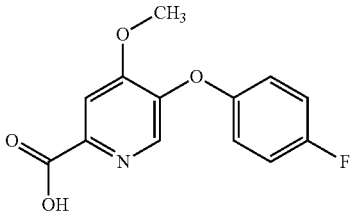 | III | 74 |
| 14 | 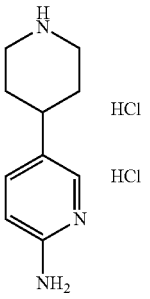 | 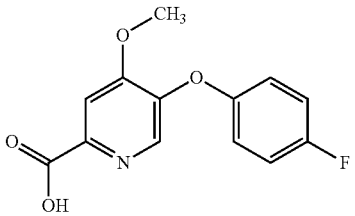 | III | 72 |
| 15 | 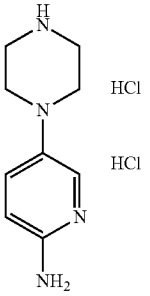 | 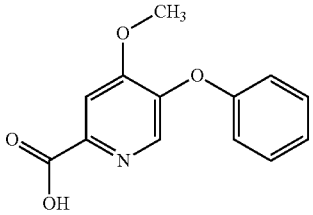 | III | 11 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 16 | 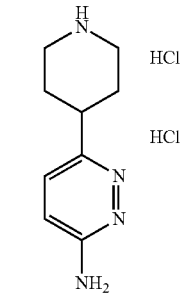 | 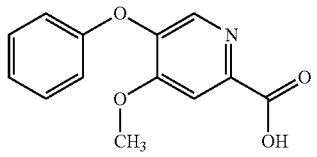 | II | 52 |
| 17 | 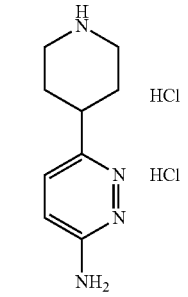 | 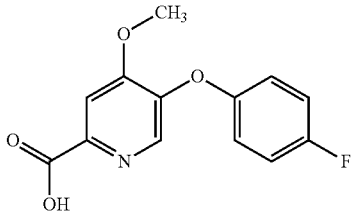 | III | 74 |
| 18 | 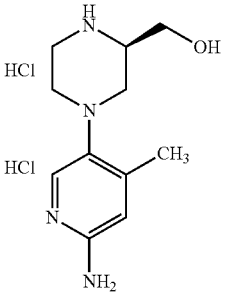 | 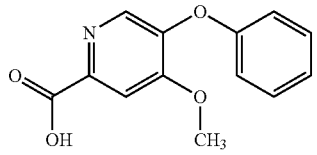 | I | 69 |
| 19 | 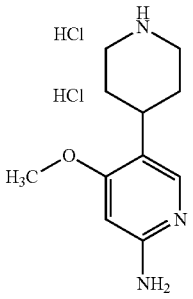 | 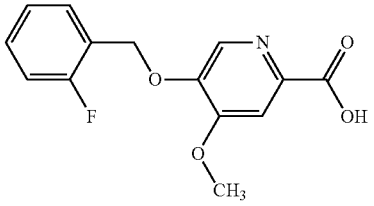 | III | 75 |
| 20 | 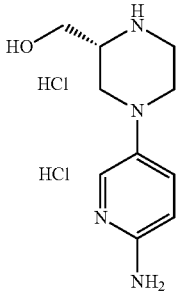 | 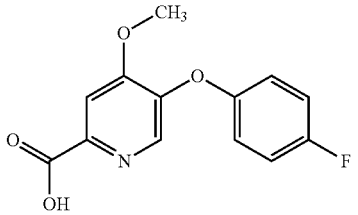 | III | 24 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 21 | 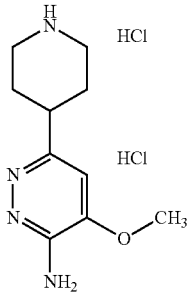 | 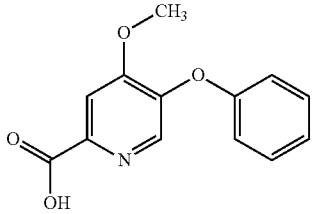 | II | 6.9 |
| 22 | 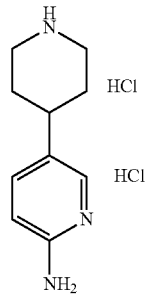 | 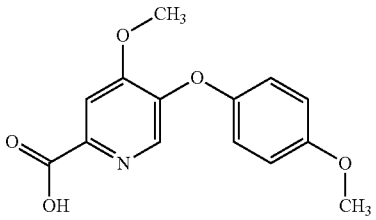 | III | 67 |
| 23 | 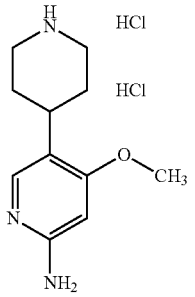 | 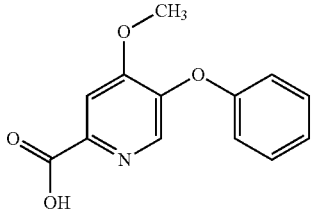 | III | 44 |
| 24 | 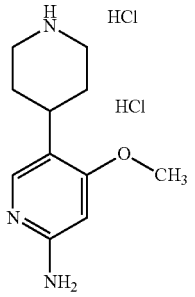 | 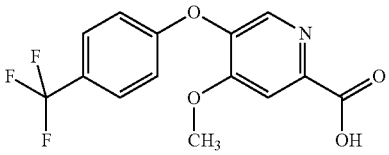 | II | 41 |
| 25 | 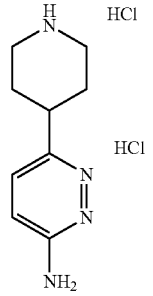 | 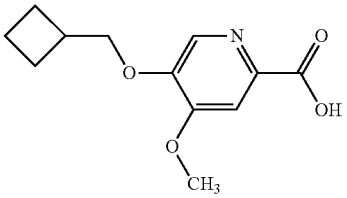 | III | 44 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 26 | 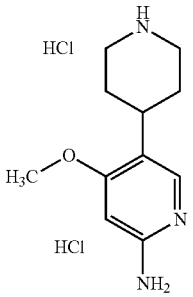 | 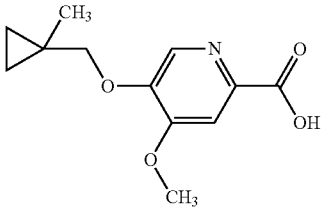 | III | 58 |
| 27 | 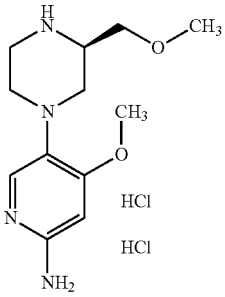 | 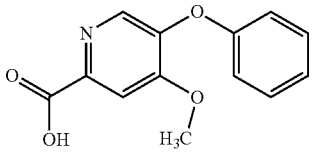 | I | 58 |
| 28 | 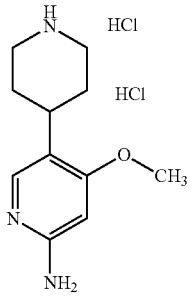 | 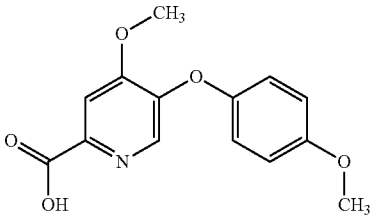 | III | 76 |
| 29 | 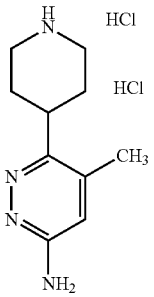 | 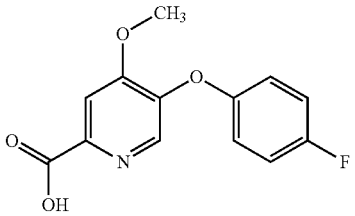 | II | 48 |
| 30 | 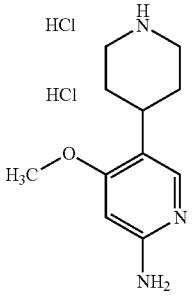 | 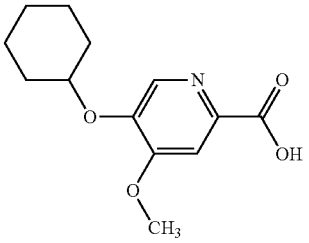 | III | 39 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 31 | 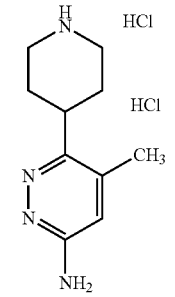 | 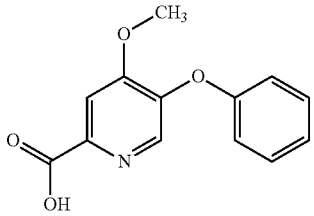 | II | 62 |
| 32 | 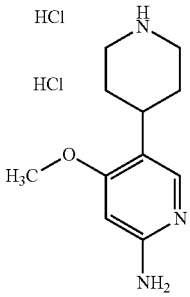 | 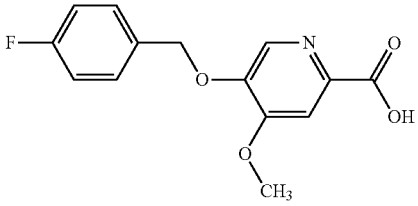 | III | 24 |
| 33 | 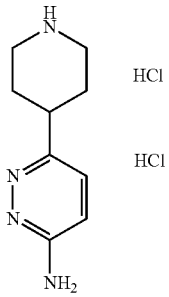 | 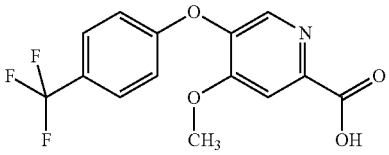 | II | 56 |
| 34 | 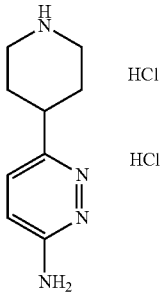 | 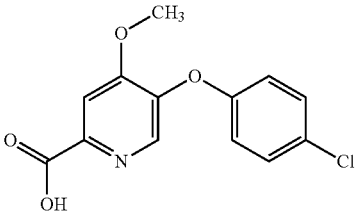 | III | 30 |
| 35 | 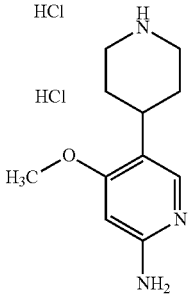 | 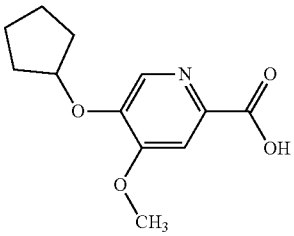 | III | 42 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 36 | 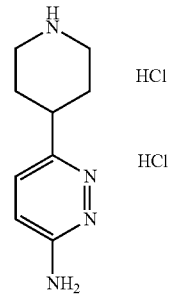 | 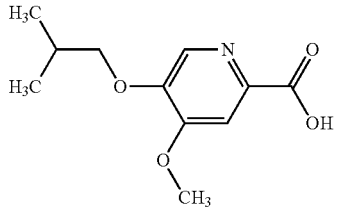 | III | 53 |
| 37 | 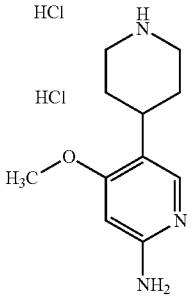 | 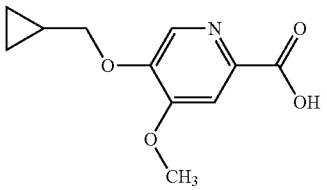 | III | 37 |
| 38 | 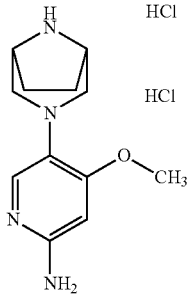 | 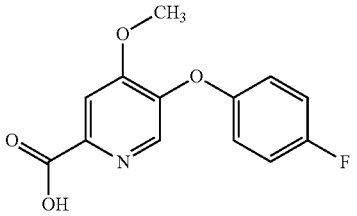 | I | 31 |
| 39 | 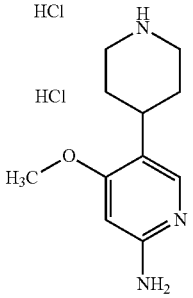 | 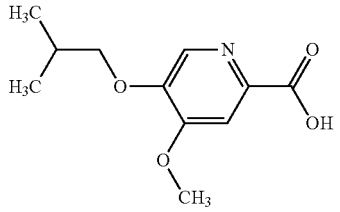 | III | 51 |
| 40 | 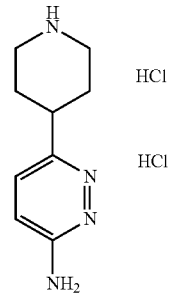 | 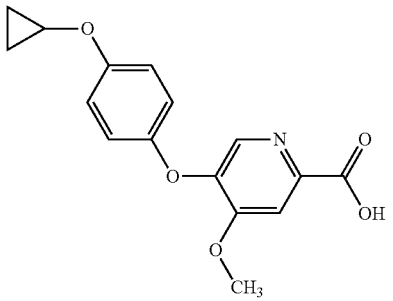 | III | 13 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 41 | 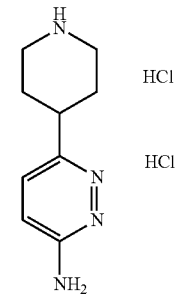 | 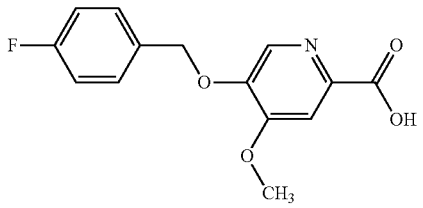 | III | 29 |
| 42 | 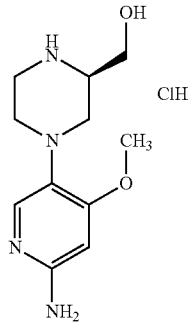 | 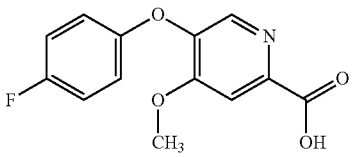 | I | 42 |
| 43 | 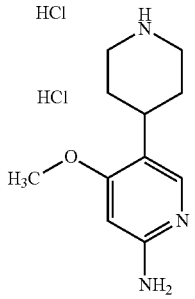 | 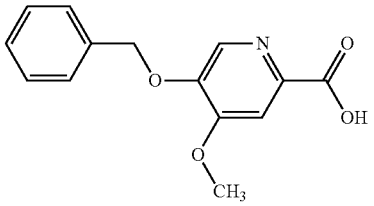 | III | 49 |
| 44 | 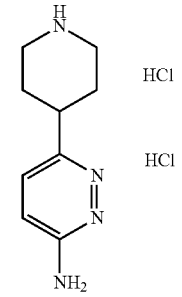 | 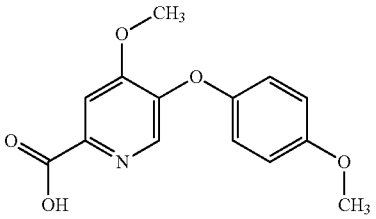 | III | 61 |
| 45 | 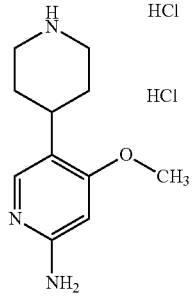 | 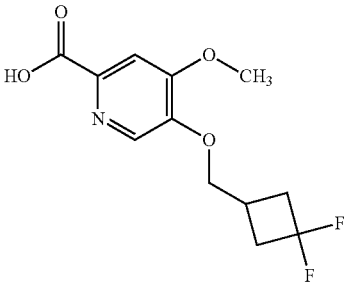 | I | 50 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 46 | 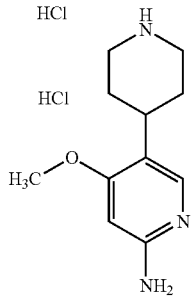 | 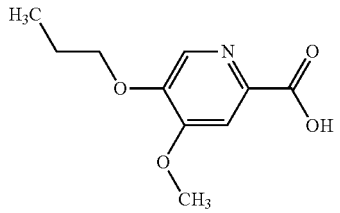 | III | 60 |
| 47 | 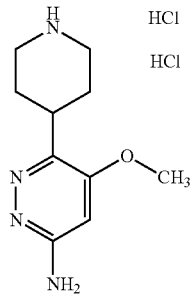 | 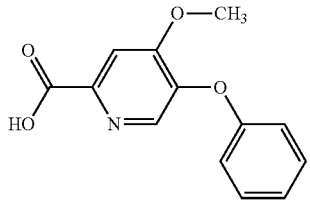 | II | 61 |
| 48 | 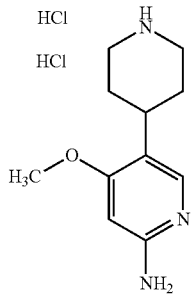 | 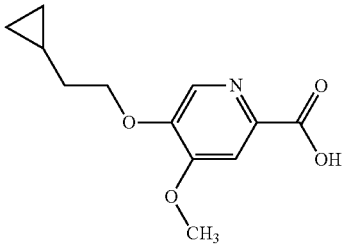 | III | 48 |
| 49 | 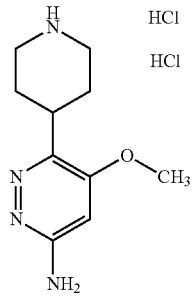 | 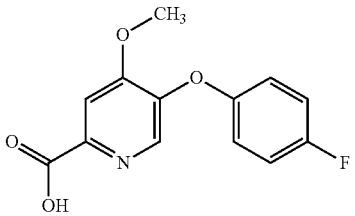 | III | 54 |
| 50 | 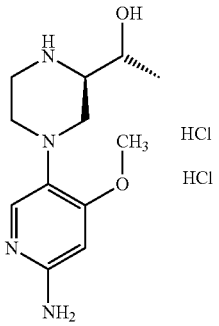 | 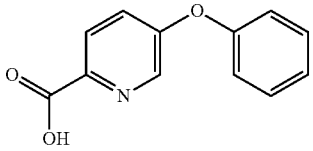 | I | 51 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 51 | 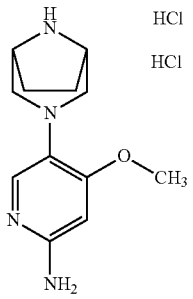 | 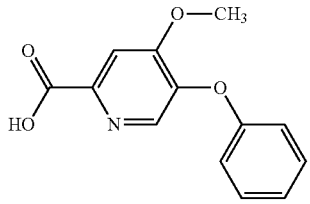 | I | 36 |
| 52 | 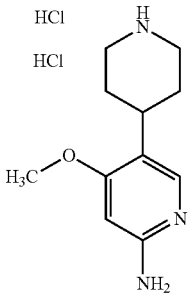 | 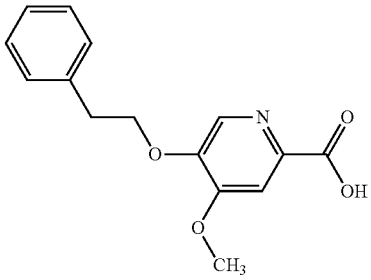 | III | 66 |
| 53 | 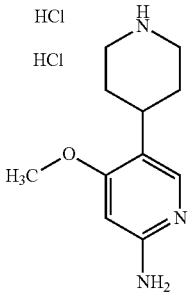 | 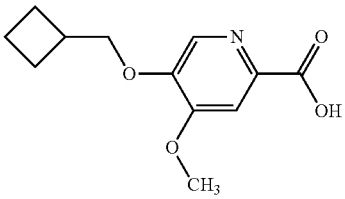 | III | 54 |
| 54 | 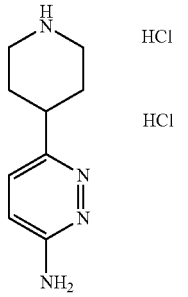 | 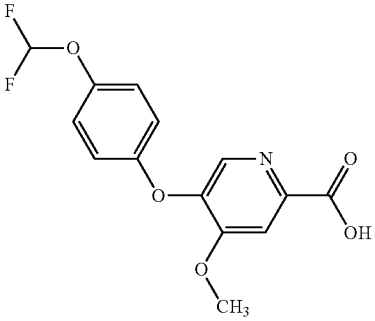 | III | 39 |
| 55 | 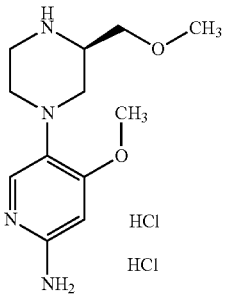 | 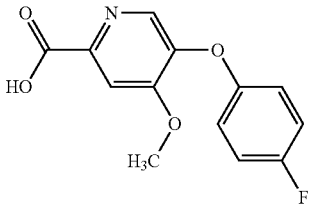 | I | 64 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 56 | 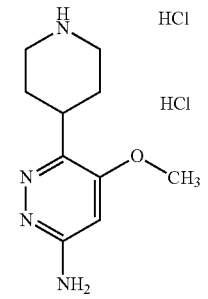 | 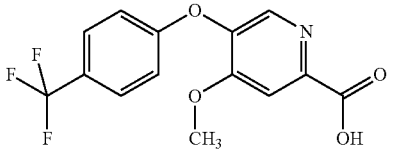 | II | 35 |
| 57 | 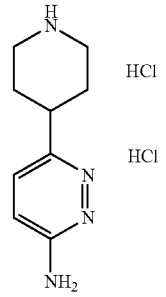 | 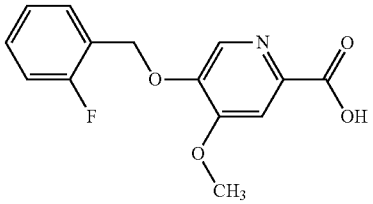 | III | 67 |
| 58 | 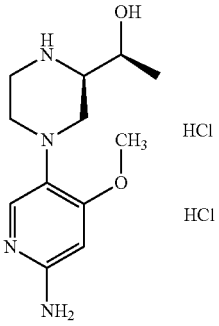 | 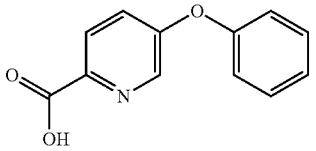 | I | 56 |
| 59 | 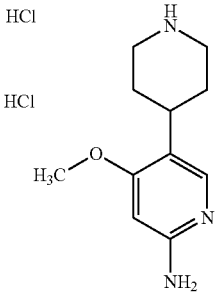 | 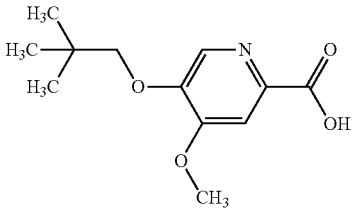 | III | 42 |
| 60 | 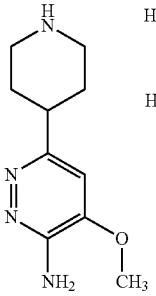 | 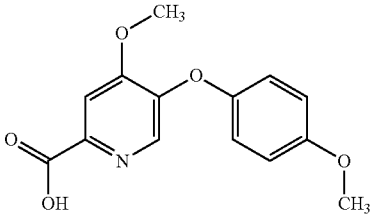 | III | 76 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 61 | 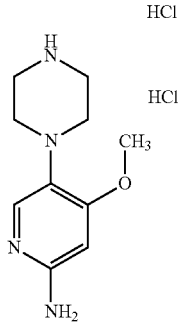 | 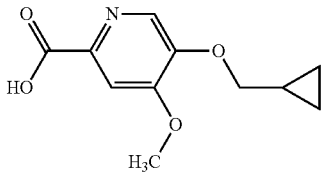 | I | 26 |
| 62 | 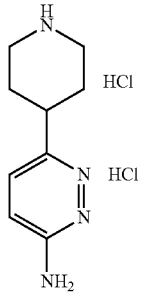 | 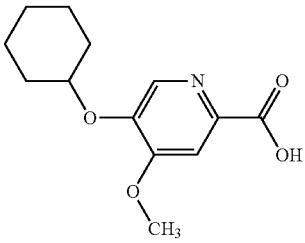 | III | 19 |
| 63 | 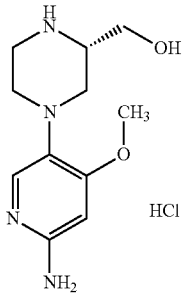 | 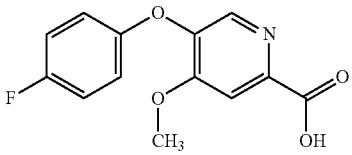 | I | 29 |
| 64 | 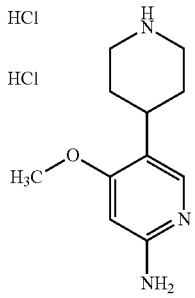 | 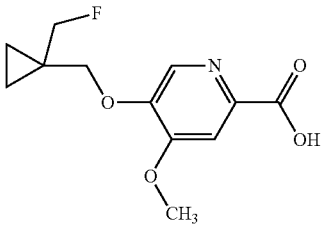 | III | 37 |
| 65 | 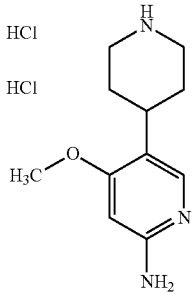 | 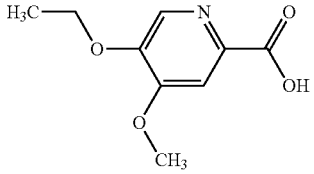 | III | 34 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 66 | 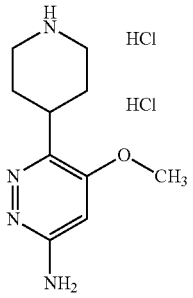 | 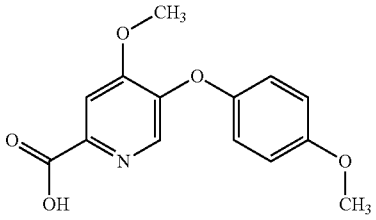 | III | 51 |
| 67 | 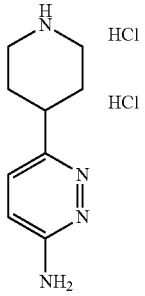 | 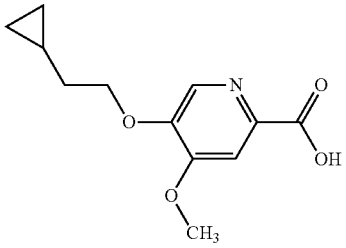 | III | 60 |
| 68 | 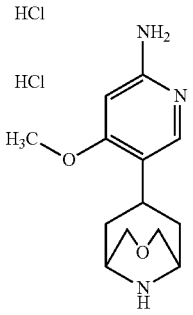 | 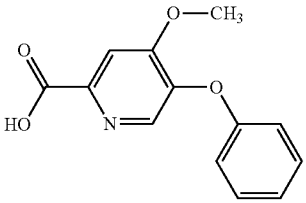 | I | 62 |
| 69 | 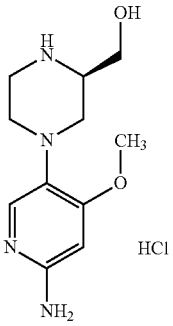 | 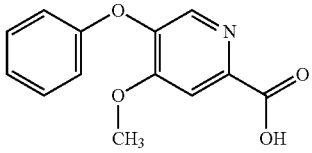 | I | 17 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 70 | 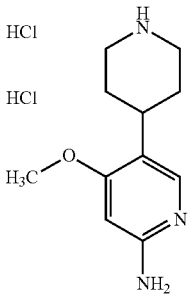 | 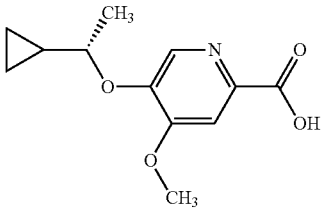 | III | 47 |
| 71 | 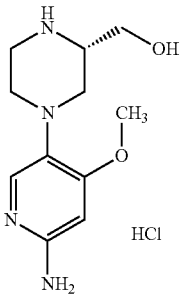 | 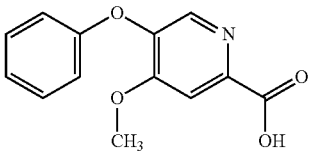 | I | 27 |
| 72 | 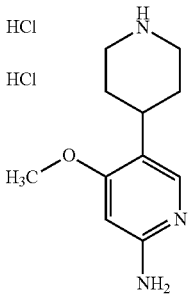 | 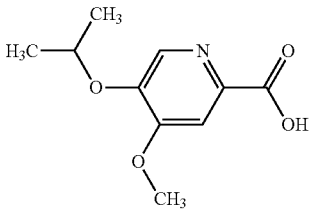 | III | 38 |
| 73 | 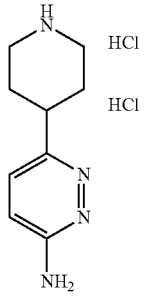 | 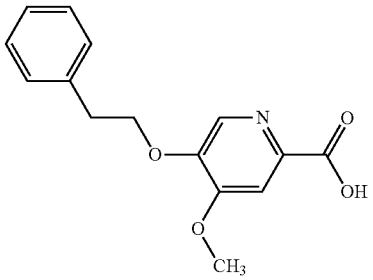 | III | 60 |
| 74 | 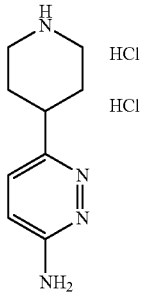 | 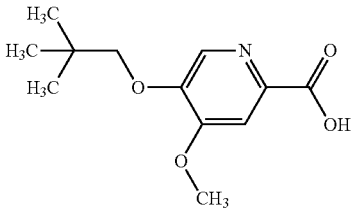 | III | 35 |

TABLE 3A-continued
General procedures for preparing compounds of the invention 1-80.
| Cpd No. | Amine Intermediate | Carboxylic acid Intermediate | Genl. Proc. | Yield % |
|---|---|---|---|---|
| 75 | 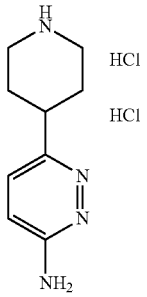 | 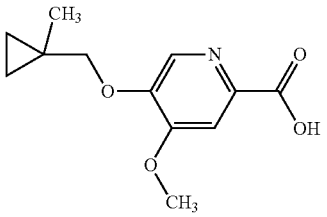 | III | 57 |
| 76 | 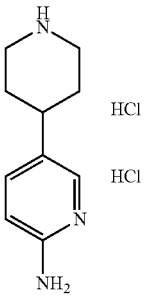 | 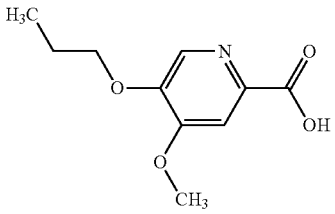 | III | 62 |
| 77 | 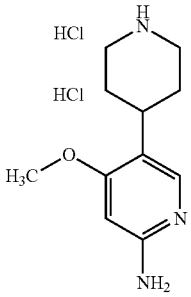 | 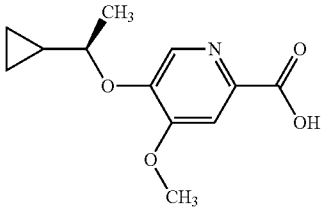 | III | 38 |
| 78 | 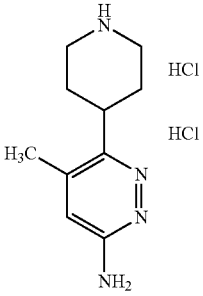 | 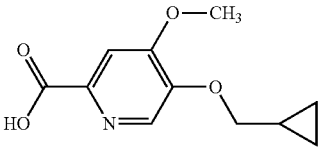 | I | 17 |
| 79 | 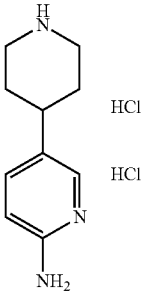 | 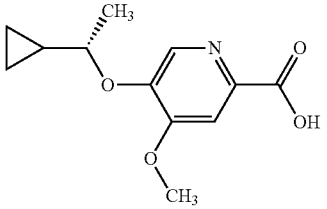 | III | 43 |

TABLE 3A-continued

General procedures for preparing compounds of the invention 1-80.

| Cpd No. | Amine Intermediate | Carboxylic acid Intermediate | Genl. Proc. | Yield % |
|---|---|---|---|---|
| 80 | 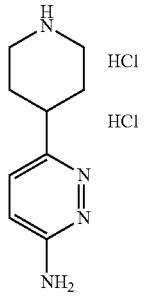 | 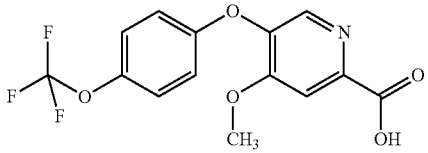 | I | 20 |

TABLE 3B

Analytical data for compounds of the invention 1-80.

| Cpd No. | ESI-MS m/z, M + H$^+$ | HPLC $R_t$ (min.) | HPLC Method |
|---|---|---|---|
| 1 | 454 | 0.47 | 1 |
| 2 | 437 | 1.07 | 5 |
| 3 | 405 | 0.83 | 1 |
| 4 | 453 | 0.86 | 1 |
| 5 | 436 | 0.44 | 1 |
| 6 | 464 | 0.80 | 3 |
| 7 | 468 | 0.44 | 1 |
| 8 | 462 | 1.02 | 5 |
| 9 | 480 | 1.08 | 5 |
| 10 | 419 | 1.02 | 5 |
| 11 | 454 | 0.79 | 1 |
| 12 | 436 | 0.78 | 1 |
| 13 | 424 | 0.80 | 1 |
| 14 | 423 | 0.87 | 1 |
| 15 | 406 | 0.79 | 1 |
| 16 | 406 | 1.52 | 6 |
| 17 | 424 | 1.38 | 2 |
| 18 | 450 | 0.43 | 1 |
| 19 | 467 | 0.90 | 3 |
| 20 | 454 | 0.77 | 1 |
| 21 | 436 | 0.78 | 1 |
| 22 | 435 | 0.83 | 1 |
| 23 | 435 | 0.83 | 1 |
| 24 | 503 | 1.93 | 6 |
| 25 | 398 | 0.75 | 3 |
| 26 | 427 | 0.80 | 3 |
| 27 | 480 | 0.50 | 1 |
| 28 | 465 | 1.02 | 1 |
| 29 | 438 | 1.58 | 2 |
| 30 | 441 | 0.86 | 3 |
| 31 | 420 | 1.48 | 2 |
| 32 | 467 | 0.91 | 3 |
| 33 | 474 | 1.91 | 6 |
| 34 | 440 | 0.83 | 1 |
| 35 | 427 | 0.80 | 3 |
| 36 | 386 | 0.73 | 3 |
| 37 | 413 | 0.71 | 3 |
| 38 | 480 | 0.94 | 5 |
| 39 | 415 | 0.79 | 3 |

TABLE 3B-continued

Analytical data for compounds of the invention 1-80.

| Cpd No. | ESI-MS m/z, M + H$^+$ | HPLC $R_t$ (min.) | HPLC Method |
|---|---|---|---|
| 40 | 462 | 0.80 | 1 |
| 41 | 438 | 0.78 | 3 |
| 42 | 484 | 0.68 | 3 |
| 43 | 449 | 0.81 | 3 |
| 44 | 436 | 0.76 | 1 |
| 45 | 463 | 0.73 | 5 |
| 46 | 401 | 0.73 | 3 |
| 47 | 436 | 1.36 | 2 |
| 48 | 427 | 0.80 | 3 |
| 49 | 454 | 0.84 | 1 |
| 50 | 450 | 0.46 | 1 |
| 51 | 462 | 0.89 | 5 |
| 52 | 463 | 0.85 | 3 |
| 53 | 427 | 0.81 | 3 |
| 54 | 472 | 0.77 | 1 |
| 55 | 498 | 0.51 | 1 |
| 56 | 504 | 1.84 | 6 |
| 57 | 438 | 0.77 | 3 |
| 58 | 450 | 0.49 | 1 |
| 59 | 429 | 0.87 | 3 |
| 60 | 466 | 0.77 | 1 |
| 61 | 414 | 0.70 | 3 |
| 62 | 412 | 0.76 | 1 |
| 63 | 484 | 0.70 | 3 |
| 64 | 445 | 0.74 | 3 |
| 65 | 387 | 0.65 | 3 |
| 66 | 466 | 0.82 | 1 |
| 67 | 398 | 0.74 | 3 |
| 68 | 477 | 0.73 | 5 |
| 69 | 466 | 0.67 | 3 |
| 70 | 427 | 0.78 | 3 |
| 71 | 466 | 0.68 | 1 |
| 72 | 401 | 0.69 | 3 |
| 73 | 434 | 0.79 | 3 |
| 74 | 400 | 0.81 | 3 |
| 75 | 398 | 0.75 | 3 |
| 76 | 372 | 0.66 | 3 |
| 77 | 427 | 0.77 | 3 |
| 78 | 398 | 1.24 | 2 |
| 79 | 398 | 0.71 | 3 |
| 80 | 490 | 2.60 | |

Synthesis of Nitro-intetmediates

[(R)-4-(6-Nitro-pyridin-3-yl)-piperazin-2-yl]-methanol hydrochloride

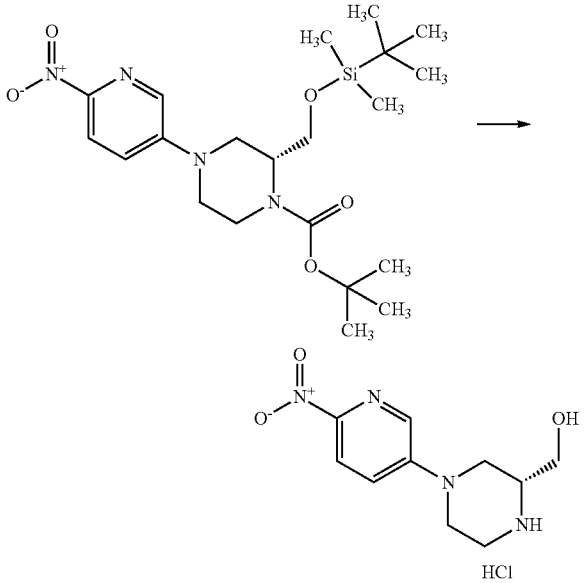

(R)-2-(tert-Butyl-dimethyl-silanyloxymethyl)-4-(6-nitro-pyridin-3-yl)-piperazine-1-carboxylic acid tert-butyl ester (1.73 g, 3.82 mmol) in DCM (10 mL) and 4M HCl (9.55 mL, 38.2 mmol) is stirred at RT for 2 h. The reaction mixture is concentrated under reduced pressure.

Yield: 950 mg (91%)

[(R)-2-Hydroxymethyl-4-(6-nitro-pyridin-3-yl)-piperazin-1yl]-(4-methoxy-5-phenoxy-pyridin-2-yl)-methanone

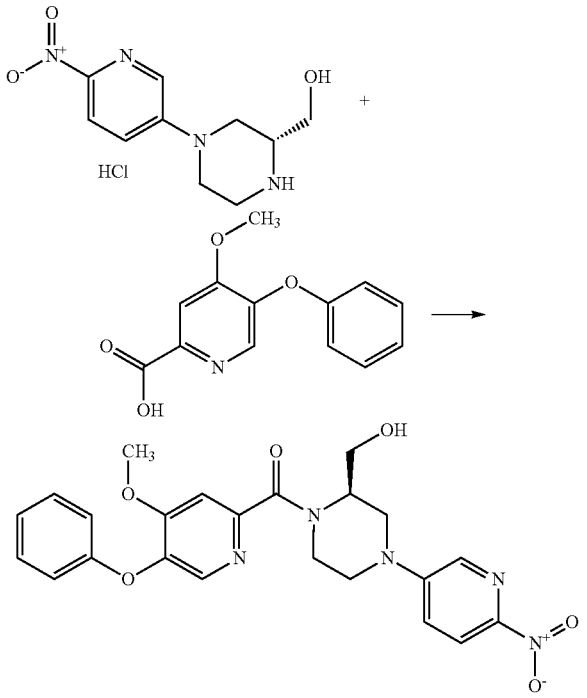

[(R)-4-(6-Nitro-pyridin-3-yl)-piperazin-2-yl]-methanol hydrochloride (60.0 mg, 0.21 mmol) and 4-methoxy-5-phenoxy-pyridine-2-carboxylic acid (42.8 mg, 0.18 mmol) in NMP (5004) with TBTU (70.1 mg, 0.22 mmol) and DIPEA (151 μL, 0.87 mmol) are stirred for 18 h at rt. The reaction mixture is purified by RP colunm chromatography (ACN/water/$NH_4HCO_3$). The residue is purified again by normal phase column chromatography (MeOH/DCM) to give the title compound.

Yield: 95 mg (93%)

[(R)-2-Hydroxymethyl-4-(6-nitro-pyridin-3-yl)-piperazin-1-yl]-[4-methoxy-5-(4-methoxy-phenoxy)-pyridin-2-yl]-methanone

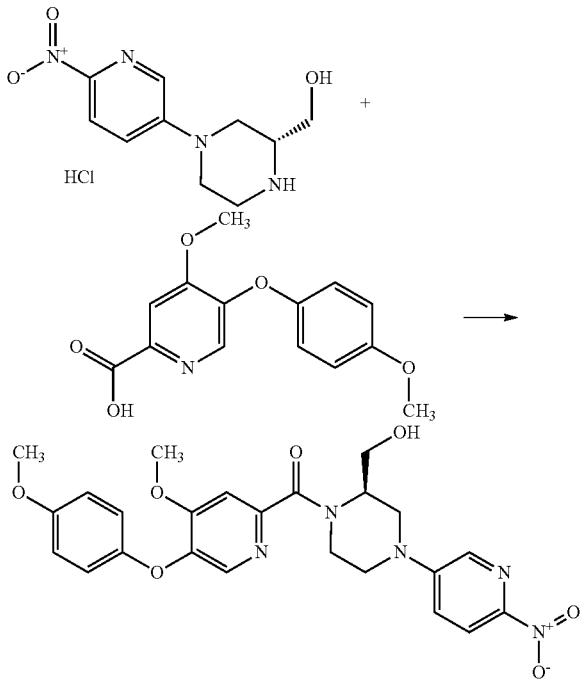

The title compound is synthesized from [(R)-4-(6-nitro-pyridin-3-yl)-piperazin-2-yl]-methanol hydrochloride (60.0 mg, 0.22 mmol) and 4-methoxy-5-(4-methoxy-phenoxy)-pyridine-2-carboxylic acid (48.1 mg, 0.18 mmol) according to the procedure described for the synthesis of the intermediate [(R)-2-hydroxymethyl-4-(6-nitro-pyridin-3-yl)-piperazin-1-yl]-(4-methoxy-5-phenoxy-pyridin-2-yl)-methanone.

Yield: 102 mg (quantiative) ESI-MS: m/z=496 $(M+H)^+$ $R_t$(HPLC): 0/78 min (Method 1) ps Procedure:

IV: Nitro intermediate (1 eq.) and Pd/C (10%) in MeOH is stirred for 20 h at RT under hydrogen atmosphere. The reaction mixture is concentrated under vacuum and purged with argon. The residue is filtered through Celite® and washed with MeOH. The filtrate is concentrated under reduced pressure and the crude product is purified by RP column chromatography (ACN/water, basic or acidic con dition).

TABLE 4

Procedures for preparing compounds of the invention 81 and 82.

| Cpd No. | Nitro-Intermediate | Genl. Proc. | Yield % | ESI-MS m/z M + H+ | HPLC $R_t$(min.) | HPLC Method |
|---|---|---|---|---|---|---|
| 81 | 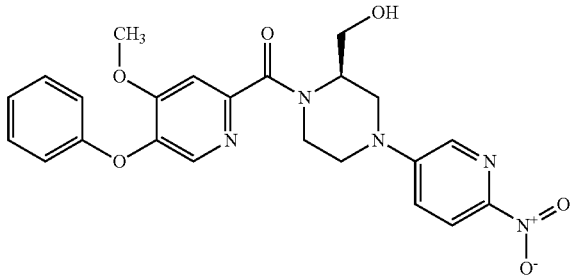 | IV | 47 | 436 | 0.75 | 1 |
| 82 | 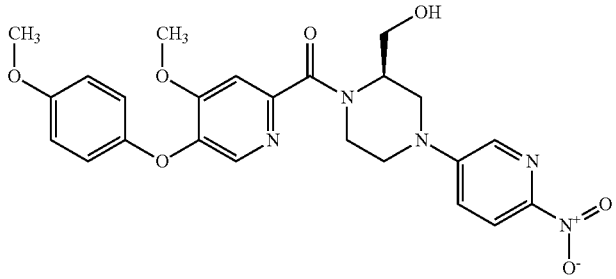 | IV | 36 | 466 | 0.74 | 1 |

Compounds of the invention 83-89 are generally prepared by reacting a carboxylic acid intermediate with an amine intermediate under conditions similar to those described for General Procedure (I) in Table 3A. Analysis of the compounds of the invention 83-89 are summarized in Table 5B.

Synthesis of Intermediates

4-Ethoxy-5-phenoxypicolinonitrile

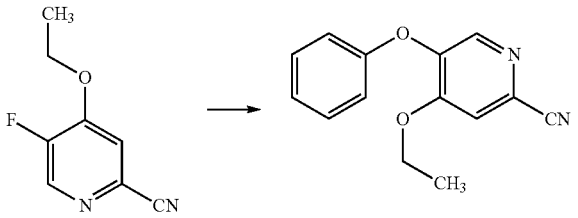

To a solution of 5-fluoro-4-isopropoxypicolinonitrile (500 mg, 3.01 mmol) in DMF (10 mL) stirred at RT under $N_2$ atmosphere, is added phenol (339.85 mg, 3.61 mmol) and $K_2CO_3$ (1.25 g, 9.03 mmol), the resulting mixture is heated to 100° C. for 3 h. The reaction mixture is then diluted with ethyl acetate (50 mL), washed with water and brine, dried over anhydrous $Na_2SO_4$, filtered and concentrated. The residue is purified by column chromatography on silica gel.

Yield: 530 mg (73%) m/z=241 $(M+H)^+$.

4-Ethoxy-5-phenoxypicolinic acid

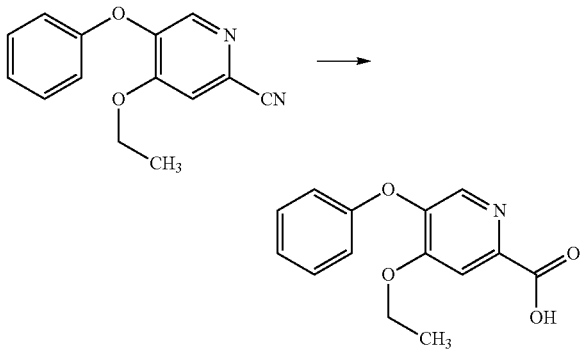

A mixture of 4-ethoxy-5-phenoxypicolinonitrile (530 mg, 2.21 mmol) in 2N sodium hydroxide solution (10 mL) is stirred at 100° C. overnight. The reaction mixture is then acidified by 1N HCl to adjust pH=4 and extracted with DCM (20 mL×2). The combined organic phases are separated and dried over $Na_2SO_4$, filtered and concentrated to give the desired product which can be used without further purification.

Yield: 420 mg (73%) m/z=260 $(M+H)^+$ tert-Butyl 6-amino-4-cyclopropoxy-1',2',3',6'-tetrahydro-[3,4'-bipyridine]-1'-carboxylate

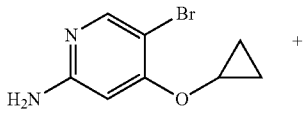

-continued

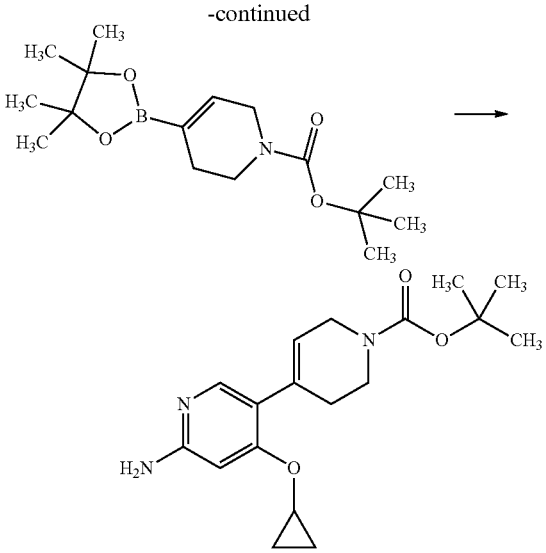

To a stirred mixture of 5-bromo-4-cyclopropoxypyridin-2-amine (2.1 g, 9.17 mmol), 4-(4,4,5,5-tetramethyl-[1,3,2]dioxaborolan-2-yl)-3,6-dihydro-2H-pyridine-1-carboxylic acid tert-butyl ester (4.25 g, 13.75 mmol) and $Cs_2CO_3$ (9.0 g, 27.50 mmol) in dioxane (60 mL) and water (12 mL) at rt under nitrogen atmosphere is added $Pd(dppf)Cl_2$ (200 mg, 0.27 mmol). The resulting mixture is stirred at 90° C. for 4 h. The reaction mixture is then poured into ice water and extracted with DCM (50 mL×3). The combined organic phases are washed with brine, dried over anhydrous $Na_2SO_4$, filtered and concentrated. The residue is purified by column chromatography on silica gel to give the desired product.

Yield: 3 g (98%) m/z=332 $(M+H)^+$.

tert-Butyl 4-(6-amino-4-cyclopropoxypridin-3-yl) piperidine-1-carboxylate

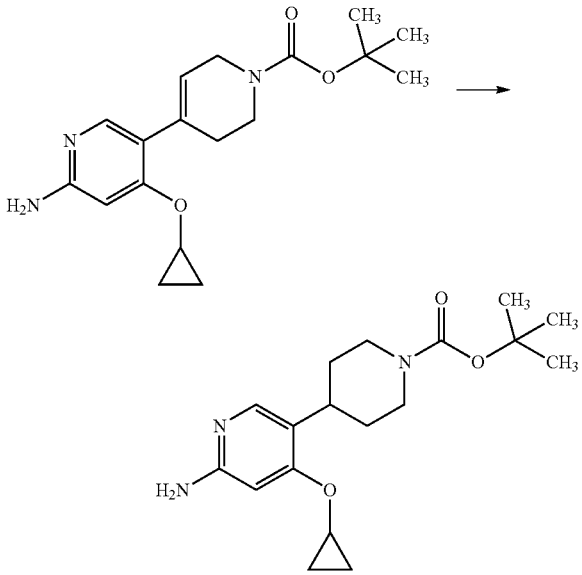

To a solution of tert-butyl 6-amino-4-cyclopropoxy-1',2',3',6'-tetrahydro-[3,4'-bipyridine]-1'-carboxylate (3g, 9.05 mmol) in EtOH (40 mL) is added $Pd(OH)_2/C$ (2 g). The resulting reaction mixture is stirred at 25° C. under hydrogen atmosphere for 16 h. The catalyst is filtered off through Celite®, and the filtrate is evaporated to dryness under reduced pressure. The residue is purified by column chromatography on silica gel to give the desired product.

Yield: 1.8 g (60%) m/z=334 $(M+H)^+$.

4-Cyclopropoxy-5-(piperidin-4-yl)pyridin-2-amine dihydrochloride

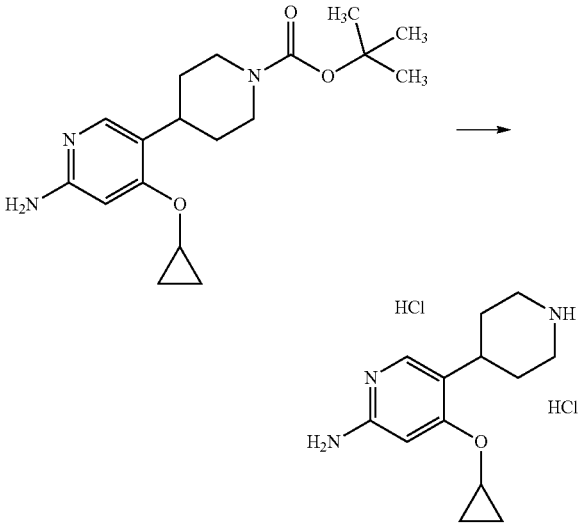

tert-Butyl 4-(6-amino-4-cyclopropoxypyridin-3-yl)piperidine-1-carboxylate (1.6 g. 4.8 mmol) is dissolved in a solution of HCl(g) in EtOH (10 mL). The reaction mixture is stirred at RT for 2 h. After completion of the reaction, the solvent is removed under reduced pressure. The crude product is then triturated with $Et_2O$ to give the desired product which can be used without farther purification.

Yield: 1 g (90%) m/z=234 $(M+H)^+$.

tert-Butyl (4-propoxypyridin-2-yl)carbamate

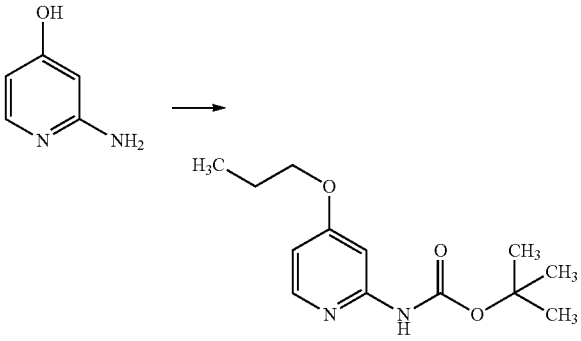

To a stirred solution of 2-aminopyridin-4-ol (1.25 g, 11.4 mmol) in N,N-dimethylacetamide (15 mL) is added cesium carbonate (7.42 g, 22.8 mmol), propylbromide (1.24 mL, 13.6 mmol) and cesium iodide (2.95 g, 11.4 mmol). The resultant mixture is stirred at 100° C. for 1 day. Di-tert-butyl dicarbonate (2.74 g, 12.6 mmol) is added to the reaction mixture and stirred at 100° C. for 16 h. The reaction mixture is diluted with water (20 mL) and extracted with EtOAc (50 mL). Phases are separated and the organic layer is concentrated. The crude mixture is purified by column chromatography on silica gel to afford the desired product Yield: 787 mg (27%) m/z=253 $(M+H)^+$.

tert-Butyl
(5-bromo-4-propoxypyridin-2-yl)carbamate

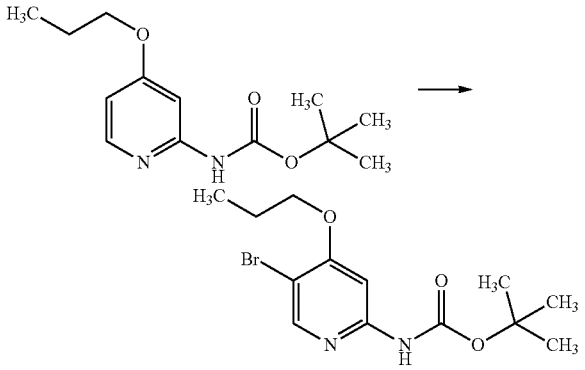

To a stirred solution of tert-butyl (4-propoxypyridin-2-yl) carbamate (0.79 g, 3.11 mmol) in acetic acid (5 mL) is added bromine (0.40 g, 2.49 mmol, in 1 mL of acetic acid) drop-wise at 0° C. After 0.5 h an additional amount of acetic acid (8 mL) is added and the reaction mixture is allowed to warm up to room temperature. After 1 h, the mixture is concentrated and purified by column chromatography on silica gel to the desired product, Yield: 255 mg (31%) m/z=331 $(M+H)^+$.

tert-Butyl 6-{[(tert-butoxy)carbonyl]amino}-4-p ropoxy-1',2',3',6'-tetrahydro-[3,4'-bipyridine]-1'-carboxylate

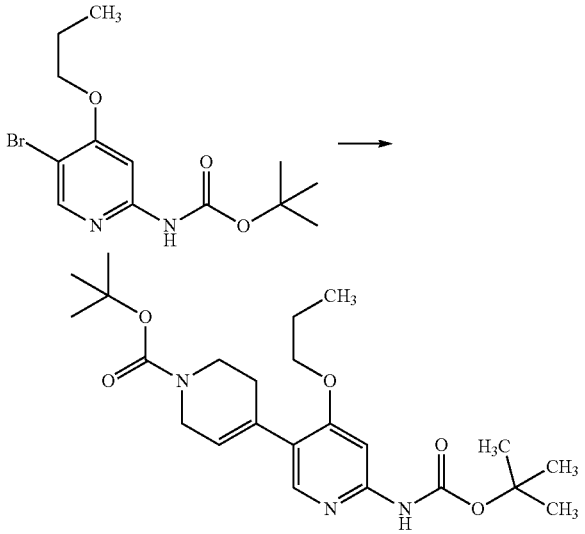

To a solution of tert-butyl (5-bromo-4-propoxypyridin-2-yl)carbamate (254 mg, 0.77 mmol) in dioxane (4 mL) is added 4-(4,4,5,5-tetramethyl-[1,3,2]dioxaborolan-2-yl)-3,6-dihydro-2H-pyridine-1-carboxylic acid tert-butyl ester (596 mg, 1.93 mmol), sodium carbonate (2M aqueous solution, 0.77 mL) and [1,1'-bis(diphenylphosphino)ferrocene]-dichloropalladium(II) (56 mg, 0.077 mmol). The reaction mixture is stirred at 100° C. for 24 h. The reaction mixture is diluted with EtOAc (10 mL) and filtered through a pad of SuperCell filtration agent. The filtrate is concentrated and purified by column chromatography on silica gel to afford the desired product.

Yield: 333 mg (quantitative) m/z=434 $(M+H)^+$.

tert-Butyl 4-(6-((tert-butoxycarbonyl)amino)-4-proxypyridin-3-yl)piperidine-1-carboxylate

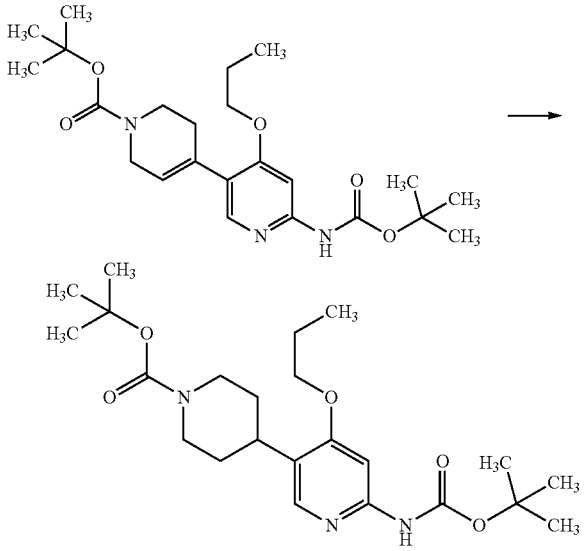

To tert-butyl 6-{[(tert-butoxy)carbonyl]amino}-4-propoxy-1',2',3',6'-tetrahydro-[3,4'-bipyridine]-1'-carboxylate (333 mg, 0.77 mmol) in EtOH (18 mL) and EtOAc (3 mL) is added palladium hydroxide on carbon (20% wet, 27 mg). The reaction mixture is stirred under a hydrogen atmosphere (43 psi) for 3 days and filtered through SuperCell filtration agent. The filtrate is concentrated under reduced pressure to afford the desired product.

Yield: 330 mg (98%) m/z=436 $(M+H)^+$.

5-(Piperidin-4-yl)-4-propoxypyridin-1-amine dihydrochloride

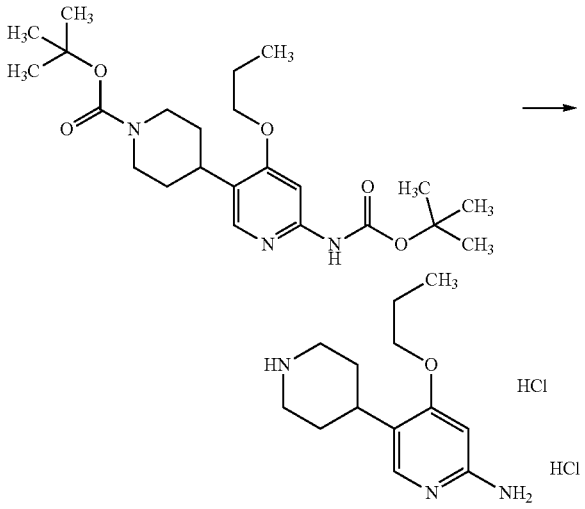

To tert-butyl 4-(6-((tert-butoxycarbonyl)amino)-4-propoxypyridin-3-yl)piperidine-1-carboxylate (330 mg, 0.76 mmol) in dichloromethane (2 mL) is added a solution is of HCl in dioxane (2.00 mL, 4M, 8.0 mmol). The reaction mixture is stirred for 16 h and concentrated. The residue is triturated with DCM and dried under vacuum to afford the desired product.

Yield: 233 mg quantitative.

4-Ethoxy-5-(piperidin-4-yl)pyridin-2-amine dihydrochloride

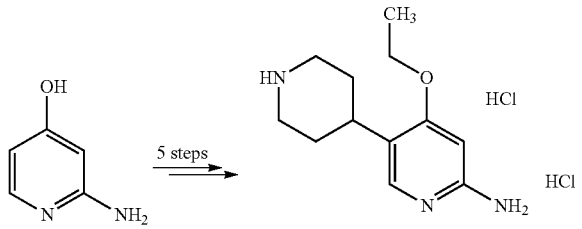

4-Ethoxy-5-(piperidin-4-yl)pyridin-2-amine dihydrochloride can be synthesized analogous to the protocol for the synthesis of 5-(piperidin-4-yl)-4-propoxypyridin-2-amine dihydrochloride, Alkylation of 2-aminopyridin-4-ol with ethylbromide and subsequent Boc protection leads to the formation of tert-butyl N-(4-ethoxypyridin-2-yl)carbamate. Bromination of tert-butyl N-(4-ethoxypyridin-2-yl)carbamate leads to the synthesis of tert-butyl (5-bromo-4-ethoxypyridin-2-yl)carbamate. Subsequent reaction with 4-(4,4,5,5-tetramethyl-[1,3,2]dioxaborolan-2-yl)-3,6-dihydro-2H-pyridine-1-carboxylic acid tert-butyl ester leads to the formation of tert-butyl 6-{[(tert-butoxy)carbonyl]amino}-4-ethoxy-1',2',3',6'-tetrahydro-[3,4'-bipyridine]-1'-carboxylate. In the next step tert-butyl 4-(6-((tert-butoxycarbonyl)amino)-4-ethoxypyridin-3-yl)piperidine-1-carboxylate is obtained via hydrogenation. Cleavage of the Boc protecting group leads to the synthesis of 4-ethoxy-5-(piperidin-4-yl)pyridin-2-amine dihydrochloride.

tert-Butyl 3-(6-aminopyridazin-3-yl)-8-azabicyclo[3.2.1]oct-2-ene-8-carboxylate

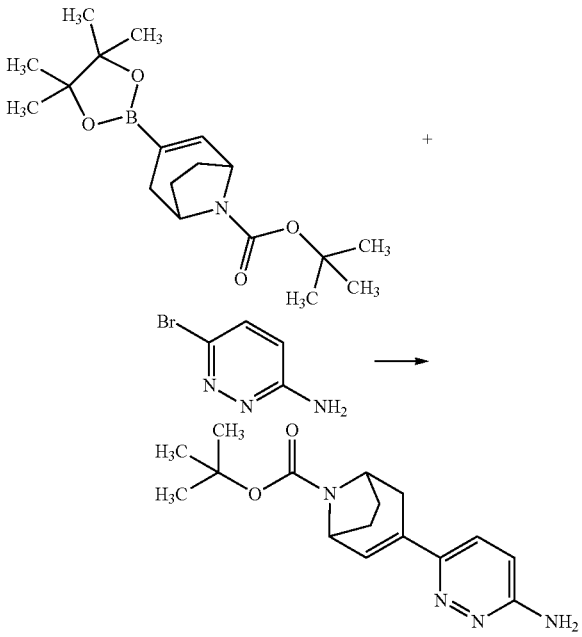

To tert-butyl 3-(4,4,5,5-tetramethyl-1,3,2-dioxaborolan-2-yl)-8-azabicyclo[3.2.1]-oct-2-ene-8-carboxylate (1.93 g, 5.75 mmol) and 6-bromopyridazin-3-amine (1.00 g, 5.75 mmol) in 1,4-dioxane (25 mL) is added 2M aq. $Na_2CO_3$ solution (11.5 mL, 23.0 mmol) and Xphos 2$^{nd}$ generation catalyst (136 mg, 0.17 mmol), The reaction mixture is degassed with argon and stirred at 100' C. for 2 h. All volatiles are evaporated under reduced pressure. The crude material is purified by normal phase chromatography to obtain the title compound.

Yield: 0.80 g (46%) ESI-MS: m/z=303 $(M+H)^+$ tert-Butyl-3-(6-arninopyridazin-3-yl)-8-azabicyclo[3.2.1]octane-8-carboxylate

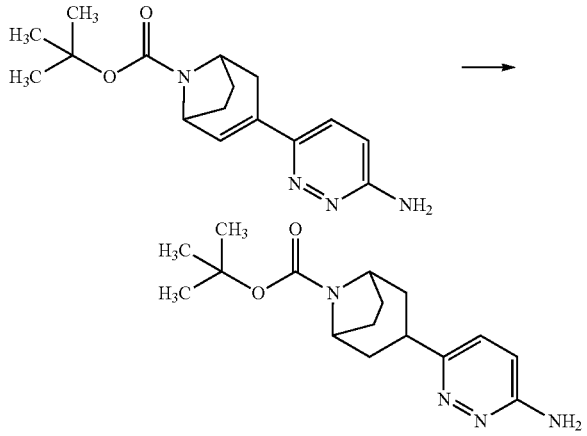

To tert-butyl 3-(6-aminopyridazin-3yl)-8-azabicyclo[3.2.1]oct-2-ene-8-carboxylate (0.80 g, 2.65 mmol) in MeOH (30 mL) is added Pd/C (250 mg) under nitrogen. The reaction mixture is degassed and hydrogenated at 3 bar hydrogen atmosphere at RT overnight. The reaction mixture is filtered and concentrated under reduced pressure.

Yield: 800 mg (quantitative) ESI-MS: m/z=305 $(M+H)^+$

6-{8Azabicyclo[3.2.1]octan-3-yl}pyridazin-3-amine dihydrochloride

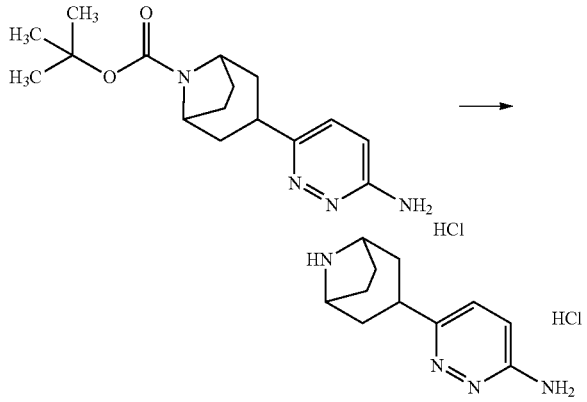

To tert-butyl 3-(6-aminopyridazin-3-yl)-8-azabicyclo[3.2.1]octane-8-carboxylate (800 mg, 2.63 mmol) in an appropriate volume of DCM is added 4M HCl in 1,4 dioxane and stirred at RT until reaction is completed. All volatiles are evaporated under reduced pressure.

Yield: 700 mg (96%) ESI-MS: m/z=205 $(M+H)^+$

2-Chloro-5-fluoro-4-methoxypyridine

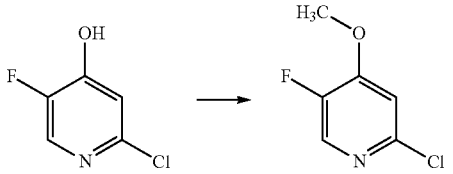

To 2-chloro-5-fluoropyridin-4-ol (1 g, 7.05 mmol) and $K_2CO_3$ (1.27 g, 9.16 mmol) in DMF (10 mL) is added iodomethane (1.15 g, 8.13 mmol) at room temperature. The resulting reaction mixture is stirred at RT for 2 h. The reaction mixture is diluted with water (20 mL) and extracted with EtOAc (30 mL×2). The combined organic phases are washed with water and brine, dried over anhydrous $Na_2SO_4$, filtered and concentrated under reduced pressure. The residue is purified by column chromatography on silica gel to give the desired product.

Yield: 1 g (91%) m/z=162 $(M+H)^+$

5-Fluoro-4-methoxypicolinonitrile

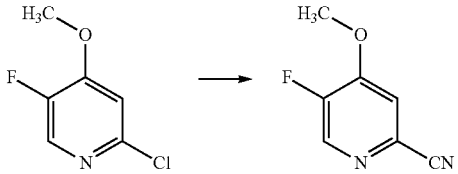

To 2-chloro-5-fluoro-4-methoxypyridine (1.0 g, 6.2 mmol), zinc cyanide (800 mg, 6.8 mmol) and dppf (34 mg, 0.62 mmol) in DMF (10 mL) stirred at RT under nitrogen atmosphere, is added $Pd2(dba)_3$ (56 mg, 0.62 mmol). The reaction mixture is stirred at 150° C. under a nitrogen atmosphere for 3 h. The reaction mixture is then diluted with water (30 mL)) and extracted with EtOAc (30 mL×2). The combined organic phases are washed with water and brine, dried over anhydrous $Na_2SO_4$, filtered and concentrated under reduced pressure. The residue is purified by column chromatography on silica gel to give the desired product.

Yield: 700 mg (74%) m/z=153 $(M+H)^+$.

4-Methoxy-5-(4-(trifluoromethyl)phenoxy)picolinonitrile

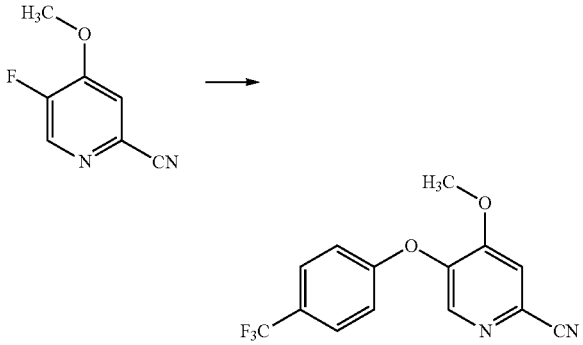

To 5-fluoro-4-methoxypicolinonitrile (700 mg, 4.6 mmol) in DMF (10 mL) is added 4-(trifluoromethyl)phenol (746 mg, 4.6 mmol) and (636 mg, 4.6 mmol). The reaction mixture is stirred at 100° C. for 16 h. The reaction mixture is diluted with water (20 mL) and extracted with EtOAc (20 mL×2). The combined organic phases are combined, washed with water and brine, dried over anhydrous $Na_2SO_4$, filtered and concentrated under reduced pressure. The residue is purified by column chromatography on silica gel to give the desired product.

Yield: 1 g (80%) m/z=295 $(M+H)^+$.

4-Methoxy-5-(4-(trifluoromethyl)phenoxy)picolinic acid

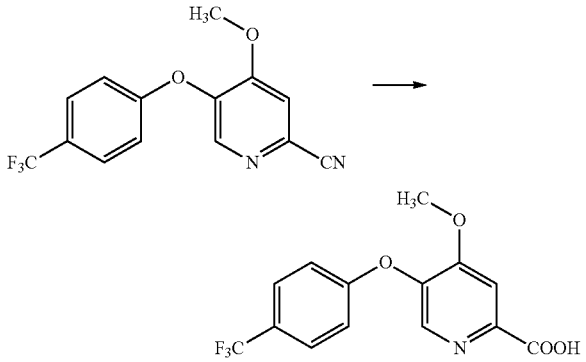

To a solution of NaOH (1.6 g, 40 mmol) in water (20 mL) is added 4-methoxy-5-(4-(trifluoromethyl)phenoxy)picolinitrile (700 mg, 2.4 mmol). The reaction mixture is stirred at 100° C. overnight. The reaction mixture is acidified by 6M HCl to adjust pH=2, extracted with EtOAc (30 mL×2). The combined organic phases are washed with water and brine, is dried over anhydrous $Na_2SO_4$, filtered and concentrated under reduced pressure to give the crude product which can be used directly without further purification;

Yield: 700 mg (94%) m/z=314 $(M+H)^+$.

2-Chloro-5-fluoropyridin-4-ol

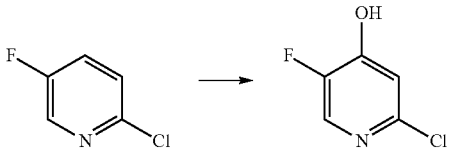

Under a nitrogen atmosphere at −78° C. to a stirred solution of 2-chloro-5-fluoropyridine (5.0 g, 38 mmol) in tetrahydrofuran (50 mL), is added lithium diisopropylamide (24.7 mL, 49.4 mmol, 2M in tetrahydrofuran) drop-wise over 30 min. The reaction mixture is stirred at −78° C. for 2 h. Afterwards a solution of trimethyl borate (7.9 g, 76.03 mmol) in tetrahydrofuran (10 mL) is added drop-wise over 20 min. After addition, the reaction mixture is stirred at RT for another 2 h. The reaction mixture is cooled to 0° C. and acetic acid (6.5 mL) is added. The reaction mixture is stirred at 0° C. for 30 min. Hydrogen peroxide (11.5 mL, 30% solution) is added drop-wise at 0° C. The reaction mixture is stirred at RT overnight. The reaction mixture is quenched with saturated aqueous $NaS_2O_4$. 5N HCl is added to the reaction mixture. After extraction with EtOAc (50 mL×3), the combined organic phases are washed with water and brine, dried over anhydrous $Na_2SO_4$, filtered and concentrated under reduced pressure. The residue is purified by silica gel chromatography to give the desired product.

Yield: 3.8 g (68%). m/z=149 $(M+H)^+$.

2-Chloro-4-ethoxy-5-fluoropyridine

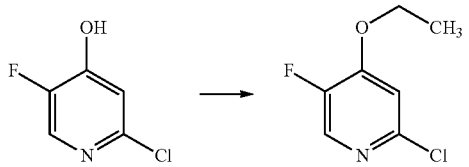

To 2-chloro-5-fluoropyridin-4-ol (2, 3.0 g, 20.33 mmol) and silver(I) carbonate (8.4 g, 30.50 mmol) is DMF (50 mL) is added iodoethane (9.51 g, 61.00 mmol) at 0° C., under a nitrogen atmosphere. The reaction mixture is stirred at room temperature for 3 h. The reaction mixture is then diluted with ethyl acetate (100 mL) and washed with water and brine, dried over anhydrous $Na_2SO_4$, filtered and concentrated under reduced pressure. The residue is purified by column chromatography on silica gel to give the desired product.

Yield: 3.0 g (84%) m/z=177 $(M+H)^+$.

4-Ethoxy-5-fluoropicolinonitrile

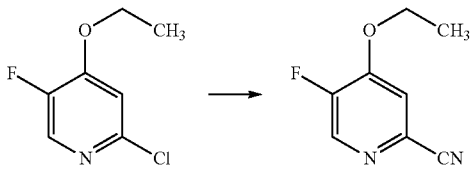

To 2-chloro-4-ethoxy-5-fluoropyridine (300 mg, 1.71 mmol) in DMF (10 mL) is added dicyanozinc (141 mg, 1.2 mmol), zinc (22.3 mg, 0.34 mmol) and $Pd(dppf)Cl_2$ (50 mg) under a nitrogen atmosphere. The reaction mixture is stirred at 150° C. for 3 h. The reaction mixture is diluted with ethyl acetate (50 mL), washed with water and brine, dried over anhydrous $Na_2SO_4$, filtered and concentrated under reduced pressure. The residue is purified by column chromatography on silica gel to give the desired product.

Yield: 220 mg (78%) LC-MS: m/z 167 $[M+H]^+$.

4-Ethoxy-5-(4-fluorophenoxy)picolinonitrile

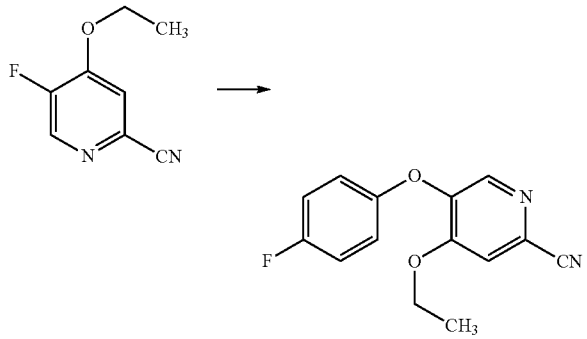

To 4-fluorophenol (202 mg, 1.81 mmol) and $K_2CO_3$ (249 mg, 1.81 mmol) in DMF (5 mL) is added 4-ethoxy-5-fluoropicolinonitrile (200 mg, 1.2 mmol) in one portion. The reaction mixture is stirred at 100° C. for 3 h. After cooling, the reaction mixture is diluted with ethyl acetate (20 mL), washed with water and brine, dried over anhydrous $Na_2SO_4$, filtered and concentrated under reduced pressure. The residue is purified by column chromatography on silica gel to give the desired product.

Yield: 220 mg (71%) m/z=259 $(M+H)^+$.

4-Ethoxy-5-(4-fluorophenoxy)picolinic acid

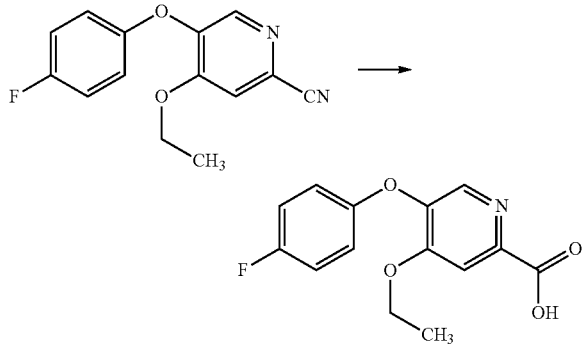

A mixture of 4-ethoxy-5-(4- fluorophenoxy)picolinonitrile (500 mg, 1.94 mmol) in an aqueous 2N sodium hydroxide solution (10 mL) is stirred at 100° C. overnight. After cooling, the reaction mixture is acidified by aqueous 1N HCl to adjust pH=4 and extracted with DCM (20 mL×2). The combined organic phases are washed with water and brine, dried over anhydrous $Na_2SO_4$, filtered and concentrated under reduced pressure to give the crude desired product.

Yield: 490 mg (91%) m/x=278 $(M+H)^+$.

TABLE 5A

Procedures for preparing compounds of the invention 83-89.

| Cpd No. | Amine Intermediate | Carboxylic acid Intermediate | Genl. Proc. | Yield % |
|---|---|---|---|---|
| 83 | 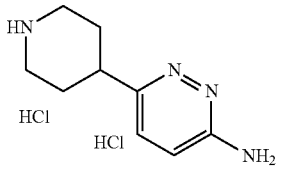 | 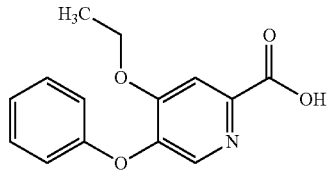 | I | 32 |

TABLE 5A-continued

Procedures for preparing compounds of the invention 83-89.

| Cpd No. | Amine Intermediate | Carboxylic acid Intermediate | Genl. Proc. | Yield % |
|---|---|---|---|---|
| 84 | 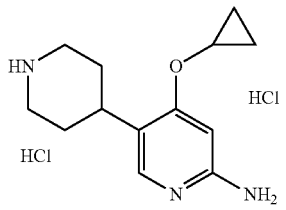 | 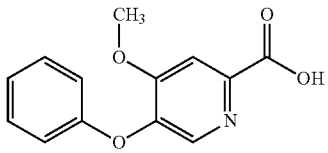 | I | 33 |
| 85 | 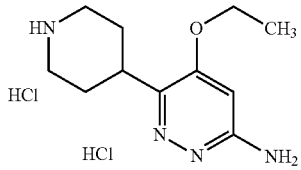 | 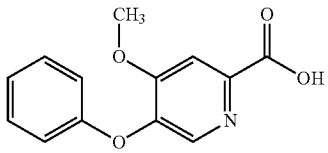 | I | 66 |
| 86 | 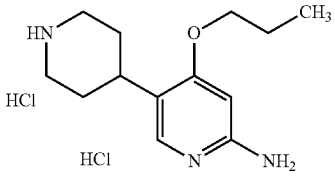 | 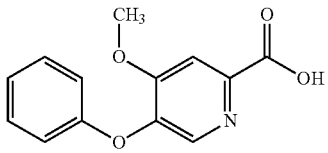 | I | 20 |
| 87 | 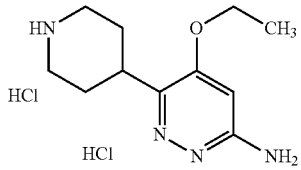 | 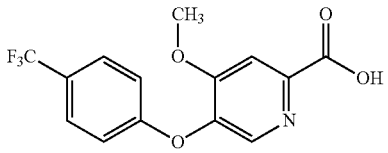 | I | 18 |
| 88 | 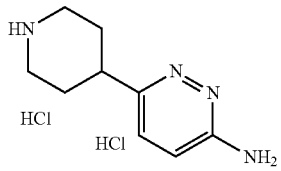 | 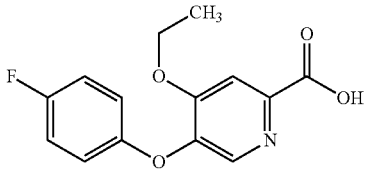 | I | 21 |
| 89 | 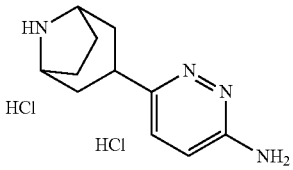 | 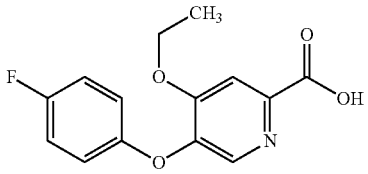 | I | 15 |

TABLE 5B

Analytical data for compounds of the invention 83-89.

| Cpd No. | ESI-MS m/z, M + H$^+$ | HPLC $R_t$ (min.) |
|---|---|---|
| 83 | 420 | 0.79 |
| 84 | 461 | 0.84 |
| 85 | 450 | 0.83 |
| 86 | 463 | 0.84 |
| 87 | 518 | 0.97 |
| 88 | 438 | 0.80 |
| 89 | 465 | 0.82 |

General Procedures:

Procedures for preparing compounds of the invention 90 and 91 are summarized in Table 6A. Analysis of the compounds of the invention 90 and 91 are summarized in Table 6B.

V: To carboxylic acid (1.0 eq.) (intermediate 2 in the following table 6A) in DMF is added DIPEA (3.0 eq.) and HATU (1.0 eq.) and the reaction mixture is stirred for 30 min at rt. Amine (1.0 eq) (intermediate 1 in the following table 6A) is added and the reaction mixture is stirred overnight. The filtered reaction mixture is purified by RP column chromatography (ACN/water+TFA or basic conditions).

TABLE 6A

General procedures for preparing compounds of the invention 90 and 91.

| Cpd No. | amine (intermediate1) | carboxylic acid (intermediate 2) | Gen. Proc. | Yield % |
|---|---|---|---|---|
| 90 | 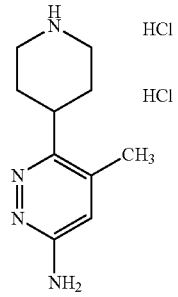 | 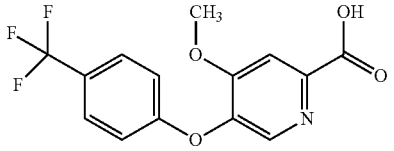 | V | 55 |
| 91 | 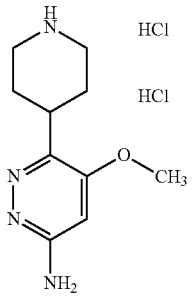 | 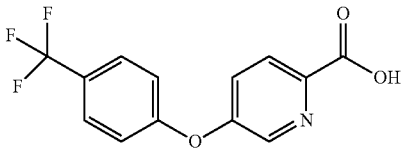 | V | 31 |

TABLE 6B

Analytical data for compounds of the invention 90 and 91.

| Cpd No. | ESI-MS m/z, M + H+ | HPLC $R_t$ (min.) |
|---|---|---|
| 90 | 488 | 0.86 (Method 7) |
| 91 | 474 | 0.87 (Method 7) |

Compounds 92 and 93

TFA salt of 4-Methoxy-5-[1-(4methoxy-5-{[3-(trifluoromethyl)-cyclobutyl]methoxy}-pyridine-2-carbonyl)piperidin-4-yl]pyridin-2-amin

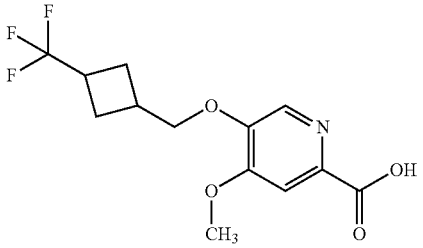

+

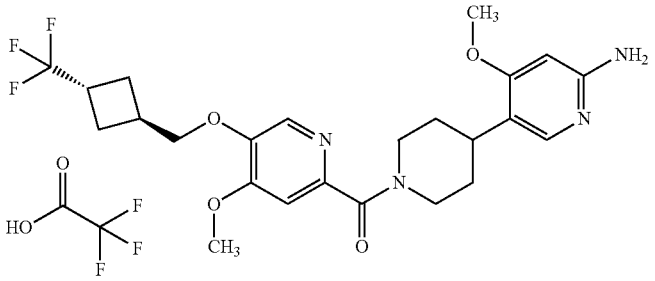

+

-continued

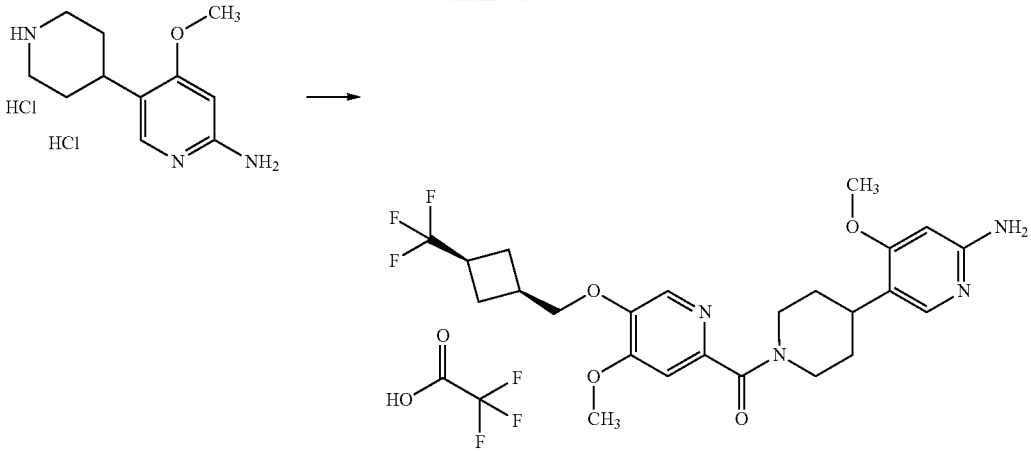

4-Methoxy-5-(3-trifluoromethyl-cyclobutylmethoxy) pyridine-2-carboxylic acid (40 mg, 0.13 mmol), DIPEA (113 μL, 0.66 mmol), HATU (54 mg, 0.144 mmol) and 4-methoxy-5-(piperidin-4-yl)pyridin-2-amine dihydrochloride (37 mg, 0.13 mmol) in DMF (2 mL) are stirred overnight at rt. The reaction mixture is purified by RP column chromatography (ACN/water+TFA) to obtain both stereoisomers.

Yield: compound 92 (trans isomer): 5 mg (6%) HPLC 0.50 min (method 12) and compound 93 (cis isomer): 8 mg (10%) HPLC $R_t$: 0.48 min (method 12), ESI-MS: m/z=495 $(M+H)^+$ Compound 94

4-Methoxy-5-{1-[4-methoxy-5-(3,3,3-trifluoro-2-methylpropoxy)pyridine-2-carbonyl]piperidin-4-yl}pyridin-2-amine

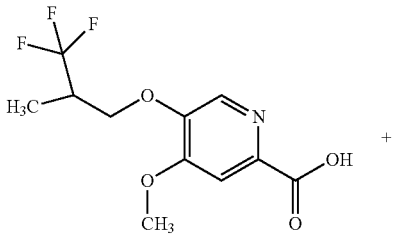

-continued

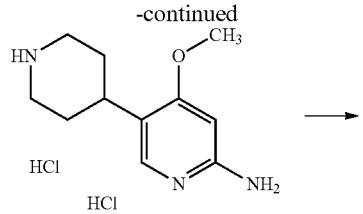

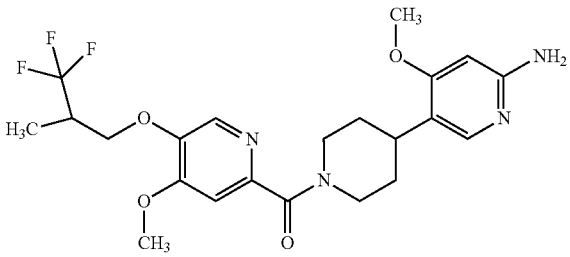

4-Methoxy-5-(3,3,3-trifluoro-2-methylpropoxy)pyridine-2-carboxylic acid (110 mg, 0.39 mmol), DIPEA (271 μL, 1.58 mmol), HATU (150 mg, 0.39 mmol) and 4-methoxy-5-(piperidin-4-yl)pyridin-2-amine dihydrochloride (121 mg, 0.43 mmol) in DMF (2 mL) are stirred 2 h at rt. The reaction mixture is purified by RP column chromatography.

Yield: 110 mg (60%) ESI-MS: m/z=469 $(M+H)^+$ HPLC $R_t$: 0.71 min (method 13)

Enantiomers of 4-Methoxy-5-(1-{4-methoxy-5-[3,3,3-trifluoro-2-methylpropoxy]pyridine-2-carbonyl}piperidin-4-yl)-pyridin-2-amine (94)

4-Methoxy-5-(1{4-methoxy-5-[2S)-3,3,3-trifluoro-2-methylpropoxyl]pyridine-2-carbonyl}piperidin-4-yl)-pyridin-2-amine and 4-Methoxy-5-(1-{4-methoxy-5-[(2R)-3,3,3-trifluoro-2-methylpropoxy]pyridine-2-carbonyl}piperidin-4-yopyridin-2-amine

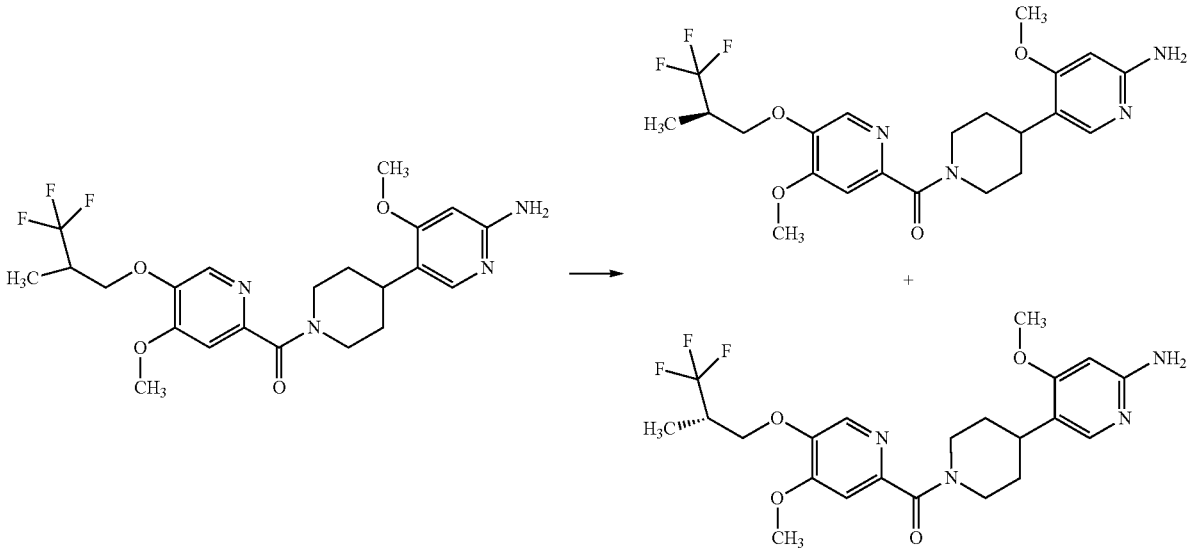

4-Methoxy-5-{1-[4-methoxy-5-(3,3,3-trifluoro-2-methylpropoxy)pyridine-2-carbonyl]piperidin-4-yl}pyridin-2-amine (292 mg, 0.62 mmol) is further separated by chiral supercritical fluid chromatography (SFC, supercritical carbonidioxide 20 mM $NH_3$ in EtOH, Chiral ART®, Amylose-SC 20×250 mm, 5 μM) to obtain both enantiomers 94a (first eluting fraction) and 94b (second eluting fraction). The stereochemistry is randomly assigned.

Yield: 70 mg (48%, compound 94a; $R_t$: 5.69 min) and 74 mg (50%, compound 94b; $R_t$: 6.23 min)

5-Hydroxy-4-methoxypyridine-2-carboxylic acid

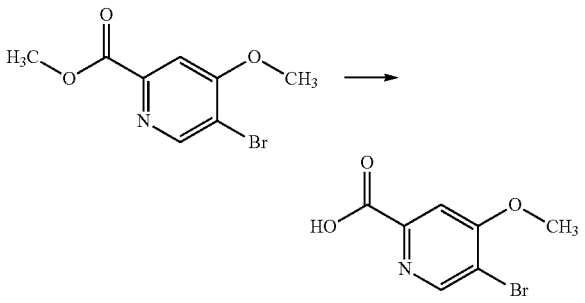

Potassium hydroxide (6.28 g, 111.98 mmol) in 50 ml water is added to methyl 5-bromo-4-methoxypyridine-2-carboxylate (5.00 g, 20.32 mmol) in 1,4-dioxane (50 ml). Di-tert-Butyl-(2',4',6'-triisopropyl-3,4,5,6-tetramethyl-biphenyl-2-yl)-phosphane (1.57 g, 3.27 mmol) and tris(dibenzylideneacetone)dipalladium(0) (949 mg, 1.04 mmol) is added under argon. The reaction mixture is stirred at 100° C. for 2 h. The reaction mixture is filtered and concentrated under reduced pressure. The residue is acidified with 4M HCl and the solid is filtered. The liquid phase is concentrated and the precipitate is collected, washed and dried.

Yield: 2.61 g (76%) ESI-MS: m/z=170 $(M+H)^+$

6-[4-(6-Amino-4-methoxypyridin-3-yl)piperidine-1-carbonyl]-4-methoxypyridin-3-ol

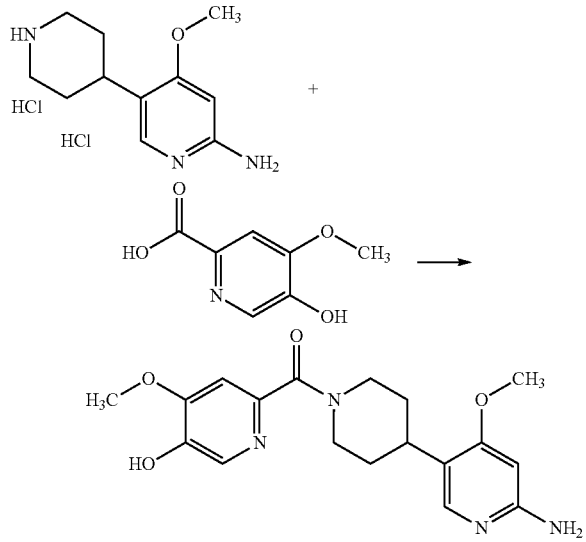

To 5-hydroxy-4-methoxypyridine-2-carboxylic acid (100 mg, 0.59 mmol) in DMF (5 mL) is added DIPEA (407 µl, 2.36 mmol) and 4-methoxy-5-(piperidin-4-yl)pyridin-2-amine dihydrochloride (331 mg, 1.18 mmol). Then HATU (225 mg, 0.59 mmol) is added. The reaction mixture is stirred overnight at RT and purified by reversed phase column chromatography to afford the title compound.

Yield: 140 mg (66%) ESI-MS: m/z=359 $(M+H)^+$ $R_t$(HPLC): 0.61 min (method 10)

General Procedures:

A procedure for preparing compound 95 of the invention is summarized in Table 7A. Analysis of the compound 95 of the invention is summarized in Table 7B.

VI: To 6-[4-(6-amino-4-methoxypyridin-3-yl)piperidine-1-carbonyl]-4-methoxypyridin-3-ol (1.0 eq.) (intermediate 2 in the following table 7A) in dioxane is added alcohol (2.4 eq.) (intermediate 1 in the following table 7A), TPP (2.7 eq.) and DTAD (2.5 eq.). The reaction mixture is stirred at 60° C. for 1 h. if the reaction shows complete conversion, the reaction mixture is purified by RP column chromatography (ACN/water+TFA).

If reaction does not show completion, additional TPP (2.7 eq.) and DTAD (2.5 eq.) are added until conversion occurs. After each addition the reaction mixture is stirred at 60° C. for 1 h. The reaction mixture is purified by RP column chromatography (ACN/water+TFA).

TABLE 7A

General procedures for preparing compound of the invention 95.

| Cpd No. | alcohol (intermediate 1) | core (intermediate 2) | Genl. Proc. | Yield % |
|---|---|---|---|---|
| 95 | 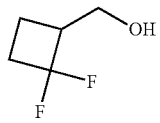 | 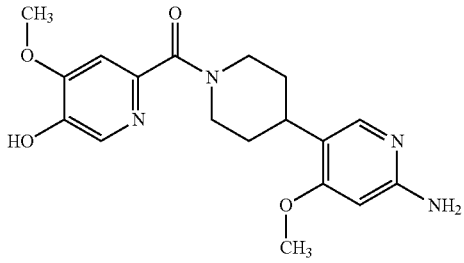 | VI | quant. |

TABLE 7B

Analytical data for compound of the invention 95.

| Cpd No. | ESI-MS m/z, M + $H^+$ | HPLC $R_t$ (min.) |
|---|---|---|
| 95 | 463 | 0.65 (Method 13) |

Alternative Preparation of Compound 1

5-{4-[5-(4-Fluorophenoxy)-4-methoxypyridine-2-carbonyl]piperazin-1-yl}-4-methoxypyridin-2-amine 5-Bromo-2-(2,5-dimethyl-1H-pyrrol-1-yl)-4-methoxypyridine

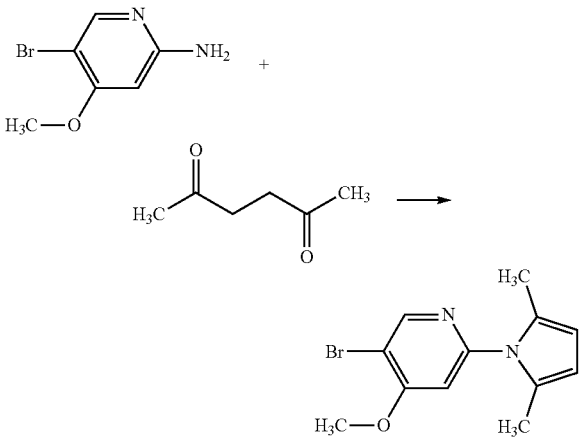

5-Bromo-4-methoxy-pyridin-2-ylamine (9.50 g, 46.79 mmol), hexane-2,5-dione (7.08 mL, 60.83 mmol) and p-toluenesulfonic acid (0.81 g, 4.68 mmol) in toluene (80 mL) are stirred over night at 120° C. using a Dean-Stark-apparatus. The reaction mixture is concentrated under reduced pressure, taken up in DCM and purified by silica gel chromatography (DCM).

Yield: 7.60 g (58%) ESI-MS: m/z=281 $[M+H]^+$ $R_t$(HPLC): 1.13 min (method 7)

1-[6-(2,5-Dimethyl-1H-pyrrol-1-yl)-4-methoxypyridin-3-yl]piperazine bis(trifluoroacetic acid)

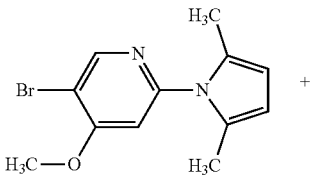

-continued

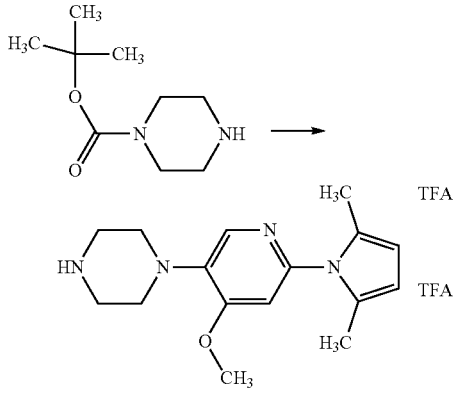

The reaction is performed under an argon-atmosphere. 5-bromo-2-(2,5-dimethyl-1 H-pyrrol-1-yl)-4-methoxyptridine (1.00 g, 3.56 mmol), tert-butyl piperazine-1-carboxylate (0.73 g, 3.92 mmol), CPhos-3G-methane sulfonate (0.30 g, 0.36 mmol) and cesium carbonate (3.48 g, 10.67 mmol) in 1,4-dioxane (15 mL) are stirred over night at 80° C. The reaction mixture is filtered and concentrated under reduced pressure. The residue is taken up in DCM (20 mL) and TFA (1.37 mL; 17.76 mmol) is added. The reaction mixture is stirred for 3 days at RT and after addition of the same amount TFA the reaction mixture is stirred overnight at 40° C. The reaction mixture is evaporated to dryness and used without further purification.

Yield: 1.80 g (98%) ESI-MS: m/z=287 $[M+H]^+$ $R_t$(HPLC): 0.67 min (method 7)

4-Methoxy-5-(piperazin-1-yl)pyridin-2-amine

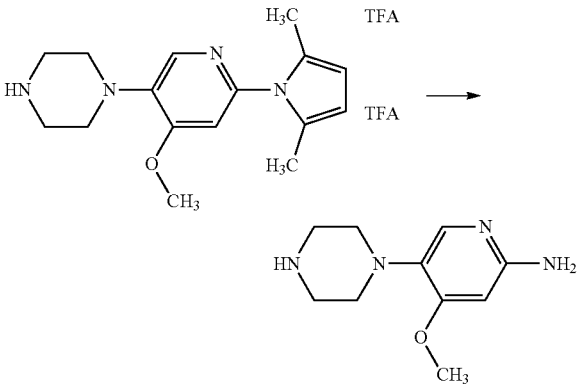

1-[6-(2,5-Dimethyl-1H-pyrrol-1-yl)-4-methoxypyridin-3-yl]piperazine bis(trifluoroacetic acid) (1.20 g, 2.33 mmol), hydroxylamine hydrochloride (0.70 g, 10.03 mmol) and triethylamine (1.00 mL, 7.11 mmol) EtOH/water (1/1; 16 mL) are stirred over night at 80° C. The organic solvent is removed under reduced pressure. The residue is purified by RP-HPLC (ACN/water+$H_3$).

Yield: 290 mg (60%) ESI-MS: m/z=209 $[M+H]^+$ $R_t$(HPLC): 0.35 min (method 11)

5-(4-Fluorophenoxy)-4-methoxypyridine-2-carbonitriel

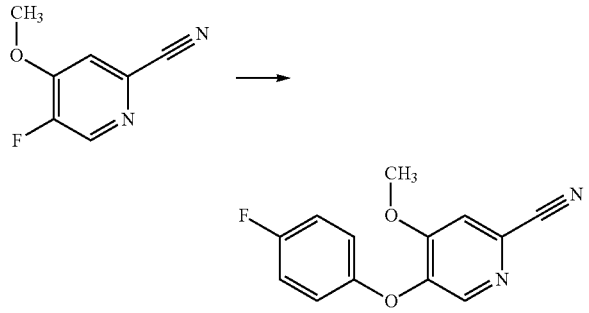

5-Fluoro-4-methoxy-pyridine-2-carbonitrile (1.00 g, 6.57 mmol), 4-fluorophenol (0.88 g; 7.89 mmol) and potassium carbonate (2.00 g; 14.46 mmol) are stirred in NMP at 105° C. for 1.5 hours. The reaction mixture is allowed to cool down to RT and extracted with EtOAc. The organic layer is washed with water and brine, separated, dried over $Na_2SO_4$, filtered and concentrated under reduced pressure. The residue is levigated with PE, filtered and dried in a drying oven at 60° C.

Yield: 1.54 g (96%) ESI-MS: m/z=245 $[M+H]^+$ $R_t$HPLC): 1.03 min (method 7)

5-(4-Fluorophenoxy)-4-methoxypyridine-2-carboxylic

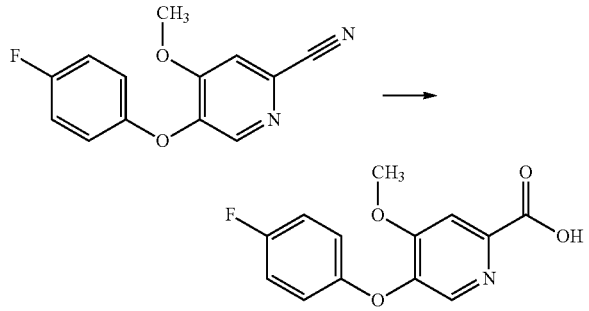

5-(4-Fluorophenoxy)-4-methoxypyridine-2-carbonitrile (1.54 g; 6.31 mmol) and NaOH (2 mol/L, aq. solution; 15.40 mL, 30.80 mmol) are stirred at 105° C. for 10 hours. The reaction mixture is allowed to cool down to RT and is left for 3 days, The resulting precipitate is filtered and levigated in water. The reaction mixture is warmed up to 50° C. and the pH is adjusted to pH7 using HCl (4 mol/L, aq. solution). The resulting precipitate is filtered, washed with EE and dried in a drying oven at 60° C.

Yield: 0.84 g (51%) ESI-MS: m/z=264 $[M+H]^+$ $R_t$(HPLC): 0.77 min (method 7)

5-{4[5-(4-Fluorophenoxy)-4-methoxypyridine-2-carbonyl]piperazin-1-yl}-4-methoxypyridin-2-amine

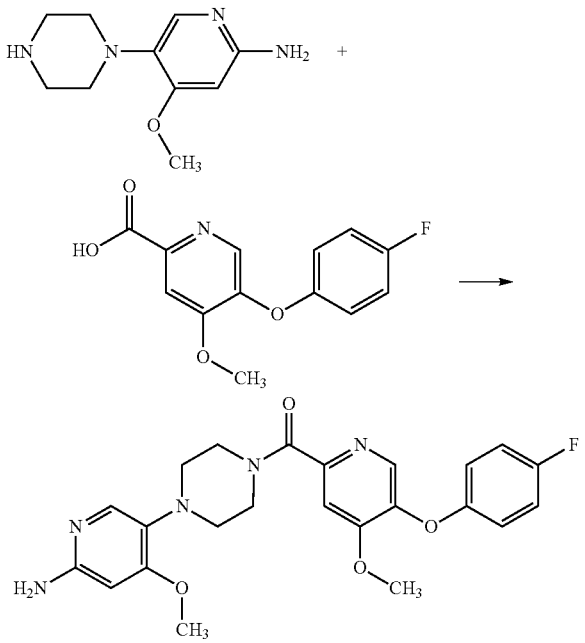

5-(4-Fluorophenoxy)-4-methoxypyridine-2-carboxylic acid (0.40 g; 1.92 mmol), HATU (0.75 g; 1.97 mmol) and DIPEA (1.16 mL; 6.72 mmol) in DMF (10 mL) are stirred for 30 minutes at RT. 4-Methoxy-5-(piperazin-1-yl)pyridin-2-amine (0.52 g; 1.98 mmol) is added and the reaction mixture is allowed to stir at RT over night. The mixture is purified by RP-HPLC (ACN/water+$NH_3$).

Yield: 0.31 g (36%) ESI-MS: m/z=454 $[M+H]^+$ $R_t$(HPLC): 0.88 min (method 11)

Alternative Preparation of Compound 39

4-Methoxy 5-{1-[4-methoxy-5-(2-methylpropoxy) pyridine-2-carbonyl]piperidin-4-yl}-pyridin-2-amine trifluoroacetic acid Methyl-4-methoxy-5-(2-methylpropoxy)pyridine-2-carhoxylate

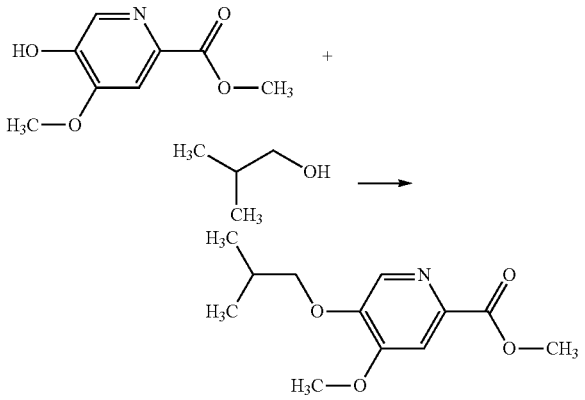

Methyl-5-hydroxy-4-methoxypyridine-2-carboxylate 0(0.40 g, 2.18 mmol), 2-methylpropan-1-ol (0.40 mL, 4.37 mmol) and TPP (1.72 g, 6.55 mmol) in THF are stirred for 10 minutes at RT. The reaction mixture is cooled in an ice bath and DTAD (1.51 g; 6.55 mmol) is added. After 30 minutes the reaction mixture is purified by RP-HPLC (ACN/water+TFA).

Yield: 0.30 g (57%) ESI-MS: m/z=240 $[M+H]^+$ $R_t$(HPLC): 0.85 min (method 7)

4-Methoxy-5-(2-methylpropoxy)-2-carboxylic acid

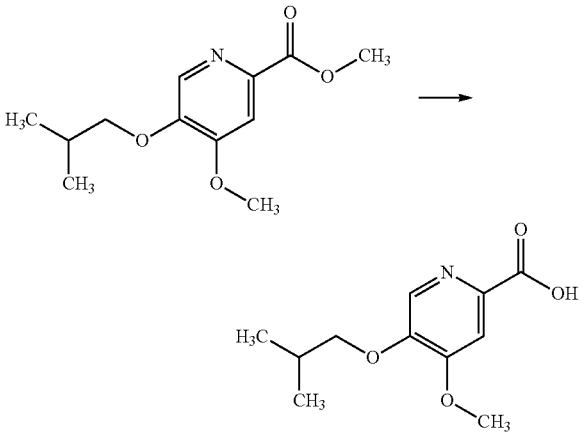

Methyl-4-methoxy-5-(2-methylpropoxy)pyridine-2-carboxylate (0.30 g; 1.25 mmol) and NaOH (4 mol/L, aq. solution; 0.47 mL; 1.88 mmol) in MeOH (8 mL) are stirred at RT for 3 days. The pH of the reaction mixture is neutralized using HCl (4 mol/Ll aq. solution) and the solvents are removed under reduced pressure. DCM and a little amount of MeOH are added to the residue. The insoluble material is littered off and the mother liquid is removed under reduced pressure. The residue is used without further purification.

Yield: 0.20 g (71%) ESI-MS: m/z=226 $[M+H]^+$ $R_t$(HPLC): 0.76 min (method 7)

tert-Butyl 6-amino-4-methoxy-1',2',3',6'-tetrahydro-[3,4'-bipyridine]-1'-carboxylate

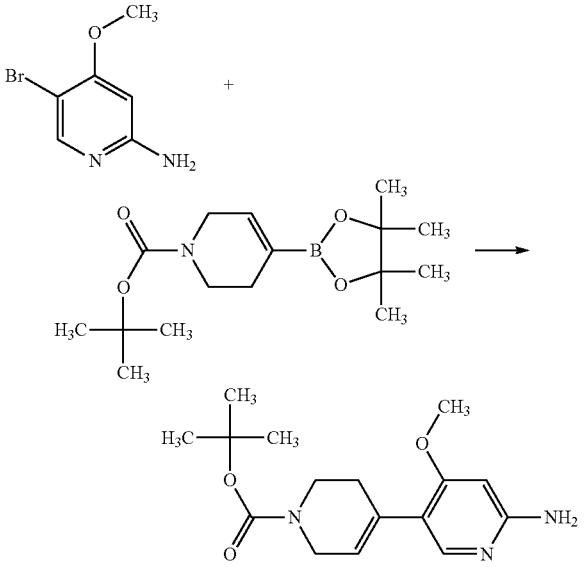

The reaction is performed under an argon-atmosphere. 5-Bromo-4-methoxypyridin-2-amine (7.40 g; 32.80 mmol), tert-butyl 4-(4,4,5,5-tetramethyl-1,3,2-dioxaborolan-2-yl)-1,2,3,6-tetrahydropyridine-1-carboxylate (11.16 g; 36.08 mmol) and sodium carbonate (2 mol/L, aq. solution; 65.60 mL; 131.21 mmol) in 1,4-dioxane (300 mL) is purged with argon. After 5 minutes Xphos $2^{nd}$ Gen. (0.77 g; 0.98 mmol) is added and the reaction mixture is stirred over night in a sealed vial at 100° C. The reaction mixture is concentrated under reduced pressure. The residue is taken up in water and extracted several times with EtOAc. The combined organic layers are dried over $Na_2SO_4$, filtered and concentrated under reduced pressure. The residue is purified by silica gel chromatography (DCM/MeOH).

Yield: 9.69 g (97%) ESI-MS: m/z=306 $[M+H]^{+60}$ $R_t$(HPLC): 0.83 mM (method 10)

tert-Butyl 4-(6-amino-4-methoxypyridin-3-yl)-piperidine-1-carboxylate

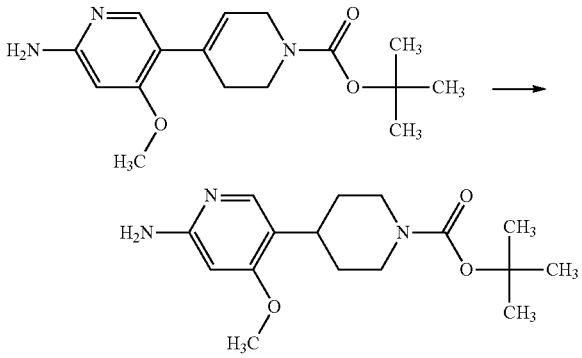

Under a hydrogen atmosphere (Parr-apparatus; 50 psi) tert-butyl 6-amino-4-methoxy-1',2',3',6'-tetrahydro-[3,4'-bipyridine]-1'-carboxylate (5.11 g; 16.73 mmol) and Pd/C (10%; 0.60 g) in MeOH (100 mL) are stirred at RT for 41.5 hours. Additional catalyst is added twice and the reaction mixture is further hydrogenated. After removal of the catalyst by filtration the mother liquid is concentrated under reduced pressure. The product is used without further purification.

Yield: 4.71 g (92%) ESI-MS: m/z=308 $[M+H]^+$ $R_t$(HPLC): 0.82 min (method 10)

4-Methoxy)-5-(piperidin-4-yl)pyridin-2-amine dihydrochloride

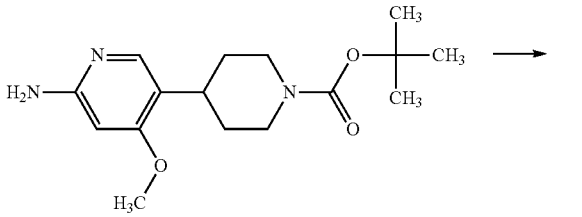

-continued

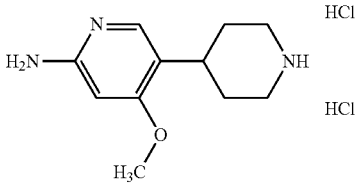

tert-Butyl 4-(6-amino-4-methoxypyridin-3-yl)-piperidine-1-carboxylate (6.90 g; 22.45 mmol) and HCl (4 mol/L; solution in 1,4-dioxane; 69.00 mL; 224.47 mmol) in DCM (89.70 mL) are stirred at RT over night. The reaction mixture is concentrated under reduced pressure. The residue is levigated in EE and filtered. The product is used without further purification.

Yield: 5.30 g (84%) ESI-MS: m/z-208 $[M+H]^+$ $R_t$(HPLC): 0.66 min (method 11)

4-Methoxy-5-{1-[4-methoxy-5-(2-methylpropoxy) pyridine-2-carbonyl]piperidin-4-yl}-pyridin-2-amine trifluoroacetic acid

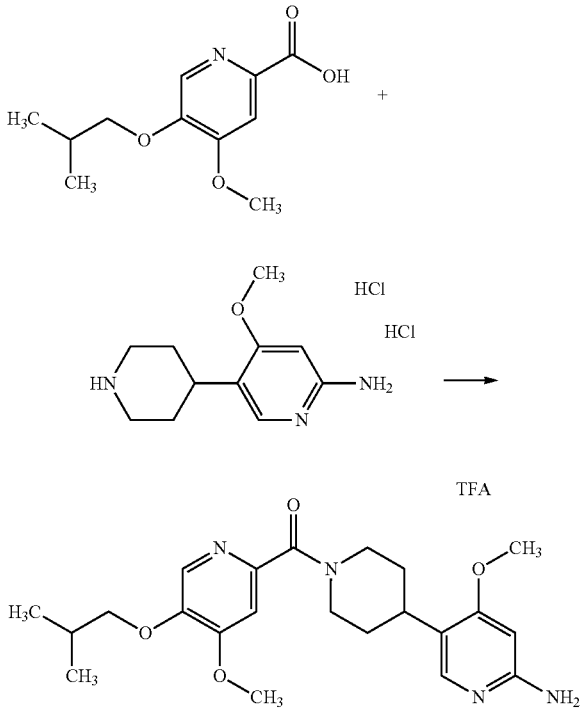

4-Methoxy-5-(2-methylpropoxy)pyridine-2-carboxylic acid (80 mg; 0.36 mmol), 4-methoxy-5-(piperidin-4-yl)pyridin-2-amine dihydrochloride (96 mg; 0.36 mmol). DIPEA (0.24 mL; 1.42 mmol) and HATU (149 mg; 0.39 mmol) in DMF (3 mL) are stirred at RT over night. The reaction mixture is purified by RP-HPLC (ACN/water+TFA).

Yield: 0.11 g (72%) ESI-MS: m/z=415 $[M+H]^+$ $R_t$(HPLC): 0.80 min (method 7)

Alternative Preparation of Compound 17

6-{1-[5-(4-Fluorophenoxy)-4-carbonyl]pimeridin-4-yl}pyridazin-3-amine tert.-Butyl 4-(6-aminopyridazin-3-yl)-1,2,3,6-tetrahydropyridine-1-carboxylate

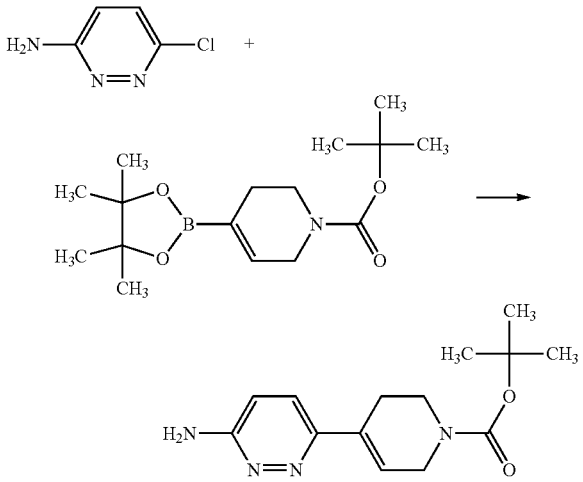

The reaction is performed under an argon-atmosphere. 6-Chloropyridazin-3-amine (5.20 g; 40.14 mmol), tert-butyl 4-(4,4,5,5-tetramethyl-1,3,2-dioxaborolan-2-yl)-1,2,3,6-tetrahydropyridine-1-carboxylate (13.65 g; 44.15 mmol) and sodium carbonate (2 mol/L, aq. solution; 80.28 mL; 160.56 mmol) in 1,4-dioxane (350 ml) are purged with argon. After 5 minutes Xphus 2$^{nd}$ Gen. (0.95 g; 1.20 mmol) is added and the mixture is stirred over night in a sealed vial at 100° C. The reaction mixture is filtered and concentrated under reduced pressure. The residue is taken up in MeOH, precipitated with water and filtered. The resulting precipitate is dried in a drying oven at 50° C. The product is used without further purification. Yield: quantitative ESI-MS: m/z=277 $[M+H]^+$ $R_t$(HPLC): 0.78 min (method 10)

tert.-Butyl 4-(6-aminopyridazin-3-yl)-piperidine-1-carboxylate

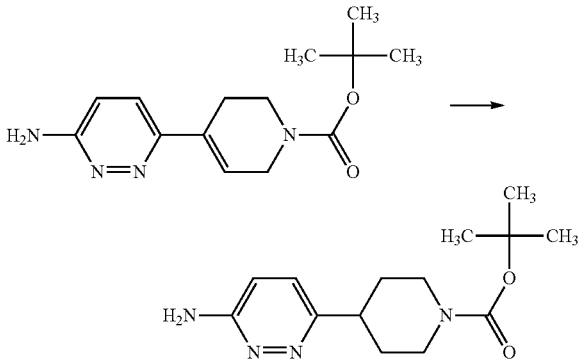

Under an hydrogen atmosphere (Parr-apparatus; 4 bar) tert.-butyl 4-(6-aminopyridazin-3-yl)-1,2,3,6-tetrahydropyridine-1-carboxylate (4.85 g; 17.55 mmol) and Pd/C (10%; 0.50 g) in MeOH (100 mL) are stirred at RT for 3 hours. After removal of the catalyst by filtration the mother liquid is concentrated under reduced pressure. The product is used without further purification.

Yield: quantitative ESI-MS: m/z=279 $[M+H]^+$ $R_t$(HPLC): 0.86 (method 11)

6-(Piperidin-4-yl)pyridazin-3-amine

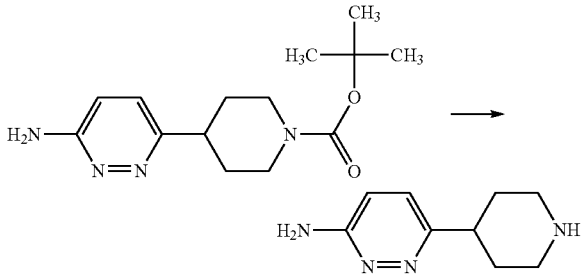

tert.-Butyl 4-(6-aminopyridazin-3-yl)-piperidine-1-carboxylate (4.89 g; 17.55 mmol) is stirred for 1 hour in TFA (20 mL; 259.25 mmol). The solvent is evaporated and the residue is purified by silica gel chromatography (DCM/MeOH+$NH_3$).

Yield: quantitative ESI-MS: m/z=179 $[M+H]^+$ $R_t$(HPLC): injection peak (method 11)

Alternatively used amine:

6-(Piperidin-4-yl)pyridazin-3-amine dihydrochloride

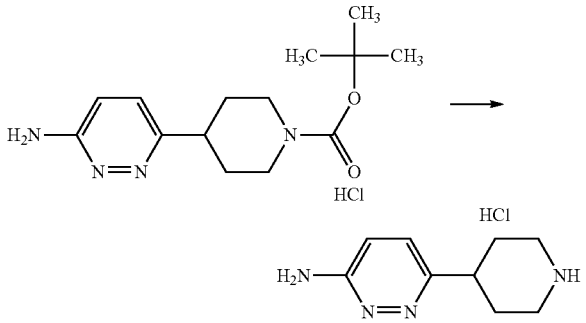

The reaction is performed using a nitrogen atmosphere. tert.-Butyl 4-(6-aminopyridazin-3-yl)-piperidine-1-carboxylate (1.00 g; 3.59 mmol) and HCl (4 mol/L, solution in 1,4-dioxane; 2.96 ml; 11.84 mmol) in ACN (6 mL) are stirred at 35°- 40° C. for 2 hours. The reaction mixture is cooled to RT and diluted with isopropylacetate. After 10 minutes of stirring the resulting precipitate is filtered off and dried in a drying oven at 45° C.

Yield: quantiative ESI-MS: m/z=179 $[M+H]^+$ $R_t$(HPLC): 0.94 min (method 14)

6-{1-[-5-(4-Fluorophenoxy)-4-methoxypyridine-2-carbonyl]piperidin-4-yl}pyridazin-3-amine

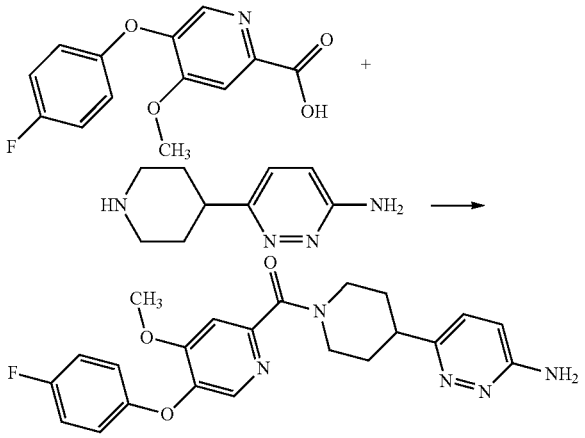

5-(4-Fluorophenoxy)-4-methoxypyridine-2-carboxylic acid (0.70 g; 2.66 mmol), HATU (1.52 g; 3.99 mmol) and DIPEA (1.83 mL; 10.64 mmol) iu DMF (20 mL) are stirred for 30 minutes. 6-(Piperidin-4-yl)pyridazin-3-amine (0.71 g; 3.98 mmol) is added and the reaction mixture is allowed to stir at RT over night. The mixture is purified by RP-HPLC (ACN/water+TFA). To remove the trifluoroacetate salt the product is taken up in water/EtOH (1.5/1) and levigated with polymer bound bicarbonate. After 30 minutes of stirring the mixture is filtered and concentrated under reduced pressure.

Yield: 180 mg (16%) ESI-MS: m/z=424 $[M+H]^+$ $R_t$(HPLC): 0.77 min (method 7)

Alternatively the title compound can be obtained as follows:

6-{1-[5-(4-Fluorophenoxy)-4-methoxypyridine-2-carbonyl]piperidin-4-yl}pyridzin-3-amine

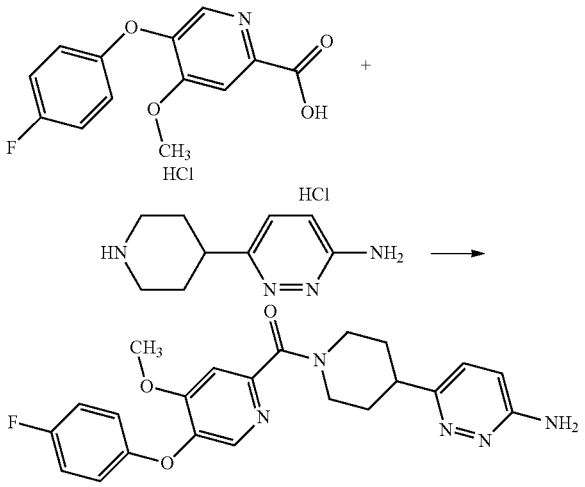

5-(4-Fluorophenoxy)-4-methoxypyridine-2-carboxylic acid (0.50 g; 1.90 mmol) and CDI (0.46 g; 2.85 mmol) in NMP (1 mL) are stirred at RT for 1 hour, 6-(Piperidin-4-yl) pyridazin-3-amine dihydrochioride (0.52 g; 2.09 mmol) and DIPEA (0.99 mL; 5.70 mmol) are added. After stirring for 3 hours the reaction mixture is diluted with water and extracted with EtOAc. The organic layer is separated, washed with water and brine, dried over $MgSO_4$ and filtered. The mother liquid is concentrated under reduced pressure and purified by silica gel chromatography (DCM/MeOH). The desired fractions are concentrated under reduced pressure and treated with ACN/ethyl ether to provide the title product in solid form.

Yield:. 0.27 g (34%) EST-MS: m/z=424 $[M+H]^+$ $R_t$(HPLC): 0.49 min (method 1)

Alternative Preparation of Compound 37

5-{1[5-Cylclopropylmethoxy)-4-methoxypyridine-2-carbonyl]piperidin-4-yl}-4-methoxypyridin-2-amine Methyl 5-(cyclopropylmethoxy)-4-methoxypyridine-2-carboxylate

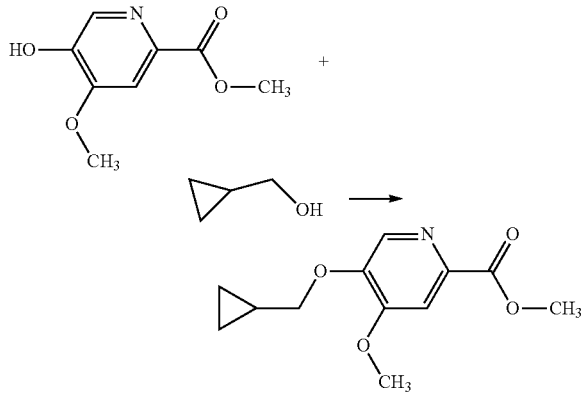

Methyl 5-hydroxy-4-methoxypyridine-2-carboxylate (0.20 g; 1.09 mmol) and cyclopropylmethanol (88 μL; 1.09 mmol) in THF (3 mL) are cooled in an ice bath. TPP (0.32 g; 1.20 mmol) and DTAD (0.28 g; 1.20 mmol) are added. The reaction mixture is allowed to warm up to RT over night. The reaction mixture is concentrated under reduced pressure and purified by RP-HPLC (ACN/water+TFA).

Yield: 0.18 g (70%) ESI-MS: m/z=238 $[M+H]^+$ $R_t$(HPLC): 0.41 min (method 12)

5-(Cyclopropylmethoxy)-4-methoxypyridine-2-carboxylic acid

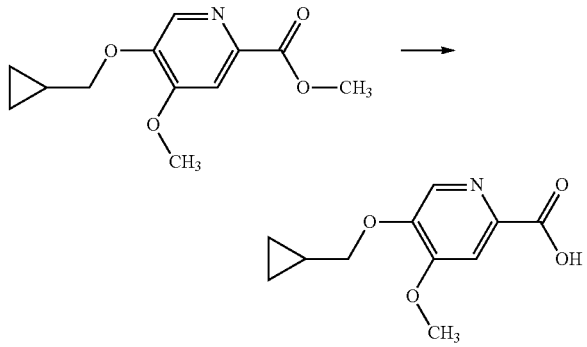

Methyl 5-(cyclopropylmethoxy)-4-methoxypyridine-2-carboxylate (0.18 g; 0.76 mmol) and NaOH (4 mol/L, aq. solution; 0.50 mL; 2.00 mmol) in MeOH (3 mL) are stirred at RT for 1 hour. The reaction mixture is concentrated under reduced pressure. The residue is taken up in water and washed with EtOAc. To the aqueous layer HCl (4 mol/L, aq. solution; 0.5 mL) is added and concentrated under reduced pressure. The product is used without further purification.

Yield: 0.13 g (74% ESI-MS: m/z=224 $[M+H]^+$ $R_t$(HPLC): 0.30 min (method 12)

5-{1-[5-(Cyclopropylmethoxy)-4-methoxypyridine-2-carbonyl]piperidin-4-yl}-4-methoxypyridin-2-amine

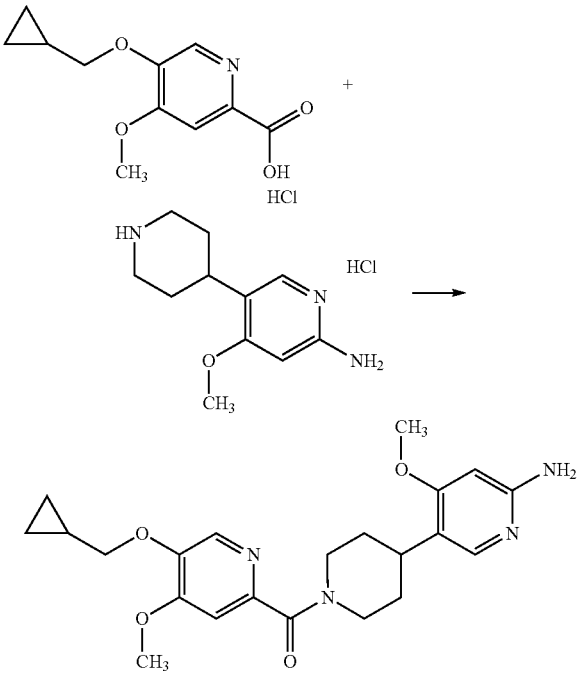

5-(Cyclopropylmethoxy)-4-methoxypyridine-2-carboxylic acid (50 mg; 0.22 mmol), 4-methoxy-5-(piperidin-4-yl) pyridin-2-amine dihydrochloride (63 mg; 0.22 mmol), DIPEA (193 μL; 1.12 mmol) and HATU (94 mg; 0.25 mmol) in DMF (2 mL) are stirred at RT over night. The resulting mixture is purified by RP-HPLC (ACN/water+$NH_3$).

Yield: 45 mg (49%) ESI-MS: m/z=413 $[M+H]^+$ $R_t$(HPLC): 0.87 min (method 11)

Alternative Preparation of Compound 90

6-(1-{4-Methoxy-5-[4-(trifluoromethy)phenoxy] pyridine-2-carbonyl}lpiperidin-4-yl)-5-methylpyridazin-3-amine trilluoroacetic acid 4-Methoxy-5-[4-(trifluoromethyl)phenoxy]pyridine-2-carbonitrile

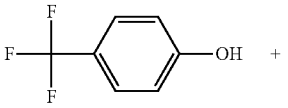

-continued

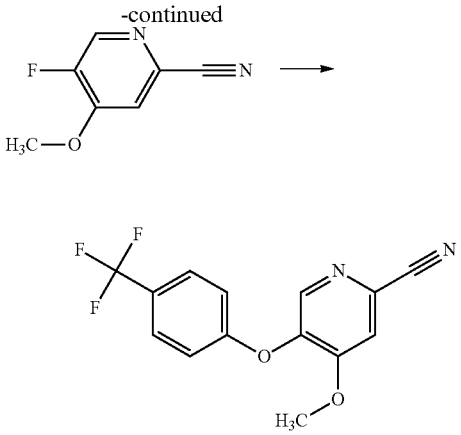

5-Fluoro-4-methoxy-pyridine-2-carbonitrile (4.69 g; 30.84 mmol), 4-trifluoromethylphenol (5.00 g; 30.84 mmol) and potassium carbonate (6.39 g; 46.27 mmol) are stirred in DMSO at 110° C. for 1 hour. The reaction mixture is allowed to cool down to RT and diluted with water. The resulting precipitate is filtered, washed with water and dried in a drying oven at 50° C.

Yield: 7.40 g (82%) ESI-MS: m/z=295 $[M+H]^+$ $R_t$(HPLC): 1.08 min (method 10)

4-Methoxy-5-[4-(trifluoromethyl)phenoxy]pyridine-2-carboxylic acid

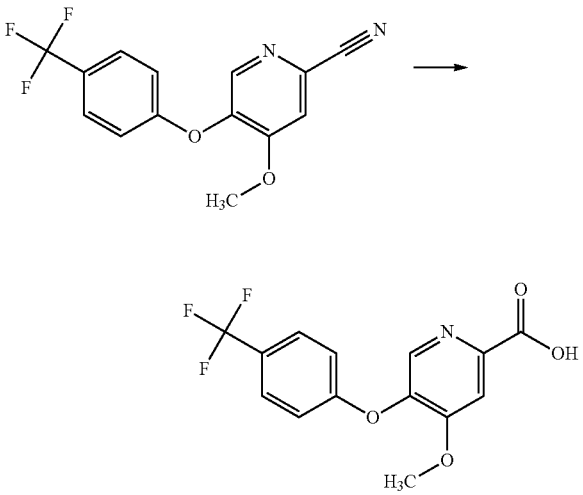

4-Methoxy-5-[4-(trifluoromethyl)phenoxy]pyridine-2-carbonitrile (7.40 g; 25.51 mmol) and NaOH (4 mol/L, aq. solution; 31.44 mL, 125.75 mmol) in MeOH (100 mL) are stirred at 70° C. over night. The reaction mixture is allowed to cool down to RT and the organic solvent is evaporated. The remaining solvent is diluted with water and adjusted to pH 3 using HCl(4 mol/L, aq. solution). The resulting precipitate is filtered and dried in a drying oven at 50° C.

Yield: 6.80 g (51%) EST-MS: m/z=314 $[M+H]^+$ $R_t$(HPLC): 0.87 min (method 10)

tert-Butyl 4-(6-amino-4-methylpyridazin-3-yl)-1,2,3,6-tetrahydropyridine-1-carboxylate

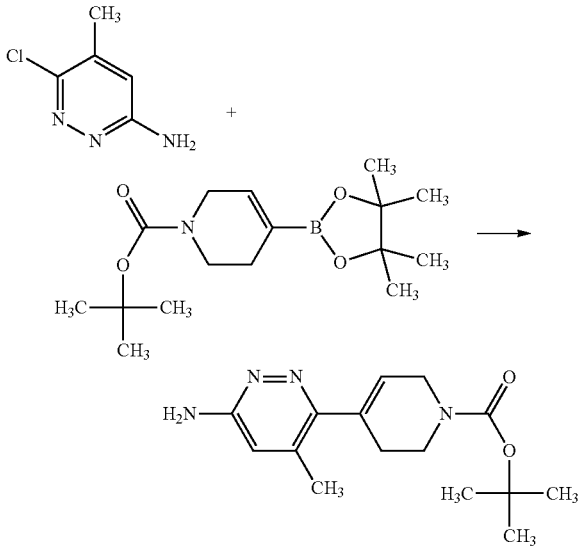

The reaction is performed underan argon-atmosphere. 6-Chloro-5-methylpyridazin-3-amine (3.00 g; 20.90 mmol), tert-butyl 4-(4,4,5,5-tetramethyl-1,3,2-dioxaborolan-2-yl)-1,2,3,6-tetrahydropyridine-1-carboxylate (7.11 g; 22.98 mmol) and sodium carbonate (2 mol/L, aq. solution; 41.79 mL; 83.58 mmol) in 1,4-dioxane (150 mL) is purged with argon. After 5 minutes Xphos 2$^{nd}$ Gen. (0.49 g; 0.63 mmol) is added and the mixture is stirred over night in a sealed vial at 100° C. The reaction mixture is concentrated under reduced pressure. The residue is taken up in water and extracted several times with EtOAc. The combined organic layers are washed with brine, dried over $Na_2SO_4$, filtered and concentrated under reduced pressure. The residue is purified by silica gel chromatography (DCM/MeOH).

Yield: 5.20 g (86%) ESI-MS: m/z=291 $[M+H]^+$ $R_t$(HPLC): 0.79 min (method 10)

tert-Butyl 4-(6-amino-4-methylpyridazin-3-yl)piperidine-1-carboxylate

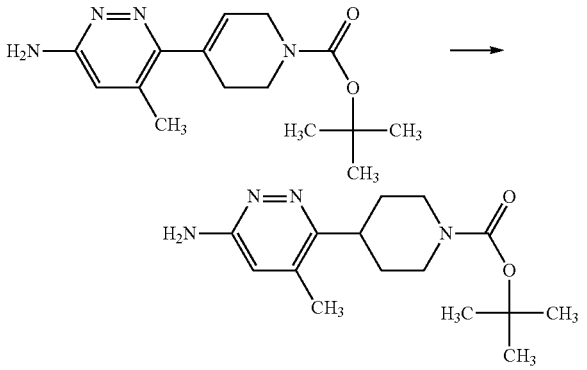

Under an hydrogen atmosphere (Parr-apparatus; 50 psi) tert-butyl 4-(6-amino-4-methylpyridazin-3-yl)1,2,3,6tetrahydropyridine-1-carboxylate (5.20 g; 17.91 mmol) and Pd/C (10%; 0.75 g) in MeOH (100 mL) are stirred at RT for 17 hours. After removal of the catalyst by filtration the mother liquid is concentrated under reduced pressure.

Yield: 5.00 g (96%) ESI-MS: m/z=293 $[M+H]^+$ $R_t$(HPLC): 0.79 min (method 10)

5-Methyl-6-(piperidin-4-yl)pyridazin-3-amine dihydrochloride

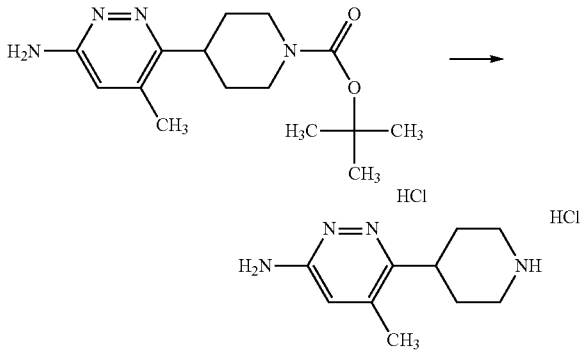

tert-Butyl 4-(6-amino-4-methylpyridazin-3-yl)piperidine-1-carboxylate (4.91 g; 16.79 mmol) and HCl(4 mol/L; solution in 1,4-dioxane; 73.65 mL; 251.90 mmol) in 1,4-dioxane (34.37 mL) are stirred at RT over night. The reaction mixture is concentrated under reduced pressure. The residue is levigated in EtOAc and filtered. The product is used without further purification.

Yield: quantitative ESI-MS: m/z=193 $[M+H]^+$ $R_t$(HPLC): 0.59 min (method 11)

6-(1-{4-Methoxy-5-[4-(trifluoromethyl)phenoxy]pyridine-2-carbonyl}ipiperidin-4-yl)-5-methylpyridazin-3-amine trifluoroacetic acid

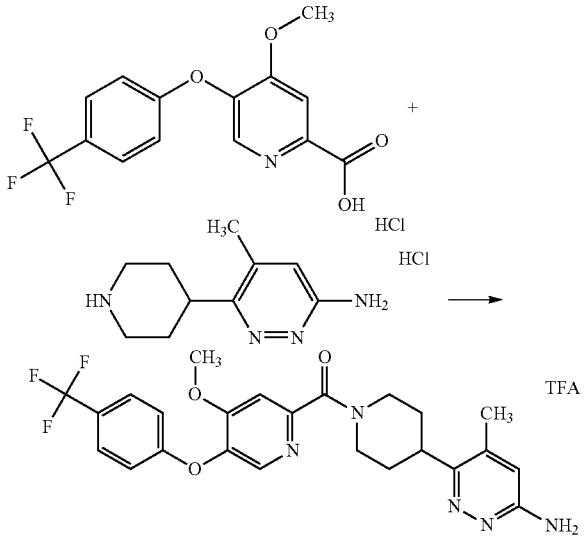

4-Methoxy-5-[4-(trifluoromethyl)phenoxy]pyridine-2-carboxylic acid (0.12 g; 0.37 mmol), HATU (0.15 g, 0.39 mmol) and DIPEA (0.19 mL; 1.11 mmol) in DMF (3 mL)

are stirred for 30 minutes. 5-Methyl-6-(piperidin-4-yl) pyridazin-3-amine dihydrochloride (0.10 g; 0.38 mmol), is added and the reaction mixture is allowed to stir at RT over night. The reaction mixture is purified by RP-HPLC (ACN/water+TFA).

Yield: 0.12 g (55%) ESI-MS: m/z=488 $[M+H]^+$ $R_t$(HPLC): 0.86 min (method 7)

Altemative Preparation of Compound 47

5-Methoxy-6-[1-(4-methoxy-5-phenoxypyridine-2-carbonyl)piperidin-4-yl]pyridazin-3-amine 4-Methoxy-5-phenoxypyridine-2-carbonitrile

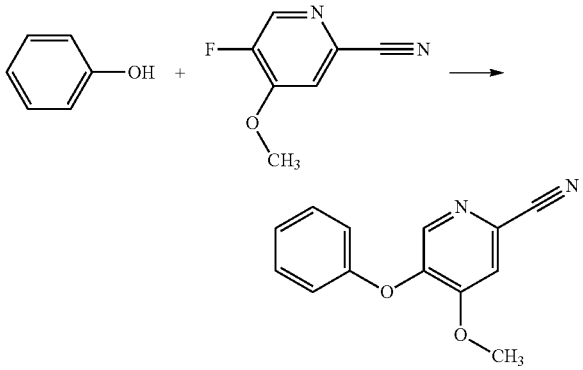

5-Fluoro-4-methoxy-pyridine-2-carbonitrile (0.40 g; 2.63 mmol), phenol (0.25 g; 2.66 mmol mmol) and potassium carbonate (0.54 g; 3.91 mmol) are stirred in DMSO (10 mL) at 110° C. for 2 hours. The reaction mixture is allowed to cool down to RT and diluted with water. The aqueous layer is extracted several times with EtOAc. The combined organic layers are dried over $Na_2SO_4$, filtered and concentrated under reduced pressure.

Yield: 0.55 g (92%) %) ESI-MS: m/z=227 $[M+H]^+$ $R_t$(HPLC): 1.01 min (method 7)

4-Methoxy-5-phenoxypyridine-2-carboxylic acid

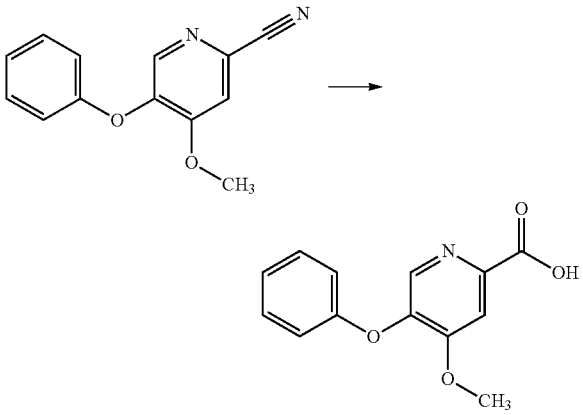

4-Methoxy-5-phenoxypyridine-2-carbonitrile (0.54 g; 2.39 mmol) and NaOH (4 mol/L, aq. solution; 3.00 mL, 12.00 mmol) in MeO H (10 mL) are stirred at 70° C. over night. The reaction mixture is allowed to cool down to RT and the organic solvent is evaporated, The remaining solvent is diluted with water and acidified to pH 3 using HCl (4 mol/L, aq. solution). The resulting precipitate is filtered and dried in a desiccator.

Yield: 0.30 g (51%) ESI-MS: m/z=246 $[M+H]^+$ $R_t$(HPLC): 0.72 min (method 10)

tert-Butyl 4-(6-{[(tert-butoxy)carbonyl]amino}-4-methoxypyridazin-3-yl)-1,2,3,6-tetrahydropyridine-1-carboxylate

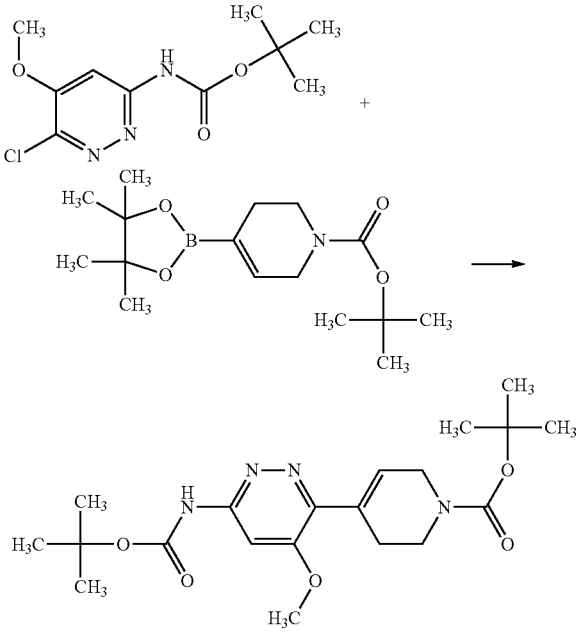

The reaction is performed under an argon-atmosphere. (6-Chloro-5-methoxy-pyridazin-3-yl)-carbamic acid tert.-butyl ester (4.00 g; 15.40 mmol), tert-butyl 4-(4,4,5,5-tetramethyl-1,3,2-dioxaborolan-2-yl)-1,2,3,6-tetrahydromidine-1-carboxylate (4.76 g; 15.40 mmol) and sodium carbonate (2 mol/L, aq. solution; 15.40 mL; 30.81 mmol) in 1,4-dioxane (80 mL) are purged with argon. After 5 minutes Xphos $2^{nd}$ Gen. (1.26 g; 1.54 mmol) is added and the mixture is stirred over night in a sealed vial at 90° C. The reaction mixture is concentrated under reduced pressure. The residue is taken up in EtOAc and washed with water and brine. The organic layer is separated and concentrated under reduced pressure. The residue is purified by silica gel chromatography (DCM/MeOH).

Yield: 4.56 g (59%)

tert-Butyl 4-(6-{[(tert-butoxy)carbonyl]amino}-4-methoxypyridazin-3yl)piperidine-1-carboxylate

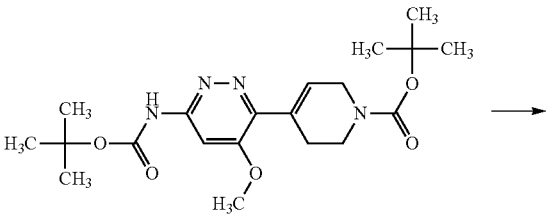

-continued

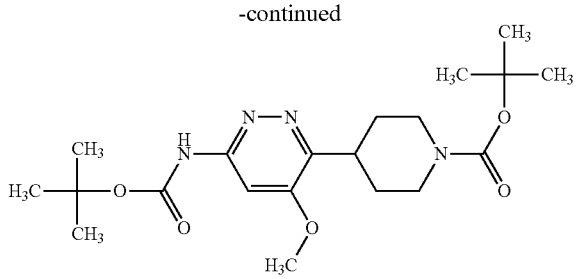

Under an hydrogen atmosphere (Parr-apparatus; 50 psi) tert-butyl 4-(6-{[(tert-butoxy)carbonyl]amino}-4-methoxypyridazin-3-yl)-1,2,3,6-tetrahydropyridine-1-carboxylate (4.55 g: 11.19 mmol) and Pd/C (10%; 3.57 g) in MeOH (45.5 mL) are stirred at 30° C. over night. After removal of the catalyst by filtration the mother liquid is concentrated under reduced pressure.

Yield: 3.67 g (80%)

5-Methoxy-6-(piperidin-4-yl)pyridazin-3-amine dihydrochloride

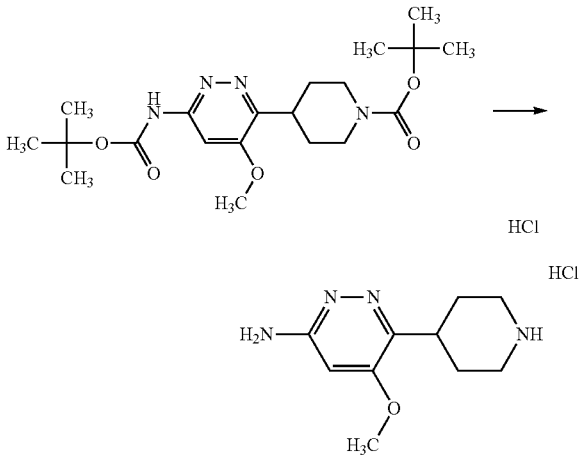

tert-Butyl 4-(6-{[tert-butoxy)carbonyl]amino}-4-methoxypyridazin-3-yl)piperidine-1-carboxylate (3.67 g; 8.98 mmol) and HCl (4 mol/L; solution in 1,4-dioxane; 55.05 mL; 134.76 mmol) in 1,4-dioxane (26.69 mL) are stirred at RT over night. The reaction mixture is concentrated under reduced pressure. The residue is levigated in EtOAc and filtered. The product is used without further purification.

Yield: 2.07 g (82%) ESI-MS: m/z=209 $[M+H]^{+60}$ $R_t$(HPLC): 0.60 min (method 11)

5-Methoxy-6-[1-(4-methoxy-5-phenoxypyridine-2-carbonyl)piperidin-4-yl]pyridazin-3-amine

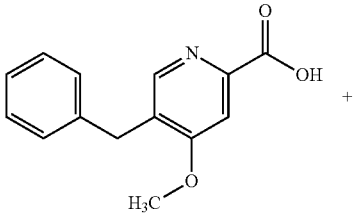

-continued

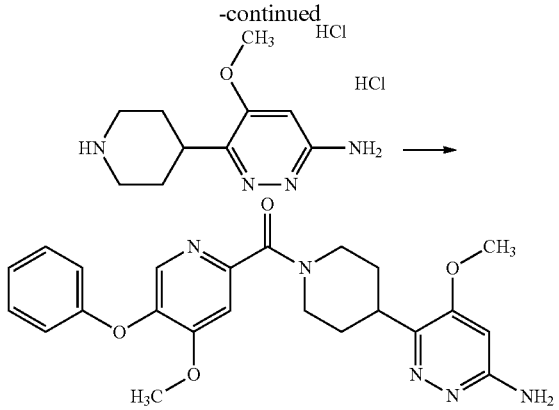

4-Methoxy-5-phenoxypyridine-2-carboxylic acid (0.10 g; 0.41 mmol), HATU (0.16 g; 0.419 mmol) and DIPEA (0.18 mL; 1.05 mmol) DMF (3 mL) are stirred for 30 minutes. 5-Methoxy-6-(piperidin-4-yl)pyridazin-3-amine dihydrochloride (0.12 g; 0.41 mmol), is added and the reaction mixture is allowed to stir at RT over night. The mixture is purified by RP-HPLC (ACN/water+$NH_3$).

Yield: 0.09 g (53%) ESI-MS: m/z=436 $[M+H]^+$ $R_t$(HPLC): 0.63 min (method 13)

Alternative Preparation of Compound 29

6-{-[5-(4-Fluorophenoxy)-4-methoxypyridine-2-carbonyl]piperidin-4-yl}-5-methylpyridazin-3-amine trifluoroacetic acid

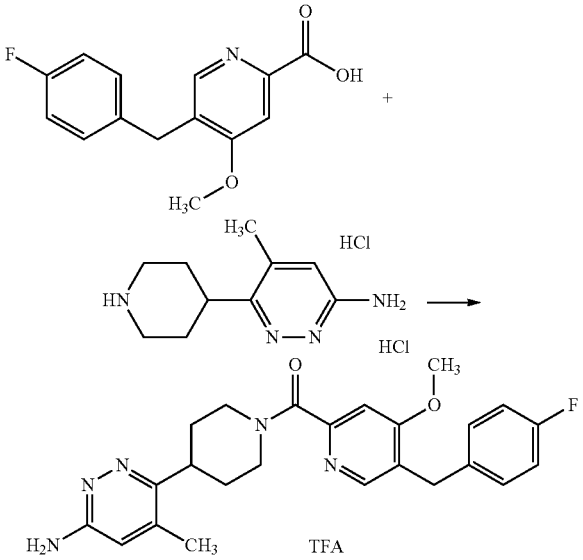

5-(4-Fluorophenoxy)-4-methoxymidine-2-carboxylic acid (60 mg; 0.23 mmol), 5-methyl-6-(piperidin-4-yl) pyridazin-3-amine dihydrochloride (60 mg; 0.23 mmol) HATU (95 mg; 0.25 mmol) and DIPEA (0.12 mL; 0.68 mmol) DMF (3 mL) are stirred at RT for 1 hour. The mixture is purified by RP-HPLC (ACN/water+TFA).

Yield: 73 mg (59%) ESI-MS: m/z=438 $[M+H]^+$ $R_t$(HPLC): 0.82 min (method 7)

Alternative Preparation of Compound 91

5-Methoxy-6-(1-{5-[4-(trifluoromethyl)phenoxy]pyridine-2-carbonyl}piperidin-4-yl)pyridazin-3-amine trifluoroacetic acid 5-[4-(Trifluoromethyl)phenoxy]pyridine-2-carbonitrile

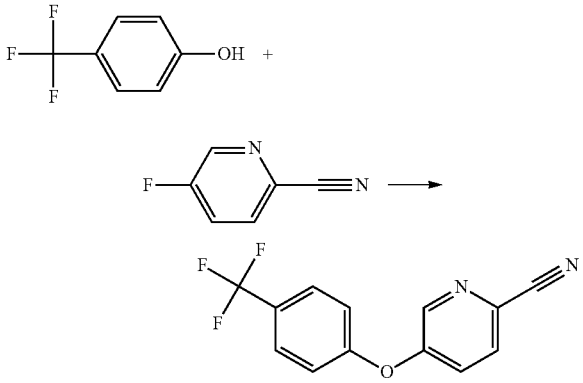

2-Cyano-5-fluoropyridine (3.54 g; 28.99 mmol), 4-trifluoromethyl-phenol (4.70 g; 28.99 mmol) and potassium carbonate (6.01 g; 43.49 mmol) are stirred inDMSO (150 mL) at 110° C. for 1 hour. The reaction mixture is diluted with water and extracted with EtOAc. The organic layer is washed with water, separated, dried over $Na_2SO_4$, filtered and concentrated under reduced pressure.

Yield: quantitative ESI-MS: m/z=265 $[M+H]^+$ $R_t$(HPLC): 1.03 turn (method 10)

5-[4-(Trifluoromethyl)phenoxy]pyridine-2-carboxylic acid

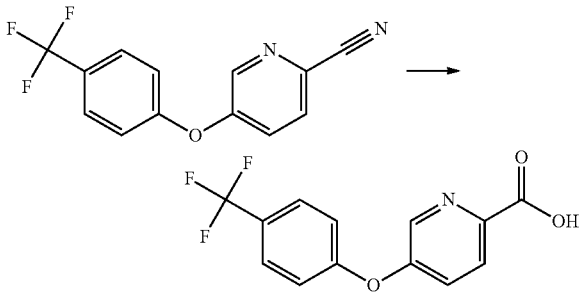

5-[4-(Trifluoromethyl)phenoxy]pyridine-2-carbonitrile (3.87 g; 14.65 mmol) and NaOH (4 mol/L, aq. solution; 18.31 mL, 73.24 mmol) in MeOH (50 mL) are stirred at 70° C. over night. The reaction mixture is concentrated under reduced pressure. The residue is taken up in water and acidified to pH3 using HCl (4 mol/L, aq. solution). The organic solvent is completely evaporated and the resulting precipitate is filtered. The residue is taken up in DCM, filtered and dried in a drying oven at 50° C.

Yield: quantitative ESI-MS: m/z=284 $[M+H]^+$ $R_t$(HPLC): 0.68 min (method 11)

5-Methoxy-6-(1-{5-[4-(trifluoromethyl)phenoxy]pyridine-2-carbonyl}piperidin-4-yl)pyridazin-3-amine trifinoroacetic acid

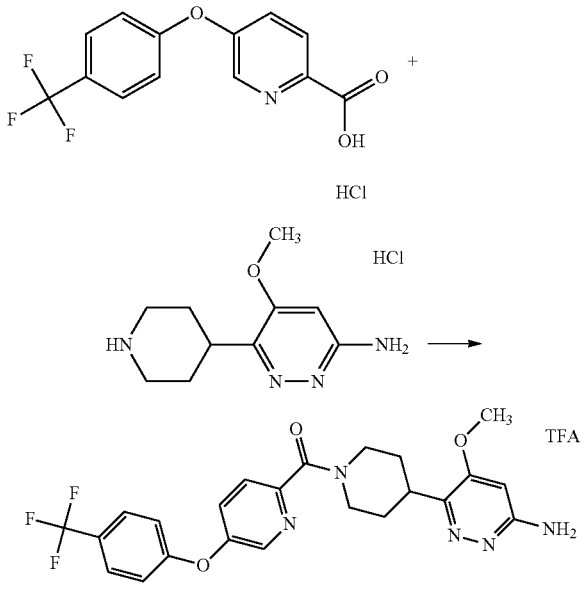

5-[4-(Trfluoromethyl)phenoxy]pyridine-2-carboxylic acid (0.10 g; 0.35 mmol), HATU (0.15 g; 0.39 mmol) and DIPEA (0.19 mL; 1.11 mmol) in DMF (3 mL) are stirred for 30 minutes at RT. 5-Methoxy-6-(piperidin-4-yl)pyridazin-3-amine dihydrochloride (0.11 g; 0.37 mmol) is added and the reaction mixture is allowed to stir at RT over night. The mixture is purified by RP-HPLC (ACN/water+TFA).

Yield: 0.06 g (31%) ESI-MS: m/z=474 $[M+H]^+$ $R_t$(HPLC): 0.87 min (method 7)

Alternative Preparation of Compound 31

6-[1-(4-Methoxy-5-phenoxypyridine-2-carbonyl)piperidin-4-yl]-5-methylpyridazin-3-amine trifluoroacetic acid

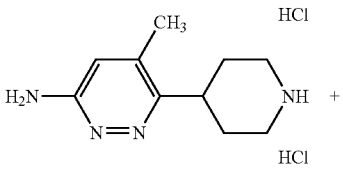

-continued

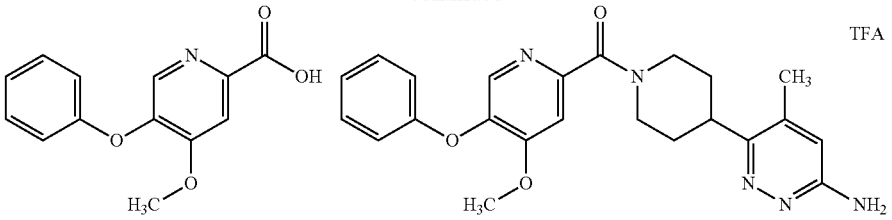

4-Methoxy-5-phenoxypyridine-2-carboxylic acid (60 mg; 0.23 mmol), 5-methyl-6-(piperidin-4-yl)pyridazin-3-amine dihydrochloride (55 mg; 0.23 mmol), HATU (95 mg; 0.25 mmol) and DIPEA (0.12 mL; 0.68 mmol) in DMF (3 mL) are stirred for 1 hour at RT. The mixture is purified by RP-HPLC(ACN/water+TFA).

Yield: 69 mg (57%) ESI-MS: m/z=420 $[M+H]^+$ $R_t$(HPLC): 0.81 min (method 7)

Assessment of Biological Activity

High Throughput Screening Assay

This screening assay measures TRPC6 (transient receptor potential cation channel, subfamily C, member 6) ion channel activation via addition either of the commercially available DAG ligand analogue OAG (1-oleoyl-2-acetyl-sn-glycerol) or of the TRPC6 agonist 1-[1-(4,5,6,7,8-pentahydrocyclohepta[21-d]thiophen-2-ylcarbonyl)-4-piperidyl]-3-hydrobenzimidazol-2-one (GSK1702934A). The assay utilizes a FLIPR fluorescent calcium sensor 4-(6-Acetoxymethoxy-2,7-diftuoro-3-oxo-9-xanthenyl)-4'-methyl-2,2'-(ethylenedioxy)dianiline-N,N,N',N'-tetraacetic acid tetrakis(acetoxymethyl) ester (Fluo4/AM) membrane potential (FMP) dye from Molecular Devices, which is a voltage sensitive indicator with a fluorescent quencher. Changes (increases) in intracellular membrane calcium concentration potential as measured by the fluorescent signal increase during membrane depolarization provide a measurement of channel activity, The commercially available HEK293/TREx line (invitrogen) was stably transthcted with a TRPC6 construct and screened by conventional calcium imaging to find clones with TRPC6 expression following stimulation with 1 μg/ml tetracycline. These cells were maintained in the growth medium recommended by the manufacturer supplemented with 100 μg/ml hygromycin to promote retention of the TRPC6 construct. After growing to near confluency, cells were plated at a density of ⁻35,000 cells/well in 384 well CellBind plates (Corning) in the presence of 1 μg/ml tetracycline, and allowed to grow for 20-30 hrs. A nearly confluent monolayer resulted. Growth media was removed from the wells and cells were then loaded with 25 mL Fluo4/AM diluted in Ringer's Solution (6.5 g NaCl, 0.42 g KCl, 0.25 g CaCl2) and 0.2 g of sodium bicarbonate; pH 7.4) supplemented with 1% Pluronic F-127 to a final concentration of 0.5 μM and incubated for 60 min, at room temperature. Dye solution was then removed from the cells by inverting plates with a sharp flick, and replaced with 25 μl Ringer's. Following ⁻0.5 hour for recovery from loading, cells were assayed using the Hamamatsu FDSS 6000 system, which permitted illumination at 485 nm. Frames were acquired at a rate of 0.2 Hz. During the assay, the plates were continuously vortexed, with pipette mixing of wells following addition of each reagent. For the screening assay, 26 μl of a diluted compound stock (at 50 μM) was added to each well for 2 minutes following the collection of a short (4 frame) baseline. 13 μl of agonist solution consisting of 125 nM GSK1702934A diluted in high-Ca2+Ringer solution (containing 90 mm Ca2+) was then added to each well, achieving a final concentration of 20 mm Ca2+ and 10 μM test compound. Data was collected for ⁻3 minutes following addition of high Ca2+Ringer. The fluorescent ratio for each well was divided by the initial fluorescent intensity for that well and the overall response was determined by averaging the fluorescent ratio of the last 4 frames acquired during the experiment excepting the final frame. Negative and Positive controls were included on each plate. Negative controls wells consisted of HEK293/TRE.x TRPC6 cells exposed to assay buffer and agonist solution, but no test compound. Positive control consisted of wells consisted of HEK293/TREx TRPC6 cells exposed to 25 μM 3-[(2-chlorophenoxy)methyl]phenyl piperidyl ketone (Chembridge) diluted in Ringer's solution and agonist solution. These controls defined zero percent and 100 percent block respectively, and intensity of each well was normalized to these values.

IC50s were determined using the above fluorescence method with the exception that instead of testing the compounds at 10 μM, compounds were tested at final concentrations of 20 μm, 6.667 μM, 2.222 μM, 0.741 μM, 0.247 μM, 0.082 μM, and 0.027 μM. Compounds were tested in triplicate at all concentrations. Standard software was used to fit IC50 curves.

TABLE 8

Antagonist effects of compounds of the invention against TRPC6 ($IC_{50}$)

| Compound No. | TRPC6 $IC_{50}$ (nM) |
|---|---|
| 1 | <27 |
| 2 | <27 |
| 3 | <27 |
| 4 | <27 |
| 5 | 27 |
| 6 | 27 |
| 7 | 27 |
| 8 | 27 |
| 9 | 27 |
| 10 | 27 |
| 11 | 27 |
| 12 | 27 |
| 13 | 27 |
| 14 | 27 |
| 15 | 27 |
| 16 | 27 |
| 17 | 29 |
| 18 | 31 |
| 19 | 32 |
| 20 | 42 |
| 21 | 43 |
| 22 | 46 |
| 23 | 54 |
| 24 | 67 |
| 25 | 70 |

TABLE 8-continued

| Antagonist effects of compounds of the invention against TRPC6 ($IC_{50}$) | |
|---|---|
| Compound No. | TRPC6 $IC_{50}$ (nM) |
| 26 | 71 |
| 27 | 75 |
| 28 | 100 |
| 29 | 110 |
| 30 | 110 |
| 31 | 120 |
| 32 | 130 |
| 33 | 82 |
| 34 | 85 |
| 35 | 94 |
| 36 | 97 |
| 37 | 160 |
| 38 | 170 |
| 39 | 170 |
| 40 | 170 |
| 41 | 180 |
| 42 | 140 |
| 43 | 140 |
| 44 | 140 |
| 45 | 150 |
| 46 | 160 |
| 47 | 220 |
| 48 | 250 |
| 49 | 250 |
| 50 | 47 |
| 51 | 290 |
| 52 | 190 |
| 53 | 210 |
| 54 | 220 |
| 55 | 220 |
| 56 | 290 |
| 57 | 300 |
| 58 | 100 |
| 59 | 340 |
| 60 | 440 |
| 61 | 500 |
| 62 | 550 |
| 63 | 670 |
| 64 | 820 |
| 65 | 830 |
| 66 | 840 |
| 67 | 560 |
| 68 | 630 |
| 69 | 630 |
| 70 | 640 |
| 71 | 850 |
| 72 | 910 |
| 73 | 1300 |
| 74 | 1400 |
| 75 | 1500 |
| 76 | 1800 |
| 77 | 2200 |
| 78 | 2800 |
| 79 | 3700 |
| 80 | <27 |
| 81 | 71 |
| 82 | 180 |
| 83 | 98 |
| 84 | 300 |
| 85 | 320 |
| 86 | 350 |
| 87 | 620 |
| 88 | 750 |
| 89 | 2100 |
| 90 | 364 |
| 91 | 414 |
| 92 | 635 |
| 93 | 595 |
| 94a | 343 |
| 94b | 351 |
| 95 | 445 |

The biological activity of the claimed compounds can also be shown using a TRPC6 patch clamp assay.

Methods of Therapeutic Use

The inhibition of TRPC6 is an attractive means for preventing and treating a variety of diseases or conditions that are exacerbated by TRPC6 activity. The compounds disclosed herein effectively inhibit TRPC6 activity. In particular, the compounds of the invention are selective ion channel inhibitors and have good metabolic stability in human microsomes. More particularly, the compounds of to the invention have very good potency and selectivity on the TRPC6 channel as compared to other TRP channels including TRPC3, TRPC5 and TRPC7. Thus, the compounds of the invention are useful for the treatment of diseases and conditions as described in the Background and Detailed Description section, including the following conditions and diseases:

cardiac conditions (e.g., cardiac :hypertrophy), hypertension (e.g., primary or secondary), pulmonary arterial hypertension (e.g., IPAH), a neurodegenerative disease or disorder (e.g., Alzheimer's disease (AD), Parkinson's disease, Huntington's disease, amyotrophic lateral sclerosis (ALS), and other brain disorders caused by trauma or other insults including aging), inflammatory diseases (e.g., asthma, chronic obstructive pulmonary disease, rheumatoid arthritis, osteoarthritis, inflammatory bowel disease, multiple sclerosis, and disorders of the immune system), preeciampsia and pregnancy-induced hypertension, kidney diseases (focal segmental glomerulosclerosis, nephrotic syndrome, diabetic nephropathy, renal insufficiency, end stage renal disease, minimal change disease), ischemia or an ischemic reperfusion injury, cancer, IPF (idiopathic pulmonary fibrosis), ARDS (acme respiratory disease syndrome), and diabetes metabolic disorders such as diabetes. Methods for preventing or treating any of the foregoing or following diseases and conditions include treating any of the symptoms associated with these diseases or conditions. For example, methods for treating kidney disease contemplate treating symptoms including, but not limited to, secondary hypertension, proteinuria, lipiduria, hypercholesterolemia, hyperlipidemia, and coagulation abnormalities.

Because of the important role that calcium regulation plays in many cellular processes including cellular activation, cytoskeletal rearrangement, gene expression, cellular trafficking and apoptotic cell death, calcium dyshomeostasis is implicated in the many diseases and disorders. These diseases and disorders include neurological and neurodegenerative diseases and disorders; inflammatory diseases and disorders such as inflammatory bowel disease and Crohn's disease; kidney disease such as hypercalcemia, kidney stones, and polycystic kidney disease; metabolic diseases and disorders including obesity and diabetes; liver and kidney diseases and disorders; chronic kidney disease, cardiovascular diseases and disorders including hypertension; respiratory diseases including COPD, IPAH, asthma, and emphysema; and cancers, including cancers of the brain, breast, kidney, cervix, prostate, gastrointestinal tract, (e.g., gastric cancer or stomach cancer), skin, and epithelia.

These disorders have been well characterized in man, but also exist with a similar etiology in other mammals, and can be treated by pharmaceutical compositions of the present invention.

Accordingly, a compound of the invention, as described herein, or a pharmaceutically acceptable salt thereof may be used for the preparation of a medicament for treating a disease or disorder mediated by TRPC6, including those mehtioned above and in the Background and Detailed Description aections.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, scram proteins, buffer substances, water, salts or electrolytes and cellulose-based substances. Preferred dosage forms include tablet, capsule, caplet, liquid, solution, suspension, emulsions, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. :Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the seventy and course of the patient's disorder or disposition thereto, and the judgment of the treating physician.

The compounds of the invention may be used alone or in combination of one or more additional therapeutic agents. Nonlimiting examples of additional therapeutic agents may include:

angiotensin II receptor antagonists (angiotensin receptor blockers (ARBs)) such as candesartan, eprosartan, candesartan, irbesartan, losartan, olmesartan, telmisartan, valsartan, azilsartan, and medoxomil;

angiotensin converting enzyme inhibitors (e.g., benazepril, captopril, enalapril, fosinopril, lisinopril, moexipril, and perindopril);

antidiabetics such as alpha-glucosidase inhibitors (e.g., miglitol and acarbose), amylin analogs (e.g., pramlintide), dipeptidyl peptidase 4 inhibitors (e.g., alogliptin, sitagliptin, saxagliptin, and linagliptin), incretin mimetics (e.g., liraglutide, exenatide, liraglutide, exenatide, dulaglutide albiglutide, and lixisenatide, insulin, meglitinides (e.g., repaglinide and nateglinide), biguanides (e.g., metformin); SGLT-2 inhibitors (e.g., canagliflozin, empaglifiozin, and dapaglitlozin), sulfonylureas (e.g., chlorpropamide, glimepiride, glyburide, glipizide, glyburide, tolazamide, and tolbutamide), and thiazolidinediones (e.g., rosiglitazone and pioglitazone);

bronchodilators including short-acting and long-action beta agonists (e,g., albuterol, levalbuterol, salmeterol, formoterol, and arformoterol) and short- and long-acting anticholinergics (ipratropium, tiotropium, umeclidinium, glycopyrrolatei), and aclidinium).

steroids such as fluticasone and budesonide;

When used as combination treatment of a pharmaceutical combination, the compounds of the invention and the one or more additional agents can be administered in the same dosage form or different dosage forms. The compounds of the invention and the one or more additional agents can be administered simultaneously or separately, as part of a regimen.

What is claimed is:

1. A compound of formula (I)

(I)

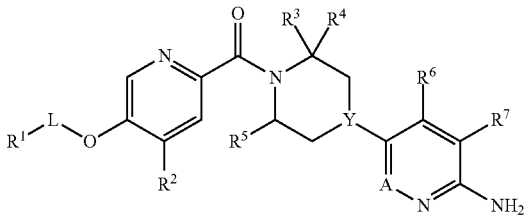

wherein

L is absent or is methylene or ethylene;

Y is CH or N;

A is CH or N;

$R^1$ is selected from the group consisting of:

$C_{1-6}$alkyl optionally substituted with 1 to 3 groups independently selected from the group consisting of halo, $C_{3-6}$cycloalkyl and $OC_{3-6}$cycloalkyl;

phenyl optionally substituted with 1 to 3 groups independently selected from the group consisting of $CF_3$, halo, $C_{3-6}$cycloalkyl, $OC_{3-6}$cycloalkyl, and $OC_{1-6}$alkyl; wherein said $OC_{1-6}$alkyl may be optionally substituted with one to three halo; and $C_{3-6}$cycloalkyl optionally substituted with 1 to 3 groups independently selected from the group consisting of halo and $C_{1-6}$alkyl optionally substituted with 1 to 3 halo;

$R^2$ is selected from the group consisting of H, $C_{1-6}$alkyl, $OCF_3$, $C_{3-6}$cycloalkyl, $OC_{3-6}$alkyl, and $OC_{3-6}$cycloalkyl;

$R^3$ is selected from the group consisting of H; C_alkyl, $C_{3-6}$cycloalkyl, and $OC_{3-6}$cycloalkyl; wherein each of the $C_{1-6}$alkyl, $C_{3-6}$cycloalkyl, or $OC_{3-6}$cycltoalkyl of the $R^3$ group may independently be optionally substituted with one to three groups each independently selected from the group consisting of halo, OH, $OC_{1-6}$ alkyl, $SC_{1-6}$alkyl, and $N(C_{1-6}alky)_2$; and wherein one to three carbon atoms of the $C_{1-6}$alkyl of the $R^3$ group may optionally be replaced one or two moieties selected from the group consisting of NH, $N(C_{1-6}alkyl)$, O, and S;

$R^4$ and $R^5$ are each independently selected from the group consisting of H and $C_{1-6}$,alkyl; or $R^3$ and $R^4$ together with the atom to which they are attached may join to form a 3-membered carbocyclyl ring; or $R^3$ and $R^5$ together with the atoms to which they are attached may join to form a 3- to 9-membered bicyclic ring, wherein said 3- to 9-membered bicyclic ring may optionally contain one to three heteroatoms selected from the group consisting of N, O, and S;

$R^6$ is selected from the group consisting of H, $C_{1-6}$alkyl, CN, $CF_3$, $OCF_3$, $C_{3-6}$cycloalkyl, $OC_{1-6}$alkyl, and $OC_{3-6}$ cycloalkyl;

$R^7$ is selected from the group consisting of H and $OC_{1-6}$ alkyl;

or a pharmaceutically acceptable salt thereof.

2. The compound according to claim 1, wherein $R^1$ is selected from the group consisting of:

$C_{1-6}$alkyl optionally substituted with 1 to 3 groups independently selected from the group consisting of halo and $C_{3-6}$cycloalkyl;

phenyl optionally substituted with 1 to 3 groups independently selected from the group consisting of $CF_3$, halo, $OC_{3-6}$cycloalkyl, and $OC_{1-6}$alkyl; wherein said $OC_{1-6}$ alkyl may be optionally substituted with one to three halo; and $C_{3-6}$cycloalkyl optionally substituted with 1 to 3 halo groups;

$R^2$ is $OC_{1-6}$alkyl;

$R^3$ is selected from the group consisting of H and $C_{1-6}$alkyl, optionally substituted with OH or $OC_{1-6}$alkyl;

$R^4$is H;

$R^5$ is H; or $R^3$ and $R^4$ together with the atom to which they are attached may join to form a 3-membered carbocyclyl ring; and R $R^3$ and $R^5$ together with the atoms to which they are attached may join to form a 3- to 9-membered bicyclic ring, wherein said 3- to 9-membered bicyclic ring may optionally contain one to three heteroatoms selected from the group consisting of N and O;

$R^6$ is selected from the group consisting of H; $C_{1-6}$alkyl, $OC_{1-6}$alkyl, and $OC_{3-6}$cycloalkyl; and $R^7$ is selected from the group consisting of H and $OC_{1-6}$ alkyl;

or a pharmaceutically acceptable salt thereof.

3. The compound according to claim 1, wherein

A is CH and Y is N; or

A is CH and Y is CH; or

A is N and Y is CH;

or a pharmaceutically acceptable salt thereof.

4. The compound according to claim 1, wherein $R^1$ is phenyl optionally substituted with a group selected from the group consisting of $CF_3$, halo, $OC_{3-6}$cycloalkyl, and $OC_{1-6}$alkyl; wherein the $OC_{3-6}$ alkyl may be optionally substituted with one to three halo;

$R^2$ is $OC_{1-6}$alkyl;

$R^3$ is selected from the group consisting of H and $C_{1-6}$alkyl optionally substituted with OH or $OC_{1-6}$alkyl;

$R^4$ is H;

$R^5$ is H; or $R^3$ and $R^4$ can together with the atom to which they are attached may join to form a 3-membered carbocyclyl ring; or $R^3$ and $R^5$ together with the atoms to which they are attached may join to form a 3- to 9-membered bicyclic ring, wherein said 3- to 9-membered bicyclic ring may optionally contain one to three heteroatoms selected from the group consisting of N and O;

$R^6$ is selected from the group consisting of H, $C_{1-6}$alky, $OC_{1-6}$alkyl, and $OC_{3-6}$cycloalkyl;

$R^7$ is selected from the group consisting of H and $OC_{1-6}$ alkyl;

or a pharmaceutically acceptable salt thereof.

5. The compound according to claim 1, wherein $R^1$ is phenyl optionally substituted with a group selected from the group consisting of $CF_3$, $OCF_3$, F, and methoxy;

$R^2$ is selected from the group consisting of methoxy or ethoxy;

$R^3$ is selected from the group consisting of H, $C_{1-6}$alkyl, 2-hydroxymethyl, methoxymethyl, and 1-hydroxyethyl;

$R^4$ is H;

$R^5$ is H; or $R^3$ and $R^4$ together with the atom to which they are attached may join to form a 3-membered carbocyclyl ring; or $R^3$ and $R^5$ together with the atoms to which they are attached may join to form a 3- to 9-membered bicyclic ring, wherein said 3- to 9-membered bicyclic ring may optionally contain one to three heteroatoms selected from the group consisting of N, O, and S;

$R^6$ is selected from the group consisting of H, methyl, methoxy, ethoxy, propoxy, and cyclopropyloxy; and $R^7$ is selected from the group consisting of H and methoxy;

or a pharmaceutically acceptable salt thereof.

6. The compound according to claim 1, wherein $R^1$ together with L represent a group selected from the group consisting of phenyl, 4-chlorophenyl, 4-fluorophenyl, 4-methoxyphenyl, 4-isopropoxyphenyl, 4-trifluoromethyiphenyl, 4-difluoromethoxyphenyl 4-cyclopropyloxyphenyl, cyclopropyl, cyclopentyl, cyclohexyl, benzyl, 2-fluorobenzyl, and phenylethyl; and $R^2$ is methoxy or ethoxy;

or a pharmaceutically acceptable salt thereof.

7. The compound according to claim 1, wherein

Y is CH and A is N;

$R^1$ together with L represent a group selected from the group consisting of phenyl, 4-chlorophenyl, 4-fluorophenyl, 4-methoxyphenyl, 4-isopropoxyphenyl, 4-trifluoromethylphenyl, 4difluoromethoxyphenyl, 4-cyclopropoxyphenyl, benzyl, 2-fluorobenzyl, and phenylethyl;

$R^2$ is methoxy or ethoxy;

$R^3$, $R^4$ and $R^5$ are each H;

$R^6$ is H, methyl, methoxy, or ethoxy; and $R^7$ is H;

or a pharmaceutically acceptable salt thereof.

8. The compound according to claim 1, wherein
Y is CH and A is CH;
$R^1$ together with L represent a group selected from the group consisting of phenyl, 4-chlorophenyi, 4-fluorophenyl, 4-methoxyphenyl, 4-trifluoromethylphenyl, cyclopentyl, cyclohexyl, benzyl, 2-fluorobenzyl, and phenylethyl;
$R^2$ is methoxy or ethoxy;
$R^3$, $R^4$ and $R^5$ are each H;
$R^6$ is H, methyl, methoxy or ethoxy; and
$R^7$ is H;
or a pharmaceutically acceptable salt thereof.

9. The compound according to claim 1, wherein
Y is N and A is CH;
$R^1$ together with L represent a group selected from the group consisting of phenyl, and 4-fluorophenyl;
$R^2$ is methoxy;
$R^3$ is selected from the group consisting of H, 2-hydroxymethyl, and hydroxyethyl;
$R^4$ is H;
$R^5$ is H; or
$R^3$ and $R^4$ together with the atom to which they are attached may join to form a 3-membered carbocyclyl ring; or
$R^3$ and $R^5$ together with the atoms to which they are attached may join to form a 3- to 9-membered bicyclic ring, wherein said 3- to 9-membered bicyclic ring may optionally contain one to three heteroatoms selected from the group consisting of N, O, and S;
$R^6$ is selected from the group consisting of H and methoxy; and
$R^7$ is H;
or a pharmaceutically acceptable salt thereof.

10. The compound according to claim 1, wherein
$R^1$ is $C_{1-6}$alkyl optionally substituted with 1 to 3 groups independently selected from the group consisting of halo and $C_{3-6}$cycloalkyl;
$R^2$ is $OC_{1-6}$alkyl;
$R^3$, $R^4$ and $R^5$ are each H;
$R^6$ is selected from the group consisting of H, $C_{1-6}$alkyl, and $OC_{1-6}$alkyl; and
$R^7$ is H;
or a pharmaceutically acceptable salt thereof.

11. The compound according to claim 1, wherein
$R^1$ together with L represent a group selected from the group consisting ethyl, propyl, isopropyl, isobutyl, cyclopropylmethyl, cyclobulylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2difluorocyclobutylmethyl, 3,3difluorocyclobutylmethyl, 3-(trifluoromethyl)cyclobutylmethyl, and 3,3,3-trifluoro-2-methyl-propyl;
$R^2$ is methoxy;
$R^3$, $R^4$ and $R^5$ are each H;
$R^6$ is selected from the group consisting of H, methyl, and methoxy; and
$R^7$ is H;
or a pharmaceutically acceptable salt thereof.

12. The compound according to claim 1, wherein
Y is CH and A is N;
$R^1$ together with L represent a group selected from the group consisting propyl, isopropyl, isobutyl, cyclopropylmethyl, cyclobutylmethyl, 2,2-dimethylpropyl, 1-cyclopropylethyl, and 2-cyclopropylethyl;
$R^2$ is methoxy;
$R^3$, $R^4$ and $R^5$ are each H;
$R^6$ is selected from the group consisting of H, methyl, and methoxy; and
$R^7$ is H;
or a pharmaceutically acceptable salt thereof.

13. The compound according to claim 1, wherein
Y is CH and A is CH;
$R^1$ together with L represent a group selected from the group consisting ethyl, propyl, isopropyl, isobutyl, cyclopropylmethyl, cyclobutylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2-difluorocyclobutylmethyl, 3,3-difluorocyclobutylmethyl, 3-(trifluoromethyl) cyclobutylmethyl, and 3,3,3-trifluoro-2-methyl-propyl;
$R^2$ is methoxy;
$R^3$, $R^4$ and $R^5$ are each H;
$R^6$ is selected from the group consisting of H, methyl, and methoxy; and
$R^7$ is H;
or a pharmaceutically acceptable salt thereof.

14. The compound according to claim 1, wherein
$R^3$ and $R^4$ together with the atom to which they are attached join to form a 3-membered carbocyclyl ring,
or a pharmaceutically acceptable salt thereof.

15. The compound according to claim 1, wherein
$R^3$ and $R^5$ together with the atoms to which they are attached join to form a 3- to 9-membered bicyclic ring, wherein said 3- to 9-membered bicyclic ring may optionally contain one to two heteroatoms independently selected from the group consisting of N and O,
or a pharmaceutically acceptable salt thereof.

16. The compound according to claim 1, selected from the group consisting of
[4-(6-Amino-4-methoxy-pyridin-3-yl)-piperazin-1-yl][5-(4-fluoro-phenoxy)-4-methoxy-pyridin-2-yl]methanone,
(6-Amino-4-methyl-3',4',5',6'-tetrahydro-2'H-[3,4']-bipyridinyi-1'-yl)[5-(4-fluoro-phenoxy)-4-methoxypyridin-2-yl]-methanone,
(6-Amino-3',4',5',6'-tetrahydro-2'H-[3,4']bipyridinyl-1'yl)-(4-methoxy-5-phenoxy-pyridin-2-yl)-methanone,
(6-Amino-4-methoxy-3',4',5',6'-tetrahydro-2'H-[3,4']bipyridinyl-l1'-yl)[5-(4-fluoro-phenoxy)-4-methoxypyridin-2-yl]-methanone,
[4-(6-Amino-4-methoxy-pyridin-3-yl)-piperazin-1-yl]-(4-methoxy-5-phenoxy-pyridin-2-yl)-methanone,
[4-(6-Amino-pyridazin-3-yl)-piperidin-1yl]-[5-(4-isopropoxy-phenoxy)-4-methoxy-pyridin-2yl]-methanone,
[(R)-4-(6-Amino-4-methyl-pyridin-3-yl)-2-hydroxymethyl-piperazin-1-yl]-[5-(4-fluoro-phenoxy)-4-methoxy-pyridin-2-yl]-methanone,
[7-(6-Amino-4-methoxy-pyridin-3-yl)-4,7-diaza-spiro[2.5]oct-4yl]-(4-methoxy-5-phenoxy-pyridin-2-yl) methanone,
[7-(6-Amino-4-methoxy-pyridin-3-yl)-4,7-diaza-spiro[2.5]oct-4-yl]-[5-(4-fluoro-phenoxy)-4-methoxy-pyridin-2-yl]-methanone,
(6-Amino-4-methyl-3',4',5',6'-tetrahydro-2'H-[3,4]bipyridinyl-1'-yl)-(4-methoxy-5-phenoxy-pyridin-2-yl) methanone,
[4-(6-Amino-5-methoxy-pyridazin-3-yl)-piperidin-1yl]-[5-(4-fluoro-phenoxy)-4-methoxy-pyridin-2-yl]-methanone,
[4-(6-Amino-pyridin-3-yl)-piperazin-1-yl]-[4-methoxy-5-(4-methoxy-phenoxy)-pyridin-2-yl]-methanone,

[4-(6-Amino-pyridin-3-yl)-piperazin-1-yl]-[5-(4-fuoro-phenoxy)-4-methoxy-pyridin-2-yl]-methanone, (6-Amino-3',4',5',6'-tetrahydro-2'H-[3,4']pyridinyl-1'yl)-[5-(4-fluoro-phenoxy)-4-methoxy-pyridin-2-yl]methanone,

[4-(6-Amino-pyridin-3-yl)-piperazin-1-yl]-(4-methoxy-5-phenoxy-pyridin-2-yl)-methanone,

[4-(6-Amino-pyridazin-3-yl)-piperidin-1-yl]-(4-methoxy-5-phenoxy-pyridin-2-yl)-methanone,

[4-(6-Amino-pyridazin-3-yl)-piperidin-1-yl]-[5-(4-fluoro-phenoxy)-4-methoxy-pyridin-2-yl]-methanone,

[(R)-4-(6-Amino-4-methyl-pyridin-3-yl)-2-hydroxymethyl-piperazin-1-yl]-(4-methoxy-5 -phenoxy-pyridin-2-yl)-methanone, (6-Amino-4-methoxy-3',4',5',6'-tetrahydro-2'H-[3,4']bipyridinyl-1'-yl)-[5-(2-fluoro-benzyloxy)-4-methoxy-pyridin-2-yl]-methanone,

[(R)-4-(6-Amino-pyridin-3-yl)-2-hydroxymethyl-piperazin-1-yl]-[5-(4-fluoro-phenoxy)-4-methoxy-pyridin-2-yl]-methanone,

[4-(6-Amino-5-methoxy-pyridazin-3-yl)-piperidin-1-yl]-(4-methoxy-5-phenoxy-pyridin-2-yl)-methanone, (6-Amino-3',4',5',6'-tetrahydro-2'H-[3,4'-]bipyridinyl-1'-yl)-[4-methoxy-5-(4-methoxy-phenoxy)-pyridin-2-yl]-methanone, (6-Amino-4-methoxy-3',4',5',6'-tetrahydro-2'H-[3,4']bipyridinyl-1'-yl)-(4-methoxy-5-phenoxy-pyridin-2-yl)-methanone, (6-Amino-4-methoxy-3',4',5',6'-tetrahydro-2'H-[3,4']bipyridinyl-1'-yl)-[4-methoxy-5-(4-trifluoromethyl-phenoxy)-pyridin-2-yl]-methanone, 45

[4-(6-Amino-pyridazin-3-yl)-piperidin-1-yl]-(5-cyclobutylmethoxy-4-methoxy-pyridin-2-yl)-methanone, (6-Amino-4-methoxy-3',4',5',6'-tetrahydro-2'H-[3,4']bipyridinyl-1'-yl)-[4-methoxy-5-(1-methyl-cyclopropyl-methoxy)-pyridin-2-yl]-methanone,

[(R)-4-(6-Amino-4-methoxy-pyridin-3-yl)-2-methoxymethyl-piperazin-1-yl]-(4-methoxy-5-phenoxy-pyridin-2-yl)-methanone, (6-Amino-4-methoxy-3',4',5',6'-tetrahydro-2'H-[3,4']bipyridinyl-1'-yl)-[4-methoxy-5-(4-methoxy-phenoxy) pyridin-2yl]-methanone, (6-Amino-4-methoxy-3',4',5',6'-tetrahydro-2'H-[3,4']bipyridinyl-1'-yl)-(5-cyclohexyloxy-4-methoxy-pyridin-2-yl)-methanone, (6-Amino-4-methoxy-3',4',5',6'-tetrahydrp-2'H-[3,4']bipyridinyl-1'-yl)-[5-(4-fluoro-benzyloxy)-4-methoxy-pyridin-2-yl]-methanone,

[4-(6-Amino-pyridazin-3-yl)-piperidin-1-yl]-[4-methoxy-5-(4-trifluoromethyl-phenoxy)-pyridin-2-yl]-methanone,

[4-(6-Amino-pyridazin-3-yl)-piperidin-1-yl]-[5-(4chloro-phenoxy)-4 -methoxy-pyridin-2-yl]-methanone, (6-Amino-4-methoxy-3',4',5',6'-tetrahydro-2'H-[3,4']bipyridiny 1'-yl)-(5-cyclopentyloxy4-methoxy-pyridin-2-yl)-methanone,

[4-(6-Amino-pyridazin-3-yl)-piperidin-1-yl]-(5-isobutoxy-4-methoxy-pyridin-2-yl)-methanone, (6-Amino-4-methoxy-3',4',5',6'-tetrahydro-2'H-[3,4']bipyridinyl-1'-yl)-(5-cyclopropylmethoxy-4-methoxy-pyridin-2-yl)-methanone,

[3-(6-Amino-4-methoxy-pyridin-3-yl)-3,8-diaza-bicyclo[3.2.1]oct-8-yl]-[5-(4-fluoro-phenoxy)-4-methoxypyridin-2-yl]-methanone, (6-Amino 4-methoxy-3',4',5',6'-tetrahydro-2'H-[3,4']bipyridinyl-1'-yl)-(5-isobutoxy-4-methoxy-pyridin-2-yl)-methanone,

[4-(6-Amino-pyridazin-3-yl)-piperidin-1-yl]-[5-(4-cyclopropoxy-phenoxy)-4-methoxy-pyridin-2-yl]-methanone,

[4-(6-Amino-pyridazin-3-yl)-piperidin-1-yl]-[5-(4-fluoro-benzyloxy)-4-methoxy-pyridin-2-yl]-methanone,

[(R)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone, (6-Amino-4-methoxy-3',4',5',6'-tetrahydro-2'H-[3,4']bipyridinyl-1'-yl)-(5-benzyloxy-4-methoxy-pyridin-2-yl)-methanone,

[4-(6-Amino-pyridazin-3-yl)-piperidin-1-yl]-[4-methoxy-5-(4-methoxy-phenoxy)-pyridin-2-yl]-methanone, (6-Amino-4-metboxy-3',4',5',6'-tetrahydro-2'H-[3,4']bipyridinyl-1'-yl)-[5-(3,3-difluoro-cyclobutylmethoxy)-4-methoxy-pyridin-2-yl]-methanone, (6-Amino-4-methoxy-3',4',5',6'-tetrahydro-2'H-[3,4']bipyridinyl-1'-yl)-(4-methoxy-5-propoxy-pyridin-2-yl)-methanone,

[4-(6-Amino-4-methoxy-pyridazin-3 -yl)-piperidin-1-yl]-(4-methoxy-5-phenoxy-pyridin-2-yl)-methanone, (6-Amino-4-methoxy-3',4',5',6'-tetrahydro-2'H-[3,4']bipyridinyl-1'-yl)-[5-(2-cyclopropyl-ethoxy)-4-methoxy-pyridin-2yl]-methanone, (1R)-1-[(2R)-4-(6-amino-4-methoxypyridin-3-yl)-1-(5-phenoxypyridine-2-carbonyl)piperazin-2-yl]ethan-1-ol,

[3-(6-Amino-4-methoxy-pyridin-3-yl)-3,8-diaza-bicylo[3.2.1]oct-8-yl]-(4-methoxy-5-phenoxy-pyridin-2-yl)-methanone, (6-Amino-4-methoxy-3',4',5',6'-tetrahydro-2'H-[3,4']bipyridinyl-1'-yl)-(4-methoxy-5-phenethyloxy-pyridin-2-yl)-methanone, (6-Amino-4-methoxy-3',4',5',6'-tetrabydro-2'H-[3,4']bipyridinyl-1'-yl)-(5-cyclobutylmethoxy-4-methoxypyridin-2-yl)-methanone,

[4-(6-Amino-pyridazin-3-yl)-piperidin-1-yl]-[5(4-difluoromethoxy-phenoxy)-4-methoxy-pyridin-2-yl]-methanone,

[(R)-4-(6-Amino-4-methoxy-pyridin-3-yl)-2methoxymethyl-piperazin-1-yl]-[5-(4-fluoro-phenoxy)-4-methoxy-pyridin-2-yl]-methanone,

[4-(6-Amino-pyridazin-3-yl)-piperidin-1-yl]-[5-(2-fluoro-benzyloxy)-4-methoxy-pyridin-2-yl]-methanone, (1S)-1-[(2R)-4-(6-amino-4-methoxypyridin-3-yl)-1-(5-phenoxypyridine-2-carbonyl)piperazin-2-yl]ethan-1-ol, (6-Amino-4-methoxy-3',4',5',6'-tetrahydro-2'H-[3,4']bipyridinyl-1'-yl)-[5-(2,2-dimethyl-propoxy)-4-methoxy-pyridin-2yl]methanone,

[4-(6-Amino-5-methoxy-pyridazin-3-yl)-piperidin-1-yl]-[4-methoxy-5-(4-methoxy-phenoxy)-pyridin-2-yl]-methanone,

[4-(6-Amino-4-methoxy-pyridin-3-yl)-piperazin-1-yl]-(5-cyclopropylmethoxy-4-methoxy-pyridin-2-yl)-methanone, [4-(6-Amino-pyridazin-3-yl)-piperidin-1-yl]-(5-cyclohexyloxy-4-methoxy-pyridin-2-yl)-methanone,

[(S)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone, (6-Amino-4-methoxy-3',4',5',6"-tetrahydro-2'H-[3,4']bipyridinyl-1'-yl)-[5-(1-fluoromethyl-cyclopropyl-methoxy)-4-methoxy-pyridin-2-yl]-methanone, (6-Amino-4-methoxy-3',4',5',6'-tetrahydro-2'H-[3,4']bipyridinyl-1'-yl)-(5-ethoxy-4-methoxy-pyridin-2-yl)-methanone,

[4-(6-Amino-pyridazin-3-yl)-piperidin-1-yl]-[5-(2-cyclopropyl-ethoxy)-4-methoxy-pyridin-2-yl]-methanone,

[7-(6-Amino-4-methoxy-pyridin-3-yl)-3-oxa-9aza-bicyclo[3.3.1]non-9-yl]-(4-methoxy-5-phenoxy-pyridin-2-yl)-methanone,

[(R)-4-(6-Amino-4-methoxy-pyridin-3-yl)-2-hydroxymethyl-piperazin-1-yl]-(4-methoxy-5-phenoxy-pyridin-2-yl)-methanone, (6-Amino-4-methoxy-3',4',5',6-tetrahydro-2'H-[3,4']bipyridinyl-1'-yl)-[5-((S)-1-cyclopropyl-ethoxy)-4-methoxy-pyridin-2-yl]-methanone,

[(S)-4-(6-Amino-4-methoxy-pyridin-3-yl)-2-hydroxymethyl-piperazin-1-yl]-(4-methoxy-5-phenoxy-pyridin-2-yl)-methanone, (6-Amino-4-methoxy-3',4',5',6'-tetrahydro-2'H-[3,4']bipyridinyl-1'-yl)-(5-isopropoxy-4-methoxy-pyridin-2-yl)-methanone,

[4-(6-Amino-pyridazin-3-yl)-piperidin-1-yl]-(4-methoxy-5-phenethyloxy-pyridin-2-yl)-methanone,

[4-(6-Amino-pyridazin-3-yl)-piperidin-1-yl]-[5-(2,2-dimethyl-propoxy)-4-methoxy-pyridin-2-yl]-methanone,

[4-(6-Amino-pyridazin-3-yl)-piperidin-1-yl]-[4-methoxy-5-(1-methyl-cyclopropylmethoxy)-pyridin-2-yl]-methanone,

[4-(6-Amino-pyridazin-3-yl)-piperidin-1-yl]-(4-methoxy-5-propoxy-pyridin-2-yl)-methanone, (6-Amino-4-methoxy-3',4',5',6'-tetrahydro-2'H-[3,4']bipyridinyl-1'-yl)-[5-((R)-1-cyclopropyl-ethoxy)-4-methoxy-pyridin-2-yl]-methanone,

[4-(6-Amino-4-methyl-pyridazin-3-yl)-piperidin-1-yl]-(5-cyclopropylmethoxy-4-methoxy-pyridin-2-yl)-methanone,

[4-(6-Amino-pyridazin-3-yl)-piperidin-1-yl]-[5-((S)-1-cyclopropyl-ethoxy)-4 -methoxy-pyridin-2-yl]-methanone,

[4-(6-Amino-pyridazin-3-yl)-piperidin-1-yl]-[4-methoxy-5-(4-trifluoromethoxy-phenoxy)-pyridin-2yl]-methanone,

[(R)-4-(6-Amino-pyridin-3-yl)-2-hydroxymethyl-piperazin-1-yl]-(4-methoxy-5-phenoxy-pyridin-2-yl)-methanone,

[(R)-4-(6-Amino-pyridin-3-yl)-2-hydroxymethyl-piperazin-1-yl]-[4-methoxy-5-(4-methoxy-phenoxy)-pyridin-2yl]-methanone,

[4-(6-Amino-pyridazin-3-yl)-piperidin-1yl]-[5-(phenoxy)-4-ethoxy-pyridin-2yl]-methanone, (6-Amino-4-cyclopropoxy-3',4',5',6'-tetrahydro-2'H-[3,4']biphyidinyl-1'-yl)-[5-(phenoxy)-4-methoxy-pyridin-2yl]-methanone, (6-Amino-4-propoxy-3',4',5',6'-tetrahydro-2'H-[3,4']bipyridinyl-1'-yl)-[5-(phenoxy)-4-methoxy-pyridin-2-yl]-methanone,

[4-(6-Amino-pyridazin-3-yl)-piperidin-1-yl]-[5-(4-fluoro-phenoxy)-4-ethoxy-pyridin-2-yl]-methanone,

[3-(6-Amino-pyridazin-3-yl)-8-aza-bicyclo[3.2.1]oct-8-yl]-[4-ethoxy-5-(4-fluoro-phenoxy)-pyridin-2-yl]-methanone, 5-Methoxy-6-(1-{5-[4-(trifluoromethyl)-phenoxy]-pyridine-2-carbonyl}piperidin-4-yl)-pyridazin-3-amine, 4-Methoxy-5-[1-(4-methoxy-5-{[trans-3-(trifluoromethyl)cyclobutyl]-methoxy}pyridine-2-carbonyl)-piperidin-4-yl]pyridin-2-amine, 4-Methoxy-5-[1-(4-methoxy-5-{[(cis-3-(trifluoromethyl)-cyclobutyl]methoxy}-pyridine-2-carbonyl)piperidin-4-yl]pyridin-2-amine, 4-Methoxy-5-(1-{4-methoxy-5-[(2)-3,3,3-trifluoro-2-methylpropoxy]-pyridine-2-carbonyl}peridin-4-yl) pyridin-2-amine, and 5-(1-{5-[(2,2-Difluorocyclobutyl)-methoxy]-4-methoxy-pyridine-2-carbonyl}-piperidin-4-yl)-4-methoxypyridin-2-amine, or a pharmaceutically acceptable salt thereof.

17. A pharmaceutical composition comprising a compound according to claim 1, or a pharmaceutically acceptable salt thereof, and optionally a pharmaceutically acceptable excipient.

18. A method for treating a disease or disorder that can be alleviated by TRPC6 inhibition the method comprising:

administering a therapeutically effective amount of a compound according to claim 1, or a pharmaceutically acceptable salt thereof, to patient in need thereof, wherein the disease or disorder is selected from the group consisting of cardiac hypertrophy, ischemia, ischemic reperfusion injury, hypertension, pulmonary arterial hypertension, idiopathic pulmonary arterial hypertension, restenosis, chronic obstructive pulmonary disease, cystic fibrosis, kizheimer's disease, Parkinson's disease, Huntington's disease, amyotrophic lateral sclerosis (ALS), trauma induced brain disorders, asthma, chronic obstructive pulmonary disease, rheumatoid arthritis, osteoarthritis, inflammatory bowel disease, multiple sclerosis, mus$^{c}$-ular dystrophy. Duchenne's muscular dystrophy, preeclampsia and pregnancy-induced hypertension, non-alcoholic steatohepatitis, minimal change disease, focal segmental glomerulosclerosis (FSGS), nephrotic syndrome, diabetic nephropathy or diabetic kidney disease (DKD), chronic kidney disease, renal insufficiency, end stage renal disease, ischemia or an ischemic reperfusion injury, idiopathic pulmonary fibrosis (IPF), acute respiratory disease syndrome (ARDS), emphysema and diabetes.

19. The compound according to claim 1, selected from the group consisting of:

[4-(6-Amino-pyridazin-3-yl)-piperidin-1-yl]-[5-(4-isopropoxy-phenoxy)-4-methoxy-pyridin-2-yl]-methanone;

[4-(6-Amino-pyridazin-3-yl)-piperidin-1-yl]-(4-methoxy-5-phenoxy-pyridin-2-yl)-methanone;

[4-(6-Amino-pyridazin-3-yl)-piperidin-1-yl]-[5-(4-fluoro-phenoxy)-4-methoxy-pyridin-2-yl]-methanone;

[4-(6-Amino-pyridazin-3-yl)-piperidin-1-yl]-[4-methoxy-5-(4-trifluoromethyl-phenoxy)-pyridin-2-yl]-methanone;

[4-(6-Amino-pyridazin-3-yl)-piperidin-1-yl]-[5-(4-chloro-phenoxy)-4-methoxy-pyridin-2-yl]--methanone;

[4-(6-Amino-pyiidazin-3-yl)-piperidin-1-yl]-[5-(4-cyclopropoxy-phenoxy)-4-methoxy-pyridin-2-yl]-methanone;

[4-(6-Amino-pyridazin-3-yl)-piperidin-1-yl]-[4-fluoro-benzyloxy)-4-methoxy-pyridin-2-yl]-methanone;

[4-(6-Amino-pyridazin-3-yl)-piperidin-1-yl]-[4-methoxy-5-(4-methoxy-phenoxy)-pyridin-2-yl]-methanone;

[4-(6-Amino-pyridazin-3-yl)-piperidin-1-yl]-[5-(4-difluoromethoxy-phenoxy)-4-methoxy-pyridin-2-yl]-methanone;

[4-(6-Amino-pyridazin-3-yl)-pipenridin-1-yl]-[5-(2-fluoro-benzyloxy)-4-methoxy-pyridin-2-yl]-methanone;

[4-(6-Amino-pyridazin-3-yl)-piperidin-1-yl]-[4-methoxy-5-(4-trifluoromethoxy-phenoxy)-pyridin-2-yl]-methanone;

[4-(6-Amino-pyridazin-3-yl)-piperidin-1-yl]-[5-(phenoxy)-4-ethoxy-pyridin-2-yl]-methanone; and

[4-(6-Amino-pyridazin-3-yl)-piperidin-1-yl]-[5-(4-fluoro-phenoxy)-4-ethoxy-pyridin-2-yl]-methanone;

or a pharmaceutically acceptable salt thereof.

20. A pharmaceutically acceptable salt of the compound according to claim 19, selected from the group consisting of:

[4-(6-Amino-pyridazin-3-yl)-piperidin-1-yl]-[5-(4-isopropoxy-phenoxy)-4-methoxy-pyridin-2-yl]-methanone;

[4-(6-Amino-pyridazin-3-yl)-piperidin-1-yl]-(4-methoxy-5-phenoxy-pyridine-2-yl)-methanone;

[4-(6-Amino-pyridazin-3-yl)-piperidin-1-yl]-[5-(4-fluoro-phenoxy)-4-methoxy-pyridin-2-yl]-methanone;

[4-(6-Amino-pyridazin-3-yl)-piperidin-1-yl]-[4-methoxy-5-(4-trifluoromethyl-phenoxy)-pyridin-2-yl]-methanone;

[4-(6-Amino-pyridazin-3-yl)-piperidin-1-yl]-[5-(4-chloro-phenoxy)-4-methoxy-pyridin-2-yl]-methanone;

[4-(6-Amino-pyridazin-3-yl)-piperidin-1-yl]-[5-(4-cyclopropoxy-phenoxy)-4-methoxy-pyridin-2-yl]-methanone;

[4-(6-Amino-pyridazin-3-yl)-piperidin-1-yl]-[5-(4-fluoro-benzyloxy)-4-methoxy-pyridin-2-yl]-methanone;

[4-(6-Amino-pyridazin-3-yl)-piperidin-1yl]-[4-methoxy-5-(4-methoxy-phenoxy)-pyridin-2-yl]-methanone;

[4-(6-Amino-pyridazin-3-yl)-piperidin-1yl]-[5-(4-difluoromethoxy-phenoxy)-4-methoxy-pyridin-2-yl]-methanone;

[4-(6-Amino-pyridazin-3-yl)-piperidin-1-yl]-[5-(2-fluoro-benzyloxy)-4-methoxy-pyridin-2-yl]-methanone;

[4-(6-Amino-pyridazin-3-yl)-piperidin-1-yl]-[4-methoxy-5-(4-trifluoromethoxy-phenoxy)-pyridin-2-yl]-methanone;

[4-(6-Amino-pyridazin-3-yl)-piperidin-1-yl]-[5-(phenoxy)-4-ethoxy-pyridin-2-yl]-methanone; and

[4-(6-Amino-pyridazin-3-yl)-piperidin-1-yl]-[5-(4-fluoro-phenoxy)-4-ethoxy-pyridin-2-yl]-methanone.

21. The compound according to claim 19, selected from the group consisting of:

[4-(6-Amino-pyridazin-3-yl)-piperidin-1-yl]-[5-(4-isopropoxy-phenoxy)-4-methoxy-pyridin-2-yl]-methanone;

[4-(6-Amino-pyridazin-3-yl)-piperidin-1-yl]-(4-methoxy-5-phenoxy-pyridin-2-yl)-methanone;

[4-(6-Amino-pyridazin-3-yl)-piperidin-1-yl]-[5-(4-fluoro-phenoxy)-4-methoxy-pyridin-2-yl]-methanone;

[4-(6-Amino-pyridazin-3-yl)-piperidin-1-yl]-[4-methoxy-5-(4-trifluoromethyl-phenoxy)-pyridin-2-yl]-methanone;

[4-(6-Amino-pyridazin-3-yl)-piperidin-1-yl]-[5-(4-chloro-phenoxy)-4-methoxy-pyridin-2-yl]-methanone;

[4-(6-Amino-pyridazin-3-yl)-piperidin-1-yl]-[5-(4-cyclopropoxy-phenoxy)-4-methoxy-pyridin-2-yl]-methanone;

[4-(6-Amino-pyridazin-3-yl)-piperidin-1-yl]-[5-(4-fluoro-benzyloxy)-4-methoxy-pyridin-2-yl]-methanone;

[4-(6-Amino-pyridazin-3-yl)-piperidin-1-yl]-[4-methoxy-5-(4-methoxy-phenoxy)-pyridin-2-yl]-methanone;

[4-(6-Amino-pyridazin-3-yl)-piperidin-1-yl]-[5-(4-difluoromethoxy-phenoxy)-4-methoxy-pyridin-2-yl]-methanone;

[4-(6-Amino-pyridazin-3-yl)-piperidin-1-yl]-[5-(2-fluoro-benzyloxy)-4-methoxy-pyridin-2-yl]-methanone;

[4-(6-Amino-pyridazin-3-yl)-piperidin-1-yl]-[4-methoxy-5-(4-trifluoromethoxy-phenoxy)-pyridin-2-yl]-mthanone;

[4-(6-Amino-pyridazin-3-yl)-piperidin-1yl]-[5-(phenoxy)-4-ethoxy-pyridin-2-yl]-methanone; and

[4-(6-Amino-pyridazin-3-yl)-piperidin-1-yl]-[5-(4-fluoro-phenoxy)-4-ethoxy-pyridin-2-yl]-methanone.

22. A compound, which is [4-(6-Amino-pyridazin-3-yl)-piperidin-1-yl]-[5-(4-isopropoxy-phenoxy)-4-methoxypyridin-2-yl]-methanone.

23. A compound, which is [4-(6-Amino-pyridazin-3-yl)-piperidin-1-yl]-(4-methoxy-5-phenoxy-pyridin-2-yl)-methanone.

24. A compound, which is [4-(6-Amino-pyridazin-3-yl)-piperidin-1yl]-[5-(4-fluoro-phenoxy)-4-methoxy-pyridin-2-yl]-methanone.

25. A compound, which is [4-(6-Amino-pyridazin-3-yl)-piperidin-1-yl]-[5-(4-difluoromethoxy-phenoxy)-4-methoxy-pyridin-2-yl]-methanone.

26. A compound, which is [4-(6-Amino-pyridazin-3-yl)-piperidin-1-yl]-[4-methoxy-5-(4-trifluoromethoxy-phenoxy)-pyridin-2-yl]-methanone.

27. A compound, which is [4-(6-Amino-pyridazin-3-yl)-piperidni-1-yl]-[5-(phenoxy)-4-ethoxy-pyridin-2-yl]-methanone.

28. The compound of claim 4, wherein $R^1$ is phenyl optionally substituted with $OCF_3$.

*29. The compound of claim 19, which is [4-(6-Amino-pyridazin-3-yl)-piperidin-1-yl]-[5-(4-isopropoxy-phenoxy)-4-methoxy-pyridin-2-yl]-methanone, or a pharmaceutically acceptable salt thereof.*

*30. The compound of claim 19, which is [4-(6-Amino-pyridazin-3-yl)-piperidin-1-yl]-(4-methoxy-5-phenoxy-pyridin-2-yl)-methanone, or a pharmaceutically acceptable salt thereof.*

*31. The compound of claim 19, which is [4-(6-Amino-pyridazin-3-yl)-piperidin1-yl]-[5-(4-fluoro-phenoxy)-4-methoxy-pyridin-2-yl]-methanone, or a pharmaceutically acceptable salt thereof.*

*32. The compound of claim 19, which is [4-(6-Amino-pyridazin-3-yl)-piperidin-1-yl]-[5-(4-difluoromethoxy-phenoxy)-4-methoxy-pyridin-2-yl]-methanone, or a pharmaceutically acceptable salt thereof.*

*33. The compound of claim 19, which is [4-(6-Amino-pyridazin-3-yl)-piperidin-1-yl]-[4-methoxy-5-(4-trifluoromethoxy-phenoxy)-pyridin-2-yl]-methanone, or a pharmaceutically acceptable salt thereof.*

*34. The compound of claim 19, which is [4-(6-Amino-pyridazin-3-yl)-piperidin-1-yl]-[5-(phenoxy)-4-ethoxy-pyridin-2-yl]-methanone, or a pharmaceutically acceptable salt thereof.*

*35. The pharmaceutically acceptable salt form of the compound of claim 19, which is [4-(6-Amino-pyridazin-3-yl)-piperidin-1-yl]-[5-(4-isopropoxy-phenoxy)-4-methoxy-pyridin-2-yl]-methanone.*

*36. The pharmaceutically acceptable salt form of the compound claim 19, which is [4-(6-Amino-pyridazin-3-yl)-piperidin-1-yl]-(4-methoxy-5-phenoxy-pyridin-2-yl)-methanone.*

*37. The pharmaceutically acceptable salt form of the compound of claim 19, which is [4-(6-Amino-pyridazin-3-yl)-piperidin-1-yl]-[5-(4-fluoro-phenoxy)-4-methoxy-pyridin-2-yl]-methanone.*

*38. The pharmaceutically acceptable salt form of the compound of claim 19, which is [4-(6-Amino-pyridazin-3-yl)-piperidin-1-yl]-[5-(4-difluoromethoxy-phenoxy)-4-methoxy-pyridin-2-yl]-methanone.*

*39. The pharmaceutically acceptable salt form of the compound of claim 19, which is [4-(6-Amino-pyridazin-3-yl)-piperidin-1-yl]-[4-methoxy-5-(4-trifluoromethoxy-phenoxy)-pyridin-2-yl]-methanone.*

*40. The pharmaceutically acceptable salt form of the compound of claim 19, which is [4-(6-Amino-pyridazin-3-yl)-piperidin-1-yl]-[5-(phenoxy)-4-ethoxy-pyridin-2-yl]-methanone.*

* * * * *